US009686995B2

(12) United States Patent
Broglie et al.

(10) Patent No.: US 9,686,995 B2
(45) Date of Patent: Jun. 27, 2017

(54) COMPOSITIONS AND METHODS TO CONTROL INSECT PESTS

(71) Applicants: E. I. DU PONT DE NEMOURS AND COMPANY, Wilmington, DE (US); Pioneer Hi-Bred International, Johnston, IA (US)

(72) Inventors: Karen E. Broglie, Landenberg, PA (US); Mani Muthalagi, Hockessin, DE (US); Kevin Kriss, Wilmington, DE (US); Albert L. Lu, West Des Moines, IA (US); James K. Presnail, Des Moines, IA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 780 days.

(21) Appl. No.: 13/791,596

(22) Filed: Mar. 8, 2013

(65) Prior Publication Data
US 2014/0250552 A1   Sep. 4, 2014

Related U.S. Application Data

(62) Division of application No. 12/868,994, filed on Aug. 26, 2010, now abandoned.

(60) Provisional application No. 61/330,484, filed on May 3, 2010, provisional application No. 61/237,880, filed on Aug. 28, 2009.

(51) Int. Cl.
| | |
|---|---|
| *A01N 57/16* | (2006.01) |
| *A01N 63/00* | (2006.01) |
| *C12N 15/113* | (2010.01) |
| *C12N 15/63* | (2006.01) |
| *C12N 15/82* | (2006.01) |
| *A01N 65/20* | (2009.01) |
| *A01N 65/44* | (2009.01) |

(52) U.S. Cl.
CPC ............ *A01N 57/16* (2013.01); *A01N 63/00* (2013.01); *A01N 65/20* (2013.01); *A01N 65/44* (2013.01); *C12N 15/113* (2013.01); *C12N 15/8218* (2013.01); *C12N 15/8286* (2013.01); *C12N 2310/11* (2013.01); *C12N 2310/531* (2013.01)

(58) Field of Classification Search
None
See application file for complete search history.

(56) References Cited

U.S. PATENT DOCUMENTS

| 7,612,194 B2 * | 11/2009 | Andersen ............ C12Q 1/6888 435/320.1 |
| 2004/0187170 A1 | 9/2004 | Plaetinck et al. |
| 2005/0261130 A1 | 11/2005 | Lennon et al. |
| 2006/0272049 A1 | 11/2006 | Waterhouse et al. |
| 2012/0164205 A1 | 6/2012 | Baum et al. |

FOREIGN PATENT DOCUMENTS

| WO | 2005110068 A2 | 11/2005 |
| WO | 2007035650 A2 | 3/2007 |

OTHER PUBLICATIONS

Baum et al (Nature Biotechnology, 25(11), pp. 1322-1326, 2007).*
Yan et al (Plant Physiology, 141, pp. 1508-1518, 2006).*
Bird et al (Biotechnology and Genetic Engineering Reviews, 9, pp. 207-227, 1991).*
Thomas et al (Plant Journal, 25, pp. 417-425, 2001).*
Baum et al, "Control of coleopteran insect pests through RNA interference," Nature Biotechnology, vol. 25 No. 11, (Nov. 1997), pp. 1322-1326 and 1 page of Supplementary Tables and 15 pages of Supplementary Figures.
International Search Report for International Application No. PCT/US2010/046762 completed Nov. 9, 2010.
International Search Report for International Application No. PCT/US2010/046762 completed Jan. 20, 2011.
Written Opinion for International Application No. PCT/US2008/087954 completed Oct. 25, 2010.

* cited by examiner

*Primary Examiner* — Elizabeth McElwain
*Assistant Examiner* — Stephen Uyeno
(74) *Attorney, Agent, or Firm* — Pioneer Hi-Bred Int'l, Inc.

(57) ABSTRACT

Methods and compositions are provided which employ a silencing element that, when ingested by a pest, such as a Coleopteran plant pest or a *Diabrotica* plant pest, decrease the expression of a target sequence in the pest. In specific embodiments, the decrease in expression of the target sequence controls the pest and thereby the methods and compositions are capable of limiting damage to a plant. The present invention provides various target polynucleotides set forth in any one of SEQ ID NOS: 1-236 or active variants and fragments thereof, wherein a decrease in expression of one or more the sequences in the target pest controls the pest (i.e., has insecticidal activity). Further provided are silencing elements which when ingested by the pest decrease the level of the target polypeptide and thereby control the pest. In specific embodiment, the pest is *D. virgifera virgifera, D. barberi, D. speciosa,* or *D. undecimpunctata howardi*. Plants, plant part, bacteria and other host cells comprising the silencing elements or an active variant or fragment thereof of the invention are also provided.

21 Claims, 2 Drawing Sheets

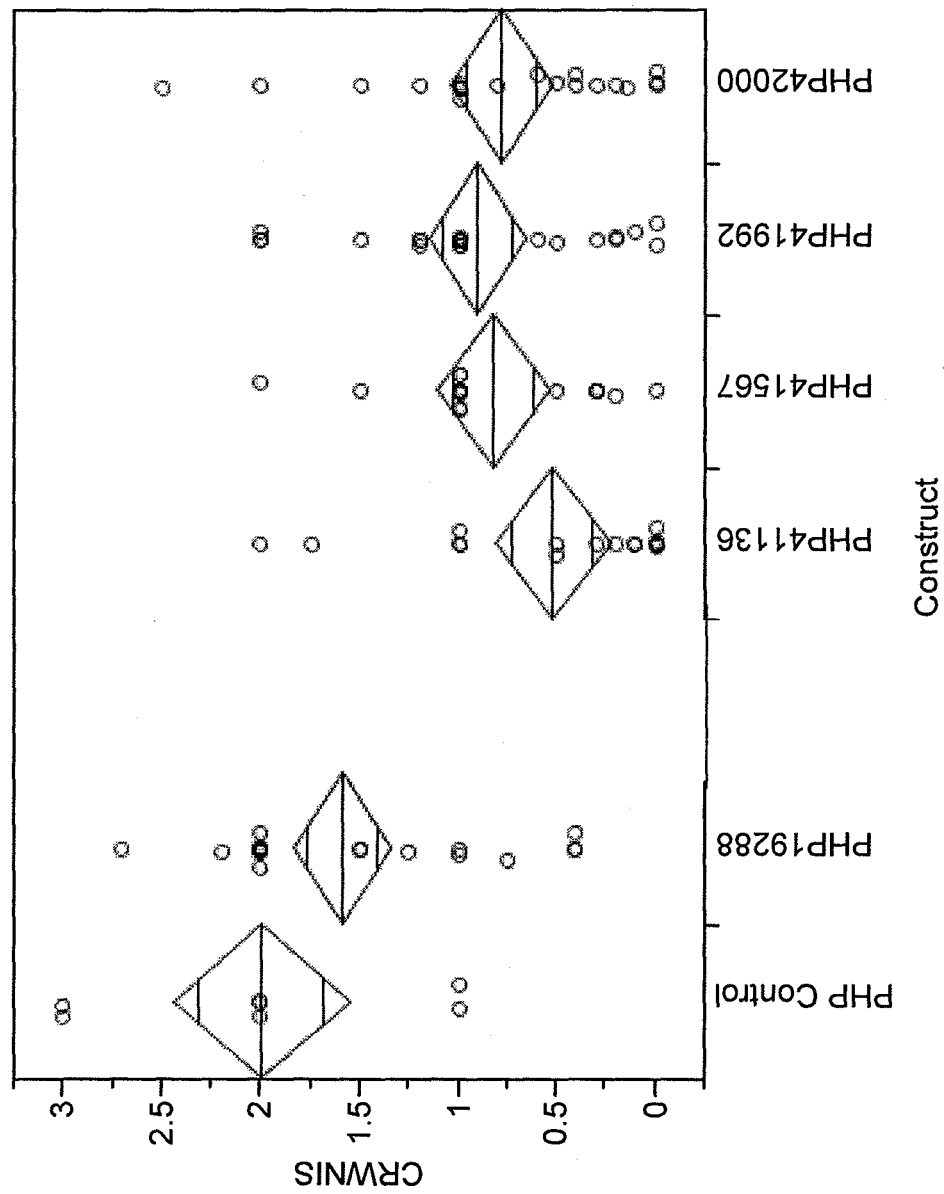

COMPOSITIONS AND METHODS TO CONTROL INSECT PESTS

CROSS-REFERENCE TO RELATED APPLICATIONS

This application is a divisional of U.S. Utility application Ser. No. 12/868,994, filed on Aug. 26, 2010, which claims the benefit of U.S. Provisional Application No. 61/330,484, filed on May 3, 2010 and U.S. Provisional Application No. 61/237,880, filed Aug. 28, 2009, the contents of which are herein incorporated by reference in their entirety.

FIELD OF THE INVENTION

The present invention relates generally to methods of molecular biology and gene silencing to control pests.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 391924SEQLIST.txt, a creation date of Aug. 25, 2010 and a size of 306 Kb. The sequence listing filed via EFS-Web is part of the specification and is hereby incorporated in its entirety by reference herein.

BACKGROUND OF THE INVENTION

Insect pests are a serious problem in agriculture. They destroy millions of acres of staple crops such as corn, soybeans, peas, and cotton. Yearly, these pests cause over $100 billion dollars in crop damage in the U.S. alone. In an ongoing seasonal battle, farmers must apply billions of gallons of synthetic pesticides to combat these pests. Other methods employed in the past delivered insecticidal activity by microorganisms or genes derived from microorganisms expressed in transgenic plants. For example, certain species of microorganisms of the genus *Bacillus* are known to possess pesticidal activity against a broad range of insect pests including *Lepidoptera, Diptera, Coleoptera, Hemiptera*, and others. In fact, microbial pesticides, particularly those obtained from *Bacillus* strains, have played an important role in agriculture as alternatives to chemical pest control. Agricultural scientists have developed crop plants with enhanced insect resistance by genetically engineering crop plants to produce insecticidal proteins from *Bacillus*. For example, corn and cotton plants genetically engineered to produce Cry toxins (see, e.g., Aronson (2002) *Cell Mol. Life Sci.* 59(3):417-425; Schnepf et al. (1998) *Microbiol. Mol. Biol. Rev.* 62(3):775-806) are now widely used in American agriculture and have provided the farmer with an alternative to traditional insect-control methods. However, these Bt insecticidal proteins only protect plants from a relatively narrow range of pests. Moreover, these modes of insecticidal activity provided varying levels of specificity and, in some cases, caused significant environmental consequences. Thus, there is an immediate need for alternative methods to control pests.

BRIEF SUMMARY OF THE INVENTION

Methods and compositions are provided which employ a silencing element that, when ingested by a pest, such as a Coleopteran plant pest including a *Diabrotica* plant pest, is capable of decreasing the expression of a target sequence in the pest. In specific embodiments, the decrease in expression of the target sequence controls the pest and thereby the methods and compositions are capable of limiting damage to a plant. The present invention provides various target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or active variants or fragments thereof, wherein a decrease in expression of one or more the sequences in the target pest controls the pest (i.e., has insecticidal activity). Further provided are silencing elements, which when ingested by the pest, decrease the level of expression of one or more of the target polynucleotides. Plants, plant parts, plant cells, bacteria and other host cells comprising the silencing elements or an active variant or fragment thereof are also provided.

In another embodiment, a method for controlling a pest, such as a Coleopteran plant pest or a *Diabrotica* plant pest, is provided. The method comprises feeding to a pest a composition comprising a silencing element, wherein the silencing element, when ingested by the pest, reduces the level of a target sequence in the pest and thereby controls the pest. Further provided are methods to protect a plant from a pest. Such methods comprise introducing into the plant or plant part a silencing element of the invention. When the plant expressing the silencing element is ingested by the pest, the level of the target sequence is decreased and the pest is controlled.

BRIEF DESCRIPTION OF THE DRAWINGS

FIG. 2 shows a corn rootworm whole plant assay. The data demonstrates that expression of SEQ ID NO: 13 (clone idvlc.pk002.j171); SEQ ID NO: 40 (clone idvlc.pk013.h1.f); SEQ ID NO:72 (clone idvlc.pk017.d14.f); and SEQ ID NO:73 (clone idvlc.pk017.e22.f) as a hairpin in a maize plant produces a maize plant, which when ingested by corn root worm, has insecticidal activity. CRWNIS refers to corn root worm nodal injury score. PHP19288 is a control plasmid lacking the silencing element.

DETAILED DESCRIPTION OF THE INVENTION

Figure 1:
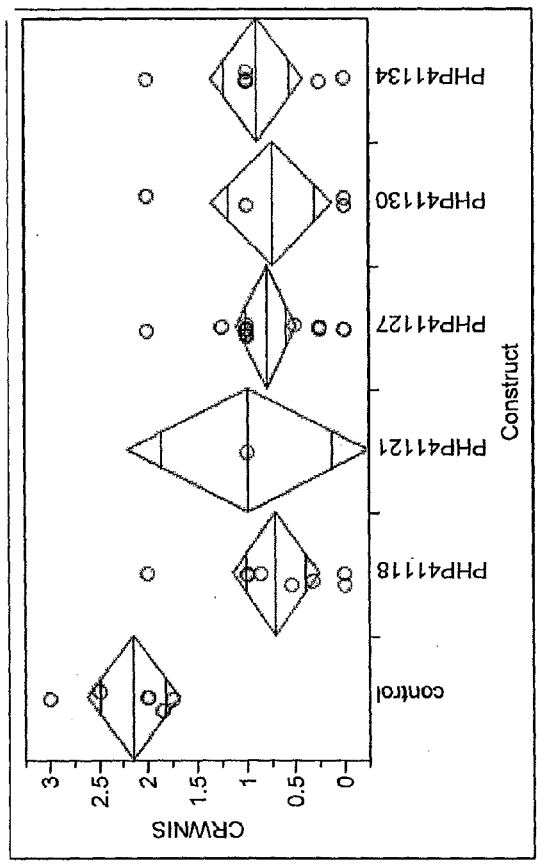
FIG. 1 shows a corn rootworm whole plant assay. The data demonstrates that expression of SEQ ID NO: 8 (clone idvlc.pk001.e9.0; SEQ ID NO: 26 (clone idvlc.pk003.p13.f); SEQ ID NO:17 (clone idvlc.pk003.f9.f); SEQ ID NO:28 (clone idvlc.pk004.d17.p); and SEQ ID NO:10 (clone idvlc.pk001.n1.f) as a hairpin in a maize plant produces a maize plant, which when ingested by corn root worm, has insecticidal activity. CRWNIS refers to corn root worm nodal injury score.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Frequently, RNAi discovery methods rely on evaluation of known classes of sensitive genes (transcription factors, housekeeping genes etc.). In contrast, the target polynucleotide set forth herein were identified based solely on high throughput screens of all singletons and representatives of all gene clusters from a cDNA library of neonate western corn rootworms. This screen allowed for the discovery of many novel sequences, many of which have extremely low or no homology to known sequences. This method provided the advantage of having no built in bias to genes that are frequently highly conserved across taxa. As a result, many novel targets for RNAi as well as known genes not previously shown to be sensitive to RNAi have been identified.

As such, methods and compositions are provided which employ a silencing element that, when ingested by a pest, such as a Coleopteran plant pest or a *Diabrotica* plant pest, is capable of decreasing the expression of a target sequence in the pest. In specific embodiments, the decrease in expression of the target sequence controls the pest and thereby the methods and compositions are capable of limiting damage to a plant or plant part. The present invention provides target polynucleotides as set forth in SEQ ID NOS: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, or 236, or active variants and fragments thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. Silencing elements designed in view of these target polynucleotides are provided which, when ingested by the pest, decrease the expression of one or more of the target sequences and thereby controls the pest (i.e., has insecticidal activity).

As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

Reducing the level of expression of the target polynucleotide or the polypeptide encoded thereby, in the pest results in the suppression, control, and/or killing the invading pathogenic organism. Reducing the level of expression of the target sequence of the pest will reduce the disease symptoms resulting from pathogen challenge by at least about 2% to at least about 6%, at least about 5% to about 50%, at least about 10% to about 60%, at least about 30% to about 70%, at least about 40% to about 80%, or at least about 50% to about 90% or greater. Hence, the methods of the invention can be utilized to control pests, particularly, Coleopteran plant pest or a *Diabrotica* plant pest.

Assays that measure the control of a pest are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. See, for example, Thomma et al. (1998) *Plant Biology* 95:15107-15111, herein incorporated by reference. See, also Baum et al. (2007) *Nature Biotech* 11:1322-1326 and WO 2007/035650 which proved both whole plant feeding assays and corn root feeding assays. Both of these references are herein incorporated by reference in their entirety. See, also the examples below.

The invention is drawn to compositions and methods for protecting plants from a plant pest, such as Coleopteran plant pests or *Diabrotica* plant pests or inducing resistance in a plant to a plant pest, such as Coleopteran plant pests or *Diabrotica* plant pests. As used herein "Coleopteran plant pest" is used to refer to any member of the Coleoptera order.

As used herein, the term "*Diabrotica* plant pest" is used to refer to any member of the *Diabrotica* genus. Accordingly, the compositions and methods are also useful in protecting plants against any *Diabrotica* plant pest including, for example, *Diabrotica adelpha*; *Diabrotica amecameca*; *Diabrotica balteata*; *Diabrotica barberi*; *Diabrotica biannularis*; *Diabrotica cristata*; *Diabrotica decempunctata*; *Diabrotica dissimilis*; *Diabrotica lemniscata*; *Diabrotica limitata* (including, for example, *Diabrotica limitata quindecimpuncata*); *Diabrotica longicornis*; *Diabrotica nummularis*; *Diabrotica porracea*; *Diabrotica scutellata*; *Diabrotica sexmaculata*; *Diabrotica speciosa* (including, for example, *Diabrotica speciosa speciosa*); *Diabrotica tibialis*; *Diabrotica undecimpunctata* (including, for example, *Diabrotica undecimpunctata duodecimnotata*; *Diabrotica undecimpunctata howardi* (spotted cucumber beetle); *Diabrotica undecimpunctata undecimpunctata* (western spotted cucumber beetle)); *Diabrotica virgifera* (including, for example, *Diabrotica virgifera virgifera* (western corn rootworm) and *Diabrotica virgifera zeae* (Mexican corn rootworm)); *Diabrotica viridula; Diabrotica wartensis; Diabrotica* sp. JJG335; *Diabrotica* sp. JJG336; *Diabrotica* sp. JJG341; *Diabrotica* sp. JJG356; *Diabrotica* sp. JJG362; and, *Diabrotica* sp. JJG365.

In specific embodiments, the *Diabrotica* plant pest comprises *D. virgifera virgifera, D. barberi, D. speciosa* or *D. undecimpunctata howardi*.

II. Target Sequences

As used herein, a "target sequence" or "target polynucleotide" comprises any sequence in the pest that one desires to reduce the level of expression. In specific embodiments, decreasing the level of the target sequence in the pest controls the pest. For instance, the target sequence can be essential for growth and development. While the target sequence can be expressed in any tissue of the pest, in specific embodiments, the sequences targeted for suppression in the pest are expressed in cells of the gut tissue of the pest, cells in the midgut of the pest, and cells lining the gut lumen or the midgut. Such target sequences can be involved in, for example, gut cell metabolism, growth or differentiation. Non-limiting examples of target sequences of the invention include a polynucleotide set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, or 236 or variants and fragments thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. As exemplified elsewhere herein, decreasing the level of expression of one or more of these target sequences in a Coleopteran plant pest or a *Diabrotica* plant pest controls the pest.

III. Silencing Elements

By "silencing element" is intended a polynucleotide which when ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Methods to assay for functional silencing elements that are capable of reducing or eliminating the level of a sequence of interest are disclosed elsewhere herein. A single polynucleotide employed in the methods of the invention can comprise one or more silencing elements to the same or different target polynucleotides. The silencing element can be produced in vivo (i.e., in a host cell such as a plant or microorganism) or in vitro.

In specific embodiments, the target sequence is not endogenous to the plant. In other embodiments, while the silencing element controls pests, preferably the silencing element has no effect on the normal plant or plant part.

As discussed in further detail below, silencing elements can include, but are not limited to, a sense suppression element, an antisense suppression element, a double stranded RNA, a siRNA, a amiRNA, a miRNA, or a hairpin suppression element. Non-limiting examples of silencing elements that can be employed to decrease expression of these target Coleopteran plant pest sequences or *Diabrotica* plant pest sequences comprise fragments and variants of the sense or antisense sequence or consists of the sense or antisense sequence of the sequence set forth in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236 or a biologically active variant or fragment thereof, including, for example, nucleotides 1-380 of SEQ ID NO: 45; nucleotides 1-266 of SEQ ID NO:50; SEQ ID NO:50; nucleotides 1-675 of SEQ ID NO:37; and nucleotides 1-132 of SEQ ID NO: 40. The silencing element can further comprise additional sequences that advantageously effect transcription and/or the stability of a resulting transcript. For example, the silencing elements can comprise at least one thymine residue at the 3' end. This can aid in stabilization. Thus, the silencing elements can have at least 1, 2, 3, 4, 5, 6, 7, 8, 9, 10 or more thymine residues at the 3' end. As discussed in further detail below, enhancer suppressor elements can also be employed in conjunction with the silencing elements disclosed herein.

By "reduces" or "reducing" the expression level of a polynucleotide or a polypeptide encoded thereby is intended to mean, the polynucleotide or polypeptide level of the target sequence is statistically lower than the polynucleotide level or polypeptide level of the same target sequence in an appropriate control pest which is not exposed to (i.e., has not ingested) the silencing element. In particular embodiments of the invention, reducing the polynucleotide level and/or the polypeptide level of the target sequence in a pest according to the invention results in less than 95%, less than 90%, less than 80%, less than 70%, less than 60%, less than 50%, less than 40%, less than 30%, less than 20%, less than 10%, or less than 5% of the polynucleotide level, or the level of the polypeptide encoded thereby, of the same target sequence in an appropriate control pest. Methods to assay for the level of the RNA transcript, the level of the encoded polypeptide, or the activity of the polynucleotide or polypeptide are discussed elsewhere herein.

i. Sense Suppression Elements

As used herein, a "sense suppression element" comprises a polynucleotide designed to express an RNA molecule corresponding to at least a part of a target messenger RNA in the "sense" orientation. Expression of the RNA molecule comprising the sense suppression element reduces or eliminates the level of the target polynucleotide or the polypeptide encoded thereby. The polynucleotide comprising the sense suppression element may correspond to all or part of the sequence of the target polynucleotide, all or part of the 5' and/or 3' untranslated region of the target polynucleotide, all or part of the coding sequence of the target polynucleotide, or all or part of both the coding sequence and the untranslated regions of the target polynucleotide.

Typically, a sense suppression element has substantial sequence identity to the target polynucleotide, typically greater than about 65% sequence identity, greater than about 85% sequence identity, about 90%, 91%, 92%, 93%, 94%, 95%, 96%, 97%, 98% or 99% sequence identity. See, U.S. Pat. Nos. 5,283,184 and 5,034,323; herein incorporated by reference. The sense suppression element can be any length so long as it allows for the suppression of the targeted sequence. The sense suppression element can be, for example, 15, 16, 17, 18, 19, 20, 22, 25, 30, 50, 100, 150, 200, 250, 300, 350, 400, 450, 500, 600, 700, 900, 1000, 1100, 1200, 1300 nucleotides or longer of the target polynucleotides set forth in any of SEQ ID NO:1-106. In other embodiments, the sense suppression element can be, for example, about 15-25, 19-35, 19-50, 25-100, 100-150, 150-200, 200-250, 250-300, 300-350, 350-400, 450-500, 500-550, 550-600, 600-650, 650-700, 700-750, 750-800, 800-850, 850-900, 900-950, 950-1000, 1000-1050, 1050-1100, 1100-1200, 1200-1300, 1300-1400, 1400-1500, 1500-1600, 1600-1700, 1700-1800 nucleotides or longer of the target polynucleotides set forth in any of SEQ ID NO:1-236.

ii. Antisense Suppression Elements

As used herein, an "antisense suppression element" comprises a polynucleotide which is designed to express an RNA molecule complementary to all or part of a target messenger RNA. Expression of the antisense RNA suppression element reduces or eliminates the level of the target polynucleotide. The polynucleotide for use in antisense suppression may correspond to all or part of the complement of the sequence encoding the target polynucleotide, all or part of the complement of the 5' and/or 3' untranslated region of the target polynucleotide, all or part of the complement of the coding sequence of the target polynucleotide, or all or part of the complement of both the coding sequence and the untranslated regions of the target polynucleotide. In addition, the antisense suppression element may be fully complementary (i.e., 100% identical to the complement of the target sequence) or partially complementary (i.e., less than 100% identical to the complement of the target sequence) to the target polynucleotide. In specific embodiments, the antisense suppression element comprises at least 85%, 90%, 91%, 92%, 93%, 94%, 95%, 96%, 97%, 98%, or 99% sequence complementarity to the target polynucleotide. Antisense suppression may be used to inhibit the expression of multiple proteins in the same plant. See, for example, U.S. Pat. No. 5,942,657. Furthermore, the antisense suppression element can be complementary to a portion of the target polynucleotide. Generally, sequences of at least 15, 16, 17, 18, 19, 20, 22, 25, 50, 100, 200, 300, 400, 450 nucleotides or greater of the sequence set forth in any of SEQ ID NO:1-236 may be used. Methods for using antisense suppression to inhibit the expression of endogenous genes in plants are described, for example, in Liu et al (2002) *Plant Physiol.* 129:1732-1743 and U.S. Pat. Nos. 5,759,829 and 5,942,657, each of which is herein incorporated by reference.

iii. Double Stranded RNA Suppression Element

A "double stranded RNA silencing element" or "dsRNA" comprises at least one transcript that is capable of forming a dsRNA either before or after ingestion by a pest. Thus, a "dsRNA silencing element" includes a dsRNA, a transcript or polyribonucleotide capable of forming a dsRNA or more than one transcript or polyribonucleotide capable of forming a dsRNA. "Double stranded RNA" or "dsRNA" refers to a polyribonucleotide structure formed either by a single self-complementary RNA molecule or a polyribonucleotide structure formed by the expression of least two distinct RNA strands. The dsRNA molecule(s) employed in the methods and compositions of the invention mediate the reduction of expression of a target sequence, for example, by mediating RNA interference "RNAi" or gene silencing in a sequence-specific manner. In the context of the present invention, the dsRNA is capable of reducing or eliminating the level or expression of a target polynucleotide or the polypeptide encoded thereby in a pest.

The dsRNA can reduce or eliminate the expression level of the target sequence by influencing the level of the target RNA transcript, by influencing translation and thereby affecting the level of the encoded polypeptide, or by influencing expression at the pre-transcriptional level (i.e., via the modulation of chromatin structure, methylation pattern, etc., to alter gene expression). See, for example, Verdel et al. (2004) *Science* 303:672-676; Pal-Bhadra et al. (2004) *Science* 303:669-672; Allshire (2002) *Science* 297:1818-1819; Volpe et al. (2002) *Science* 297:1833-1837; Jenuwein (2002) *Science* 297:2215-2218; and Hall et al. (2002) *Science* 297:2232-2237. Methods to assay for functional dsRNA that are capable of reducing or eliminating the level of a sequence of interest are disclosed elsewhere herein. Accordingly, as used herein, the term "dsRNA" is meant to encompass other terms used to describe nucleic acid molecules that are capable of mediating RNA interference or gene silencing, including, for example, short-interfering RNA (siRNA), double-stranded RNA (dsRNA), micro-RNA (miRNA), hairpin RNA, short hairpin RNA (shRNA), post-transcriptional gene silencing RNA (ptgsRNA), and others.

In specific embodiments, at least one strand of the duplex or double-stranded region of the dsRNA shares sufficient sequence identity or sequence complementarity to the target polynucleotide to allow for the dsRNA to reduce the level of expression of the target sequence. As used herein, the strand that is complementary to the target polynucleotide is the "antisense strand" and the strand homologous to the target polynucleotide is the "sense strand."

In another embodiment, the dsRNA comprises a hairpin RNA. A hairpin RNA comprises an RNA molecule that is capable of folding back onto itself to form a double stranded structure. Multiple structures can be employed as hairpin elements. In specific embodiments, the dsRNA suppression element comprises a hairpin element which comprises in the following order, a first segment, a second segment, and a third segment, where the first and the third segment share sufficient complementarity to allow the transcribed RNA to form a double-stranded stem-loop structure.

The "second segment" of the hairpin comprises a "loop" or a "loop region." These terms are used synonymously herein and are to be construed broadly to comprise any nucleotide sequence that confers enough flexibility to allow self-pairing to occur between complementary regions of a polynucleotide (i.e., segments 1 and 3 which form the stem of the hairpin). For example, in some embodiments, the loop region may be substantially single stranded and act as a spacer between the self-complementary regions of the hairpin stem-loop. In some embodiments, the loop region can comprise a random or nonsense nucleotide sequence and thus not share sequence identity to a target polynucleotide. In other embodiments, the loop region comprises a sense or an antisense RNA sequence or fragment thereof that shares identity to a target polynucleotide. See, for example, International Patent Publication No. WO 02/00904, herein incorporated by reference. In specific embodiments, the loop region can be optimized to be as short as possible while still providing enough intramolecular flexibility to allow the formation of the base-paired stem region. Accordingly, the loop sequence is generally less than 1000, 900, 800, 700, 600, 500, 400, 300, 200, 100, 50, 25, 20, 19, 18, 17, 16, 15, 10 nucleotides or less.

The "first" and the "third" segment of the hairpin RNA molecule comprise the base-paired stem of the hairpin structure. The first and the third segments are inverted repeats of one another and share sufficient complementarity to allow the formation of the base-paired stem region. In specific embodiments, the first and the third segments are fully complementary to one another. Alternatively, the first and the third segment may be partially complementary to each other so long as they are capable of hybridizing to one another to form a base-paired stem region. The amount of complementarity between the first and the third segment can be calculated as a percentage of the entire segment. Thus, the first and the third segment of the hairpin RNA generally share at least 50%, 60%, 70%, 80%, 85%, 90%, 91%, 92%, 93%, 94%, 95%, 96%, 97%, 98%, 99%, up to and including 100% complementarity.

The first and the third segment are at least about 1000, 500, 475, 450, 425, 400, 375, 350, 325, 300, 250, 225, 200, 175, 150, 125, 100, 75, 60, 50, 40, 30, 25, 22, 20, 19, 18, 17, 16, 15 or 10 nucleotides in length. In specific embodiments, the length of the first and/or the third segment is about 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 19 nucleotides, about 10 to about 20 nucleotides, about 19 to about 50 nucleotides, about 50 nucleotides to about 100 nucleotides, about 100 nucleotides to about 150 nucleotides, about 100 nucleotides to about 300 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides, about 600 nt, about 700 nt, about 800 nt, about 900 nt, about 1000 nt, about 1100 nt, about 1200 nt, 1300 nt, 1400 nt, 1500 nt, 1600 nt, 1700 nt, 1800 nt, 1900 nt, 2000 nt or longer. In other embodiments, the length of the first and/or the third segment comprises at least 10-19 nucleotides, 10-20 nucleotides; 19-35 nucleotides, 20-35 nucleotides; 30-45 nucleotides; 40-50 nucleotides; 50-100 nucleotides; 100-300 nucleotides; about 500-700 nucleotides; about 700-900 nucleotides; about 900-1100 nucleotides; about 1300-1500 nucleotides; about 1500-1700 nucleotides; about 1700-1900 nucleotides; about 1900-2100 nucleotides; about 2100-2300 nucleotides; or about 2300-2500 nucleotides. See, for example, International Publication No. WO 0200904. In non-limiting examples the first stem of the hairpin comprises nucleotides 1-380 of SEQ ID NO: 45; nucleotides 1-266 of SEQ ID NO:50; nucleotides 1-675 of SEQ ID NO:37; or nucleotides 1-132 of SEQ ID NO: 40 or active variants and fragments thereof. In specific embodiments, the first and the third segment comprise at least 20 nucleotides having at least 85% complementary to the first segment. In still other embodiments, the first and the third segments which form the stem-loop structure of the hairpin comprises 3' or 5' overhang regions having unpaired nucleotide residues.

In specific embodiments, the sequences used in the first, the second, and/or the third segments comprise domains that are designed to have sufficient sequence identity to a target polynucleotide of interest and thereby have the ability to decrease the level of expression of the target polynucleotide. The specificity of the inhibitory RNA transcripts is therefore generally conferred by these domains of the silencing element. Thus, in some embodiments of the invention, the first, second and/or third segment of the silencing element comprise a domain having at least 10, at least 15, at least 19, at least 20, at least 21, at least 22, at least 23, at least 24, at least 25, at least 30, at least 40, at least 50, at least 100, at least 200, at least 300, at least 500, at least 1000, or more than 1000 nucleotides that share sufficient sequence identity to the target polynucleotide to allow for a decrease in expression levels of the target polynucleotide when expressed in an appropriate cell. In other embodiments, the domain is between about 15 to 50 nucleotides, about 19-35 nucleotides, about 20-35 nucleotides, about 25-50 nucleotides, about 19 to 75 nucleotides, about 20 to 75 nucleotides, about 40-90 nucleotides about 15-100 nucleotides 10-100 nucleotides, about 10 to about 75 nucleotides, about 10 to about 50 nucleotides, about 10 to about 40 nucleotides, about 10 to about 35 nucleotides, about 10 to about 30 nucleotides, about 10 to about 25 nucleotides, about 10 to about 20 nucleotides, about 10 to about 19 nucleotides, about 50 nucleotides to about 100 nucleotides, about 100 nucleotides to about 150 nucleotides, about 150 nucleotides to about 200 nucleotides, about 200 nucleotides to about 250 nucleotides, about 250 nucleotides to about 300 nucleotides, about 300 nucleotides to about 350 nucleotides, about 350 nucleotides to about 400 nucleotides, about 400 nucleotide to about 500 nucleotides or longer. In other embodiments, the length of the first and/or the third segment comprises at least 10-20 nucleotides, at least 10-19 nucleotides, 20-35 nucleotides, 30-45 nucleotides, 40-50 nucleotides, 50-100 nucleotides, or about 100-300 nucleotides.

In specific embodiments, the domain of the first, the second, and/or the third segment has 100% sequence identity to the target polynucleotide. In other embodiments, the domain of the first, the second and/or the third segment having homology to the target polypeptide have at least 50%, 60%, 70%, 80%, 85%, 90%, 91%, 92%, 93%, 94%, 95%, 96%, 97%, 98%, 99%, or greater sequence identity to a region of the target polynucleotide. The sequence identity of the domains of the first, the second and/or the third segments to the target polynucleotide need only be sufficient to decrease expression of the target polynucleotide of interest. See, for example, Chuang and Meyerowitz (2000) *Proc. Natl. Acad. Sci. USA* 97:4985-4990; Stoutjesdijk et al. (2002) *Plant Physiol.* 129:1723-1731; Waterhouse and Helliwell (2003) *Nat. Rev. Genet.* 4:29-38; Pandolfini et al. *BMC Biotechnology* 3:7, and U.S. Patent Publication No. 20030175965; each of which is herein incorporated by reference. A transient assay for the efficiency of hpRNA constructs to silence gene expression in vivo has been described by Panstruga et al. (2003) *Mol. Biol. Rep.* 30:135-140, herein incorporated by reference.

The amount of complementarity shared between the first, second, and/or third segment and the target polynucleotide or the amount of complementarity shared between the first segment and the third segment (i.e., the stem of the hairpin structure) may vary depending on the organism in which gene expression is to be controlled. Some organisms or cell types may require exact pairing or 100% identity, while other organisms or cell types may tolerate some mismatching. In some cells, for example, a single nucleotide mismatch in the targeting sequence abrogates the ability to suppress gene expression. In these cells, the suppression cassettes of the invention can be used to target the suppression of mutant genes, for example, oncogenes whose transcripts comprise point mutations and therefore they can be specifically targeted using the methods and compositions of the invention without altering the expression of the remaining wild-type allele.

Any region of the target polynucleotide can be used to design the domain of the silencing element that shares sufficient sequence identity to allow expression of the hairpin transcript to decrease the level of the target polynucleotide. For instance, the domain can be designed to share sequence identity to the 5' untranslated region of the target polynucleotide(s), the 3' untranslated region of the target polynucleotide(s), exonic regions of the target polynucleotide(s), intronic regions of the target polynucleotide(s), and any combination thereof. In specific embodiments, a domain of the silencing element shares sufficient homology to at least about 15, 16, 17, 18, 19, 20, 22, 25 or 30 consecutive nucleotides from about nucleotides 1-50, 25-75, 75-125, 50-100, 125-175, 175-225, 100-150, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of the target sequence. In some instances to optimize the siRNA sequences employed in the hairpin, the synthetic oligodeoxyribonucleotide/RNAse H method can be used to determine sites on the target mRNA that are in a conformation that is susceptible to RNA silencing. See, for example, Vickers et al. (2003) *J. Biol. Chem* 278:7108-7118 and Yang et al. (2002) *Proc. Natl. Acad. Sci. USA* 99:9442-9447, herein incorporated by reference. These studies indicate that there is a significant correlation between the RNase-H-sensitive sites and sites that promote efficient siRNA-directed mRNA degradation.

The hairpin silencing element may also be designed such that the sense sequence or the antisense sequence do not correspond to a target polynucleotide. In this embodiment, the sense and antisense sequence flank a loop sequence that comprises a nucleotide sequence corresponding to all or part of the target polynucleotide. Thus, it is the loop region that determines the specificity of the RNA interference. See, for example, WO 02/00904, herein incorporated by reference.

In addition, transcriptional gene silencing (TGS) may be accomplished through use of a hairpin suppression element where the inverted repeat of the hairpin shares sequence identity with the promoter region of a target polynucleotide to be silenced. See, for example, Aufsatz et al. (2002) *PNAS* 99 (Suppl. 4): 16499-16506 and Mette et al. (2000) *EMBO J* 19(19):5194-5201.

In other embodiments, the dsRNA can comprise a small RNA (sRNA). sRNAs can comprise both micro RNA (miRNA) and short-interfering RNA (siRNA) (Meister and Tuschl (2004) *Nature* 431:343-349 and Bonetta et al. (2004) *Nature Methods* 1:79-86). miRNAs are regulatory agents comprising about 19 ribonucleotides which are highly efficient at inhibiting the expression of target polynucleotides. See, for example Javier et al. (2003) *Nature* 425: 257-263, herein incorporated by reference. For miRNA interference, the silencing element can be designed to express a dsRNA molecule that forms a hairpin structure containing a 19-nucleotide sequence that is complementary to the target polynucleotide of interest. The miRNA can be synthetically made, or transcribed as a longer RNA which is subsequently cleaved to produce the active miRNA. Specifically, the miRNA can comprise 19 nucleotides of the sequence having homology to a target polynucleotide in sense orientation and 19 nucleotides of a corresponding antisense sequence that is complementary to the sense sequence.

When expressing an miRNA, it is recognized that various forms of an miRNA can be transcribed including, for example, the primary transcript (termed the "pri-miRNA") which is processed through various nucleolytic steps to a shorter precursor miRNA (termed the "pre-miRNA"); the pre-miRNA; or the final (mature) miRNA is present in a duplex, the two strands being referred to as the miRNA (the strand that will eventually basepair with the target) and miRNA*. The pre-miRNA is a substrate for a form of dicer that removes the miRNA/miRNA* duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) *Genes & Development* 18:2237-2242 and Guo et al. (2005) *Plant Cell* 17:1376-1386).

The methods and compositions of the invention employ silencing elements that when transcribed "form" a dsRNA molecule. Accordingly, the heterologous polynucleotide being expressed need not form the dsRNA by itself, but can interact with other sequences in the plant cell or in the pest gut after ingestion to allow the formation of the dsRNA. For example, a chimeric polynucleotide that can selectively silence the target polynucleotide can be generated by expressing a chimeric construct comprising the target sequence for a miRNA or siRNA to a sequence corresponding to all or part of the gene or genes to be silenced. In this embodiment, the dsRNA is "formed" when the target for the miRNA or siRNA interacts with the miRNA present in the cell. The resulting dsRNA can then reduce the level of expression of the gene or genes to be silenced. See, for example, US Application Publication 2007-0130653, entitled "Methods and Compositions for Gene Silencing", herein incorporated by reference. The construct can be designed to have a target for an endogenous miRNA or alternatively, a target for a heterologous and/or synthetic miRNA can be employed in the construct. If a heterologous and/or synthetic miRNA is employed, it can be introduced into the cell on the same nucleotide construct as the chimeric polynucleotide or on a separate construct. As discussed elsewhere herein, any method can be used to introduce the construct comprising the heterologous miRNA.

IV. Variants and Fragments

By "fragment" is intended a portion of the polynucleotide or a portion of the amino acid sequence and hence protein encoded thereby. Fragments of a polynucleotide may encode protein fragments that retain the biological activity of the native protein. Alternatively, fragments of a polynucleotide that are useful as a silencing element do not need to encode fragment proteins that retain biological activity. Thus, fragments of a nucleotide sequence may range from at least about 10, about 15, about 19 nucleotides, about 20 nucleotides, about 22 nucleotides, about 50 nucleotides, about 75 nucleotides, about 100 nucleotides, 200 nucleotides, 300 nucleotides, 400 nucleotides, 500 nucleotides, 600 nucleotides, 700 nucleotides and up to the full-length polynucleotide employed in the invention. Alternatively, fragments of a nucleotide sequence may range from 1-50, 25-75, 75-125, 50-100, 125-175, 175-225, 100-150, 100-300, 150-200, 200-250, 225-275, 275-325, 250-300, 325-375, 375-425, 300-350, 350-400, 425-475, 400-450, 475-525, 450-500, 525-575, 575-625, 550-600, 625-675, 675-725, 600-650, 625-675, 675-725, 650-700, 725-825, 825-875, 750-800, 875-925, 925-975, 850-900, 925-975, 975-1025, 950-1000, 1000-1050, 1025-1075, 1075-1125, 1050-1100, 1125-1175, 1100-1200, 1175-1225, 1225-1275, 1200-1300, 1325-1375, 1375-1425, 1300-1400, 1425-1475, 1475-1525, 1400-1500, 1525-1575, 1575-1625, 1625-1675, 1675-1725, 1725-1775, 1775-1825, 1825-1875, 1875-1925, 1925-1975, 1975-2025, 2025-2075, 2075-2125, 2125-2175, 2175-2225, 1500-1600, 1600-1700, 1700-1800, 1800-1900, 1900-2000 of any one of SEQ ID NO: 1-236. Methods to assay for the activity of a desired silencing element are described elsewhere herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. A variant of a polynucleotide that is useful as a silencing element will retain the ability to reduce expression of the target polynucleotide and, in some embodiments, thereby control a pest of interest. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the polypeptides employed in the invention. Variant polynucleotides also include synthetically derived polynucleotide, such as those generated, for example, by using site-directed mutagenesis, but continue to retain the desired activity. Generally, variants of a particular polynucleotide of the invention (i.e., a silencing element) will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides employed in the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

A method is further provided for identifying a silencing element from the target polynucleotides set froth in SEQ ID NO:1-236. Such methods comprise obtaining a candidate fragment of any one of SEQ ID NO:1-236 which is of sufficient length to act as a silencing element and thereby reduce the expression of the target polynucleotide and/or control a desired pest; expressing said candidate polynucleotide fragment in an appropriate expression cassette to produce a candidate silencing element and determining is said candidate polynucleotide fragment has the activity of a silencing element and thereby reduce the expression of the target polynucleotide and/or controls a desired pest. Methods of identifying such candidate fragments based on the desired pathway for suppression are known. For example, various bioinformatics programs can be employed to identify the region of the target polynucleotides that could be exploited to generate a silencing element. See, for example, Elbahir et al. (2001) *Genes and Development* 15:188-200, Schwartz et al. (2003) *Cell* 115:199-208, Khvorova et al. (2003) *Cell* 115:209-216. See also, siRNA at Whitehead (jura.wi.mit.edu/bioc/siRNAext/) which calculates the binding energies for both sense and antisense siRNAs. See, also genscript.com/ssl-bin/app/rnai?op=known; Block-iT™ RNAi designer from Invitrogen and GenScript siRNA Construct Builder.

V. DNA constructs

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The polynucleotide encoding the silencing element or in specific embodiments employed in the methods and compositions of the invention can be provided in expression cassettes for expression in a plant or organism of interest. It is recognized that multiple silencing elements including multiple identical silencing elements, multiple silencing elements targeting different regions of the target sequence, or multiple silencing elements from different target sequences can be used. In this embodiment, it is recognized that each silencing element can be contained in a single or separate cassette, DNA construct, or vector. As discussed, any means of providing the silencing element is contemplated. A plant or plant cell can be transformed with a single cassette comprising DNA encoding one or more silencing elements or separate cassettes comprising each silencing element can be used to transform a plant or plant cell or host cell. Likewise, a plant transformed with one component can be subsequently transformed with the second component. One or more silencing elements can also be brought together by sexual crossing. That is, a first plant comprising one component is crossed with a second plant comprising the second component. Progeny plants from the cross will comprise both components.

The expression cassette can include 5' and 3' regulatory sequences operably linked to the polynucleotide of the invention. "Operably linked" is intended to mean a functional linkage between two or more elements. For example, an operable linkage between a polynucleotide of the invention and a regulatory sequence (i.e., a promoter) is a functional link that allows for expression of the polynucleotide of the invention. Operably linked elements may be contiguous or non-contiguous. When used to refer to the joining of two protein coding regions, by operably linked is intended that the coding regions are in the same reading frame. The cassette may additionally contain at least one additional polynucleotide to be cotransformed into the organism. Alternatively, the additional polypeptide(s) can be provided on multiple expression cassettes. Expression cassettes can be provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), a polynucleotide comprising the silencing element employed in the methods and compositions of the invention, and a transcriptional and translational termination region (i.e., termination region) functional in plants. In other embodiment, the double stranded RNA is expressed from a suppression cassette. Such a cassette can comprise two convergent promoters that drive transcription of an operably linked silencing element. "Convergent promoters" refers to promoters that are oriented on either terminus of the operably linked silencing element such that each promoter drives transcription of the silencing element in opposite directions, yielding two transcripts. In such embodiments, the convergent promoters allow for the transcription of the sense and anti-sense strand and thus allow for the formation of a dsRNA.

The regulatory regions (i.e., promoters, transcriptional regulatory regions, and translational termination regions) and/or the polynucleotides employed in the invention may be native/analogous to the host cell or to each other. Alternatively, the regulatory regions and/or the polynucleotide employed in the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide encoding the silencing element, may be native with the plant host, or may be derived from another source (i.e., foreign or heterologous) to the promoter, the polynucleotide comprising silencing element, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The polynucleotide encoding the silencing element can be combined with constitutive, tissue-preferred, or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

An inducible promoter, for instance, a pathogen-inducible promoter could also be employed. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-la promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved.

Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the *epidermis* of the root tip and that the TR2' gene is root specific in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

In one embodiment of this invention the plant-expressed promoter is a vascular-specific promoter such as a phloem-specific promoter. A "vascular-specific" promoter, as used herein, is a promoter which is at least expressed in vascular cells, or a promoter which is preferentially expressed in vascular cells. Expression of a vascular-specific promoter need not be exclusively in vascular cells, expression in other cell types or tissues is possible. A "phloem-specific promoter" as used herein, is a plant-expressible promoter which is at least expressed in phloem cells, or a promoter which is preferentially expressed in phloem cells.

Expression of a phloem-specific promoter need not be exclusively in phloem cells, expression in other cell types or tissues, e.g., xylem tissue, is possible. In one embodiment of this invention, a phloem-specific promoter is a plant-expressible promoter at least expressed in phloem cells, wherein the expression in non-phloem cells is more limited (or absent) compared to the expression in phloem cells. Examples of suitable vascular-specific or phloem-specific promoters in accordance with this invention include but are not limited to the promoters selected from the group consisting of: the SCSV3, SCSV4, SCSV5, and SCSV7 promoters (Schunmann et al. (2003) *Plant Functional Biology* 30:453-60; the rolC gene promoter of *Agrobacterium rhizogenes*(Kiyokawa et al. (1994) *Plant Physiology* 104:801-02; Pandolfini et al. (2003) *BioMedCentral (BMC) Biotechnology* 3:7, (website designated as: biomedcentral.com/1472-6750/3/7); Graham et al. (1997) *Plant Mol. Biol.* 33:729-35; Guivarc'h et al. (1996); Almon et al. (1997) *Plant Physiol.* 115:1599-607; the rolA gene promoter of *Agrobacterium rhizogenes* (Dehio et al. (1993) *Plant Mol. Biol.* 23:1199-210); the promoter of the *Agrobacterium tumefaciens* T-DNA gene 5 (Korber et al. (1991) *EMBO J.* 10:3983-91); the rice sucrose synthase RSs1 gene promoter (Shi et al. (1994) *J. Exp. Bot.* 45:623-31); the CoYMV or *Commelina* yellow mottle badnavirus promoter (Medberry et al. (1992) *Plant Cell* 4:185-92; Zhou et al. (1998) *Chin. J. Biotechnol.* 14:9-16); the CFDV or coconut foliar decay virus promoter (Rohde et al. (1994) *Plant Mol. Biol.* 27:623-28; Hehn and Rhode (1998) *J. Gen. Virol.* 79:1495-99); the RTBV or rice tungro bacilliform virus promoter (Yin and Beachy (1995) *Plant J.* 7:969-80; Yin et al. (1997) *Plant J.* 12:1179-80); the pea glutamin synthase GS3A gene (Edwards et al. (1990) *Proc. Natl. Acad. Sci. USA* 87:3459-63; Brears et al. (1991) *Plant J.* 1:235-44); the inv CD111 and inv CD141 promoters of the potato invertase genes (Hedley et al. (2000) *J. Exp. Botany* 51:817-21); the promoter isolated from *Arabidopsis* shown to have phloem-specific expression in tobacco by Kertbundit et al. (1991) *Proc. Natl. Acad. Sci. USA* 88:5212-16); the VAHOX1 promoter region (Tornero et al. (1996) *Plant J.* 9:639-48); the pea cell wall invertase gene promoter (Zhang et al. (1996) *Plant Physiol.* 112:1111-17); the promoter of the endogenous cotton protein related to chitinase of US published patent application 20030106097, an acid invertase gene promoter from carrot (Ramloch-Lorenz et al. (1993) *The Plant J.* 4:545-54); the promoter of the sulfate transporter geneSultrl; 3 (Yoshimoto et al. (2003) *Plant Physiol.* 131:1511-17); a promoter of a sucrose synthase gene (Nolte and Koch (1993) *Plant Physiol.* 101:899-905); and the promoter of a tobacco sucrose transporter gene (Kuhn et al. (1997) *Science* 275-1298-1300).

Possible promoters also include the Black Cherry promoter for Prunasin Hydrolase (PH DL1.4 PRO) (U.S. Pat. No. 6,797,859), Thioredoxin H promoter from cucumber and rice (Fukuda A et al. (2005). *Plant Cell Physiol.* 46(11): 1779-86), Rice (RSs1) (Shi, T. Wang et al. (1994). *J. Exp. Bot.* 45(274): 623-631) and maize sucrose synthese −1 promoters (Yang., N-S. et al. (1990) *PNAS* 87:4144-4148), PP2 promoter from pumpkin Guo, H. et al. (2004) *Transgenic* Research 13:559-566), At SUC2 promoter (Truernit, E. et al. (1995) *Planta* 196(3):564-70., At SAM-1 (S-adenosylmethionine synthetase) (Mijnsbrugge K V. et al. (1996) *Planr. Cell. Physiol.* 37(8): 1108-1115), and the Rice tungro bacilliform virus (RTBV) promoter (Bhattacharyya-Pakrasi et al. (1993) *Plant J.* 4(1):71-79).

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in The Operon, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992)

*Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

VI. Compositions Comprising Silencing Elements

One or more of the polynucleotides comprising the silencing element can be provided as an external composition such as a spray or powder to the plant, plant part, seed, a pest, or an area of cultivation. In another example, a plant is transformed with a DNA construct or expression cassette for expression of at least one silencing element. In either composition, the silencing element, when ingested by an insect, can reduce the level of a target pest sequence and thereby control the pest (i.e., a Coleopteran plant pest including a *Diabrotica* plant pest, such as, *D. virgifera virgifera*, *D. barberi*, or *D. undecimpunctata howardi*). It is recognized that the composition can comprise a cell (such as plant cell or a bacterial cell), in which a polynucleotide encoding the silencing element is stably incorporated into the genome and operably linked to promoters active in the cell. Compositions comprising a mixture of cells, some cells expressing at least one silencing element are also encompassed. In other embodiments, compositions comprising the silencing elements are not contained in a cell. In such embodiments, the composition can be applied to an area inhabited by a pest. In one embodiment, the composition is applied externally to a plant (i.e., by spraying a field or area of cultivation) to protect the plant from the pest.

The composition of the invention can further be formulated as bait. In this embodiment, the compositions comprise a food substance or an attractant which enhances the attractiveness of the composition to the pest.

The composition comprising the silencing element can be formulated in an agriculturally suitable and/or environmentally acceptable carrier. Such carriers can be any material that the animal, plant or environment to be treated can tolerate. Furthermore, the carrier must be such that the composition remains effective at controlling a pest. Examples of such carriers include water, saline, Ringer's solution, dextrose or other sugar solutions, Hank's solution, and other aqueous physiologically balanced salt solutions, phosphate buffer, bicarbonate buffer and Tris buffer. In addition, the composition may include compounds that increase the half-life of a composition. Various insecticidal formulations can also be found in, for example, US Publications 2008/0275115, 2008/0242174, 2008/0027143, 2005/0042245, and 2004/0127520, each of which is herein incorporated by reference.

It is recognized that the polynucleotides comprising sequences encoding the silencing element can be used to transform organisms to provide for host organism production of these components, and subsequent application of the host organism to the environment of the target pest(s). Such host organisms include baculoviruses, bacteria, and the like. In this manner, the combination of polynucleotides encoding the silencing element may be introduced via a suitable vector into a microbial host, and said host applied to the environment, or to plants or animals.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be stably incorporated into the genome of the cell (e.g., chromosome, plasmid, plastid, or mitochondrial DNA), converted into an autonomous replicon, or transiently expressed (e.g., transfected mRNA).

Microbial hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the sequences encoding the silencing element, and desirably, provide for improved protection of the components from environmental degradation and inactivation.

Such microorganisms include bacteria, algae, and fungi. Of particular interest are microorganisms such as bacteria, e.g., *Pseudomonas*, *Erwinia*, *Serratia*, *Klebsiella*, *Xanthomonas*, *Streptomyces*, *Rhizobium*, *Rhodopseudomonas*, *Methylius*, *Agrobacterium*, *Acetobacter*, *Lactobacillus*, *Arthrobacter*, *Azotobacter*, *Leuconostoc*, and *Alcaligenes*, fungi, particularly yeast, e.g., *Saccharomyces*, *Cryptococcus*, *Kluyveromyces*, *Sporobolomyces*, *Rhodotorula*, and *Aureobasidium*. Of particular interest are such phytosphere bacterial species as *Pseudomonas syringae*, *Pseudomonas fluorescens*, *Serratia marcescens*, *Acetobacter xylinum*, *Agrobacteria*, *Rhodopseudomonas spheroides*, *Xanthomonas campestris*, *Rhizobium melioti*, *Alcaligenes entrophus*, *Clavibacter xyli* and *Azotobacter vinlandir*, and phytosphere yeast species such as *Rhodotorula rubra*, *R. glutinis*, *R. marina*, *R. aurantiaca*, *Cryptococcus albidus*, *C. diffluens*, *C. laurentii*, *Saccharomyces rosei*, *S. pretoriensis*, *S. cerevisiae*, *Sporobolomyces rosues*, *S. odorus*, *Kluyveromyces veronae*, and *Aureobasidium pollulans*.

A number of ways are available for introducing the polynucleotide comprising the silencing element into the microbial host under conditions that allow for stable maintenance and expression of such nucleotide encoding sequences. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (2000); *Molecular Cloning: A Laboratory Manual* (3rd ed.; Cold Spring Harbor Laboratory Press, Plainview, N.Y.); Davis et al. (1980) *Advanced Bacterial Genetics* (Cold Spring Harbor Laboratory, Cold Spring Harbor, N.Y.); and the references cited therein.

Suitable host cells include the prokaryotes and the lower eukaryotes, such as fungi. Illustrative prokaryotes, both Gram-negative and Gram-positive, include Enterobacteriaceae, such as *Escherichia*, *Erwinia*, *Shigella*, *Salmonella*, and *Proteus*; Bacillaceae; Rhizobiceae, such as *Rhizobium*; Spirillaceae, such as photobacterium, *Zymomonas*, *Serratia*, *Aeromonas*, *Vibrio*, *Desulfovibrio*, *Spirillum*; Lactobacillaceae; Pseudomonadaceae, such as *Pseudomonas* and *Acetobacter*; Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of the invention include ease of introducing the coding sequence into the host, availability of expression systems, efficiency of expression, stability in the host, and the presence of auxiliary genetic capabilities. Characteristics of interest for use as a pesticide microcapsule include protective qualities, such as thick cell walls, pigmentation, and intracellular packaging or formation of inclusion bodies; leaf affinity; lack of mammalian toxicity; attractiveness to pests for ingestion; and the like. Other considerations include ease of formulation and handling, economics, storage stability, and the like.

Host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

The sequences encoding the silencing elements encompassed by the invention can be introduced into microorganisms that multiply on plants (epiphytes) to deliver these components to potential target pests. Epiphytes, for example, can be gram-positive or gram-negative bacteria.

The silencing element can be fermented in a bacterial host and the resulting bacteria processed and used as a microbial spray in the same manner that *Bacillus thuringiensis* strains have been used as insecticidal sprays. Any suitable microorganism can be used for this purpose. *Pseudomonas* has been used to express *Bacillus thuringiensis* endotoxins as encapsulated proteins and the resulting cells processed and sprayed as an insecticide Gaertner et al. (1993), in *Advanced Engineered Pesticides*, ed. L. Kim (Marcel Decker, Inc.).

Alternatively, the components of the invention are produced by introducing heterologous genes into a cellular host. Expression of the heterologous sequences results, directly or indirectly, in the intracellular production of the silencing element. These compositions may then be formulated in accordance with conventional techniques for application to the environment hosting a target pest, e.g., soil, water, and foliage of plants. See, for example, EPA 0192319, and the references cited therein.

In the present invention, a transformed microorganism can be formulated with an acceptable carrier into separate or combined compositions that are, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention (i.e., at least one silencing element) are normally applied in the form of compositions and can be applied to the crop area, plant, or seed to be treated. For example, the compositions may be applied to grain in preparation for or during storage in a grain bin or silo, etc. The compositions may be applied simultaneously or in succession with other compounds. Methods of applying an active ingredient or a composition that contains at least one silencing element include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions comprising the silencing element can be in a suitable form for direct application or as a concentrate of primary composition that requires dilution with a suitable quantity of water or other dilutant before application.

The compositions (including the transformed microorganisms) can be applied to the environment of an insect pest (such as a Coleoptera plant pest or a *Diabrotica* plant pest) by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the composition(s) and/or transformed microorganism(s) may be mixed with grain to protect the grain during storage. It is generally important to obtain good control of pests in the early stages of plant growth, as this is the time when the plant can be most severely damaged. The compositions can conveniently contain another insecticide if this is thought necessary. In an embodiment of the invention, the composition(s) is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, in an inert carrier, and dead cells of a *Bacillus* strain or transformed microorganism of the invention.

VII. Plants, Plant Parts, and Methods of Introducing Sequences into Plants

In one embodiment, the methods of the invention involve introducing a polynucleotide into a plant. "Introducing" is intended to mean presenting to the plant the polynucleotide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the polynucleotide of the invention may be introduced into plants by contacting plants with a virus or viral nucleic acids. Generally, such methods involve incorporating a nucleotide construct of the invention within a viral DNA or RNA molecule. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

VIII. Methods of Use

The methods of the invention comprise methods for controlling a pest (i.e., a Coleopteran plant pest, including a *Diabrotica* plant pest, such as, *D. virgifera virgifera, D. barberi,* or *D. undecimpunctata howardi*). The method comprises feeding to a pest a composition comprising a silencing element of the invention, wherein said silencing element, when ingested by a pest (i.e., a Coleopteran plant pest including a *Diabrotica* plant pest, such as, *D. virgifera virgifera, D. barberi,* or *D. undecimpunctata howardi*), reduces the level of a target polynucleotide of the pest and thereby controls the pest. The pest can be fed the silencing element in a variety of ways. For example, in one embodiment, the polynucleotide comprising the silencing element is introduced into a plant. As the Coleopteran plant pest or *Diabrotica* plant pest feeds on the plant or part thereof expressing these sequences, the silencing element is delivered to the pest. When the silencing element is delivered to the plant in this manner, it is recognized that the silencing element can be expressed constitutively or alternatively, it may be produced in a stage-specific manner by employing the various inducible or tissue-preferred or developmentally regulated promoters that are discussed elsewhere herein. In specific embodiments, the silencing element is expressed in the roots, stalk or stem, leaf including pedicel, xylem and phloem, fruit or reproductive tissue, silk, flowers and all parts therein or any combination thereof.

In another method, a composition comprising at least one silencing element of the invention is applied to a plant. In such embodiments, the silencing element can be formulated in an agronomically suitable and/or environmentally acceptable carrier, which is preferably, suitable for dispersal in fields. In addition, the carrier can also include compounds that increase the half life of the composition. In specific embodiments, the composition comprising the silencing element is formulated in such a manner such that it persists in the environment for a length of time sufficient to allow it to be delivered to a pest. In such embodiments, the composition can be applied to an area inhabited by a pest. In one embodiment, the composition is applied externally to a plant (i.e., by spraying a field) to protect the plant from pests.

In certain embodiments, the constructs of the present invention can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.*

12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxy-alkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, U.S. application Ser. No. 12/351,093, entitled "*Compositions and Methods for the Suppression of Target Polynucleotides*", filed Jan. 9, 2009 and herein incorporated by reference in its entirety.

As used herein, a "suppressor enhancer element" comprises a polynucleotide comprising the target sequence to be suppressed or an active fragment or variant thereof. It is recognize that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element. Thus, in specific embodiments, the suppressor enhancer element comprises a polynucleotide set forth in SEQ ID NO: 1-236 or an active variant or fragment thereof It is recognized that multiple suppressor enhancer elements from the same target sequence or from different target sequences, or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the invention have an improved loading of RNAi into the phloem of the plant than would be observed with the expression of the silencing element construct alone and, thus provide better control of phloem feeding insects by an RNAi approach. In specific embodiments, the plants, plant parts, and plant cells of the invention can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell, or phloem when compared to an appropriate control. In other embodiments, the increase in the level of RNAi in the plant, plant part, plant cell, or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Methods to assay for an increase in the level of RNAi are discussed elsewhere herein.

The following examples are offered by way of illustration and not by way of limitation.

EXPERIMENTAL

Example 1: In Vitro Transcript dsRNA Screening Method

A cDNA library was produced from neonate western corn rootworm larvae by standard methods. A selected cDNA clone containing an expressed sequence tag is amplified in a PCR using universal primers to the plasmid backbone and flanking the EST insert. The universal primers also contain T7 RNA polymerase sites. 1 ul of the PCR reaction is used as the template for an in vitro transcription (IVT) reaction to produce long double stranded RNAs. Following enzymatic digestion and removal of the DNA template and single stranded RNA, the IVT reaction products are incorporated into artificial insect diet as described below.

Insect Bioassays 2.5 ul of the IVT reaction are added to a given well of a 96 well microtiter plate. 25 ul of molten lowmelt Western corn rootworm diet are added to the sample and shaken on an orbital shaker to mix the sample and diet. Once the diet has solidified, neonate rootworms are added to the well. An average of 5 neonates is added to each well. After the plate is infested, the plate is sealed with mylar and a single hole in punched in the mylar over each well to allow air exchange. 4 replicate wells are produced for each sample. The assay is scored for activity 7 days post infestation. The possible scores are dead, severely stunted (little or now growth but alive), stunted (growth to second instar but not equivalent to controls), or no activity. Samples demonstrating mortality or severe stunting were advanced to confirmation. Primary assays and confirmation assays were performed with the southern corn rootworm.

Following confirmation, a simple dose response assay was performed with both southern and western corn rootworms. Samples for dose response assays were produced in the same manner with the following modification; samples were further purified using column purification prior to enzymatic treatment. Samples were also normalized to 0.5 ug/ul and all samples were evaluated by gel electrophoresis. Dose response assays were performed with the following rates; 50, 25, 12, 6, 3, and 1.5 ppm Example 2. Sequences Having Insecticidal Activity DNA sequences which encode double stranded RNAs which were shown to have insecticidal activity against corn rootworms using the assay described in Example 1 are set forth below. Non-limiting examples of target polynucleotides are set forth below in Table 1.

TABLE 1

```
SEQ ID NO: 1
>iwm2c.pk005.e1.fis1

SEQ ID NO: 2
>iwm2c.pk004.b13.fis1

SEQ ID NO: 3
>iwm2s.pk003.o11.fis1

SEQ ID NO: 4
>iwm2c.pk002.e24.fis1

SEQ ID NO: 5
>iwm2c.pk002.e24.fis1

SEQ ID NO: 6
>iwm2c.pk011.n17.fis1

SEQ ID NO: 7
>idv1c.pk001.d141.fis1
```

TABLE 1-continued

SEQ ID NO: 8
>idv1c.pk001.e9.fis1

SEQ ID NO: 9
>idv1c.pk001.m5.f.fis1

SEQ ID NO: 10
>idv1c.pk001.n1.f.fis1

SEQ ID NO: 11
>idv1c.pk002.c5.f.fis1

SEQ ID NO: 12
>idv1c.pk002.f20.f.fis1

SEQ ID NO: 13
>idv1c.pk002.j17.f.fis1

SEQ ID NO: 14
>idv1c.pk002.n13.f.fis1

SEQ ID NO: 15
>idv1c.pk003.d6.f.fis1

SEQ ID NO: 16
>idv1c.pk003.f8.f.fis1

SEQ ID NO: 17
>idv1c.pk003.f9.f.fis1

SEQ ID NO: 18
>idv1c.pk003.j4.f.fis1

SEQ ID NO: 19
>idv1c.pk003.j6.f.fis1

SEQ ID NO: 20
>idv1c.pk003.j20.f.fis1

SEQ ID NO: 21
>idv1c.pk003.l1.f.fis1

SEQ ID NO: 22
>idv1c.pk003.m1.f.fis1

SEQ ID NO: 23
>idv1c.pk003.m10.f.fis1

SEQ ID NO: 24
>idv1c.pk003.o13.f.fis1

SEQ ID NO: 25
>idv1c.pk003.o22.f.fis1

SEQ ID NO: 26
>idv1c.pk003.p13.f.fis1

SEQ ID NO: 27
>idv1c.pk004.b12.f.fis1

SEQ ID NO: 28
>idv1c.pk004.d17.f.fis1

SEQ ID NO: 29
>idv1c.pk004.f20.f.fis1

SEQ ID NO: 30
>idv1c.pk004.k5.f.fis1

SEQ ID NO: 31
>idv1c.pk004.l15.f.fis1

SEQ ID NO: 32
>idv1c.pk004.n6.f.fis1

SEQ ID NO: 33
>idv1c.pk004.o4.f.fis1

TABLE 1-continued

SEQ ID NO: 34
>idv1c.pk004.o9.f.fis1

SEQ ID NO: 35
>idv1c.pk004.p1.f.fis1

SEQ ID NO: 36
>idv1c.pk013.a15.f.fis1

SEQ ID NO: 37
>idv1c.pk013.b11.f.fis1

SEQ ID NO: 38
>idv1c.pk013.c21.f.fis1

SEQ ID NO: 39
>idv1c.pk013.d22.f.fis1

SEQ ID NO: 40
>idv1c.pk013.h1.f.fis1

SEQ ID NO: 41
>idv1c.pk013.h14.f.fis1

SEQ ID NO: 42
>idv1c.pk013.k1.f.fis1

SEQ ID NO: 43
>idv1c.pk014.a19.f.fis1

SEQ ID NO: 44
>idv1c.pk014.b9.f.fis1

SEQ ID NO: 45
>idv1c.pk014.b17.f.fis1

SEQ ID NO: 46
>idv1c.pk014.c14.f.fis1

SEQ ID NO: 47
>idv1c.pk014.d11.f.fis1

SEQ ID NO: 48
>idv1c.pk014.f3.f.fis1

SEQ ID NO: 49
>idv1c.pk014.j2.f.fis1

SEQ ID NO: 50
>idv1c.pk014.k23.f.fis1

SEQ ID NO: 51
>idv1c.pk014.m5.f.fis1

SEQ ID NO: 52
>idv1c.pk014.m13.f.fis1

SEQ ID NO: 53
>idv1c.pk014.n16.f.fis1

SEQ ID NO: 54
>idv1c.pk014.n23.f.fis1

SEQ ID NO: 55
>idv1c.pk014.o1.f.fis1

SEQ ID NO: 56
>idv1c.pk015.a16.f.fis1

SEQ ID NO: 57
>idv1c.pk015.b8.f.fis1

SEQ ID NO: 58
>idv1c.pk015.g10.f.fis1

SEQ ID NO: 59
>idv1c.pk015.l13.f.fis1

TABLE 1-continued

SEQ ID NO: 60
>idv1c.pk015.n19.f.fis1

SEQ ID NO: 61
>idv1c.pk015.p2.f.fis1

SEQ ID NO: 62
>idv1c.pk016.a9.f.fis1

SEQ ID NO: 63
>idv1c.pk016.f12.f.fis1

SEQ ID NO: 64
>idv1c.pk016.f21.f.fis1

SEQ ID NO: 65
>idv1c.pk016.h15.f.fis1

SEQ ID NO: 66
>idv1c.pk016.h19.f.fis1

SEQ ID NO: 67
>idv1c.pk016.j12.f.fis1

SEQ ID NO: 68
>idv1c.pk016.j15.f.fis1

SEQ ID NO: 69
>idv1c.pk016.k9.f.fis1

SEQ ID NO: 70
>idv1c.pk016.p18.f.fis1

SEQ ID NO: 71
>idv1c.pk017.c3.f.fis1

SEQ ID NO: 72
>idv1c.pk017.d14.f.fis1

SEQ ID NO: 73
>idv1c.pk017.e22.f.fis1

SEQ ID NO: 74
>idv1c.pk017.f1.f.fis1

SEQ ID NO: 75
>idv1c.pk017.h14.f.fis1

SEQ ID NO: 76
>idv1c.pk017.n19.f.fis1

SEQ ID NO: 77
>idv1c.pk017.p2.f.fis1

SEQ ID NO: 78
>idv1c.pk018.a5.f.fis1

SEQ ID NO: 79
>idv1c.pk018.c11.f.fis1

SEQ ID NO: 80
>idv1c.pk018.d5.f.fis1

SEQ ID NO: 81
>idv1c.pk018.d14.f.fis1

SEQ ID NO: 82
>idv1c.pk018.e10.f.fis1

SEQ ID NO: 83
>idv1c.pk018.e20.f.fis1

SEQ ID NO: 84
>idv1c.pk018.f19.f.fis1

SEQ ID NO: 85
>idv1c.pk018.f22.f.fis1

TABLE 1-continued

SEQ ID NO: 86
>idv1c.pk018.g20.f.fis1

SEQ ID NO: 87
>idv1c.pk018.h21.f.fis1

SEQ ID NO: 88
>idv1c.pk018.m5.f.fis1

SEQ ID NO: 89
>idv1c.pk019.c4.f.fis1

SEQ ID NO: 90
>idv1c.pk019.i5.f.fis1

SEQ ID NO: 91
>idv1c.pk019.k3.f.fis1

SEQ ID NO: 92
>idv1c.pk019.l7.f.fis1

SEQ ID NO: 93
>idv1c.pk020.a8.f.fis1

SEQ ID NO: 94
>idv1c.pk020.b11.f.fis1

SEQ ID NO: 95
>idv1c.pk020.g17.f.fis1

SEQ ID NO: 96
>idv1c.pk020.i7.f.fis1

SEQ ID NO: 97
>idv1c.pk020.i24.f.fis1

SEQ ID NO: 98
>idv1c.pk020.k19.f.fis1

SEQ ID NO: 99
>idv1c.pk020.l3.f.fis1

SEQ ID NO: 100
>idv1c.pk020.p23.f.fis1

SEQ ID NO: 101
>idv1c.pk021.c21.f.fis1

SEQ ID NO: 102
>idv1c.pk021.d22.f.fis1

SEQ ID NO: 103
>idv1c.pk021.g16.f.fis1

SEQ ID NO: 104
>idv1c.pk021.h12.f.fis1

SEQ ID NO: 105
>idv1c.pk021.m20.f.fis1

SEQ ID NO: 106
>idv1c.pk004.j11.f.fis1

SEQ ID NO: 107
>idv1c.pk001.o20.f

SEQ ID NO: 108
>idv1c.pk002.a20.f

SEQ ID NO: 109
>idv1c.pk002.c15.f

SEQ ID NO: 110
>idv1c.pk002.i21.f

SEQ ID NO: 111
>idv1c.pk024.b23.f

TABLE 1-continued

SEQ ID NO: 112
>idv1c.pk024.e1.f

SEQ ID NO: 113
>idv1c.pk024.e24.f

SEQ ID NO: 114
>idv1c.pk024.k17.f

SEQ ID NO: 115
>idv1c.pk024.m13.f

SEQ ID NO: 116
>idv1c.pk024.n1.f

SEQ ID NO: 117
>idv1c.pk024.o3.f

SEQ ID NO: 118
>idv1c.pk025.a4.f

SEQ ID NO: 119
>idv1c.pk025.c5.f

SEQ ID NO: 120
>idv1c.pk025.c23.f

SEQ ID NO: 121
>idv1c.pk025.d18.f

SEQ ID NO: 122
>idv1c.pk025.d20.f

SEQ ID NO: 123
>idv1c.pk025.f24.f

SEQ ID NO: 124
>idv1c.pk025.j20.f

SEQ ID NO: 125
>idv1c.pk025.l10.f

SEQ ID NO: 126
>idv1c.pk026.a16.f

SEQ ID NO: 127
>idv1c.pk026.b23.f

SEQ ID NO: 128
>idv1c.pk026.d22.f

SEQ ID NO: 129
>idv1c.pk026.e6.f

SEQ ID NO: 130
>idv1c.pk026.g12.f

SEQ ID NO: 131
>idv1c.pk026.h15.f

SEQ ID NO: 132
>idv1c.pk026.i12.f

SEQ ID NO: 133
>idv1c.pk026.j18.f

SEQ ID NO: 134
>idv1c.pk026.k13.f

SEQ ID NO: 135
>idv1c.pk027.b21.f

SEQ ID NO: 136
>idv1c.pk027.c7.f

SEQ ID NO: 137
>idv1c.pk027.k4.f

TABLE 1-continued

SEQ ID NO: 138
>idv1c.pk027.p21.f

SEQ ID NO: 139
>idv1c.pk028.b7.f

SEQ ID NO: 140
>idv1c.pk028.c22.f

SEQ ID NO: 141
>idv1c.pk028.h6.f

SEQ ID NO: 142
>idv1c.pk028.i16.f

SEQ ID NO: 143
>idv1c.pk028.m11.f

SEQ ID NO: 144
>idv1c.pk028.o18.f

SEQ ID NO: 145
>idv1c.pk029.a17.f

SEQ ID NO: 146
>idv1c.pk029.d16.f

SEQ ID NO: 147
>idv1c.pk029.i22.f

SEQ ID NO: 148
>idv1c.pk029.j20.f

SEQ ID NO: 149
>idv1c.pk029.k11.f

SEQ ID NO: 150
>idv1c.pk029.l22.f

SEQ ID NO: 151
>idv1c.pk030.e10.f

SEQ ID NO: 152
>idv1c.pk030.e21.f

SEQ ID NO: 153
>idv1c.pk030.h13.f

SEQ ID NO: 154
>idv1c.pk030.h23.f

SEQ ID NO: 155
>idv1c.pk030.l9.f

SEQ ID NO: 156
>idv1c.pk030.m22.f

SEQ ID NO: 157
>idv1c.pk030.o7.f

SEQ ID NO: 158
>idv1c.pk031.a11.f

SEQ ID NO: 159
>idv1c.pk031.e16.f

SEQ ID NO: 160
>idv1c.pk031.g2.f

SEQ ID NO: 161
>idv1c.pk031.g22.f

SEQ ID NO: 162
>idv1c.pk031.i13.f

SEQ ID NO: 163
>idv1c.pk031.m3.f

TABLE 1-continued

SEQ ID NO: 164
>idv1c.pk032.b4.f

SEQ ID NO: 165
>idv1c.pk032.e16.f

SEQ ID NO: 166
>idv1c.pk032.f14.f

SEQ ID NO: 167
>idv1c.pk032.m9.f

SEQ ID NO: 168
>idv1c.pk033.a15.f

SEQ ID NO: 169
>idv1c.pk033.b14.f

SEQ ID NO: 170
>idv1c.pk033.m3.f

SEQ ID NO: 171
>idv1c.pk033.n10.f

SEQ ID NO: 172
>idv1c.pk033.n18.f

SEQ ID NO: 173
>idv1c.pk034.e8.f

SEQ ID NO: 174
>idv1c.pk034.p24.f

SEQ ID NO: 175
>idv1c.pk035.f21.f

SEQ ID NO: 176
>idv1c.pk035.g1.f

SEQ ID NO: 177
>idv1c.pk035.h19.f

SEQ ID NO: 178
>idv1c.pk035.j4.f

SEQ ID NO: 179
>idv1c.pk035.m1.f

SEQ ID NO: 180
>idv1c.pk035.o13.f

SEQ ID NO: 181
>idv1c.pk036.a14.f

SEQ ID NO: 182
>idv1c.pk036.e18.f

SEQ ID NO: 183
>idv1c.pk036.f4.f

SEQ ID NO: 184
>idv1c.pk036.f9.f

SEQ ID NO: 185
>idv1c.pk036.i17.f

SEQ ID NO: 186
>idv1c.pk036.i20.f

SEQ ID NO: 187
>idv1c.pk036.k23.f

SEQ ID NO: 188
>idv1c.pk034.k22.f

SEQ ID NO: 189
>idv1c.pk002.c7.f

TABLE 1-continued

SEQ ID NO: 190
>idv1c.pk002.f18.f

SEQ ID NO: 191
>idv1c.pk002.i23.f

SEQ ID NO: 192
>idv1c.pk002.j24.f

SEQ ID NO: 193
>idv1c.pk002.m16.f

SEQ ID NO: 194
>idv1c.pk002.n13.f

SEQ ID NO: 195
>idv1c.pk024.c7.f

SEQ ID NO: 196
>idv1c.pk024.j15.f

SEQ ID NO: 197
>idv1c.pk025.b17.f

SEQ ID NO: 198
>idv1c.pk025.f3.f

SEQ ID NO: 199
>idv1c.pk025.i8.f

SEQ ID NO: 200
>idv1c.pk025.l17.f

SEQ ID NO: 201
>idv1c.pk025.o24.f

SEQ ID NO: 202
>idv1c.pk025.p9.f

SEQ ID NO: 203
>idv1c.pk026.f20.f

SEQ ID NO: 204
>idv1c.pk026.p8.f

SEQ ID NO: 205
>idv1c.pk026.p22.f

SEQ ID NO: 206
>idv1c.pk027.a14.f

SEQ ID NO: 207
>idv1c.pk027.g7.f

SEQ ID NO: 208
>idv1c.pk027.k23.f

SEQ ID NO: 209
>idv1c.pk028.b17.f

SEQ ID NO: 210
>idv1c.pk028.f11.f

SEQ ID NO: 211
>idv1c.pk029.c3.f

SEQ ID NO: 212
>idv1c.pk029.f5.f

SEQ ID NO: 213
>idv1c.pk029.j4.f

SEQ ID NO: 214
>idv1c.pk030.b23.f

SEQ ID NO: 215
>idv1c.pk030.f9.f

TABLE 1-continued

SEQ ID NO: 216
>idv1c.pk030.g11.f

SEQ ID NO: 217
>idv1c.pk031.c20.f

SEQ ID NO: 218
>idv1c.pk031.d1.f

SEQ ID NO: 219
>idv1c.pk031.j1.f

SEQ ID NO: 220
>idv1c.pk031.j6.f

SEQ ID NO: 221
>idv1c.pk031.p16.f

SEQ ID NO: 222
>idv1c.pk032.a16.f

SEQ ID NO: 223
>idv1c.pk032.f11.f

SEQ ID NO: 224
>idv1c.pk032.i21.f

SEQ ID NO: 225
>idv1c.pk032.n18.f

SEQ ID NO: 226
>idv1c.pk032.p5.f

SEQ ID NO: 227
>idv1c.pk033.d24.f

SEQ ID NO: 228
>idv1c.pk033.j21.f

SEQ ID NO: 229
>idv1c.pk033.o9.f

SEQ ID NO: 230
>idv1c.pk033.p15.f

SEQ ID NO: 231
>idv1c.pk033.p16.f

SEQ ID NO: 232
>idv1c.pk034.i2.f

SEQ ID NO: 233
>idv1c.pk034.j6.f

SEQ ID NO: 234
>idv1c.pk035.i17.f

SEQ ID NO: 235
>idv1c.pk035.k18.f

SEQ ID NO: 236
>idv1c.pk036.i19.f

SEQ ID NO: 237
Construct expressing SEQ ID NO: 8 as a hairpin RNA. The construct comprises: UBI1ZM promoter 5'UTR and 1$^{st}$ intron operably linked to SEQ ID NO: 8 operably linked to the ADH1 intron operably linked to the complement of SEQ ID NO: 8.

SEQ ID NO: 238
Construct expressing SEQ ID NO: 26 as a hairpin RNA. The construct comprises: UBI1ZM promoter 5'UTR and 1$^{st}$ intron operably linked to SEQ ID NO: 26 operably linked to the ADH1 intron operably linked to the complement of SEQ ID NO: 26.

SEQ ID NO: 239
Construct expressing SEQ ID NO: 17 as a hairpin RNA. The construct comprises: UBI1ZM promoter 5'UTR and 1$^{st}$ intron operably linked to SEQ ID NO: 17 operably linked to the ADH1 intron operably linked to the complement of SEQ ID NO: 17.

TABLE 1-continued

```
SEQ ID NO: 240
Construct expressing SEQ ID NO: 28 as a hairpin RNA. The construct comprises: UBI1ZM
promoter 5'UTR and 1st intron operably linked to SEQ ID NO: 28 operably linked to the
ADH1 intron operably linked to the complement of SEQ ID NO: 28.

SEQ ID NO: 241
Construct expressing SEQ ID NO: 28 as a hairpin RNA. The construct comprises: UBI1ZM
promoter 5'UTR and 1st intron operably linked to SEQ ID NO: 28 operably linked to the
ADH1 intron operably linked to the complement of SEQ ID NO: 28.

SEQ ID NO: 242
Construct expressing SEQ ID NO: 13 as a hairpin RNA. The construct comprises: UBI1ZM
promoter 5'UTR and 1st intron operably linked to SEQ ID NO: 13 operably linked to the
ADH1 intron operably linked to the complement of SEQ ID NO: 13.

SEQ ID NO: 243
Construct expressing SEQ ID NO: 40 as a hairpin RNA. The construct comprises: UBI1ZM
promoter 5'UTR and 1st intron operably linked to SEQ ID NO: 40 operably linked to the
ADH1 intron operably linked to the complement of SEQ ID NO: 40.

SEQ ID NO: 244
Construct expressing SEQ ID NO: 72 as a hairpin RNA. The construct comprises: UBI1ZM
promoter 5'UTR and 1st intron operably linked to SEQ ID NO: 72 operably linked to the
ADH1 intron operably linked to the complement of SEQ ID NO: 72.

SEQ ID NO: 245
Construct expressing SEQ ID NO: 73 as a hairpin RNA. The construct comprises: UBI1ZM
promoter 5'UTR and 1st intron operably linked to SEQ ID NO: 73 operably linked to the
ADH1 intron operably linked to the complement of SEQ ID NO: 73

SEQ ID NO: 246
Construct expressing SEQ ID NO: 15 as a hairpin RNA. The construct comprises: UBI1ZM
promoter 5'UTR and 1st intron operably linked to SEQ ID NO: 15 operably linked to the
ADH1 intron operably linked to the complement of SEQ ID NO: 15.

SEQ ID NO: 247
Construct expressing SEQ ID NO: 18 as a hairpin RNA. The construct comprises: UBI1ZM
promoter 5'UTR and 1st intron operably linked to SEQ ID NO: 18 operably linked to the
ADH1 intron operably linked to the complement of SEQ ID NO: 18.

SEQ ID NO: 248
Construct expressing nt 1-380 of SEQ ID NO: 45 as a hairpin RNA. The construct comprises:
UBI1ZM promoter 5'UTR and 1st intron operably linked to nt 1-380 of SEQ ID NO: 45
operably linked to the ADH1 intron operably linked to the complement of nt 1-380 of SEQ ID
NO: 45.

SEQ ID NO: 249
Construct expressing nt 1-675 of SEQ ID NO: 37 as a hairpin RNA. The construct comprises:
UBI1ZM promoter 5'UTR and 1st intron operably linked to nt 1-675 of SEQ ID NO: 37
operably linked to the ADH1 intron operably linked to the complement of nt 1-675 of SEQ ID
NO: 37.

SEQ ID NO: 250
Construct expressing SEQ ID NO: 29 as a hairpin RNA. The construct comprises: UBI1ZM
promoter 5'UTR and 1st intron operably linked to SEQ ID NO: 29 operably linked to the
ADH1 intron operably linked to the complement of SEQ ID NO: 29.

SEQ ID NO: 251
Construct expressing nt 1-266 of SEQ ID NO: 50 as a hairpin RNA. The construct comprises:
UBI1ZM promoter 5'UTR and 1st intron operably linked to nt 1-266 of SEQ ID NO: 50
operably linked to the ADH1 intron operably linked to the complement of 1-266 of SEQ ID
NO: 50.

SEQ ID NO: 252
Construct expressing nt 16-585 of SEQ ID NO: 47 as a hairpin RNA. The construct
comprises: UBI1ZM promoter 5'UTR and 1st intron operably linked to nt 16-585 of SEQ ID
NO: 47 operably linked to the ADH1 intron operably linked to the complement of nt 16-585
of SEQ ID NO: 47.
```

Example 3. Transformation of Maize

Immature maize embryos from greenhouse donor plants are bombarded with a plasmid containing the silencing element of the invention operably linked to either a tissue specific, tissue selective, or constitutive promoter and the selectable marker gene PAT (Wohlleben et al. (1988) *Gene* 70:25-37), which confers resistance to the herbicide Bialaphos. In one embodiment, the constructs will express a long double stranded RNA of the target sequence set forth in table 1. Such a construct can be linked to the dMMB promoter. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the silencing element of interest operably linked to either the tissue specific, tissue selective, or constitutive promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in a particle gun. All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Plants are monitored and scored for the appropriate marker, such as the control of a Coleoptera plant pest, such as a *Diabrotica* plant pest and have insecticidal activity. For example, $R_0$ plant roots are fed to western corn rootworm larvae (WCR, *Diabrotica virgifera*). Transgenic corn roots are handed-off in Petri dishes with MSOD medium containing antibiotics and glyphosate for in vitro selection. Two WCR larvae are infested per root in each dish with a fine tip paintbrush. The dishes are sealed with Parafilm to prevent the larvae from escaping. The assays are placed into a 27° C., 60% RH Percival incubator incomplete darkness. Contamination and larval quality are monitored. After six days of feeding on root tissue, the larvae are transferred to WCR diet in a 96 well plate. The larvae are allowed to feed on the diet for eight days making the full assay fourteen days long. Larval mass and survivorship are recorded for analysis. A one-way ANOVA analysis and a Dunnett's test is performed on the larval mass data to look for statistical significance compared to an untransformed negative control. WCR larvae stunting is measured after feeding on two events and compared to growth of larvae fed on negative control plants.

In other assays, transgenic corn plants ($R_e$) generated are planted into 10-inch pots containing Metromix after reaching an appropriate size. When plants reach the V4 growth stage, approximately 1000 Western corn rootworm (WCR, *Diabrotica virgifera*) eggs are infested into the root zone. Non-transgenic corn of the same genotype is infested at a similar growth stage to serve as a negative control. Eggs are pre-incubated so hatch occurs within 24 hours of infestation. Larvae are allowed to feed on the root systems for 3 weeks. Plants are removed from the soil and washed so that the roots can be evaluated for larval feeding. Root damage is rated using a Node Injury Scale (NIS) to score the level of damage where a 0 indicates no damage, a 1 indicates that one node of roots is pruned to within 1.5 inches, a 2 indicates that 2 nodes are pruned, while a 3 indicates that 3 nodes are pruned, Because the plants being used for evaluation are directly out of tissue culture after transformation and because transformation events are unique, only a single plant is evaluated per event at this time. The plants in the assay that present signs or symptoms of larval feeding indicate that a successful infestation is obtained. Negative control plant roofs are moderately to severely damaged averaging whereas roots of the transgenic plants provide substantial control of larval feeding, with about 0.2 or less on the Node Injury Scale.

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCl, 0.10 g/l pyridoxine HCl, and 0.40 g/l glycine brought to volume with polished D-I $H_2O$) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCl, 0.10 g/l pyridoxine HCl, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

Example 4. *Agrobacterium*-Mediated Transformation of Maize

For *Agrobacterium*-mediated transformation of maize with a silencing element of the invention, the method of Zhao is employed (U.S. Pat. No. 5,981,840, and PCT patent publication WO98/32326; the contents of which are hereby incorporated by reference). Such as a construct can, for example, express a long double stranded RNA of the target sequence set forth in table 1. Such a construct can be linked to the dMMB promoter. Briefly, immature embryos are isolated from maize and the embryos contacted with a suspension of *Agrobacterium*, where the bacteria are capable of transferring the polynucleotide comprising the silencing element to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants. Assays for insecticidal activity can be performed as described above in Example, 5.

Example 5. Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the examples above by the method of particle gun bombardment (Klein et al. (1987) *Nature*, 327:70).

Soybean Embryogenic Suspension Culture Initiation

Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying the silencing element of interest are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (Bio-Whitaker Molecular Applications) and the DNA fragments containing silencing element of interest are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS 1000/HE instrument disk. Each 5 µl aliquot contains approximately 0.375 mg gold per bombardment (i.e. per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for the appropriate marker or the ability of the plant, when injected with the silencing elements, to control the Coleopteran plant pest or the *Diabrotica* plant pest.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot.

Media Recipes

| SB 196 - FN Lite liquid proliferation medium (per liter) | |
| --- | --- |
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO$_3$ | 2.83 gm |
| (NH$_4$)$_2$ SO$_4$ | 0.463 gm |
| Asparagine | 1.0 gm |
| Sucrose (1%) | 10 gm | pH 5.8

FN Lite Stock Solutions

| Stock # | | 1000 ml | 500 ml |
| --- | --- | --- | --- |
| 1 | MS Fe EDTA 100x Stock | | |
| | Na$_2$ EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL—Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL—Cat#11117-066); 1 ml B5 vitamins 1000× stock; 60 g maltose; 750 mg MgCl2 hexahydrate; 5 g activated charcoal; pH 5.7; and, 2 g gelrite.

SB 103 solid medium (per liter) comprises: 1 pkg. MS salts (Gibco/BRL—Cat#11117-066); 1 ml B5 vitamins 1000× stock; 60 g maltose; 750 mg MgCl2 hexahydrate; pH 5.7; and, 2 g gelrite.

SB 71-4 solid medium (per liter) comprises: 1 bottle Gamborg's B5 salts w/sucrose (Gibco/BRL—Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide Example 6. Expression of Silencing Elements in Maize The silencing elements set forth in SEQ ID NO: 8, 26, 17, 28 and 10 were expressed in a maize plant as hairpins and the plant was tested for insecticidal activity against corn root worms. The sequences set forth in SEQ ID NO: 8, 26, 17, 28 and 10 were engineered to be expressed as a hairpin. The constructs comprised the following components: the maize ubiquitin promoter/5'UTR/1$^{st}$ intron operably linked SEQ ID NO:8, 26, 17, 28 or 10:: ADH1 intron:: complement of SEQ ID NO:8, 26, 17, 28 and 10. Plasmids PHP41121, PHP41134, PHP41127, PHP41130, PHP41118 were generated as summarized below in Table 2.

TABLE 2

| SEQ ID NO of silencing element | SEQ ID NO of construct w/ promoter and silencing element | Clone name of silencing element | Sequence homology of the silencing element | Plasmid name |
| --- | --- | --- | --- | --- |
| 8 | 237 | idvlc.pk001.e9.f | Ribosomal protein s10E | PHP41121 |
| 26 | 238 | idvlc.ph003.p13.f | Ribosomal protein | PHP41134 |
| 17 | 239 | idvlc.pk003.f9.f | 27 kD proteinase | PHP41127 |
| 28 | 240 | idvlc.pk004.d17.f | Tribolium | PHP41130 |
| 10 | 241 | idvlc.pk001.n1.f | No hits | PHP41118 |

Maize plants were transformed with Plasmids PHP41121, PHP41134, PHP41127, PHP41130, PHP41118 and plants expressing the silencing elements denoted in Table 2 were transplanted from 272V plates into greenhouse flats containing Fafard Superfine potting mix. Approximately 10 to 14 days after transplant, plants (now at growth stage V2-V3) were transplanted into treepots containing Fafard Superfine potting mix. At 14 days post greenhouse send date, plants were infested with 100 eggs of western corn root worms (WCRW)/plant. For later sets, a second infestation of 100 eggs WCRW/plant was done 14 days after the first infestation and scoring was at 14 days after the second infestation. 21 days post infestation, plants were scored using CRWNIS. Those plants with a score of ≤0.5 are transplanted into large pots containing SB300 for seed. As shown in FIG. 1, each of SEQ ID NO: 8, 26, 17, 28 and 10 had insecticidal activity.

Example 7 Insect Bioassays 2.5 ul of an in-vitro transcription reaction which synthesized one of the sequences set forth in SEQ ID NO: 107-236 were added to a given well of a 96 well microtiter plate. 25 ul of molten lowmelt western corn rootworm diet were added to the sample and shaken on an orbital shaker to mix the sample and diet. Once the diet had solidified, neonate rootworms were added to the well. An average of 5 neonates were added to each well. After the plate was infested, the plate was sealed with mylar and a single hole was punched in the mylar over each well to allow air exchange. 4 replicate wells were produced for each sample. The assay was scored for activity 7 days post infestation. Table 3 provides insecticidal bioassay data employing the southern corn rootworm. The possible scores are dead (D), severely stunted (SS; little or no growth but alive), stunted (S; growth to second instar but not equivalent to controls), contaminated (c), or no activity.

Following confirmation, a simple dose response assay was performed with both southern and western corn rootworms. See, Tables 4 and 5 below. Samples for dose response assays were produced in the same manner described above with the following modification: samples were further purified using column purification prior to enzymatic treatment. Samples were also normalized to 0.5 ug/ul and all samples were evaluated by gel electrophoresis. Dose response assays were performed with the following rates: crude, 0.5, 0.25, 0.0125 ppm, and 0.125 dilutions (equivalent to 51, 25, 12.5 and 6 ppm).

TABLE 3

Insecticidal Bioassay Data Against Southern Corn Root Worm

| Clone name | | | | | |
|---|---|---|---|---|---|
| idv1c.pk001.o20.f | S | S | S | S | S |
| idv1c.pk002.a20.f | S | S | S | S | S |
| idv1c.pk002.c7.f | SS | SS | SS | SS | SS |
| idv1c.pk002.c15.f | S | S | S | S | S |
| idv1c.pk002.f18.f | SS | SS | S | SS | SS |
| idv1c.pk002.i21.f | S | S | S | S | S |
| idv1c.pk002.i23.f | SS | SS | SS | SS | SS |
| idv1c.pk002.j24.f | SS | SS | SS | SS | SS |
| idv1c.pk002.m16.f | SS | SS | SS | SS | SS |
| idv1c.pk002.n13.f | SS | SS | SS | SS | SS |
| idv1c.pk024.b23.f | S | S | S | S | S |
| idv1c.pk024.c7.f | SS | SS | D | SS | SS |
| idv1c.pk024.e1.f | S | S | S | S | S |
| idv1c.pk024.e24.f | S | S | S | S | S |
| idv1c.pk024.j15.f | SS | SS | SS | SS | SS |
| idv1c.pk024.k17.f | S | S | S | S | S |
| idv1c.pk024.m13.f | S | S | S | S | S |
| idv1c.pk024.n1.f | S | S | S | S | S |
| idv1c.pk024.o3.f | S | S | S | S | S |
| idv1c.pk025.a4.f | S | S | S | S | S |
| idv1c.pk025.b17.f | SS | SS | SS | SS | SS |
| idv1c.pk025.c5.f | S | S | S | S | S |
| idv1c.pk025.c23.f | S | SS | S | S | S |
| idv1c.pk025.d18.f | S | S | S | S | S |
| idv1c.pk025.d20.f | S | S | S | S | S |
| idv1c.pk025.f3.f | SS | SS | SS | SS | SS |
| idv1c.pk025.f24.f | S | S | S | S | S |
| idv1c.pk025.i8.f | SS | SS | SS | S | SS |
| idv1c.pk025.j20.f | S | S | S | S | S |
| idv1c.pk025.l10.f | S | S | S | S | S |
| idv1c.pk025.l17.f | SS | S | SS | SS | SS |
| idv1c.pk025.o24.f | SS | SS | SS | SS | SS |
| idv1c.pk025.p9.f | SS | SS | S | SS | SS |
| idv1c.pk026.a16.f | S | S | S | S | S |
| idv1c.pk026.b23.f | S | S | S | S | S |
| idv1c.pk026.d22.f | S | S | S | S | S |
| idv1c.pk026.e6.f | S | S | S | S | S |
| idv1c.pk026.f20.f | SS | SS | SS | SS | SS |
| idv1c.pk026.g12.f | S | S | S | S | S |
| idv1c.pk026.h15.f | S | S | S | S | S |

TABLE 3-continued

Insecticidal Bioassay Data Against Southern Corn Root Worm

| Clone name | | | | | |
|---|---|---|---|---|---|
| idv1c.pk026.i12.f | S | S | S | S | S |
| idv1c.pk026.j18.f | S | S | S | S | S |
| idv1c.pk026.k13.f | S | S | S | S | S |
| idv1c.pk026.p8.f | SS | SS | S | S | SS |
| idv1c.pk026.p22.f | SS | SS | SS | SS | SS |
| idv1c.pk027.a14.f | SS | SS | SS | SS | SS |
| idv1c.pk027.b21.f | S | S | S | S | S |
| idv1c.pk027.c7.f | S | S | S | S | S |
| idv1c.pk027.g7.f | SS | SS | SS | SS | SS |
| idv1c.pk027.k4.f | S | S | S | S | S |
| idv1c.pk027.k23.f | SS | SS | SS | SS | SS |
| idv1c.pk027.p21.f | S | S | S | S | S |
| idv1c.pk028.b7.f | S | S | S | S | S |
| idv1c.pk028.b17.f | S | SS | SS | S | SS |
| idv1c.pk028.c22.f | S | S | S | S | S |
| idv1c.pk028.f11.f | SS | SS | SS | SS | SS |
| idv1c.pk028.h6.f | S | S | S | S | S |
| idv1c.pk028.i16.f | S | S | S | S | S |
| idv1c.pk028.m11.f | S | S | S | S | S |
| idv1c.pk028.o18.f | S | S | S | S | S |
| idv1c.pk029.a17.f | S | S | S | S | S |
| idv1c.pk029.c3.f | SS | SS | SS | SS | SS |
| idv1c.pk029.d16.f | S | S | S | S | S |
| idv1c.pk029.f5.f | SS | SS | SS | S | SS |
| idv1c.pk029.i22.f | S | S | S | S | S |
| idv1c.pk029.j4.f | SS | SS | SS | SS | SS |
| idv1c.pk029.j20.f | S | S | S | S | S |
| idv1c.pk029.k11.f | S | S | S | S | S |
| idv1c.pk029.l22.f | S | S | S | S | S |
| idv1c.pk030.b23.f | SS | SS | SS | SS | SS |
| idv1c.pk030.e10.f | S | S | S | S | S |
| idv1c.pk030.e21.f | S | S | S | S | S |
| idv1c.pk030.f9.f | SS | SS | SS | SS | SS |
| idv1c.pk030.g11.f | SS | SS | SS | SS | SS |
| idv1c.pk030.h13.f | S | S | S | S | S |
| idv1c.pk030.h23.f | S | S | S | S | S |
| idv1c.pk030.l9.f | S | S | S | S | S |
| idv1c.pk030.m22.f | S | S | S | S | S |
| idv1c.pk030.o7.f | S | S | S | S | S |
| idv1c.pk031.a11.f | S | S | S | S | S |
| idv1c.pk031.c20.f | SS | SS | SS | SS | SS |
| idv1c.pk031.d1.f | SS | SS | SS | SS | SS |
| idv1c.pk031.e16.f | S | S | S | S | S |
| idv1c.pk031.g2.f | S | S | S | S | S |
| idv1c.pk031.g22.f | S | S | S | S | S |
| idv1c.pk031.i13.f | S | S | S | S | S |
| idv1c.pk031.j1.f | SS | SS | SS | SS | SS |
| idv1c.pk031.j6.f | SS | SS | SS | SS | SS |
| idv1c.pk031.m3.f | S | S | S | S | S |
| idv1c.pk031.p16.f | SS | SS | SS | SS | SS |
| idv1c.pk032.a16.f | SS | SS | SS | SS | SS |
| idv1c.pk032.b4.f | S | S | S | S | S |
| idv1c.pk032.e16.f | S | S | S | S | S |
| idv1c.pk032.f11.f | SS | SS | SS | SS | SS |
| idv1c.pk032.f14.f | S | S | S | S | S |
| idv1c.pk032.i21.f | SS | SS | SS | SS | SS |
| idv1c.pk032.m9.f | S | S | S | S | S |
| idv1c.pk032.n18.f | SS | SS | SS | SS | SS |
| idv1c.pk032.p5.f | SS | SS | SS | SS | SS |
| idv1c.pk033.a15.f | S | S | S | S | S |
| idv1c.pk033.b14.f | S | S | S | S | S |
| idv1c.pk033.d24.f | SS | SS | SS | SS | SS |
| idv1c.pk033.j21.f | SS | SS | SS | SS | SS |
| idv1c.pk033.m3.f | S | S | S | S | S |
| idv1c.pk033.n10.f | S | S | S | S | S |
| idv1c.pk033.n18.f | S | S | S | S | S |
| idv1c.pk033.o9.f | SS | SS | SS | SS | SS |
| idv1c.pk033.p15.f | SS | SS | SS | SS | SS |
| idv1c.pk033.p16.f | SS | SS | SS | SS | SS |
| idv1c.pk034.e8.f | S | S | S | S | S |
| idv1c.pk034.i2.f | SS | SS | SS | SS | SS |
| idv1c.pk034.j6.f | SS | SS | SS | SS | SS |
| idv1c.pk034.p24.f | S | S | S | S | S |
| idv1c.pk035.f21.f | S | S | S | S | S |
| idv1c.pk035.g1.f | S | S | S | S | S |
| idv1c.pk035.h19.f | S | S | S | S | S |

TABLE 3-continued

Insecticidal Bioassay Data Against Southern Corn Root Worm

| Clone name | | | | | |
|---|---|---|---|---|---|
| idv1c.pk035.i17.f | SS | SS | SS | SS | SS |
| idv1c.pk035.j4.f | S | S | S | S | S |
| idv1c.pk035.k18.f | SS | SS | SS | SS | SS |
| idv1c.pk035.m1.f | S | S | S | S | S |
| idv1c.pk035.o13.f | S | S | S | S | S |
| idv1c.pk036.a14.f | S | S | S | S | S |
| idv1c.pk036.e18.f | S | S | S | S | S |
| idv1c.pk036.f4.f | S | S | S | S | S |
| idv1c.pk036.f9.f | S | S | S | S | S |
| idv1c.pk036.i17.f | S | S | S | S | S |
| idv1c.pk036.i19.f | SS | SS | SS | SS | SS |
| idv1c.pk036.i20.f | S | S | S | S | S |
| idv1c.pk036.k23.f | S | S | S | S | S |

*columns in Table 3 represent replicate wells 1, 2, 3, and 4 and the average.

TABLE 4

Insect Bioassays Against Southern and Western Corn Root Worm.

| Clone name | Seq id | SCRW | | | | WCRW | | | | SCRW 2 | | | |
|---|---|---|---|---|---|---|---|---|---|---|---|---|---|
| | | Crude | 0.5 | 0.25 | 0.125 | Crude | 0.5 | 0.25 | 0.125 | Crude | 0.5 | 0.25 | 0.125 |
| idv1c.pk034.k22.f | DNA directed polymerase | SS | S | S | S | D | D | S | S | SS | S | S | S |
| idv1c.pk002.c7.f | regulatory; prolactin; binding element | SS | S | N | N | S | S | N | N | SS | N | N | N |
| idv1c.pk002.f18.f | cadherin like | S | N | N | N | S | N | N | N | S | N | N | N |
| idv1c.pk002.i23.f | mitochondrial NADH dehydrogenase Fe—S protein | S | N | N | N | S | S | S | S | S | S | N | N |
| idv1c.pk002.j24.f | Human DNA sequence from clone RP5-858M22 | S | S | N | N | N | N | N | N | S | S | N | N |
| idv1c.pk002.m16.f | conserved hypothetical protein | SS | N | N | N | SS | N | N | N | SS | S | N | N |
| idv1c.pk002.n13.f | 16s ribosomal RNA gene | S | N | N | N | SS | SS | N | N | S | S | N | N |
| idv1c.pk024.c7.f | conserved hypothetical protein | SS | N | N | N | SS | SS | N | N | SS | S | N | N |
| idv1c.pk024.j15.f | | SS | N | N | N | N | N | N | N | SS | N | N | N |
| idv1c.pk025.b17.f | cadherin like | SS | S | N | N | SS | SS | S | N | SS | S | N | N |
| idv1c.pk025.f3.f | alpha tubulin | SS | SS | S | S | SS | SS | N | N | SS | SS | S | S |
| idv1c.pk025.i8.f | chromaffin granule amine transporter | SS | S | S | S | SS | SS | SS | S | SS | S | N | S |
| idv1c.pk025.l17.f | Cytochrome b561 domain-containing protein 2 | S | S | N | N | S | S | N | N | S | S | N | N |
| idv1c.pk025.o24.f | ATP-dependent RNA helicase | N | N | N | N | SS | S | N | N | S | N | N | N |
| idv1c.pk025.p9.f | conserved insect hypothetical protein | S | N | N | N | N | N | N | N | S | N | N | N |
| idv1c.pk026.f20.f | NADH-ubiquinone oxidoreductase 24 kDa subunit | S | S | N | N | SS | N | N | N | S | S | N | N |
| idv1c.pk026.p8.f | Sec61 gamma subunit alpha | SS | N | N | N | SS | SS | S | S | SS | S | S | N |
| idv1c.pk026.p22.f | no hits | S | N | N | N | SS | S | N | N | S | N | N | N |
| idv1c.pk027.a14.f | conserved insect sequence | S | N | N | N | N | N | N | N | S | N | N | N |
| idv1c.pk027.g7.f | conserved hypothetical protein | SS | SS | S | S | S | S | S | S | SS | SS | S | S |
| idv1c.pk027.k23.f | low homology to zebrafish sequence | SS | N | N | N | SS | S | S | S | SS | N | N | N |
| idv1c.pk028.b17.f | highly similar to conserved drosophila sequence | SS | S | N | N | SS | SS | SS | SS | SS | S | N | N |
| idv1c.pk028.f11.f | | S | S | N | N | S | N | N | N | S | S | N | N |
| idv1c.pk029.c3.f | dynein heavy chain of insects | SS | N | N | N | S | S | S | S | SS | N | N | N |
| idv1c.pk029.f5.f | COP9 complex homolog subunit 6 | SS | S | N | N | SS | SS | SS | SS | SS | S | N | N |
| idv1c.pk029.j4.f | acyl-coa dehydrogenase | S | S | S | S | SS | SS | S | S | S | S | S | S |
| idv1c.pk030.b23.f | Lancl1 protein [Tribolium castaneum] | SS | S | N | N | SS | SS | SS | S | SS | S | S | N |
| idv1c.pk030.f9.f | no hits | S | N | N | N | S | N | N | N | S | S | S | N |
| idv1c.pk030.g11.f | aspartate aminotransferase | SS | SS | S | S | SS | N | N | N | SS | SS | S | S |

TABLE 4-continued

Insect Bioassays Against Southern and Western Corn Root Worm.

| Clone name | Seq id | SCRW | | | | WCRW | | | | SCRW 2 | | | |
| --- | --- | --- | --- | --- | --- | --- | --- | --- | --- | --- | --- | --- | --- |
| | | Crude | 0.5 | 0.25 | 0.125 | Crude | 0.5 | 0.25 | 0.125 | Crude | 0.5 | 0.25 | 0.125 |
| idv1c.pk031.c20.f | low-density lipoprotein receptor, | SS | S | N | N | SS | SS | N | N | SS | S | N | N |
| idv1c.pk031.d1.f | chaperonin | SS | S | S | N | SS | SS | SS | S | SS | S | S | N |
| idv1c.pk031.j1.f | 1,4-dihydroxy-2-naphthoate octaprenyltransferase | S | N | N | N | N | N | N | N | S | N | N | N |
| idv1c.pk031.j6.f | no hits | S | N | N | N | SS | SS | SS | N | S | N | N | N |
| idv1c.pk031.p16.f | ribosomal protein S12 | S | S | S | S | SS | SS | SS | SS | S | S | S | S |
| idv1c.pk032.a16.f | DEAD box ATP-dependent RNA helicase | S | S | S | S | SS | SS | N | N | S | S | S | S |
| idv1c.pk032.f11.f | ribosomal protein L4e | SS | SS | SS | S | SS | SS | SS | N | SS | SS | SS | S |
| idv1c.pk032.i21.f | conserved hypothetical protein | SS | S | S | S | SS | SS | S | N | SS | S | S | S |
| idv1c.pk032.n18.f | similar to pol-like protein | S | S | S | S | SS | SS | S | S | SS | S | S | S |
| idv1c.pk032.p5.f | no hits | S | S | S | S | SS | SS | S | N | S | S | S | S |
| idv1c.pk033.d24.f | sodium pump alpha subunit; | SS | S | N | N | N | N | N | N | SS | SS | S | N |
| idv1c.pk033.j21.f | proteasome subunit alpha type 6 | SS | S | S | N | SS | SS | SS | S | SS | S | S | N |
| idv1c.pk033.o9.f | similar to Uncharacterized protein ZK1236.4 [*Acyrthosiphon pisum*] | S | S | S | N | S | S | N | N | S | S | S | N |
| idv1c.pk033.p15.f | ribosomal protein L35Ae | SS | SS | S | N | S | S | N | N | SS | SS | SS | N |
| idv1c.pk033.p16.f | similar to ribosomal protein L10Ae | S | S | S | S | S | S | S | S | S | S | S | S |
| idv1c.pk034.i2.f | cadherin-like gene | S | N | N | N | SS | SS | SS | N | SS | S | N | N |
| idv1c.pk034.j6.f | conserved hypothetical protein | SS | S | N | N | S | S | S | N | SS | S | S | N |
| idv1c.pk035.i17.f | ryanodine receptor-like protein [*Tribolium castaneum*] | N | N | N | N | SS | SS | N | N | S | N | N | N |
| idv1c.pk035.k18.f | conserved hypothetical protein | S | N | N | N | SS | S | N | N | S | N | N | N |
| idv1c.pk036.i19.f | predicted protein | SS | S | N | N | SS | S | S | N | SS | SS | SS | S |

TABLE 5

Insect Bioassays Against Southern and Western Corn Root Worm.

| Clone name | 1° assay result | 1st Confirmation | 2nd Confirmation | SCRW dose response #1 | | | | SCRW does response #2 | | | |
| --- | --- | --- | --- | --- | --- | --- | --- | --- | --- | --- | --- |
| | | | | Crude | 0.5 | 0.25 | 0.125 | Crude | 0.5 | 0.25 | 0.125 |
| idv1c.pk001.o20.f | S | SS | SS | S | N | N | N | S | N | N | N |
| idv1c.pk002.a20.f | S | SS | SS | S | N | N | N | N | N | N | N |
| idv1c.pk002.c15.f | S | S | N | SS | S | N | N | SS | SS | S | N |
| idv1c.pk002.i21.f | S | SS | SS | SS | S | N | N | SS | S | S | S |
| idv1c.pk024.b23.f | S | SS | SS | SS | N | N | N | S | S | N | N |
| idv1c.pk024.e1.f | S | S | S | S | S | N | N | S | S | N | N |
| idv1c.pk024.e24.f | S | S | S | S | S | N | N | S | N | N | N |
| idv1c.pk024.k17.f | S | S | S | SS | N | N | N | SS | SS | N | N |
| idv1c.pk024.m13.f | S | S | S | S | N | N | N | S | S | N | N |
| idv1c.pk024.n1.f | S | S | S | S | S | S | S | S | S | N | N |
| idv1c.pk024.o3.f | S | SS | SS | S | S | S | S | N | N | N | N |
| idv1c.pk025.a4.f | S | SS | S | S | S | N | N | S | N | N | N |
| idv1c.pk025.c5.f | S | N | N | N | N | N | N | S | N | N | N |
| idv1c.pk025.c23.f | S | N | N | S | N | N | N | S | N | N | N |
| idv1c.pk025.d18.f | S | S | N | SS | SS | N | N | SS | SS | S | N |
| idv1c.pk025.d20.f | S | S | S | S | S | S | S | S | S | N | N |
| idv1c.pk025.f24.f | S | SS | SS | S | S | S | S | S | S | S | N |
| idv1c.pk025.j20.f | S | SS | SS | S | N | N | N | S | S | N | N |
| idv1c.pk025.l10.f | S | S | S | S | N | N | N | S | N | N | N |
| idv1c.pk026.a16.f | S | SS | SS | S | N | N | N | S | N | N | N |
| idv1c.pk026.b23.f | S | S | S | S | N | N | N | S | N | N | N |
| idv1c.pk026.b22.f | S | S | S | N | N | N | N | N | N | N | N |
| idv1c.pk026.e6.f | S | S | S | S | N | N | N | S | S | N | N |
| idv1c.pk026.g12.f | S | S | S | SS | S | N | N | SS | SS | N | N |

TABLE 5-continued

Insect Bioassays Against Southern and Western Corn Root Worm.

| Clone name | 1° assay result | 1st Confirmation | 2nd Confirmation | SCRW dose response #1 | | | | SCRW does response #2 | | | |
|---|---|---|---|---|---|---|---|---|---|---|---|
| | | | | Crude | 0.5 | 0.25 | 0.125 | Crude | 0.5 | 0.25 | 0.125 |
| idv1c.pk026.h15.f | S | N | N | S | N | N | N | N | N | N | N |
| idv1c.pk026.i12.f | S | N | N | N | N | N | N | N | N | N | N |
| idv1c.pk026.j18.f | S | S | N | S | S | N | N | SS | N | N | N |
| idv1c.pk026.k13.f | S | SS | SS | S | S | S | S | S | S | S | N |
| idv1c.pk027.b21.f | S | N | N | S | N | N | N | N | N | N | N |
| idv1c.pk027.c7.f | S | N | N | N | N | N | N | N | N | N | N |
| idv1c.pk027.k4.f | S | SS | SS | SS | N | N | N | SS | S | N | N |
| idv1c.pk027.p21.f | S | SS | SS | SS | S | N | N | SS | S | N | N |
| idv1c.pk028.b7.f | S | SS | SS | S | N | N | N | N | N | N | N |
| idv1c.pk028.c22.f | S | SS | SS | SS | N | N | N | SS | S | N | N |
| idv1c.pk028.h6.f | S | SS | SS | SS | N | N | N | SS | N | N | N |
| idv1c.pk028.i16.f | S | N | N | S | N | N | N | S | N | N | N |
| idv1c.pk028.m11.f | S | N | N | S | N | N | N | S | N | N | N |
| idv1c.pk028.o18.f | S | S | SS | S | S | S | S | S | S | S | N |
| idv1c.pk029.a17.f | S | S | S | S | S | S | S | S | N | N | N |
| idv1c.pk029.d16.f | S | S | S | S | S | S | S | S | S | S | S |
| idv1c.pk029.i22.f | S | S | S | SS | SS | S | S | SS | SS | S | N |
| idv1c.pk029.j20.f | S | S | S | SS | SS | S | S | SS | S | S | S |
| idv1c.pk029.k11.f | S | N | N | SS | S | N | N | SS | S | S | S |
| idv1c.pk029.l22.f | S | S | SS | S | S | N | N | S | N | N | N |
| idv1c.pk030.e10.f | S | S | S | SS | S | S | S | SS | S | S | S |
| idv1c.pk030.e21.f | S | S | S | SS | S | S | S | SS | SS | S | S |
| idv1c.pk030.h13.f | S | S | S | S | S | S | S | SS | S | S | S |
| idv1c.pk030.h23.f | S | SS | S | SS | SS | S | S | SS | S | S | N |
| idv1c.pk030.l9.f | S | N | N | S | N | N | N | S | S | N | N |
| idv1c.pk030.m22.f | S | N | N | S | N | N | N | S | N | N | N |
| idv1c.pk030.o7.f | S | S | SS | SS | S | N | N | SS | S | N | N |
| idv1c.pk031.a11.f | S | S | S | SS | S | S | S | SS | S | S | S |
| idv1c.pk031.e16.f | S | S | S | S | N | N | N | N | N | N | N |
| idv1c.pk031.g2.f | S | SS | SS | SS | S | S | N | SS | S | S | N |
| idv1c.pk031.g22.f | S | S | S | S | N | N | N | SS | S | N | N |
| idv1c.pk031.i13.f | S | SS | SS | SS | S | S | N | SS | N | N | N |
| idv1c.pk031.m3.f | S | S | S | SS | S | S | N | SS | S | S | N |
| idv1c.pk032.b4.f | S | S | S | SS | S | N | N | SS | S | N | N |
| idv1c.pk032.e16.f | S | S | S | S | S | S | S | S | S | N | N |
| idv1c.pk032.f14.f | S | N | N | S | N | N | N | S | N | N | N |
| idv1c.pk032.m9.f | S | SS | SS | SS | N | N | N | SS | S | N | N |
| idv1c.pk033.a15.f | S | N | N | N | N | N | N | S | N | N | N |
| idv1c.pk033.b14.f | S | N | N | S | N | N | N | S | N | N | N |
| idv1c.pk033.m3.f | S | S | S | SS | N | N | N | SS | N | N | N |
| idv1c.pk033.n10.f | S | SS | SS | S | S | S | S | S | S | N | N |
| idv1c.pk033.n18.f | S | SS | SS | S | N | N | N | S | N | N | N |
| idv1c.pk034.e8.f | S | S | S | S | N | N | N | S | N | N | N |
| idv1c.pk034.p24.f | S | S | N | S | S | N | N | S | N | N | N |
| idv1c.pk035.f21.f | S | S | S | S | S | S | S | S | S | S | N |
| idv1c.pk035.g1.f | S | S | N | S | N | N | N | S | N | N | N |
| idv1c.pk035.h19.f | S | SS | SS | S | N | N | N | N | N | N | N |
| idv1c.pk035.j4.f | S | SS | SS | SS | S | S | S | SS | SS | S | S |
| idv1c.pk035.m1.f | S | S | S | S | S | S | S | S | S | S | N |
| idv1c.pk035.o13.f | S | S | S | S | N | N | N | S | N | N | N |
| idv1c.pk036.a14.f | S | S | N | SS | S | S | N | SS | S | S | N |
| idv1c.pk036.e18.f | S | S | S | S | S | N | N | S | S | S | N |
| idv1c.pk036.f4.f | S | S | S | S | S | N | N | S | S | N | N |
| idv1c.pk036.f9.f | S | S | S | SS | S | S | N | SS | S | S | N |
| idv1c.pk036.i17.f | S | S | S | S | S | S | N | S | S | S | N |
| idv1c.pk036.i20.f | S | S | S | SS | SS | N | N | SS | SS | S | N |
| idv1c.pk036.k23.f | S | S | S | S | S | N | N | S | S | S | N |

Example 8. Expression of Silencing Elements in Maize

The silencing elements set forth in SEQ ID NO: 13, 40, 72 and 73 were expressed in a maize plant as hairpins and the plants were tested for insecticidal activity against corn root worms. The sequences set forth in SEQ ID NO: 13, 40, 72 and 73 were engineered to be expressed as a hairpin. The constructs comprised the following components: the maize ubiquitin promoter/5'UTR/1$^{st}$ intron operably linked to one of SEQ ID NO: 13, 40, 72 and 73::the ADH1 intron::complement of the corresponding SEQ ID NO. Plasmids PHP41136, PHP41567, PHP41992, PHP42000 were generated as summarized below in Table 6. PHP19288 was a control plasmid which lacked a silencing element.

TABLE 6

| SEQ ID NO of silencing element | SEQ ID NO of construct w/ promoter and silencing element | Clone name of silencing element | Plasmid name |
|---|---|---|---|
| 13 | 242 | idv1c.pk002.j17.f | PHP41136 |
| 40 | 243 | idv1c.pk013.h1.f | PHP41567 |

TABLE 6-continued

| SEQ ID NO of silencing element | SEQ ID NO of construct w/ promoter and silencing element | Clone name of silencing element | Plasmid name |
|---|---|---|---|
| 72 | 244 | idv1c.pk017.d14.f | PHP41992 |
| 73 | 245 | idv1c.pk017.e22.f | PHP42000 |

Maize plants were transformed with plasmids PHP41136, PHP41567, PHP41992, PHP42000, and PHP19288 (control lacking silencing element) and plants expressing the silencing elements denoted in Table 6 were transplanted from 272V plates into greenhouse flats containing Fafard Superfine potting mix. Plants were infected (100 eggs per plant) 14 days post green house send date and a second infestation (150 eggs per plant) was performed 14 days later. The scoring for insecticidal activity was done 14 days later (28 days post first infection). Each of SEQ ID NO: 13, 40, 72 and 73 had insecticidal activity in this assay.

As shown in FIG. 2, significant efficacy was shown with the PHP41136, PHP41567, PHP41992, and PHP42000 constructs. No significant difference between PHP41136 and the PHP positive control was seen. Table 7 provides a summary of the data shown in FIG. 2.

TABLE 7

OneWay Anova

Summary of Fit

| | |
|---|---|
| Rsquare | 0.440885 |
| Adj Rsquare | 0.412145 |
| Root Mean Square Error | 0.654125 |
| Mean of Response | 1.270885 |
| Observations (or Sum Wgts) | 226 |

TABLE 7-continued

Analysis of Variance

| Source | DF | Sum of Squares | Mean Square | F Ratio | Prob > F |
|---|---|---|---|---|---|
| Construct | 11 | 72.20360 | 6.56396 | 15.3407 | <.0001* |
| Error | 214 | 91.56622 | 0.42788 | | |
| C. Total | 225 | 163.76982 | | | |

Means for Oneway Anova

| Level | Number | Mean | Std Error | Lower 95% | Upper 95% |
|---|---|---|---|---|---|
| PHP Control | 20 | 1.96000 | 0.14627 | 1.672 | 2.2483 |
| PHP19288 | 22 | 1.59545 | 0.13946 | 1.321 | 1.8703 |
| PHP41136 | 16 | 0.52813 | 0.16353 | 0.206 | 0.8505 |
| PHP41567 | 17 | 0.82941 | 0.15865 | 0.517 | 1.1421 |
| PHP41992 | 23 | 0.91304 | 0.13639 | 0.644 | 1.1819 |
| PHP42000 | 21 | 0.78810 | 0.14274 | 0.507 | 1.0695 |

Std Error uses a pooled estimate of error variance

Example 9 Insect Bioassays 2.5 ul of an in-vitro transcription reaction which synthesized one of the sequences set forth in SEQ ID NO: 13, 40, 72 and 73 was added to a given well of a 96 well microtiter plate. 25 ul of molten lowmelt western corn rootworm diet were added to the sample and shaken on an orbital shaker to mix the sample and diet. Once the diet solidified, neonate rootworms were added to the well. An average of 5 neonates was added to each well. After the plate was infested, the plate was sealed with mylar and a single hole was punched in the mylar over each well to allow air exchange. 4 replicate wells were produced for each sample. The assay was scored for activity 7 days post infestation. Dose response assays were performed with the following rates: 50, 25, 12.5, 6.5, 3.2, and 1.5 ppm. Table 8 provides insecticidal bioassay data employing the southern corn rootworm. The possible scores are dead (D), severely stunted (SS; little or no growth but alive), stunted (S; growth to second instar but not equivalent to controls), contaminated (c), or no activity.

TABLE 8

Comparison of T0 activity and dsRNA assay results

| | Gene id | | | | | | | | | | | | | |
|---|---|---|---|---|---|---|---|---|---|---|---|---|---|---|
| | SCRW | | | | | | WCRW equivalent to 5 ng/cm2 | | | | | | | |
| | 50 ppm | 25 ppm | 12.5 ppm | 6.5 ppm | 3.2 ppm | 1.5 ppm | 50 ppm | 25 ppm | 12.5 ppm | 6.5 ppm | 3.2 ppm | 1.5 ppm | PHP# | T0Gene testing results |
| Proteosome subunit alpha type 3 | SS | SS | SS | | | | SS | SS | SS | SS | SS | SS | 41136 | good |
| Low homology to sea urchin reverse transcriptase | N | N | N | N | N | N | SS | SS | SS | SS | SS | SS | 41129 | poor |
| Mosquito conserved hypo. Prot. | SS | SS | SS | SS | SS | SS | SS | SS | SS | SS | SS | SS | 41124 | poor |
| Syntaxin | ss | ss | ss | N | N | N | N | N | N | N | N | N | 41558 | poor |
| Ribosomal protein L27E | SS | SS | SS | SS | SS | SS | S | S | N | N | N | N | 41567 | good |
| No hits | SS | SS | S | N | N | N | S | N | N | N | N | N | 41549 | poor |
| Proteosome beta subunit | SS | SS | SS | SS | SS | SS | S | S | S | S | N | N | 41999 | poor |
| Cadherin like | S | S | S | S | S | S | SS | SS | SS | SS | S | S | 41992 | good |
| Ribosome biogenesis regulatory homolog | S | S | N | N | N | N | SS | SS | SS | SS | S | S | 42000 | good |

Example 10. Expression of Silencing Elements in Maize

The silencing elements set forth in the various SEQ ID NOs denoted in Table 9 were expressed in a maize plant (via the FASTcorn highthoughput screening methods) as hairpins and the various plants were tested for insecticidal activity against corn root worms. The sequences set forth in the SEQ ID NOs denoted in Table 9 were engineered to be expressed as a hairpin. The constructs comprised the following components: the maize ubiquitin promoter/5′UTR/1$^{st}$ intron operably linked SEQ ID NO set forth in Table 9:: ADH1 intron:: complement of the SEQ ID NO: set forth in Table 9. The various plasmids having these silencing expression constructs were generated as summarized below in Table 9.

TABLE 9

| Row Labels | SEQ ID NO making up one stem of the hairpin | Clone name of silencing element | SEQ ID NO of full length expression vector | Pass | Weak pass | # tested | % rtPCR (+) | % actives of rtPCR+ | Diet assay activity |
|---|---|---|---|---|---|---|---|---|---|
| PHP44742 | nt 1-380 of SEQ ID NO: 45 | idv1c.pk014.b17.f | 248 | 100.0% | 0.0% | 19 | 90 | 100 | s |
| PHP44107 | 8 | idv1c.pk001.e9.f | 237 | 94.7% | 0.0% | 19 | 95 | 100 | ss |
| PHP44118 | 15 | idv1c.pk003.d6.f | 246 | 55.0% | 10.0% | 20 | 70 | 100 | s |
| PHP44747 | nt 1-266 of SEQ ID NO: 50 | idv1c.pk014.k23.f | 251 | 40.0% | 13.3% | 15 | 67 | 50 | ss |
| PHP44116 | 18 | idv1c.pk003.j4.f | 247 | 31.6% | 10.5% | 19 | 25 | 100 | ss |
| PHP44109 | 29 | idv1c.pk004.f20.f | 250 | 30.0% | 10.0% | 20 | 58 | 63 | SS |
| PHP44750 | nt 1-675 of SEQ ID NO: 37 | idv1c.pk013.b11.f | 249 | 30.0% | 0.0% | 10 | 50 | 33 | s |
| PHP44119 | 9 | idv1c.pk001.m5.f | | 26.3% | 0.0% | 19 | No data | No data | ss |
| PHP44117 | 14 | idv1c.pk002.n13.f | | 26.3% | 5.3% | 19 | 0 | 0 | s |
| PHP44744 | nt 1-132 of SEQ ID NO: 40 | idv1c.pk013.h1.f | 243 | 21.1% | 5.3% | 19 | 68 | 38 | s |
| PHP44748 | nt 16-585 of SEQ ID NO: 47 | idv1c.pk014.d11.f | 252 | 17.6% | 5.9% | 17 | 83 | 25 | s |
| PHP44211 | 54 | idv1c.pk014.n23.f | | 15.0% | 0.0% | 20 | No data | No data | s |
| PHP44208 | 32 | idv1c.pk004.n6.f | | 12.5% | 25.0% | 8 | No data | No data | s |
| PHP45641 | 92 | idv1c.pk019.l7.f | | 12.5% | 0.0% | 8 | 50 | 12 | s |
| PHP44115 | 12 | idv1c.pk002.f20.f | | 10.0% | 10.0% | 20 | No data | No data | ss |
| PHP44122 | 27 | idv1c.pk004.b12.f | | 10.0% | 0.0% | 20 | No data | No data | ss |
| PHP44120 | 25 | idv1c.pk003.o22.f | | 10.0% | 15.0% | 20 | No data | No data | s |
| PHP44121 | 21 | idv1c.pk003.l1.f | | 10.0% | 5.0% | 20 | No data | No data | s |
| PHP44746 | 46 | idv1c.pk014.c14.f | | 9.1% | 18.2% | 11 | 40 | 25 | s |
| PHP44976 | 66 | idv1c.pk016.h19.f | | 7.7% | 0.0% | 13 | 92 | 8 | ss |
| PHP44213 | 23 | idv1c.pk003.m10.f | | 5.6% | 0.0% | 18 | No data | No data | s |
| PHP44113 | 26 | idv1c.pk003.p13.f | | 5.3% | 5.3% | 19 | No data | No data | ss |
| PHP44114 | 24 | idv1c.pk003.o13.f | | 5.3% | 5.3% | 19 | No data | No data | s |
| PHP44745 | 33 | idv1c.pk004.o4.f | | 5.3% | 0.0% | 19 | 76 | 0 | s |
| PHP44210 | 11 | idv1c.pk002.c5.f | | 5.0% | 0.0% | 20 | No data | No data | ss |
| PHP44106 | 10 | idv1c.pk001.n1.f | | 5.0% | 15.0% | 20 | No data | No data | s |
| PHP44112 | 28 | idv1c.pk004.d17.f | | 0.0% | 0.0% | 17 | No data | No data | ss |
| PHP44216 | 20 | idv1c.pk003.j20.f | | 0.0% | 0.0% | 12 | No data | No data | ss |
| PHP44220 | 13 | idv1c.pk002.j17.f | | 0.0% | 0.0% | 20 | No data | No data | ss |
| PHP44209 | 56 | idv1c.pk015.a16.f | | 0.0% | 0.0% | 14 | No data | No data | s* |
| PHP44212 | 38 | idv1c.pk013.c21.f | | 0.0% | 0.0% | 20 | No data | No data | s* |
| PHP44215 | 39 | idv1c.pk013.d22.f | | 0.0% | 0.0% | 18 | No data | No data | s* |
| PHP44217 | 53 | idv1c.pk014.n16.f | | 0.0% | 0.0% | 13 | No data | No data | s* |
| PHP44221 | 48 | idv1c.pk014.f3.f | | 0.0% | 0.0% | 10 | No data | No data | s* |
| PHP44743 | 48 | idv1c.pk013.k1.f | | 0.0% | 0.0% | 20 | 37 | 0 | s* |
| PHP44756 | 49 | idv1c.pk014.j2.f | | 0.0% | 0.0% | 20 | 0 | 0 | s* |
| PHP44757 | 61 | idv1c.pk015.p2.f | | 0.0% | 0.0% | 20 | 80 | 0 | s* |
| PHP44975 | 65 | idv1c.pk016.h15.f | | 0.0% | 0.0% | 5 | 31 | 0 | s* |
| PHP44977 | 68 | idv1c.pk016.j15.f | | 0.0% | 0.0% | 6 | 30 | 0 | s* |
| PHP44982 | 75 | idv1c.pk017.h14.f | | 0.0% | 0.0% | 11 | 55 | 0 | s* |
| PHP44989 | 84 | idv1c.pk018.f19.f | | 0.0% | 0.0% | 9 | 45 | 0 | s* |
| PHP44991 | 87 | idv1c.pk018.h21.f | | 0.0% | 0.0% | 12 | 60 | 0 | s* |
| PHP44992 | 91 | idv1c.pk019.k3.f | | 0.0% | 0.0% | 5 | 25 | 0 | s* |
| PHP45629 | 99 | idv1c.pk020.l3.f | | 0.0% | 0.0% | 13 | 80 | 0 | s* |
| PHP45635 | 104 | idv1c.pk021.h12.f | | 0.0% | 0.0% | 6 | 30 | 0 | s* |
| PHP45636 | 98 | idv1c.pk020.k19.f | | 0.0% | 0.0% | 14 | 70 | 0 | s* |
| PHP45638 | 97 | idv1c.pk020.i24.f | | 0.0% | 0.0% | 7 | 35 | 0 | s* |
| PHP45640 | 95 | idv1c.pk020.g17.f | | 0.0% | 0.0% | 15 | 75 | 0 | s* |
| PHP44111 | 17 | idv1c.pk003.f9.f | | 0.0% | 0.0% | 19 | No data | No data | s |
| PHP44204 | 16 | idv1c.pk003.f8.f | | 0.0% | 0.0% | 20 | No data | No data | s |
| PHP44205 | 34 | idv1c.pk004.o9.f | | 0.0% | 0.0% | 13 | No data | No data | s |
| PHP44206 | 43 | idv1c.pk014.a19.f | | 0.0% | 0.0% | 17 | No data | No data | s |
| PHP44207 | 22 | idv1c.pk003.m1.f | | 0.0% | 0.0% | 20 | No data | No data | s |
| PHP44214 | 41 | idv1c.pk013.h14.f | | 0.0% | 0.0% | 18 | No data | No data | s |
| PHP44218 | 19 | idv1c.pk003.j6.f | | 0.0% | 0.0% | 20 | No data | No data | s |
| PHP44219 | 52 | idv1c.pk014.m13.f | | 0.0% | 0.0% | 20 | No data | No data | ss |
| PHP44222 | 31 | idv1c.pk004.l15.f | | 0.0% | 5.6% | 18 | No data | No data | s |
| PHP44223 | 36 | idv1c.pk013.a15.f | | 0.0% | 5.3% | 19 | No data | No data | s |
| PHP44739 | 44 | idv1c.pk014.b9.f | | 0.0% | 0.0% | 4 | 0 | No data | s |
| PHP44741 | 51 | idv1c.pk014.m5.f | | 0.0% | 0.0% | 3 | 0 | 0 | s |

TABLE 9-continued

| Row Labels | SEQ ID NO making up one stem of the hairpin | Clone name of silencing element | SEQ ID NO of full length expression vector | Pass | Weak pass | # tested | % rtPCR (+) | % actives of rtPCR+ | Diet assay activity |
|---|---|---|---|---|---|---|---|---|---|
| PHP44749 | 57 | idv1c.pk015.b8.f | | 0.0% | 0.0% | 3 | 0 | 0 | s |
| PHP44752 | 60 | idv1c.pk015.n19.f | | 0.0% | 0.0% | 10 | 70 | 0 | s |
| PHP44753 | 71 | idv1c.pk017.c3.f | | 0.0% | 0.0% | 19 | 85 | 0 | s |
| PHP44973 | 59 | idv1c.pk015.l13.f | | no data | no data | 0 | 24 | No data | s* |
| PHP44978 | 69 | idv1c.pk016.k9.f | | no data | no data | 0 | 10 | No data | s* |
| PHP45630 | 102 | idv1c.pk021.d22.f | | no data | no data | 0 | 5 | No data | s* |
| PHP45631 | 105 | idv1c.pk021.m20.f | | no data | no data | 0 | 30 | No data | s* |
| PHP45637 | 96 | idv1c.pk020.i7.f | | no data | no data | 0 | 15 | No data | s* |
| PHP45639 | 94 | idv1c.pk020.b11.f | | no data | no data | 0 | 15 | No data | s* |

Maize plants were transformed with PHP plasmids and plants expressing the silencing elements denoted in Table 9 were transplanted from 272V plates into greenhouse flats containing Fafard Superfine potting mix. Approximately 10 to 14 days after transplant, plants (now at growth stage V2-V3) were transplanted into treepots containing Fafard Superfine potting mix. At 14 days post greenhouse send date, plants were infested with 100 eggs of western corn root worms (WCRW)/plant. For later sets, a second infestation of 100 eggs WCRW/plant was done 14 days after the first infestation and scoring was at 14 days after the second infestation. 21 days post infestation, plants were scored using CRWNIS. Those plants with a score of ≤0.5 are transplanted into large pots containing SB300 for seed. "Pass" as denoted in Table 9 is a Nodal injury score of 0.2 to 0. "Weak pass" as denoted in Table 9 is a score from >0.2 to 0.75 which was the cut off for advancing an event. "% rtPCR" as denoted in Table 9 is the percent of the 20 events with demonstrated expression of the hairpin as determined by rtPCR. "% actives of rtPCR" as denoted in Table 9 is the percent of rtPCR positives that also passed the CRWNIS test. So this last number could be 100% even if only 10 of 20 events were rtPCR positive if all 10 also passed the CRWNIS test. The "diet assay activity" summarizes the data previously presented herein denoting either stunted (s) or severely stunted (ss) activity when the hairpins mixed with the CRW diet and fed directly to the bugs.

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated polynucleotide comprising a heterologous promoter operably linked to a nucleotide sequence encoding a double stranded RNA, wherein the double stranded RNA targets a Coleopteran plant pest target nucleotide sequence, wherein the Coleopteran plant pest target nucleotide sequence comprises:
   a) the nucleotide sequence set forth in SEQ ID NO: 8, or the full length complement thereof; or
   b) the nucleotide sequence comprising at least 95% sequence identity to SEQ ID NO: 8, or the full length complement thereof;
   wherein said double stranded RNA has insecticidal activity against a Coleopteran plant pest.

2. The isolated polynucleotide of claim 1, wherein said Coleopteran plant pest is a *Diabrotica* plant pest.

3. An expression cassette comprising the polynucleotide of claim 1.

4. The expression cassette of claim 3 comprising the construct of SEQ ID NO: 237.

5. The expression cassette of claim 3, wherein said double stranded RNA comprises a hairpin RNA.

6. The expression cassette of claim 3, wherein said polynucleotide is flanked by a first operably linked convergent promoter at one terminus of the polynucleotide and a second operably linked convergent promoter at the opposing terminus of the polynucleotide, wherein the first and the second convergent promoters are capable of driving expression of the double stranded RNA.

7. A host cell comprising a heterologous expression cassette of claim 3.

8. A plant cell having stably incorporated into its genome a heterologous polynucleotide comprising a nucleotide sequence encoding a double stranded RNA, wherein the double stranded RNA targets a Coleopteran plant pest target nucleotide sequence, wherein the Coleopteran plant pest target nucleotide sequence comprises:
   a) the nucleotide sequence set forth in SEQ ID NO: 8, or the full length complement thereof; or,
   b) the nucleotide sequence comprising at least 95% sequence identity to SEQ ID NO: 8, or the full length complement thereof;
   wherein said double stranded RNA has insecticidal activity against a Coleoptera plant pest.

9. The plant cell of claim 8, wherein the Coleopteran plant pest is a *Diabrotica* plant pest.

10. The plant cell of claim 8, wherein said double stranded RNA comprises a hairpin RNA.

11. The plant cell of claim 8, wherein said polynucleotide is operably linked to a heterologous promoter.

12. The plant cell of claim 8, wherein said plant cell is from a monocot.

13. The plant cell of claim 8, wherein said plant cell is from a dicot.

14. A plant or plant part comprising a plant cell of claim 8.

15. A transgenic seed comprising the heterologous polynucleotide encoding the double stranded RNA of claim 8.

16. A double stranded RNA comprising a nucleotide sequence complementary to:
   a) the nucleotide sequence set forth in SEQ ID NO: 8 or
   b) a nucleotide sequence comprising at least 95% sequence identity to the nucleotide sequence set forth in SEQ ID NO: 8.

17. The double stranded RNA of claim 16, wherein said Coleoptera plant pest is a *Diabrotica* plant pest.

18. The double stranded RNA of claim 16, wherein the double stranded RNA comprises a hairpin RNA.

19. The double stranded RNA of claim 16, further comprising an agriculturally acceptable carrier.

20. The double stranded RNA of claim 16, wherein the double stranded RNA is expressed in a plant, plant part, or plant cell.

21. The double stranded RNA of claim 16, wherein the double stranded RNA is expressed in a microorganism.

* * * * *

```
                      SEQUENCE LISTING

<160> NUMBER OF SEQ ID NOS: 252

<210> SEQ ID NO 1
<211> LENGTH: 1442
<212> TYPE: DNA
<213> ORGANISM: Diabrotica virgifera virgifera
<220> FEATURE:
<221> NAME/KEY: misc_feature
<222> LOCATION: 189, 190, 191, 192, 193, 194, 195, 196, 197, 198, 199,
      200, 201, 202, 203, 204, 205, 206, 207, 208, 209, 210, 211, 212,
      213, 214, 215, 216, 217, 218, 219, 220, 221, 222, 223, 224,
      225, 226, 227, 228
<223> OTHER INFORMATION: n = A,T,C or G

<400> SEQUENCE: 1
gcacgaggcg tcaagcaagg ccagtcagtg aaaaattacc tgccaaccat cctctgctta      60
caggacagcg tgtacttgat gctctttttcc catgtgtaca gggtggtact actgccattc     120
ccggagcttt cggttgtgga aaaactgtaa tttcacaatc tctttccaaa tattccaact     180
ctgatgtcnn nnnnnnnnnn nnnnnnnnnn nnnnnnnnnn nnnnnnnnct gaagtattga     240
gagatttccc tgaattgact gttgaaattg acgggcacac tgaatctatt atgaaacgta     300
ccgcattggt cgccaacaca tctaacatgc ctgtagctgc tcgtgaagct tctatctata     360
ctggtattac tcttttctgaa tacttccgtg atatgggtta caacgtatct atgatggctg     420
actcgacatc acgttgggcc gaagctttga gagaaatttc aggtcgtttg gctgaaatgc     480
```

```
ctgccgattc cggttatccg gcttacttag gtgcccgttt ggcttccttc tacgaacgtg      540
ctggtcgcgt taaatgttta ggtaatccag acagagaagg atccgtttca attgtaggag      600
ccgtatcacc tcctggtggt gatttctcag atcctgttac cactgctact cttggtattg      660
tacaggtgtt ctggggtttg gacaagaaac ttgcccaacg taagcacttc ccttcagtag      720
actggcttgg atcatattcc aaatatttaa gagcattgga cgacttttat gacaaaaact      780
tccaagagtt tattcctctt agaaccaaag ttaaggaaat tcttcaggaa gaagatgatc      840
tagccgaaat tgtgcagctg gtaggtaaag catctctggc agaaacggac aaaatcacct      900
tggaaattgc caggcttctt aaagaagatt tcttgcaaca aaactcatac tcttcttatg      960
acagattctg tccattctat aaaactgtcg gtatgttgag aaacatgatc ggtttgtacg     1020
acatggcgag acacgctgta gaatcaaccg cacaatcaga aaataagatc acttggaacg     1080
taataagaga ttcaatgagt ggaattttat atcaacttag cagtatgaaa tttaaggatc     1140
ccgtaaaaga tggtgaagct aaaatcaagg cagattttga tcaattatat gaagatattc     1200
agcaggcctt cagaaactta gaagattaaa tcttttttaag gaaatttttcc tattttgttc     1260 atcagtgtaa gttaaaaaat atagcgatat ttatcaaaaa gaataataag gcctctatcc     1320
ctcacttctg tgaatattaa tatggccgta ctaaagatag taactaaaga taggttttct     1380
cttttttgat attatcctgt acaaaataaa ttatgtaaat tgttaaaaaa aaaaaaaaa      1440 aa                                                                    1442
```

<210> SEQ ID NO 2
<211> LENGTH: 1098
<212> TYPE: DNA
<213> ORGANISM: Diabrotica virgifera virgifera

<400> SEQUENCE: 2

```
gcccaacgta agcacttccc ttcagtagac tggcttggat catattccaa atatttaaga       60
gcattggacg acttttatga caaaaacttc caagagttta ttcctcttag aaccaaagtt      120
aaggaaattc ttcaggaaga agatgatcta gccgaaattg tgcagctggt aggtaaagca      180
tctctggcag aaacggacaa aatcaccttg gaaattgcca ggcttcttaa agaagatttc      240
ttgcaacaaa actcatactc ttcttatgac agattctgtc cattctataa aactgtcggt      300
atgttgagaa acatgatcgg tttgtacgac atggcgagac acgctgtaga atcaaccgca      360
caatcagaaa ataagatcac ttggaacgta ataagagatt caatgagtgg aattttatat      420
caacttagca gtatgaaatt taaggatccc gtaaagatg gtgaagctaa atcaaggca       480 gattttgatc aattatatga agatattcag caggccttca gaacttaga agattaaatc       540 ttttaagga aattttccta ttttgttcat cagtgtaagt ttaaaaatat agcgatattt      600
atcaaaaaga ataataaggc ctctatccct cacttctgtg aatattaata tggccgtact      660
aatgatagta actaaagata ggttttctct ttttgatat tatcctgtac aaaataaatt       720
atgtaaattg ttgaatatgt gtatagtttt tttgggtgag ggtacagtgc ttattaaata      780 cttttaaac atttttcccg ccattccaat tactattaag ttttttcgtt ttaatacttt      840
tttaaatata caggtgctta atatcgttta tatttcagt attacttggt tttcttcatg       900
taaattgttt taaatttttc ttttacccctt ttaatcttgt atattacatt acccaattaa     960
agttaattgt acagattaag ataaacgagt atccttataac atcttattaga ttgttagaat   1020 caataaatgt agtgtaattg ttctgttttg aacaaataaa tgcatcatta ttgttgttta    1080
```

| | |
|---|---:|
| aaaaaaaaaa aaaaaaaa | 1098 |

<210> SEQ ID NO 3
<211> LENGTH: 1766
<212> TYPE: DNA
<213> ORGANISM: Diabrotica virgifera virgifera

<400> SEQUENCE: 3

| | |
|---|---:|
| tttttatccc gtgagatatt tttgcagtcc ttttaataaa attcttcata attcaccatg | 60 |
| aagggctgcg ttttcaacat cgacaacggt tatttggaag gcctgtgtcg tggctttaaa | 120 |
| tgtgggatcc tgaaacaatc cgattatttg aatttggtcc agtgtgaaac tcttgaagat | 180 |
| ttaaaactgc acttgcaagg cactgactat ggaactttt tggccaatga accttcacct | 240 |
| ttgtcagtat ccgtcatcga ttcaagactt cgagaaaaac tcgtgattga gttccagcac | 300 |
| atgcgtaacc aagcagtaga gcctctctcg acatttatgg acttcattac ctacagttac | 360 |
| atgatcgaca acataatttt gcttattaca ggaactcttc accagagacc aatcagtgaa | 420 |
| ttaatcccta aatgtcaccc tctaggtagc ttcgagcaaa tggaagccat ccacgtagct | 480 |
| gctactccag ctgagttata caacgctgta ttggtggaca caccacttgc tccattcttc | 540 |
| gttgattgca tcagtgaaca agatttggat gaaatgaaca ttgaaattat cagaaacacc | 600 |
| ttatacaaag cttacttgga agcattttat accttctgca aggaaattgg aggtactact | 660 |
| gccgatagca tgtgtgaaat tttggctttt gaggcagata gacgtgctat tattattact | 720 |
| atcaactcgt ttggcactga attaagcaaa gatgaccgtg ctaagttgta ccctcgctgt | 780 |
| ggaagactca accccgatgg tttggctgct ctagtgagag ccgaggacta cgaccaagtt | 840 |
| aaagcagttg ctgaatacta cgctgaatat tccaaactgt ttgaaggagc tggcaacaac | 900 |
| ccgggagaca aaacattgga agacaaattc tttgaatacg aagtacgtct taacatcaat | 960 |
| gctttcatgc aacagtttca ctttggggtg ttctactctt acttgaaatt gaaggaacag | 1020 |
| gaatgcagaa atattgtatg gattgctgaa tgtgtagctc aaaaacacag ggctaaaatc | 1080 |
| gataactaca tcccaatatt ctaaaggaat ttcttgtttg cactattgtt tgcattccat | 1140 |
| ttggctcatt tagttcttag tgtcagtaag tggaattatc aaaagtatca gttttatga | 1200 |
| ttcagatgta ctattcagac cttcagacaa atccagttag tacaatgttt tcgtttcaca | 1260 |
| tttattatca actacatctt tcagtcgtcc aagattgtta tgaaattaaa tatacattaa | 1320 |
| atgtgttgat gttttaacaa tacatagcaa atcctcaaaa agaacaataa aaagactcgc | 1380 |
| agtttatttt gaaggaaaat ccattgagta ttaatgtatc ctaaaatatg taatcataaa | 1440 |
| attacatggt catatcagtt ttatcgcctt tcagaaattt gctgttacct atccttattg | 1500 |
| tttattatat tttttaatga tcggtatgtt tttgatatta ttttagtttt ctggaaataa | 1560 |
| tattgcacaa attcttagtt atctgattca acatgtatca atgctttgtt gagtcatatc | 1620 |
| ataaatatta ttatgttttc tgtgtataaa gcgtagctag gccaaaatgt tatttctgtt | 1680 |
| gtatatgtaa gaataaataa aattatatgt atctgaaaaa aaaaaaaaa aaaaaaaaa | 1740 |
| aaaaaaaaaa aaaaaaaaa aaaaaa | 1766 |

<210> SEQ ID NO 4
<211> LENGTH: 1016
<212> TYPE: DNA
<213> ORGANISM: Diabrotica virgifera virgifera

<400> SEQUENCE: 4

| | |
|---|---:|
| gtgacatttg cttcagaact ttgaaactca caacacccac atatggagac ttaaaccatt | 60 |

```
tggtatccct cacaatgtcc ggtgtaacca cctgtcttag gttcccaggt cagttgaatg      120
ctgatcttag aaaattggct gtcaacatgg ttcccttccc ccgtctccac ttcttcatgc      180
ccggattcgc tccactcacc tcaagaggca gccaacaata cagagcgttg acagttccag      240
agctcacaca gcaaatgttt gatgccaaga acatgatggc ggcttgtgat cccagacacg      300
gaaggtacct tacagtagct gcagtattca gaggtaggat gtcaatgaaa gaagttgacg      360
aacagatgct caacatccag aacaagaaca gcagctactt cgtcgaatgg atccccaaca      420
acgttaaaac agccgtttgt gatatcccac caagaggtct caagatgtct gccactttca      480
tcggcaactc aaccgccatc caagaattgt tcaaacgtat ctccgaacag tttacagcta      540
tgttcaggag gaaagctttc ttgcattggt acaccggaga aggtatggat gaaatggaat      600
tcacggaagc agaatccaac atgaacgact tggtatcaga ataccaacag taccaagaag      660
ccacagctga cgaagatgcc gaattcgacg aagaccagga agccgaagtc gacgagaact      720
aaatttcata cgttaatttt ggatctgaaa tcaaagcttt ataactttta tatttgtctc      780
ctctcctttt attttttatt taagcatgtt ttttgtacag tctctacatt cccgtttgta      840
aatttcgaat acactactta aattattcca agactgactt tttgttgctt gtgtttctgg      900
aatttcagga agtgtttaga tatttaacat gttttgcgaa ctgtttttt atgaataggc       960 attaaaactg ctgccattac ttataaaaaa aaaaaaaaa aaaaaaaaaa aaaaaa          1016

<210> SEQ ID NO 5
<211> LENGTH: 1016
<212> TYPE: DNA
<213> ORGANISM: Diabrotica virgifera virgifera

<400> SEQUENCE: 5
gtgacatttg cttcagaact ttgaaactca caacacccac atatggagac ttaaaccatt       60
tggtatccct cacaatgtcc ggtgtaacca cctgtcttag gttcccaggt cagttgaatg      120
ctgatcttag aaaattggct gtcaacatgg ttcccttccc ccgtctccac ttcttcatgc      180
ccggattcgc tccactcacc tcaagaggca gccaacaata cagagcgttg acagttccag      240
agctcacaca gcaaatgttt gatgccaaga acatgatggc ggcttgtgat cccagacacg      300
gaaggtacct tacagtagct gcagtattca gaggtaggat gtcaatgaaa gaagttgacg      360
aacagatgct caacatccag aacaagaaca gcagctactt cgtcgaatgg atccccaaca      420
acgttaaaac agccgtttgt gatatcccac caagaggtct caagatgtct gccactttca      480
tcggcaactc aaccgccatc caagaattgt tcaaacgtat ctccgaacag tttacagcta      540
tgttcaggag gaaagctttc ttgcattggt acaccggaga aggtatggat gaaatggaat      600
tcacggaagc agaatccaac atgaacgact tggtatcaga ataccaacag taccaagaag      660
ccacagctga cgaagatgcc gaattcgacg aagaccagga agccgaagtc gacgagaact      720
aaatttcata cgttaatttt ggatctgaaa tcaaagcttt ataactttta tatttgtctc      780
ctctcctttt attttttatt taagcatgtt ttttgtacag tctctacatt cccgtttgta      840
aatttcgaat acactactta aattattcca agactgactt tttgttgctt gtgtttctgg      900
aatttcagga agtgtttaga tatttaacat gttttgcgaa ctgtttttt atgaataggc       960 attaaaactg ctgccattac ttataaaaaa aaaaaaaaa aaaaaaaaaa aaaaaa          1016

<210> SEQ ID NO 6
<211> LENGTH: 1374
<212> TYPE: DNA
```

-continued

```
<213> ORGANISM: Diabrotica virgifera virgifera

<400> SEQUENCE: 6
ggacaacttc gtgtttggac agtctggagc tggaaacaac tgggccaagg gacattacac      60
agaaggtgct gaattagttg attcagtatt agatgttgta aggaaagaag ctgaatcatg     120
tgattgttta caaggattcc aactcacaca ctcacttgga ggtggtactg gatcaggtat     180
gggtaccctc cttatctcaa aaatccgtga agaataccca gacagaatta tgaacacata     240
ctcagtagtc ccctcaccca aagtatcaga taccgtagta gaaccataca acgccacact     300
ttcagtacat caattggtag aaaacacaga tgaaacatac tgtattgata atgaagctct     360
ctatgacatt tgcttcagaa ctttgaaact cacaacaccc acatatggag acttaaacca     420
tttggtatcc ctcacaatgt ccggtgtaac cacctgtctt aggttcccag gtcagttgaa     480
tgctgatctt agaaaattgg ctgtcaacat ggttcccttc ccccgtctcc acttcttcat     540
gcccggattc gctccactca cctcaagagg cagccaacaa tacagagcgt tgacagttcc     600
agagctcaca cagcaaatgt ttgatgccaa gaacatgatg gcggcttgtg atcccagaca     660
cggaaggtac cttacagtag ctgcagtatt cagaggtagg atgtcaatga aagaagttga     720
cgaacagatg ctcaacatcc agaacaagaa cagcagctac ttcgtcgaat ggatccccaa     780
caacgttaaa acagccgttt gtgatatccc accaagaggt ctcaagatgt ctgccacttt     840
catcggcaac tcaaccgcca tccaagaatt gttcaaacgt atctctgaac agtttacagc     900
tatgttcagg aggaaagctt tcttgcattg gtacaccgga gaaggtatgg atgaaatgga     960
attcacggaa gcagaatcca acatgaacga cttggtatca gaataccaac agtaccaaga    1020
agccacagct gacgaagatg ccgaattcga cgaagaccag gaagccgaag tcgacgagaa    1080
ctaaatttca tacgttaatt ttggatctga aatcaaagct ttataacttt tatatttgtc    1140
tcctctcctt ttattttta tttaagcatg ttttttgtac agtctctaca ttcccgtttg    1200
taaatttcga atacactact taaattattc caagactgac tttttgttgc ttgtgtttct    1260
ggaatttcag gaagtgttta gatatttaac atgttttgcg aactgttttt ttatgaatag    1320
gcattaaaac tgctgccatt acttataaaa aaaaaaaaaa aaaaaaaaaa aaaa          1374

<210> SEQ ID NO 7
<211> LENGTH: 1128
<212> TYPE: DNA
<213> ORGANISM: Diabrotica virgifera virgifera

<400> SEQUENCE: 7
ggggagttca gaatttgtga atagagattg accaaaatga aagcggcttg tattattaca      60
ctattactac ctgttgtatt aagttacaaa gctaacttaa atcctctttc aaatgagttt     120
ataaactata tcaatagcaa gcaaaacaca tgggttgctg gaaagaactt tgatgagaaa     180
ctttcaatcc aagaaataaa aaatttatta ggagcgagaa aaaggagttt aggagatgta     240
aaaggattta tgcacagtga agatattcaa gttccagatt ctttcgatgc aagggaaaac     300
tggaaagact gttcagatgt tatcagcact attgtagacc aatctgcttg tggatcttgc     360
tgggcaatgt ctgcagcatc tgcaatgagt gacagacgat gcatagtcac ccagggaaag     420
cttaaagtgc ctgtttctgc tgaaaattta ttgtcttgtt gcgatgactg tggatttgga     480
tgcgccggag gatatataga tgatgcatgg tcgttttggc aagagaatgg aattactaca     540
ggaggtcttt acggcagcaa ccagggttgt caatcatatt cgcttcaacc ttgtgaacat     600
catacaaatg gtactaaagt gcaatgcagt actttgaact acggcacacc ttcttgcaga     660
```

-continued agcgatcaat gtgacgatac cgcactaaat tataagtccg agttaactta tgcctcaggt 720
ccagtgaatt actatactac agttcccaat atgcaaaagg aaatattgac aaatggtccg 780
atacaaactc gttttgatgt gtacagcgat ttcttcagtt acaaaagtgg tgtttatcaa 840
catgtcgctg gagattatgt aggaggacat gccgtcagag ttttaggttg gggagtagag 900
aatggagtcg cttattggtt ggctgctaat tcatggaatg aagattgggg agacaaggga 960
ttgtttaaaa taattcgcgg aacaaatgaa tgcagtttcg agaatggtat ggttgcgtca 1020
actccaagag tctaattcta aacaaaatat tggaaatagg cttaattctg gtttatttta 1080
aataaaacac ttgatcccaa aaaaaaaaaa aaaaaaaaaa aaaaaaaa 1128

<210> SEQ ID NO 8
<211> LENGTH: 600
<212> TYPE: DNA
<213> ORGANISM: Diabrotica virgifera virgifera

<400> SEQUENCE: 8
ggggctttct gatttttgac agcttctata gaagtttatc aagatgttga tgccaaaaaa 60
gaatagagta tgtatttacg aatacctctt caaagaggga gtcatggtag ctaaaaaaga 120
ttaccatgcc ccaaaacacc tcgaactaga aactatccct aaccttcaag taattaaggc 180
tttacaatca cttaaatcaa aaggttacgt aaaggaacaa ttcgcctgga ggcattatta 240
ttggtatttg actaactctg gcatcgaata cctccgcaca ttcttacact tacctggaga 300
aattgtccca tctaccttga aacgcccagc aaggacagaa accacccgtc ctagaccagc 360
tgctctcaga tctgagacat ctaaaccttc agaagaccgt gcaggataca gaaggactcc 420
tggaggccct ggagctgaca agaaagctga tgttggtcca ggaactggag atgttgagtt 480
caggcaagga ttcggacgtg gacgggcacc acaataaatt tattgataag ttaattttta 540
taaattgatc agccaataaa aagtttggtt aaaaaaaaaa aaaaaaaaaa aaaaaaaaaa 600

<210> SEQ ID NO 9
<211> LENGTH: 1874
<212> TYPE: DNA
<213> ORGANISM: Diabrotica virgifera virgifera

<400> SEQUENCE: 9 ttttttttt ttttttttt ttttttttc tttatttgtc caagtttaat ttacagatca 60
caaataatgc aatgcaagta ataagtcaat tagttattaa aaatacattg atactccaat 120
attagtatat aaaagaaaca aaacatatca aaattattta agtagtggag tccaaataga 180
ctatttcttc ttttgggctt tttctgcagc ttttgtgact tttccggcgc tgggatcttt 240
gaaggcaacg ctcttgatga ctcctactgc aacggtttgc ctcatgtcac ggacagcaaa 300
acgtccaagg ggtgggaatt cttggaatga ttctacacac atgggcttgg tgggtaccaa 360
gttgacaatg gcggcatcac cagatttgat ggctttggga ttttcttcag tggtcttacc 420
agaacgacgg tcaacctttt ctttgccaaa aggatcgata ggccgtgctt tcgcagtccc 480
tatgcatact gaacatcagg atcaagccag cttttgccct tttgctctac gcgaggtttc 540
tgtcctcgct gagctggcct taggacacct gcgttattct ttgacagacg taccgcccca 600
gtcaaactcc ccgcctggca gtgtcctcga atcgaatcag gctggaggta agttgacgct 660
cgaaacgaag cacacggacg ctagccgagt atccgaaagg caagccttat cggaaccacg 720
aaaccgacga acggcacaac gcaacgaaac gtcactccgt gccctcggct caagaatacc 780

-continued

| | |
|---|---|
| gtgacagtcg cagcctcgtg agcgaacgac gcacgcgttt cgccttaccg agtaagtaaa | 840 |
| gaaacgatga aagtagtggt atttcaccgg cgatgttgcc atctcccact tatgctacac | 900 |
| ctctcatgtc tccttacaat gccagactag agtcaagctc aacagggtct tctttccccg | 960 |
| ctaattttc caagcccgtt cccttggcag tggtttcgct agatagtggg tagggacagt | 1020 |
| gggaatctcg ttaatccatt catgcgcgtc actaattaga tgacgaggca tttggctacc | 1080 |
| ttaagagagt catagttact cccgccgttt acccgcgctt gcttgaattt cttcactttg | 1140 |
| acattcagag cactgggcag aaatcacatt gtgtcaacac ccgctggggc catcgcaatg | 1200 |
| ctttgtttta attagacagt cggattcccc tagtccgtgc cagttctgag ctgaccgttg | 1260 |
| aatggcggcc gaagaggaca tccaagcacc cgaaagtaac tcagagcctc gcagcaagac | 1320 |
| ggttccgcgg gaggccaagg cacgggaccg aactcggatc catgaaaccc aactcgtaag | 1380 |
| aattaggctc acttcacctc acccaggccc ggcacgtcag ccatgaccca cttcctcgcc | 1440 |
| aagcccgaca cgccccgatc ctcagagcca atccttatcc cgaagttacg gatccaattt | 1500 |
| gccgacttcc cttacctaca ttattctatc gactagaggc tcttcacctt ggagacctgc | 1560 |
| tgcggatatg ggtacgaacc ggtgcgagcc tccacgtggc cctctcctgg attttcaagg | 1620 |
| ttcgaggaga agatccggac accgctgcaa ctgcggtgct cttcgcgttc caaaccatat | 1680 |
| ctccctgcta gaggattcca tggaactcga acgcttatac agaaaagaaa actcttcccg | 1740 |
| gatctctcga cgacgtctcc aggtcctttt gggttacccc gacgaactct cttgcgaggg | 1800 |
| cccgactttt tgacggttcc gctaccgggt tccggaatag gaaccggatt ccctttcgcc | 1860 |
| caatgggtgt gccc | 1874 |

<210> SEQ ID NO 10
<211> LENGTH: 816
<212> TYPE: DNA
<213> ORGANISM: Diabrotica virgifera virgifera

<400> SEQUENCE: 10

| | |
|---|---|
| tttttttttt tttttttttt tttttttttt cagagagatt cccatcaacg taaataatca | 60 |
| gggtatttat tcacatgtcc ctacgttctt atcatcatgt aaaaggagtt ttgactatac | 120 |
| atattttgaa acatttaaa tggggccctc agaacaacag tggactaagt cacaaattca | 180 |
| gcattttag attaatatat caataaaagc agcaaaatta atcttccga ttaacaggga | 240 |
| cctacacaac ctacctctat atttggctag atgatgctac ataatttgta gctttatctc | 300 |
| ataaacataa tgaaaatatg aatgcaaaga ttgcatttat ctcaaaactt agttttgag | 360 |
| cttatgccac tgttgctgat agcctcaaat attaacatgt tgacagacat aacatctata | 420 |
| gatgtctaat ttccattgaa acgtctagat gacatttta aaataacgaa ttgtgcatat | 480 |
| tcaaactaca tctatagatg catatgaaat atgacatgaa catacattgt cgtcatcaat | 540 |
| atgtttacaa aactcattgt ttccatattg acagtctaat tctataccc gtatctgcaa | 600 |
| aaaaacttaa tttccaattt tcgtggcaaa cgactaacaa aacagttatc catctataca | 660 |
| caaaactctg atctaaacaa aaattctag gaacctctaa taccagtcat ctaatacctc | 720 |
| gtaactgaat atctttagac ttgataagaa aaaaaaaca gaaaaaacct acttgacaaa | 780 |
| tctcttggca gatacgggct attagaatta gacccc | 816 |

<210> SEQ ID NO 11
<211> LENGTH: 579
<212> TYPE: DNA
<213> ORGANISM: Diabrotica virgifera virgifera

<400> SEQUENCE: 11

```
ggggcttttta catcaaaaat ttctttagct gttgtcggtt aaggaacagc ttacaaaatg    60
aaattcaaca aattagtaac cgcttcaaga agcaaaaata ggaaaaggca tttcacagcc   120
ccatcccaca tcagaagaac ccttatgtcc gcacccttgt ctaaagaact tagacaaaag   180
tacaatgtta gcactatgcc aatccgcaag gacgatgaag tacaagttgt aaggggggcac   240
tacaaaggct agcaagtagg taaagttgta caagtataca ggaagaaatt cgttatctac   300
attgaaagga tccagagaga aaaagccaat ggagctagtg tatatgtagg aatccaccct   360
tcaaagttg ttattgttaa acttaaaatg acaaggaca ggaagaagat cattgacaga    420
agagccaaag gacgtttggc tgctttgggc aaagacaaag gaaatacac tgaagaatca    480
gctgcctcag ctgtagaaac atcttaagtg taataagtaa ttttttaataa taaaataata   540
taaagttcca aaaaaaaaaa aaaaaaaaa aaaaaaaa                            579
```

<210> SEQ ID NO 12
<211> LENGTH: 585
<212> TYPE: DNA
<213> ORGANISM: Diabrotica virgifera virgifera

<400> SEQUENCE: 12

```
gggggctggc agtttgctgt cttaatgttg acatttttat atattggaaa aaatgtcgaa    60
agttgaattt aaacaagata tgcccccaca agggggctac aatccaatta actataaaag   120
agttccagcc aaaactttat ttggaggatg ggccttaatc gggggctacc ttggcatgac   180
tgcaggagcg gcgtatttat attatttaaa cgttaaggca gtaaaaactc gagaacttga   240
attaaagggc gccagcttag cgctgtatcc aatacttatg gctgaaagag accgtgaata   300
tatgaagcaa ttaaggagaa atagagatga agaacgtgaa ttaatgaaaa atgttgaagg   360
atggcagacg ggtacatggt atggtgaacc catctacaag actaaagaca agatactct    420
tattcatccc ctattccatg aatattacat tcacagttct acaaggact acactgttcg    480
tgcaaacgtt ggtttgatgt cttaaatttt tattctattg taatttagta gcgaaattta   540
aatattaaat tgtaaatatg aaaaaaaaaa aaaaaaaaa aaaaa                    585
```

<210> SEQ ID NO 13
<211> LENGTH: 1043
<212> TYPE: DNA
<213> ORGANISM: Diabrotica virgifera virgifera

<400> SEQUENCE: 13

```
ggggagtcgt caacatcaat ttcaagtttc aagaaaaagc aaatcactac gacttgccgg    60
attttgtagt agtgttaatt ttgtattaaa aaatcaaaat gagttctatt ggaactgggt   120
acgatttatc agcttcccaa ttctctcctg atggaagagt atttcaagtt gaatatgcaa   180
tgaaagcagt tgaaaatagt ggcaccgtaa taggcctccg aggtacagat ggcattgtat   240
tggctgctga aaagctcatt atgtcaaaat tgcatgaacc aagtacaaat aaacgaattt   300
tcaacattga taaacacata ggaatggcat tttcaggctt aatagctgat gcaaggcaaa   360
tcgttgagat tgctagaaaa gaagcatcaa attatagaca tcaatatggt tcaaatattc   420
ctcttaaaata cctaaatgat agagtaagca tgtacatgca tgcatacact ttatacagtg   480
ctgttagacc atttggttgc agtgtcatct tggccagtta tgaagatagt gacccatcta   540
tgtatctgat tgatccatct ggagttagct atggatactt tggatgtgct acaggtaaag   600
```

```
caaaacagtc tgcaaagact gaaatagaaa aattgaagat ggggaatcta acatgcaaag    660
aacttgttaa agaagcagcc aaaatcattt atttggtcca tgatgagctg aaggataaga    720
attttgaact ggaactttca tgggtatgca agatacgaa tggtttacat accaaagtgc     780
ctgaatcagt gtttgctgat gcagaaaaag ctgccaaaca agcaatggaa gcagattcag    840
aatcagatac agaagatatg taataactac atttagtttt taatatttcg ctgatggtgg    900
ctgttcttac aatatttcgt gtgttatgtt catatattat gtaatactgt gagaatttcc    960
atttcaagga taggtttata acttttttt ctaataaata cataacttta tgtcaaaaaa     1020
aaaaaaaaaa aaaaaaaaaa aaa                                             1043

<210> SEQ ID NO 14
<211> LENGTH: 601
<212> TYPE: DNA
<213> ORGANISM: Diabrotica virgifera virgifera

<400> SEQUENCE: 14
gggataatca ttagtttttt tattgaaagc tggaatgaag ggttggatga aaaaaaaaac      60
tgtctttatt taatttataa agaattttat ttttaagtta aaaagcttaa attttttaa     120 aagacgagaa gaccctatag agtttataa aattattaat aagtttttt agtattaaat      180 ttatttatat aataaattta tttaattggg gtgattaaaa aataaattta acttttttta    240
tattattata ttaattaata atttttgat ccaattttt tgattataag aataaattac      300
cttagggata acagcgtaat tttattggag agttcaaatc ggtaataaag attgcgacct    360
cgatgttgga ttaaagttta taattggtgt agcagctata ttattaagtc tgttcgactt    420
ttaaaatttt acatgatctg agtttaaacc ggtgtgagcc aggttggttt ctatctttaa    480
tttattaata tattttagta cgaaaggacc aaatatataa aataattttt atatttagat    540
aaatattaaa aaaaaaaaa aaaaaaag caaaaaaaaa aaaaaaaaaa aaaaaaaaa        600 a                                                                     601

<210> SEQ ID NO 15
<211> LENGTH: 913
<212> TYPE: DNA
<213> ORGANISM: Diabrotica virgifera virgifera

<400> SEQUENCE: 15
gggggcagtt atttcgactt ttcatgcttg tcataaaata aaattaaaat atatccggcg      60
aggtgttgac tagcggattt ttttagattc aacaatctta ttttataaaa taattagtta    120
aaatgatgca acagctaat aatgcatatt atcccgatta ttccactgct ccaatgcaac     180
gtcaaattaa cccctatgca gataatggag ggagtgtagt agcaatagca ggtgaagact    240
ttgtaataat tggtgcagat acacgtttga gtactggatt ttccatttat accagagaac    300
aaaacaaact tttcccacta tcaggcacta ctgttttggg ttgtgcagga tgttggtgtg    360
acactctaac attaaccaga atccttaaat ctcgcatgca gatgtaccaa caagagcata    420
acaaaacaat gtctacaact gcatgtgccc agatgttgtc aaccatgctc tactacaaga    480
gattctttcc ttattatata tcaaacattc tagtaggttt agataatgaa ggaaagggct    540
gtgtttacag ctatgatcct attggacatt gtgaaaaagc tacgtataga gcaggtggtt    600
cagctggagc tcttcttcag cctctgttgg acaatcaaat tggacagaag aacatgctta    660
aaacatctgg ggaacctctt agtcaggaga agctctgtc tacccttaaa gatgtattta     720
tttctgctgc tgaaagagac atctacactg gagatagcgt acttataaat attattacta    780
```

```
aagatggagt aaaggaagag tccttccagt tgagacggga ttagaagcaa gtggttttgt    840
ttatattttc ttatgtgtaa ttcaaatata ctttctaaat aaacaaaaaa aaaaaaaaaa    900
aaaaaaaaaa aaa                                                       913

<210> SEQ ID NO 16
<211> LENGTH: 681
<212> TYPE: DNA
<213> ORGANISM: Diabrotica virgifera virgifera

<400> SEQUENCE: 16
ggggatttcg ttggtttaac gattgatagt aactataaat tcaaattaca gatcagatgt     60
atatatatat ataaacacgc aaaaatgctt ggctataaaa tgaaaaatgt aactgcaata    120
ttagatgacg ttatatataa aaataaataa aatctgctgt tgatattgta gttcattagt    180
tttgaaaaat aagcagtact aactttaatc ttgtgccaaa ttagttttat tgttaatatt    240
aatattttca cccaaataag agaaatggat gacgtgcaac tgggtcctgt gagtattagc    300
atgatagaag ataatttata tttaggagga ttggcagctg cgaaaaattt ggaagtttta    360
aagaagtaca acattactca tattcttacc atagatatat gtccattacc aagaactgta    420
acagaacaaa gaaatttagt taccagattt atacagttgt cagaccaacc aagagaagat    480
ttgctttcat attttgatga aacagattta tttattaatg aaggaaggga aagggaatt    540 gttttggttc attgttattt tggtgtttct agaagtgcca ctgttgttat tgcccatata    600
atgaaaaaat accagatgag ttactttgag gcatttgata tggtaaaagc tgaaaaaaaa    660
aaaaaaaaaa aagaaaaaa a                                               681

<210> SEQ ID NO 17
<211> LENGTH: 1109
<212> TYPE: DNA
<213> ORGANISM: Diabrotica virgifera virgifera

<400> SEQUENCE: 17
gggggagtag ttgttttat tgtgagatga tttcgaagtt caccctggtt ttcttggttt     60
gcattgtcgc accagcgata ggtgatccac cagttccaga atggagtgac acttatagcg    120
tagaaggaac tatccatttg ccttatgcag aaatagtaga gccttttccat gcttggtatg    180 atggaaaatc taaaaattcg cgcattgatt actacaatgg gacggctaag acataccaac    240
ttggaggaaa tggaaatggt gtccaactga aagtagttcc attcactaca gaggaggtcc    300
taaaccaaat aacgtgcttc cagatcaatg gaactgaaga cgatccagtg actcctcaat    360
cgattttgcc agatttagaa ggatttgaat atcaaggcat acaggagtat ggagatagag    420
aactagaggt atggtttcta aaaactgtcc agttagaaaa agaaaacgaa tacactctat    480
gggttgtccg agatgagcat ggtaaagcta ttccagttaa atatgatatg agaggataca    540
attcgttatt gggaagccac tacgatcatt actatttgct atacacatcg aagtcttaca    600
ggactcacaa gattgatccc tccgtttttg aagtagaaac taatagtgaa tgcagaagtt    660
ttcctggacc cggaaatcaa catgttcaca tcatgaaccc catggccgaa tacattcgtc    720
ccgaaaaaag tgagcacgtg gactcaagct ttggcgattt tataaataac cacaacaaaa    780
attacgcaga cacaaaagaa cacgttttta gaaagaggt tttccgtcaa aacgtcaggt    840
tcatcgaatc tgtcaaccga caaaataaag gtaagtgtta tagtagggga gcaaagtagg    900
tgtgctaaat ttgcagtcac tcgagagtta tggcgaccta ttgggttgtg attattaggt    960
```

```
cctaaaacca aaaaaagtta agtaaaattt tccatttcca acaatcgttt tttccgatta    1020
tagcgtcatc tatccataat tcgaaaaaat gtctctaata aaagttgctt attttttacga   1080 aaaaaaaaaa aaaaaaaaa aaaaaaaaa                                       1109

<210> SEQ ID NO 18
<211> LENGTH: 400
<212> TYPE: DNA
<213> ORGANISM: Diabrotica virgifera virgifera

<400> SEQUENCE: 18
gggggatttt ctctagtttg caggaagcag gaatttcagt aaagaaataa gattaaaatg      60
gcagacaaag tagaaaaggt tgccagacca atgaaattcc cttacacatt cagtgcaaaa     120
attgcacaat tcccaatcaa gcactacttg aagaaccaat ggatctggaa atactatgct     180
atttctcttg tagtatgtct tccagtcttc aactcgatta gtaaactggc caactctcct     240
ggaaacgttg ctaaatgggc agagattcgc agaagagaag ctgctgaaca tcatcactaa     300
gaaaattttt tttatagtaa ttagtctgcc aattgttttg ttctaattta atttctatta     360
aatacatgta gaaaaaaaaa aaaaaaaaa aaaaaaaaa                             400

<210> SEQ ID NO 19
<211> LENGTH: 800
<212> TYPE: DNA
<213> ORGANISM: Diabrotica virgifera virgifera

<400> SEQUENCE: 19
gggaagcagt ggtatcaacg cagagtggcc attacggccg gggtagttct agcgttctag      60
ttctatagtt gttgtgtagt attttctgtg tagtttgtga ttttccctat tgtgcatttg     120
tatattttat ttatttattt atatatttac gatcagtaag aacattttac ataaattcaa     180
taagcatata gattcgtgta aaaaaatgcc aaagctatcc aaaaaaaatc aaaaaaaagt     240
aggcgctcaa caagactcgt taccgagaaa tgacagaact actgactgta cctcaaattc     300
acattcacat tctggtaatg gtgaaactac ttatcatagc gcaaattcaa attctgttgc     360
tcttgaaagt agttcatcaa atgcccaaat tcaaattagc accatacctc caataaatga     420
taattcttcg ccaaacagct cctttgatca aactgcacct acaagttcaa gtttacctga     480
gggaagagta cactccgaaa gaattaattt tcgtcctaga agagccagtt tggtaacact     540
gagacgtgaa aaagttacag ctttgaggaa gacacataaa aatatgagaa aaaataaagc     600
tgtaacaagt tttaaatctt ttgctcaagc cgaaattcaa catgtatctc ttcccagcca     660
ggagaatttg aaatctcgag gatcaattgt gaatttggtc actaaaagaa aaaacacaaa     720
tgaagaatgt tcatcccatg gctcccttac agaatcagat atgggtaacc aaaaaaaaaa     780
aaaaaaaaaa aaaaaaaaa                                                 800

<210> SEQ ID NO 20
<211> LENGTH: 1105
<212> TYPE: DNA
<213> ORGANISM: Diabrotica virgifera virgifera

<400> SEQUENCE: 20
gggagccctt atttctccta ttgctatata cgcagctgaa acatggactc tcaaaaaaat      60
caatcgaagt aagatcgaag ccttcgaaat gtaggtctac agaattattg tacccgtgtc     120
caggagagaa cacagaacca acctgtcaat tctgaaagag cttcatataa aagacaaggt     180
attaaaaaaa gtataccgac catacttaaa ttactttggt aaagtaacga ttactatacg     240
```

```
aagaggcaaa tcgttacttt gattactctg attacttcgt accaatcgta tcagagcgag    300
taacgactat tgtatctact ttgattactt cgtatcagag cgaataacga ctattgtatc    360
tactttgatt actctgatta cttcgtacca atcgtatcag agcgagtaac aactattgta    420
cctactttga ttattctgat tacttcgtac caatcgtatc agagcgagta acaactattg    480
tcagggccgc gtttaggtca aatgacgccc taggcaattc tctagtagcc gcccttcaaa    540
catgtaccat ttttgcgaaa aaaacgcaa gcagaatttt ttatttaaat aagaatgtta    600
ttgcacaaat ctcggtgttc ttcaaataat gtttagaaat gtgttaaaaa tattctttat    660
tttacatcag gcgtaatgtt acatattact attataagta tgtttgagcg tttggaactg    720
tgtccaatgc atgcgtttta atgcatgata cgtagaaatt gcctgtttgt agccgcacct    780
acttgttcga ttttaaatga gagatgcatt gaaaacatta ctcaagcact atgtgtttat    840
agctttgttt aacaataaaa aaattaattt ttagcgatgc aaataatcaa aaccggtata    900
atttgacatg cactttccaaa tgcggtaagc agaattgcta ttttattttt taatcaaaag    960
ttattcggat tcaaaaattg caattttccg atattttgaa agttcaaccg cgtctatctc   1020
gaaaactatg catcctacga aaaaacttta acaacatttt ttgcttagaa tgacccaaaa   1080
aaaaaaaaaa aaaaaaaaaa aaaaa                                          1105
```

<210> SEQ ID NO 21
<211> LENGTH: 936
<212> TYPE: DNA
<213> ORGANISM: Diabrotica virgifera virgifera

<400> SEQUENCE: 21

```
ggggctcat tgtagtagcg ccaggcgcgg aaacgtgagt gctaaaacac agtgatcgta     60
ctagtccaaa acatctttta tattttccta cttttatatc taattgtata gtttcgttat    120
ttttattact tagaagttta tattttctca tcgtttttata cgcttctggt aaggattttt    180
atacattaaa caatattact tgcttgggta agttatgttt tattttgaaa tatagcattg    240
taaccttttt taaatctttt atttttttta tttttctttt tctttaaca tactactgat    300 acgctgcaga ggtccatgcg ttttcaattt tttaggatct tttgataact ttttaaaat    360 gtaacacatt tagaaagacc gttgaaaagt tcgccctttt agaccgcgga ggcagtgacg    420
tagctgacag gtccgcaagg cggggggccc cgacattagg agggataagt agagatctct    480
ctagtcagag ataagtactt actttcgatc ttttcgtaat tacgtactta ctttcgatct    540
tttcgtaatt acctctgttt tccttccatt gcatgtgatc tttgtatata ttcttaata    600 ttttacagaa aacgtaagtg tgtctacaaa atgttttgca tatttgtgta aaattaatca    660
aaatatctta aaaccagtag tcaattaaaa aaatatttaa aaatgttgtg caataaacct    720
tgcggtattt actgaagtgt ttcacacctg tttgaagtta aatatcaagg tttatttttt    780
ggccgggaat ttaaaggttg tggtatattt acttttttaca attaataatg ggatcaactg    840
attgggtata tagggtgatc aaattatacc ttgtagttca atatcttcgt tgccagaaga    900
gatgcaggaa aaaaaaaaaaa aaaaaaaaaaa aaaaaa                            936
```

<210> SEQ ID NO 22
<211> LENGTH: 812
<212> TYPE: DNA
<213> ORGANISM: Diabrotica virgifera virgifera

<400> SEQUENCE: 22

```
gggaaagcac taaaaaatgc aggatacaaa tttgacattg catatacatc tgtccttaca      60
agagctcaga acacacttaa ttcaataatc aaagaaattg ccaagagaa tttggaaact      120 ataaaaactt ggagactcaa tgaaagacat tatggtggcc tcactggctt aaataaagca     180
gaaacagcag caaatatgg agatgagcag gtagctattt ggcggcgcag ttttgacatt      240
ccacctccac caatggaacc tgaccatgct tattatgata ccattgtaaa agatgcccga     300
tatgctgatg gtcctgcacc agatcagttt cctaaatttg aatccttaaa gctaacaatt     360
gagcgtactt taccccttctg gaatgaaact gttgttccac aaattaaggc tggaaaacag   420
atcttaattg cagcacatgg taacagtttg agaggaattg taaagcatct agaccagctt    480
actgatgacc aaattatgca gttgaatttg ccaacaggaa ttccatttgt ctacacatta    540
gatgaaaatt tgaaaccaat aaagagttta gaattcctag gagatccaga aactgtgaaa    600
aaggctatgg aagctgtagc tgcccaagga aaagccaaat aagcattatt tattatttat    660
tgttttaatt tatatcaaaa tcatttattg ttagatattt gatgtgtaat gaataaatgg    720
ttaggctgaa ttgtaaaact cagcagaaat gttatgtgca agacattaaa gcatattctt    780
ctcaaaaaaa aaaaaaaaa aaaaaaaaa aa                                      812

<210> SEQ ID NO 23
<211> LENGTH: 1127
<212> TYPE: DNA
<213> ORGANISM: Diabrotica virgifera virgifera

<400> SEQUENCE: 23 ggggaagta ttctgtagaa aactgataag tatattgctt ttctcattta tttatgtggt      60
taaatagtga gttagtgttg gtcaacgtag atgataacaa ctgaacattg aataaactac    120
aagaataatg ttaagcataa aaattctgtt atgtatgttg ctggcacacc aatctgcggt    180
agaagctgta tataatgttg gagttggacg agccgattgc acaggaccat cagcagaaat    240 tactttatg ggttatgcca aatccggtca gaaaggatgt ggtatccatt taaggcagtt     300
ttcaagagca tttgtgatta agatgagaa cactctagtt gcatttgtga caattgacac     360
atgtatgatg aaccatcccc taaaacaagc ggtaatagat aaattggatc taaaatatcc    420 caatgtatt actctaaaga atacaattct cagtggaaca cacagtcaca gcacacctgg    480
aggtttcctc aaggatgtaa tgttggacat accaagctcg ggatattgta agaaaacctt    540
taacgcattg gtagcaggaa ttgtaaaatc catagataaa gcatacaaca atcaagttga    600
agcaagaatc ttttacagca ctactacagt aactaataca aacaggaaca gaagtccagc    660
tgcttacctc tataatccag aatcagaaag aaaaaagtaa gtgtaatact agataataat    720
actttaaact ttattaagta taataaaatt aataacgtac aaaatactca aaattaacat    780
ttatttccaa attaccatat aaatataatt ttaataattc tgggactcaa acattgtaa     840 tttatttttg cttattaata ataataaatt gtacaaataa attctatttg tcactctaaa   900
cacaaataag atgttgctgt tctttacgac agtctcctgg cgactagtgt cataactttt   960
atactcgcat tttaatggcc atcattaata gtggagtcaa tggagttttt acttaggaaa   1020
aaaatcaaac aagagaggac tgtttataac ttcattcaga aatgtatcat aaacaacaca   1080
tcaaaaagtt ctactccaaa aaaaaaaaaa aaaaaaaaa aaaaaa                    1127

<210> SEQ ID NO 24
<211> LENGTH: 869
<212> TYPE: DNA
<213> ORGANISM: Diabrotica virgifera virgifera
```

<400> SEQUENCE: 24

```
gggccaatag tcccatgaaa gcagcctacg attattacaa gaaatgttca aagacaggaa      60
attgcttgcc accagtaagc ctccttcctg gcaaccaaaa ggaaggcgaa gttcaactgc     120
aaccaatcga tctcaagaaa aatccatttt taaacggagt ttatgaagcc ggaagttctg     180
ctgacttctc caggtcttcg tctgagacga aatccaatgg agcctctctt gatagtgacg     240
cgtccaatgc gagatttgcg ataactggag ccaacgatga ggacaacgag gtatctccca     300
gccagaggat tccatgcaaa ggtgatggaa aagtgtgcgt gcccaaggac gcttgcgtca     360
atggtgtggt caccaaacat agaggaagcg cattgcagat caaacaaaat aattatctaa     420
gtaaacattc agatccacaa agccaggcgt tgttagaaaa tgtgaattca aaatattact     480
actacacgag aacaaaagga ttattcagga tatgttaccc aaaagaaagg ccgcctactg     540
taaagacata cttgagtcct ttggaaacgc attgtaacaa tgtaaattac tacattcccg     600
atgaaaataa cgataccaag gacttcactg acgatgcttg gacaagatta catatgggac     660
gatccatgat agctctcttt atcatatcgt tcatagctgt ctttgctgcc ttctgcaccg     720
gggtcactgg atgttggaag aggtctccag gaaatattac agccactgca atacttatgc     780
tgctagcatg tttgttgagt gctggtgcta tgggtctatg gcacggagtg gaatattaca     840
aaaaaaaaa aaaaaaaaaa aaaaaaaa                                         869
```

<210> SEQ ID NO 25
<211> LENGTH: 569
<212> TYPE: DNA
<213> ORGANISM: Diabrotica virgifera virgifera

<400> SEQUENCE: 25

```
ggggagttcg attccggcag cggacggcga ctctgtgaaa gttgatcgct taaacgtttc      60
tacacgtggt gcacgtgctc cgtaccgaga cgacgacgaa gagaagacgc cggcgtcgcg     120
acgcgagtag acgacaacgt ggttgaacaa gtgtggaagt gccggcatgt tgcactgagt     180
gaagtgacag agttgtgcgc atgtgaggaa aggatgtcaa gggattaaag gcggcatca      240
tggtgagctg tttaaggtta gtaaattcca tactgctggc gcttgactga gaataatgag     300
taagtgttta atagtgattt aatatagttt cttgaacttt tattcaggaa agattcaagt     360
aaatgtgata cagtaggcgg tactgtagac taaagaaag cttatttaa attttaggaa     420
atattatttt taatattatt ttttgatag tttttttata gattttaatt atattgaaaa     480
agttgacatg ttgtgtaatg tctggctaat tggctcggcc aaggccatca aattcactca     540
aaaaaaaaaa aaaaaaaaa aaaaaaaa                                         569
```

<210> SEQ ID NO 26
<211> LENGTH: 576
<212> TYPE: DNA
<213> ORGANISM: Diabrotica virgifera virgifera

<400> SEQUENCE: 26

```
ggggcttttt cacaatgcag gcaccaacga caaagccaaa aagagatcca atccactctg      60
tccaagtttt tggcagaaag aaatcagcta cagccgtagc ttattgcaaa agaggtagag     120
gagtcttgag ggtaaatggc agacctctca gccaagtgga gcctaaaatg ctccaagaca     180
aacttcaaga acccattctt cttccttgga aggacaaatt ctctgctgtt gacatcagag     240
ttagagtaaa tggtggtgga catgtttccc aaatttatgc tattagacaa gctatctcaa     300
```

```
aggctttggt agcttattac caaaaatatg ttgatgaagc atcaaagaag gaattgaagg    360
atatccttat ccaatatgac cgtaccttgt tggtagccga tcccagacgc tgcgaaccca    420
agaaattcgg tggtccaggt gctcgtgccc gctaccaaaa atcttaccgt taagttcttt    480
tttagattta atgttgtgtt tcttgtatgt attaagatat caacaataaa cacaattttt    540
tcccgcaaaa aaaaaaaaaa aaaaaaaaaa aaaaaa                              576

<210> SEQ ID NO 27
<211> LENGTH: 1118
<212> TYPE: DNA
<213> ORGANISM: Diabrotica virgifera virgifera

<400> SEQUENCE: 27
ggggcaccaa ttaatccttt ttaattagta cgtgtatacc tataagaaaa atcaataaaa     60
tacatattcg atagttcgct gctgaagtga caggcaaaga gaaaatgaag gtgattcttt    120
gtttactggg ggttgttacc ttagtactga gcactcccgt gtaccaggaa gacttacaga    180
aatattatcc tcaaggatca attccatgcc cattcttcaa gaaagacgcc agttttaatg    240
catcttccga tgatattaaa gtttatttta gaaacaaaga tcatcctgag agttcagtac    300
caatagacat taacgatagt tcggaagtcg atgcgttggg atttcacca  aataaagata    360 caatgtttgt tgtccacggc tggcacaacg tcacgactc  gccagtctgc gatgagatat    420
ccaaagctgt cctccagaac gacgacataa acgtttttcct aatcgattgg aacaaaatcg    480
ccagcaacct ctacttagta gcttacaaag cagttccagg ggtcggtcaa ttactaggaa    540
cactcattag aaatttggtc aacaacaata aattggattt gaataaagct tctatcgttg    600
gccattcttt gggagctcat gtcgctggat tggccggagc tgaactcaac ggacgggtta    660
gtaacattgt aggtctggac cctgctctac catgcttctc atacaacgat atcagtacaa    720
gattggaccc ctccgatgca caatacgtcg aggtaataca cacatgcgca ggtttactcg    780
gttttgatgt agatattgga cactcagatt attaccctaa tggcggaaaa gatcaacccg    840
gttgcacttt ggatgttgta ggaatgtgca gacacagtag atcatattac tactatgcgg    900
aatctttaat tagtggagga tttgctgcaa acaatgtaa  ttgctacaaa gattttaaca    960
acaatcaatg taatggagga acatccaata tgggagaata atatatcaac aaaagtgcca   1020
aaggcggata ctacctcaac acaaatagtc agtcaccata tgcccaacat tgatataaat   1080
gtataataga aaaaaaaaaa aaaaaaaaaa aaaaaaaa                           1118

<210> SEQ ID NO 28
<211> LENGTH: 955
<212> TYPE: DNA
<213> ORGANISM: Diabrotica virgifera virgifera

<400> SEQUENCE: 28
ggggattaca aactgaactc aacaacctct tttcatcttc gacccgtttg ccggcgttag     60
cttgtaaaac atttctgtta aaatcacgaa ccatccgtta aaagaaatgg cagatgaata    120 ttttttttgct ttaaccctca aaggtaaaaa cagtgaaatc tgggatccag aagcgaaggg    180
agcagaggat taccaagggg gacacaaatt gatcattaaa caagctttgt tgggacccga    240
agcccaagaa ggtgaagtaa atgttgtaca agtagaagct atgacgtgga aagactcagt    300
taaaatccca attgccacac taaaagccgg aggcccaaat aaccaagtat tgttagatct    360
gtcattccca gacccaccag tcacattttc acttatacaa ggtaatggac cagttcacat    420
tgtaggccat catttaattg gtagtccgat ggaagaattc gatgaaatgg atgaattaga    480
```

```
agaggaaatg ttggatgatg aagaagggga agaaggagcc gaggaagatg aggatgaaga      540
tgaacccaaa gccaaaaaag caaaatcagc gactaacgcc aagggcaaaa ctcccgtaaa      600
aaacaattca aaggctgcaa agaaataaac aagttcatct aatccccaaa ccacctcctt      660
tgtaatgtta agttagtttt ttaatgtatc tcgggagttg ttatacatcc attaacagat      720
caaccgtaac aatttctctt aaatataagt ataatatttt atgtttcttg acgtcataag      780
attttgtgaa agtttctttt attccaggtg taactcttag ttttaatgtg atcaatattt      840
ttaagctgga aacgtattta tttcctttga aatcatccaa ttttgttgta aatatgcagc      900
cctcattaaa ccattttttg tagcaaaaaa aaaaaaaaaa aaaaaaaaaa aaaaa           955
```

<210> SEQ ID NO 29
<211> LENGTH: 422
<212> TYPE: DNA
<213> ORGANISM: Diabrotica virgifera virgifera

<400> SEQUENCE: 29

```
gggggaaata tatactacaa tgaagttttt aagatcgaca gtgtgctaca ttgccatctt       60
ggcaattctc tttaccctct gtgccgatga ggttgaagga aggagaaaaa ttttgatggg      120
gcgaaaaagc attaccagga catatcttcg tggaaatgct gttcctgcgt atgtgataat      180
aatccttgta ggaattggtc aactcatcct gggaggata ttgtacgttg cattgaggaa       240
gaagatcatt gctgcacctg taacggcatc atatgcagtg gctagacaag aaccataaat      300
tttatttgtc tagaatatta ttttctaaat atgcatcttt tttaaattat tgtctacgta      360
aataataagt ctagaaatat ataaaaattg tcaaaaaaaa aaaaaaaaaa aaaaaaaaa       420 aa                                                                    422
```

<210> SEQ ID NO 30
<211> LENGTH: 2911
<212> TYPE: DNA
<213> ORGANISM: Diabrotica virgifera virgifera

<400> SEQUENCE: 30

```
gggggtgcga agctaccatc cgtgggatta tgcctgaacg cctctaaggc cgatccttt       60 ggcttgaaga gttttcagca agaggtgtca gaaaagttac cacagggata actggcttgt     120
ggcggccaag cgttcatagc gacgtcgctt tttgatcctt cgatgtcggc tcttcctatc     180
attgcgaagc agaattcgcc aagcgttgga ttgttcaccc atagacaggg aacgtgagct     240
gggtttagac cgtcgtgaga caggttagtt ttaccctact gatgactcgt cgttgcgata     300
gtaatcctgc tcagtacgag aggaaccgca ggttcggaca tttggttgac gcacttactc     360
gagcgggtaa tggtgcgaag ctaccatccg tgggattatg cctgaacgcc tcctcaaagt     420
cacaagatga gtgtaacgcc acctacagat ctacacaaga agaagaacc acgatagcat      480 cgacagacag tggtaatggc cgacgaccgc gacgagggaa tttaaaata cgaaatgttg      540 taaaaggaga ggcaccaaaa agaagagtag atggttcgaa aaatcaatga aaagctagtt     600
gaacgttcag tttctttaa aaagaaagt tttgtagatt tgaaacaac accgcacaca       660 tcttatgaa aatgtaatgt cactcaagtg caattgaatt tgcctgaata tattggtctc      720
gaagttacaa tcatttcagg tcgttgcgcc aactctgaat ttttattaat aacggtgcat     780
attgatataa ataaaacata aaactaaaat caaatgggta tgagtgagaa agaatgtga      840 atcggcagtt cataaatctt tctgaaagta ttaaggtctc ttatcttata gataaatgac     900
```

-continued

| | | |
|---|---|---|
| aaagcacttc tagtgatgca ccgcaaaata aaggtcaacc tcacgctcgg gtaacctgtt | 960 |
| ttcaatagcg actagactaa tagtatttgt aaataggaca gttttatgga cttcaaaatg | 1020 |
| tgattctaca atttacgcgg atattaatca aaattcggag ttggcgcagt gatgtgagat | 1080 |
| tattgtaatt tctaaacgaa tctatttatg taaattttat tgtgtttgag tgacattaca | 1140 |
| tcaaccataa gatgtgtgtg gggccctttt ggcgaattt gccataaaaa aattaatttg | 1200 |
| gaggcttttt aactagctcc aagagttgta cagaaagata tgccgctatt aatattgttt | 1260 |
| cgcaacaaat agatcatttt gattacttaa aaaagtaca atgaatcata ctaagttatt | 1320 |
| ttttgttgta ctatccgttg caagataatt tggatagtaa atttaaacta attcaactaa | 1380 |
| atatattaaa attttcgttc catctacttc cattttcttt tattttttt tataacgagt | 1440 |
| ggatcaacaa aatgagcatt tttttatatt ttaattgtga tttgaaagtg tattttaagt | 1500 |
| gggagatgat gatgttcgag tctattaact gtacgttact tatcacaatc tattttgtat | 1560 |
| ggattttcat acaagaact ttagtttgtt gattattatt taataaacta cattttattt | 1620 |
| aaaatgtact gtttaacgaa tcatgtaacg atcacgctcc tgcgcagtaa acaaaatatg | 1680 |
| ttccaacaaa cagatgatcg ttcatcgcat cgtccttcca attgttccaa caaaaattgt | 1740 |
| gatcgtccaa tgacagtgtt gcgacgatca ttttagtact ctgatactat aaaaattgtg | 1800 |
| tgttggaaga aacctaatgt aactgcgcca ttttgaactc agatgtttct taggtatgcc | 1860 |
| cagggtagta gttcccttaa agaaaaaaaa gtgggaaaat gtttaggttt ctatttatta | 1920 |
| acaaatcaca tattggatgg acagtctgca tctttttttg tcagtataga taaaaaatcc | 1980 |
| tgttcttata atgctaactt gattatcaaa cgactgctaa gccttagatt gaagcctcat | 2040 |
| acgcaccaaa ctgcctaatt tagatacaaa attagccaaa ctaaatcttc gaatacccaa | 2100 |
| aacacttaaa ttattgccat ccatatgtct agtgtgtaaa gacaaccaga aaaacctgat | 2160 |
| tactgatact aggagtgtaa aatataagct gagggccctg acatctgacg agttgatgaa | 2220 |
| gaatatatct tcctatagaa actgttaaaa aaacggtaat attaaatgcg aaacacggag | 2280 |
| ctacgatgag aagaaaaaat ttggtcctct aaccactaca agaaaggtcc aaaggtgttg | 2340 |
| taatatttga tcttatacag tataactcat gatcaaacaa cgtagagagc aaatatgaga | 2400 |
| acatcaaatg tatgttaata ttccgttggg gtgagttgac ggaattaatt aaaaataagt | 2460 |
| gtaacgacga acagtaatat atttatttat tttgggtgaa caagcggcgt gttttgctta | 2520 |
| tatctcgaaa gagggttgat tgttagcgaa ccgaggattt gtctgcatcg tttgcgtgct | 2580 |
| gtgtagagac tggcctccgg accaccacct ttatgtcaac tagttttgcg gttttgagat | 2640 |
| aatgaccaga aagggccata cattctgcat ctccttttaa gaaccttttt gtattttaag | 2700 |
| aagttgacat aacgagtgtg gcactctggg catcgcaatc tattagtgtt tccttgaatg | 2760 |
| aaacattaat cacaatctgt ttaaaggata acatttcgtt tctcgaaatc aacggcatat | 2820 |
| ggtttgtata tcacatgtgg atttaaatg accaatgccg tttcattttg agaaaagcca | 2880 |
| tgaaaaaaaa aaaaaaaaaa aaaaaaaaaa a | 2911 |

<210> SEQ ID NO 31
<211> LENGTH: 1287
<212> TYPE: DNA
<213> ORGANISM: Diabrotica virgifera virgifera

<400> SEQUENCE: 31

| | |
|---|---|
| gggagacaag aggcagctac tattaacgat acatcgctct ctcgttagtg ttcatatttt | 60 |
| acgtgtagtg taacagaaag tgcagttttt tattcaccat gtctaaccgc aacatcccta | 120 |

```
tcaaaatggg tgacttcagt gttatcgaca cggagtttag cagcatcagg gaaaggttcg      180
acgccgaaat gaggaaaatg gaagaagaaa tgaacaaatt cagatctgaa cttaccagta      240
gggaagcgaa caacttcttc agaagcacaa ccagcatgtc gtacgaatct gaaacggtga      300
ctggtggaaa taagtcttca tcgacgtcca gttcaacgac acagcaaagc agcacaggat      360
cagatttagc ccacagagca ccaagtggtg atgtcagaac atggtacgac gacctcaact      420
ctcccctaat ccaacaggac ggtaacgaaa agagcctaaa attaagattc gacgttagtc      480
agtatgctcc agaagaaatt gtagtcaaaa ctgttgataa taaactcttg gttcacgccg      540
agcacgaaga gaaaacagaa tcaaaatccg tatacagaga atacaatagg gaattcttgc      600
tgcctaaagg aacaaatccc gaacacatca agagctcatt aagtaaagat ggcgtcctca      660
ctgtcgaagc acctctccca gctatcacct cagggggaaaa attaattcca atccaacatt      720
aagtaattta aaattccttg taagccttcg aagcgtttat gtccgctagt aaatactcat      780
cgattaatta tttaaaatgt aacaactcat gtgactaaca aaattttttat tttatttcat      840 ttttaaaacc tggcaacgtt gtctggcttg tttaggataa gtcacaaatt tagtgttggc      900
tctaaagtac ttactgtcta cacagcacaa gtcacaaatc gttaaataca ccataaaacct      960 catgcatcgt tgccggatgg ttcaaaagct catactattt gtgactatct tcttgatggc     1020
ggtcgtaaac ttgaaggttg attaacatcc tttcacaaag cttaattatg caatgaaaat     1080 aattttttaac aactttatttt gtgacaaaaa aattgaagct aatgtaaaat tgtttggtta     1140
aattcttgtg aaggtctatg gttcgatgtt caataaccag caatttcacc gtaggcgtag     1200
tgtaacaaat tgtatcatgt gtaggatatt tacgaataaa ttatttttaa tctcgttaaa     1260
aaaaaaaaaa aaaaaaaaaa aaaaaaaa                                        1287
```

<210> SEQ ID NO 32
<211> LENGTH: 560
<212> TYPE: DNA
<213> ORGANISM: Diabrotica virgifera virgifera

<400> SEQUENCE: 32

```
gggatcacgt gaataaatta caatatttct tcaaaatccc ttgacgcatc cccttgtaca       60
caatactgat aacatggtat tcggtataga tgttatcggt attgtggaca ggggcgcgcg      120
ttaaggtatt ttgaagaaat attgtgattt attcacgtga tcactccgtc tgttaggtag      180
acggagttat tttatgttcg taacaggtag tctgtatttc ttttaaggca aatatttggt      240
ccgtcgttga tctattgttt ctaaaacctg cctggtattc tcccaatact ttttccgaat      300
attgatttag cctttttctt atacagtatg cggcaaaata aacagtacct actgaaatga      360
atattgaaat gtttatgatg atttatatat ctagtataca tgatatagcc ttgcaaactt      420
tattcacgac gacgcatgtt cccgataaac agatgttaaa gatgtcctct ggtcagtgac      480
ggatctacgg ggagggaaaa tgagaaaatt ttttccccta acaaggttca aaaaaaaaaa      540 aaaaaaaaa aaaaaaaaa                                                    560
```

<210> SEQ ID NO 33
<211> LENGTH: 807
<212> TYPE: DNA
<213> ORGANISM: Diabrotica virgifera virgifera

<400> SEQUENCE: 33

```
gggggacagt tcaatatgga tccactactt tactggttca tatttgttac gttaatatgt       60
```

| | |
|---|---|
| acgctaggta ttctaggaag ttacttaatg ttttctataa taagagatag ctgttttaag | 120 |
| agaaagaaac aaaaagatac tgtgatggta atatatgaac cagattttca tccagcatgt | 180 |
| ctgagtaagt tacagtatga taaacatgat gttgaagatt taacgagaat cgaaagaaat | 240 |
| tccaagacgg ggtttagaag actaagtttt caaaatgaag tatttggtaa gcagtttgaa | 300 |
| ggattattgg gtgagaaaag acaatctgtt gacaaggaaa gtgatgtgtt tgtatctacc | 360 |
| aacactcttg acaaaagcat tacatcaatt acagaagaag atgaagaatc agacgatagt | 420 |
| tttgatcgag atactgtcag cgtagacatt gaagtatcag acgaggtaag agaagtttta | 480 |
| agaaccgaaa aagaagctaa gaaggtcgag aaagaaatga acaggtttgc aggtggtaca | 540 |
| aacgatttac aatattacga aatcaatgag aagtatataa aattaatgat ttctctttgt | 600 |
| gatatggaat gcagctccat cgagtgcaga aaacacaaaa acagagtttt aagttacatc | 660 |
| gagcaatgtc agaaccaact caaattaaaa tctctgaagt ctaaataatt attttattt | 720 |
| gcttggagat gtaattatta taaatatatt ttaaatataa gtttagtata aacagccaaa | 780 |
| aaaaaaaaaa aaaaaaaaaa aaaaaaa | 807 |

<210> SEQ ID NO 34
<211> LENGTH: 981
<212> TYPE: DNA
<213> ORGANISM: Diabrotica virgifera virgifera

<400> SEQUENCE: 34

| | |
|---|---|
| ggggattcta aacttttcga actaacaaac aagatggcaa ccaaatttt agttctcgcc | 60 |
| gcattcattg cagtagctaa agccggttct tatggatcag gtttcggcta cgccgcgcca | 120 |
| gctgttgtcg ctcacggatc tcacgatgcc atctctacct actccactgt gcaacatcat | 180 |
| gctccagccg tacactccta tgctgctcac gctcccctcg ttcatgctcc agttgcccat | 240 |
| tcctacgcag ctcctttggt tcaagctcca gtcgctcacg cttacgctgc tcccgttgct | 300 |
| cacgttcacg ctgaaccctc tgcaccagcc cattacgact tcgcatatgg agtaagtgac | 360 |
| ccccacaccg gagatgctaa gagccaacac gaatctcgtc gtggagatgt tgttcacgga | 420 |
| agctactccc tcgtagaatc cgatggaacc aaacgtaccg tagactacac tgctgatcca | 480 |
| caccatggat ttaatgctgt tgtacacaaa gaacctaccg tacatgctgt tgctccagtt | 540 |
| gttgccaaaa tcgtagtccc agtagcacat gctgctccag tagctcatgc tgcttatgct | 600 |
| gctccagcgg ttcatgccgc ttactctgct ccagcagttc atgctgctta ctctgctcca | 660 |
| gcagttcatg ccgcttactc tgctccagtt gtccatgctg cccacgctgc cccagttgcc | 720 |
| catgctgctt atgctggtcc agttgcccac gccgcttatg cagcaccagc tctacatgga | 780 |
| tacgctggct ctgttgctca tggttacgct gctccttttgg ctcatggtca tcatgcttat | 840 |
| gctgctcatg ctccagtcct ttcacataac ttgtggtaat tctagaaagg aaaaattgta | 900 |
| gattttgtat ataaattatt tatactgctt gcattacaat aaaagattgt ggaaaaaaaa | 960 |
| aaaaaaaaaa aaaaaaaaa a | 981 |

<210> SEQ ID NO 35
<211> LENGTH: 1160
<212> TYPE: DNA
<213> ORGANISM: Diabrotica virgifera virgifera

<400> SEQUENCE: 35

| | |
|---|---|
| ggggagtaaaa ttaaactgca gtgattaaca atgaaagttg ttattatttt cgcttttatc | 60 |
| tgcaatattg catttgtagc tcatgtttac ccggaatact aaaacaata tcgctgcaag | 120 |

```
gcatcttcgg aaaattatag tgaatgcttt ctaaataagc tcagaaatac tctgccctac    180
tacgttaaag gcattcctga attagatata cctccatttg atccgtttac actacctata    240
tacagtcgca atgtaaacat attgggaaac aagattagtg cgactttcaa aaattcgatt    300
gtaactggac taaggaactc tattattcat aatgctaagg ttgatctgaa taacaactat    360
gcagaaataa gcgttactat tccttggttg gatatggcca cagagtatga tatttctggt    420
gaattctttc aatacccact agatgtgaag ggtacttta aaggaaatat aactgacatt    480
caacttttct caaaatctac tctacaaact ttcaaaaata acggtgaaga ttattataaa    540
tttgataaaa taaccaaaa agtacaaatt ggaggaggcc atattgaaat aacaactaca    600
gataaagatc ttatgccgat agttcaaaca atacaagaat attttaatga gcatcccaga    660
ggcttcttta acttgatatt gccattcaca ttggaatacg cacaagacct actcagagaa    720
tttggcaatg aatatttagc caatcttcct gcttctgaat ggttaccgca gtaaacataa    780
atttgaaaaa aatagtagac ttagtagttt aaacaacata gttttttagt taaaaaaatt    840
gaccgtagta tttaaataat ataatgacaa taatgttgtt gatgatcagt tgagatatat    900
ctatccgcta ttctatggaa aattccagaa atgcaatgca ttttgaatta tgcccataag    960
tggagtaatt cgttctagca gcatatagcc tacatgttca aatggactga gacccgtatc   1020
ttctgttgac catagcaata catacatttc ctcgtagaac acttttttgt gattattatt   1080
tttactttgt gagtattttg tatatgtgaa ataaaaatat tatattttgc aaaaaaaaaa   1140
aaaaaaaaaa aaaaaaaaa                                                1160
```

`<210>` SEQ ID NO 36
`<211>` LENGTH: 721
`<212>` TYPE: DNA
`<213>` ORGANISM: Diabrotica virgifera virgifera

`<400>` SEQUENCE: 36

```
ggggtcactt taattgtcag taggaactga gtgctagttc aaggtagacg tacgttgacg     60
agcgtgtagc aaagttgttc gtttcggatt ttgttttcg taggtagatt aatatggatt    120
atagtaagac atggctggga ggcattaaaa aatgcagctt ctgtgcatgt cttccagaaa    180
aatatagcaa tgaatgggtt aaaggcgcct cacgcttctc tgagttacct aggacattct    240
tggtattaat ttttctattt tgcttcaagt aatattgtcc tcatggctta gtggcgggaa    300
gcaagatcat attagtcgcc gtttcgcaaa atgaagcata tttcataaat atctgtgggt    360
ataaagtatt ctccaagcga agctccagaa tgctgcagaa tgcaggagct ttatagccaa    420
gtctgaagtg aatacagagc aatatcatta ataagtcatg ttcttaaatt atttctaaaa    480
attataaaaa ctgtcagagt gatgatgata gccaacttgg atttagaaag gaattaggaa    540
taaaagatgc attatttact tttaatgtga taactcaaaa atgcatggat tatgtttgtg    600
aatctgcatg tttgttactt taatttttaa attgtatttt ttttttaaatt ttaaaaagca    660 tttgacaaag taagacatga aatattagtc caaaaaaaaa aaaaaaaaa aaaaaaaaaa    720 a                                                                    721
```

`<210>` SEQ ID NO 37
`<211>` LENGTH: 928
`<212>` TYPE: DNA
`<213>` ORGANISM: Diabrotica virgifera virgifera

`<400>` SEQUENCE: 37

```
ggggtttagt atgtcttaga gcattatggt tactcttcca atcattggat gatcgttctc    60
caatgcggta tcctgtatat taccacttaa tacaaattgc gaaacagaca gaatctgtaa   120
aattagtgtt tcaagatatc aaccatctaa agcaacagtt tgccaattgc cttccgtcta   180
atgaacagct tcaaaagctt tataggcttt tacatgaagt actggttaaa tcaaatcaaa   240
gtgagcaggc tgctttagtg atgattgaac ttcttggtac atacactgac aaaaatgctt   300
ctcatgccag agaagacgcc atccgttgca ttgtatcagc actagctgat cccaacacat   360
tccttcttga tccattgtta tcactaaaac ctgtcagatt tttggagggt gatttaatac   420
atgaccttt aaacatcttt gttagtgaaa atttgtccac ctacctcaag ttttacaatg   480
aacataagga atttgtgagt gcacaaggtt taaatcatga acagaatatg caaaaaatga   540
gactgctttc cttcatgcag cttgctgaga gtaatcctga aatatctttt gatgtcatcg   600
aaaaggagtt acagatgaaa ccagacgaag ttgaaagctt tattattgaa gtattaaaaa   660
ccaagttagt tcgtgcaaga atggatcaat cttcccggaa agtctttgtg tccagcacaa   720
tgcacaggac tttcggaagg gcacaatggc aacaactgcg ggacttactg cactcttgga   780
ggggaaatat aagttctgtt caagacggta tgaagactat cgccgctgct cagctagaac   840
ttatgaacca caacagtaa tgataatgaa gttttcataa cttttaataa aacgttgaaa   900
aaaaaaaaa aaaaaaaaa aaaaaaa                                         928
```

<210> SEQ ID NO 38
<211> LENGTH: 1339
<212> TYPE: DNA
<213> ORGANISM: Diabrotica virgifera virgifera

<400> SEQUENCE: 38

```
ggggaatata attaattcaa taattagaat tagaaatatc tcgttggaac agttgtagat    60
attcataatg gagagtaact tgggttatca aaatgggagt caaagtagag aacaagactt   120
tcaaaaactg tcgcagacca tcggtaccag catacagaaa atatcacaaa atgtgtcttc   180
tatgcagcgg atggtcaatc aaataggaac ccatcaagat tcgcctgaat tgagaaagca   240
attcattcc attcaacact acacccagca gttagtaaag gacacaaatg gatacatcaa   300
agaccttagc catattccac catctctatc acaatccgag cagagacaaa ggaaaatgca   360
gagggagagg cttcaagatg agtacaccag tgcattgaat ttgtttcaaa acgtccagag   420
aagtacagca tacaaagaaa aggagcaggt caataaggct aaggcccagg tgtatggaga   480
accccattta attggatata agtccaagga ccaacaactc atagaactgc aagacaataa   540
ttcgaggcaa atgcaaatgc aagaggagtc aaatctaagg gaattagaag aacaggaaca   600
gtcaataaga cagttggaga gcgacatcaa cgatgtcaac ctaattttca agaattagg    660
aacccttgtg cacgaacagg gcgaagtgat agacagtatc gaggccaacg tggaaagaac   720
caccgacttc gtcagccaag gtgcccaaca actccgcgaa gctagtacgt tgaaaaacaa   780
agtaagaaga aagaagctga tcatgttgat gatcgctgct ctagttttaa ctatactcat   840
aataataatc gttgtatccg tgaaacgtta aaatagtatt atggtaatga tattaaaaat   900
gtgatgattt aaatgattgt ggtaagtaga taggaaatat tcatgaacta cacatcctta   960
cttattattt tatcttattt ggtgaagctc ccagttcctt aaccctttc ttggcaaacc  1020
gatataaaac tgtgaaaact ctgtttctt tatattcatg cccttctaga attatttaaa  1080
aatttatgaa ataatatttt ccctttaat ttattcctaa gtaccaaatt tgaatgtgtt  1140
acaaatttgt tacgttgcca agaataccat accccttatt accactgatg gtccatgcat  1200
```

```
tttctaaggt tgaaccgat ttctcagaac aaagttaaaa tttcttttat ctgagttcat    1260
gggagtgctc tcgcgtcaca acaccccct atccccatta aatttttagga aaaaaaaaa    1320 aaaaaaaaaa aaaaaaaaa                                                1339
```

<210> SEQ ID NO 39
<211> LENGTH: 533
<212> TYPE: DNA
<213> ORGANISM: Diabrotica virgifera virgifera

<400> SEQUENCE: 39

```
ggggctttta tttccgcttg atagtcaaga aaggtgtca agatgacatg taaaaggcgc      60
aatggagggc gctccaagca cggccgtggt cacgtaaagc cagttcgatg caccaactgt    120
gctagatgcg ttcccaagga taaggcaatc aagaagttcg tcatcagaaa cattgttgaa    180
gccgccgctg tgagagatat tactgaggca tcagtatatc aagcttacgt tctccccaag    240
ctctatgcga agctccacta ctgtgtatcc tgcgctatcc acagcaaagt tgtgcgtaat    300
agaagcaaaa aggataggag agtcagaact cctccacaga gaaacttccc tggtagggac    360
aatgctagag ttcagcaaca acaacctagg aagtaaactg tttctttagt tttacaataa    420
aatttaagaa aaaataaaaa aaaaaaaaaa aaaaaaaaaa aaaaaaaaaa aaaaaaaaaa    480
aaaaaaaaaa aaaaaaaaaa aagggaaaaa aaaaaaaaaa aaaaaaaaaa aaa           533
```

<210> SEQ ID NO 40
<211> LENGTH: 535
<212> TYPE: DNA
<213> ORGANISM: Diabrotica virgifera virgifera

<400> SEQUENCE: 40

```
ggggcttttt cagcagttgt caaagcactg ccacaatggg taaaataatg aaatcaggaa     60
aagtcgtatt ggtcctcggg ggccgatacg ccggcagaaa agccgtagtc gtcaaaacct    120
acgatgaagg tacatcagat aaacaatacg gacatgcctt agtagctgga attgataggt    180
acccaaggaa aatccacaaa cgcatgggca aaggcaaaat gcacaagagg tccaagatca    240 agcctttat caaagtattg aactacaacc atctcatgcc cactagatac tctgtagatt    300
tggcatcaga cttgaaagtt gtacccaagg acctcaaaga tgccatgaag aggaagaagg    360
ctagattcca gacccgtgtc aaatttgagg aaaggtataa gcaaggaaag aacaaatggt    420
tcttccaaaa attgaggttc taggctgtag atttaatttt ataattgtac acttttttatt    480 ttgagaataa aatgtggata aatgcaaaaa aaaaaaaaaa aaaaaaaaaa aaaaa          535
```

<210> SEQ ID NO 41
<211> LENGTH: 788
<212> TYPE: DNA
<213> ORGANISM: Diabrotica virgifera virgifera

<400> SEQUENCE: 41

```
ggggaactgt caaatataac cttaaataat atttatttac gtgtgtgtct tgtttccata     60
gttttagctt tttttcttt aatttaaaaa gatgagtgac gatagtgata actttgaata    120
tgtagacgat gagatagatg ataaaaactca caataaaacta gtggataacg ttttttaaagt   180 taaataaagt tcaacatgtc aaaagtgcac atagaactga agctgccact aaagtgtctg    240
aatttaatct agtaaaatcc ctttcgaata aaaatttagt gcatgttaat gaattaacga    300
gcgttttaaa gggaaggaag tctcttcagc tgtctaataa aattaaatct acaagtaata    360
```

| | |
|---|---|
| tcagcaagac attgcctaaa cctctagaaa agccacaagc tgaacgtatt aaacgagctt | 420 |
| taaactatga gaaagcgaaa ttaaaattgg atagatggga agctcttgtt caggctaata | 480 |
| gatcagctgc acaattatcg ttcccttta aatagtgatga gaaagtaaag gtcattgaga | 540 |
| aacgggccat atcttacccc ttatctttca gagttaaatc ggaccttcag aaaaatttgg | 600 |
| aaaatataga ttcacaaata gaagagtatc acatagatac agtagaaaag aagaagatg | 660 |
| aagactatcc acttcactta gaagaattaa aggaaaaaaa agaaaagaac tagccaaact | 720 |
| tcgtgcacac cagagtttta agaagcaaa agctagacaa aaaaaaaaaa aaaaaaaaa | 780 |
| aaaaaaaa | 788 |

<210> SEQ ID NO 42
<211> LENGTH: 444
<212> TYPE: DNA
<213> ORGANISM: Diabrotica virgifera virgifera

<400> SEQUENCE: 42

| | |
|---|---|
| ggggaacgaa gtggccattt cttacagata attccacatg ccaaccattc ataagataaa | 60 |
| gcaaggcatc gtcgtgttct tgttgaaact ctagtagtcg gtatgggccc actatccaat | 120 |
| ttccaataat tctaatccaa ccagtaactt tttgtgacac ttctgtatga tctccttgaa | 180 |
| tataatcagg gttgttaaca acgcaactga atatttccgt agagggcgct tcaaaaatcc | 240 |
| gtagaaatcc gtagtacaaa aatctgacag aaaatgacac ttggcagacc aaaaaaagaa | 300 |
| gaagaatgac acttgacata caaaaaaaga agaagaatga cacttgacag accaaaaaaa | 360 |
| gaagaataat gacacttgac agaccaaaaa gaagaagaat ggcacttgac acaccaaaaa | 420 |
| aaaaaaaaaa aaaaaaaaaa aaaa | 444 |

<210> SEQ ID NO 43
<211> LENGTH: 472
<212> TYPE: DNA
<213> ORGANISM: Diabrotica virgifera virgifera

<400> SEQUENCE: 43

| | |
|---|---|
| gaggtttaca tattttcaag ttgtccaaaa atatccacat gtcttcgagg taattgagat | 60 |
| ggtagtccag acctttaaaa catttttaaa ttcatttggg tgacatatat atattggtgg | 120 |
| aattgaatat gtcaaattta tttattactt caatagtata taagtcttgc agctgttacg | 180 |
| tttaaaattt gagtagctta cttaactgtc gtatttgaaa agtgtgttgg tcgaatatgc | 240 |
| gcctcgttag ttatttctag ttgctttttg taaatttgga ggatcaaaaa ataaataagc | 300 |
| ttatgattaa ttgtttatat gggaggtggg ccgcagttga aatgaaaaaa aataatttta | 360 |
| ttaacgtttc gacgcccaaa tcgggtgccg ttgtcaaaat acaaatatt attaaaataa | 420 |
| acaaaagtgt tgttgctaag cgaaaaaaaa aaaaaaaaaa aaaaaaaaaa aa | 472 |

<210> SEQ ID NO 44
<211> LENGTH: 497
<212> TYPE: DNA
<213> ORGANISM: Diabrotica virgifera virgifera

<400> SEQUENCE: 44

| | |
|---|---|
| ggggcttatt cacaattatt aaaataataa atggatatga ccaattatca gtaagtgaaa | 60 |
| cagaattcat tggtataaat ttcatatctg taatccgtct acccgtaaag gaaaccagaa | 120 |
| ccaatagtat taatttattt tctgaaatac agggcatgcc tttgtttaca taatatttgc | 180 |
| atactaaacct ttgaaacgtt attcctgaag atctacattt gcttctgctg ctccaactgc | 240 |

```
gttgaggaca ggacagacac attttatgca atatgttaat aatactataa aagtatccga    300
attaaaaaaa atattcttaa aaagcacaaa taaaacaaac aacgatcacg ccacacacga    360
caaggccggg caaggtggcc aagatgccaa gatggccgaa gtgaggtcgt tcgttggtcg    420
tttttagtca cgtgatgcca tcgtgatgcc ctctctaagc ggcatgcgaa aaaaaaaaa    480
aaaaaaaaaa aaaaaaa                                                  497
```

<210> SEQ ID NO 45
<211> LENGTH: 809
<212> TYPE: DNA
<213> ORGANISM: Diabrotica virgifera virgifera

<400> SEQUENCE: 45

```
ggggaagtaa ttctgctaaa aattttacac tcctttggat tggaggaaga attacaattt     60
tcattattaa atatctattt gaaataaaat aacaattgca caaggtgtag taaaaaggtg    120
ggtcatgaat aaaataaaat attctgggaa taaaaatagt tccattgaac ctaagttacc    180
ttagtacaaa ggtgcacata aaaaagtta taactctttg agcttataaa ataaaaatcg    240
agaatatcga aaaatattag aggttaaaat gggcatttga cattattatg gtaggaaaat    300
ctttaaaaaa atagtagtga aattttcaca gccgataaaa attttatagg ggctttattc    360
ccttaacctc cccccccccc aaaccttat gtacgttcca gttaaattat tatttagtcc    420
tggagggga tgtgtcacca acacgatatt ttttttcctt atttctctga actaattgtg    480
ataccattag ttaaacacaa tatttctaaa acttttttgc tgactatttt gtcgatgaac    540
cagttgttat atgcggcttt ttttcacatg ttatgagagg ttattaaaat tattgttaaa    600
ttatttatt gtagtttaaat gtgtaagcca gttcccacat tcaaacctgt cagaggtgag    660
ctaagatatt ggttggcgac aatgtttgtg gacatcaggg ccggttttgt ggttttgag    720
cgccccggc aaaataaaat ttgtcgccca ttcatacaag aatatacaaa tttactccga    780
aaaaaaaaaa aaaaaaaaa aaaaaaaa                                       809
```

<210> SEQ ID NO 46
<211> LENGTH: 1728
<212> TYPE: DNA
<213> ORGANISM: Diabrotica virgifera virgifera

<400> SEQUENCE: 46

```
ggggagtaaa gaataattcg gtgtttaccc ttattaagtg aagttttttt actacgaagt     60
gtactgtgtg ggagacaaaa aaaaacatga agaatctgtt gttcttgttt gggtttatca    120
gtatttatc agtattgcta gccgcagatg ttcgcctggt agacttagat ccaccagaag    180
ctcaacagca aatagaacaa caggaccagt ctcttcacta tgcgccaaaa gtagaatcaa    240
atgttcccgc agtaagatat ttgggaaacg aacctcacaa tgttctggaa gatatttact    300
tagctagaca gtatcacgga caagacggaa taggaggata cctttatgga tacaacatcc    360
cagatattgc caaaactgag aaaaaagttg ctggtggaga tttaagaggg gcgtacaatt    420
acattaatga tgatgggcc gaaatcaagg tcgaatattg ggacgatgga actggattcc    480
atcaaatcga taatgttcct aaaatcttac ccaagccaat tgaagagtct ccggaagtta    540
aagctgaaaa ggataagttt ctagcaagat ggcatgaaga ggccgagaga atcaacgtc    600
cagttgcttc cccctatgat gctgatggta attacgctag cggaccatta tcgctccagg    660
gacaagctga atttaagaaa atgtttgaaa atcaaccccc aaggtcagta ctaccaacaa    720
```

```
cctagctcta gttctggagt ttaccagcaa aacggacaat atcaacccgc tggacaatac      780
caacaaactg acaataccca acaaactgga cagtaccaac aacctggaca gtaccaacaa      840
cctggacagt atcatcaatc tggtcaaatt aaacaagttc aacaaccagg acccccttcaa    900 caaggtcaat attatcaatc atctaaatcg caatcttctg gtcagcacca acaacctggt     960
caataccaac caactgatca ataccaacaa actggtcaat accaacaacc aggtcaacaa    1020
gtttctgttc agcaattaac caatcctaat caaatcgatt acactggagc atacagtgaa    1080
agccaaaact cttacgcaaa cccaactcca acaaaccat ctggtcaata cacgccagtt     1140
gcttcaagct ccaaccagta cagccaacaa ggaggatatc aacagcctgg acaacaccaa    1200
caaggtgcat atcaacaaag tggaacaaat cagcaaccag gatcatacca acaaggtgca    1260
taccagcaga gtggagcaaa tcaacaacca ggatcatacc aacagggtgg tcaataccac    1320
caatctggac agtaccagcc ctccgataac tcaaaatcaa accaagttga taattccggt    1380
gattacgata aaagctggga caacgagggc caatatgata aaaatacga tgaagaagaa     1440 ggctccactg ggcccccaaa gggattcttc tataagtttg attaccctgt aggaaaaatt    1500
gttcagaaag gagaaatcgc tagagttgga gatctgaaaa atgcgtatag tcaaaataaa    1560
gctgcgtacg aatcccaagt aagttcaggc cactcgggtt cagctgcttc ccaaagcagt    1620
tactcatatg gttcttaact ttaagctgtg ataatgtatt ttatagattt ttaggagaat    1680
aaaaaatata ttactttcaa aaaaaaaaaa aaaaaaaaa aaaaaaaa                  1728

<210> SEQ ID NO 47
<211> LENGTH: 962
<212> TYPE: DNA
<213> ORGANISM: Diabrotica virgifera virgifera

<400> SEQUENCE: 47
gggacggttt tacgtgggaa cagcccaaaa cactacaact aaactgacaa ccttccgtaa      60
caatatttta gaaatctttt attgacgcac tagatgcctc cttctagatt ttaagtttag     120
aaaaaacttc tgtgattggc gctctgaacc ttgagaccga cgcgattttt tgcctctctg     180
aatcggaaac attctacaga gcaaagtatc gcgtactaac aagtaactgt cgcaaaacgt     240
gcccacagat tcccgatata gaccacagtg gcgtttcaag cgttactgca attcagtgtg     300
agtcaaacgt tcagtttcaa gttagatatt actcgcacat tgtgttgtgt ttaagagaaa     360
aaataatttg gaaagagca tttctataaa cactccggac tgtattggga atggtggtca     420
tccatgcatg aaaagttctt gcaaaaacaa tatttatata ttatgtattt tatacaactc     480
atcagtgttc actggttgta aattatattt tattctaatt ttttaaccta caactctaca     540
ttccttgtta ttttaaaata atcgtcaaat taacatagaa tttgcaagaa acatgtacaa     600
tgggcattta agatctgctg ccgtttgata tagaattccc ttagtgttaa ttttattgat     660
ttgattttgt aaactgtaga tgaataatta ttgtagatga tagtttgaat gtatagattt     720
tattgtacct atgtaattta ttatgagagg ataaaacgat ctatatgttg tatacaattg     780
atttaagtaa gtttggtaga tgtattgtcc aatgtagatc gtaaaatttg gtgtaatttt    840
ttatagcata gtttattttt taaataaccc aactgatact ctattgctct attcaaattg     900 tgctttttt gtctaagaaa taaaatagtt gtgaaaaaaa aaaaaaaaaa aaaaaaaaa      960 aa                                                                    962

<210> SEQ ID NO 48
<211> LENGTH: 1146
```

```
<212> TYPE: DNA
<213> ORGANISM: Diabrotica virgifera virgifera

<400> SEQUENCE: 48
ggggattggt gttcaagtca agtcaagttt gttgagtaaa atcaaactag tttgacttga      60
tgcatctcta atatctgcca taaattgaag gactccagta ttcaatccga atatgtttca     120
acgtaaatgt aaattctaca tgacaaaaac tcagttctta atagatggac acaacatttc     180
agcgaacatc taaatattaa cgatattgaa gaaggttaca acatagaaaa tcaacaaaat     240
ctacatcatc aactacacac tgaagaccca acaagagaag aagtatcaac tgccatccta     300
aaactcaaag acaataaagc cctgaatctg ttctgatctg tataaaaagg tggtgatcat     360
ttgcagcaat ccataaatta atagtactga tatggcagaa tgaactggat ccagaaaagg     420
gaataatacg tccgttgcat aaaaaaggtg atcaactgga ttgtaagaac tatataggca     480
ttactctact agcatctacg tataaaatct tcggcaatgt attgtttgaa agactgaaac     540
ttttcacaaa ggatattgtt ggtcaatatc aatgcggatt cactgctgga agtcaacta      600
tacatcaaat tcaagcacat agacagattc tagaaaagtc aatagaatat aacatagata     660
cccaccatct cttcgtcgac ttcaaagcag cctatgacag tgttaaaaga actgcattat     720
ataatgcaat gattgacttt gggatcccac cgaatttggt taagttgacc caactaacaa     780
tgcaaaatgt aagctcgtgc gttagaattc aaggagaaaa ctggacattc tttgacatta     840
ataatggtct aaggtctaag acaggggac gcgctggcgt gtctcctctt taatattcct      900
tggaaaggc agtgagaaaa ttaaatatta gaatgaatgg aagtattttt aatagatcga      960
cgcaaattct cgcattcgct gacgatatag ttatagtggg cagaagtgtg agagacatgg    1020
tgcagtattt taaaagactt gcggacgcgg caagtgaatt aggacttgtg atacacgagg    1080
aaaaaaacaa atatatgttg gtttctaaaa actcccgaaa aaaaaaaaaa aaaaaaaaa     1140
aaaaaa                                                               1146

<210> SEQ ID NO 49
<211> LENGTH: 630
<212> TYPE: DNA
<213> ORGANISM: Diabrotica virgifera virgifera

<400> SEQUENCE: 49
ggggagtcag tgttgcgatc gtccagcagt cttccaaaaa ttgacgtgtt ttctggaata      60
aacaatatgt gattgagtgc ttttttaacct taaaaatcaa aaagtttctt gtgatagtga    120
agtgaaatac ttaaaataat agacaatgtt tgcgaacgga caggtagtag gtgatggtac    180
ctgggacctt cgggttttg tcacagatct acaaacggag aggttgattc gcgtaaaagg      240
agatgtccac attggcggag tgatgttgag gctggtcgag gacctagaaa tttcaatgga    300
ttggtctgac catgcgcttt ggtggcccga taaaaatata tggctgacaa gaacaagatc    360
tactctcgac caatgcggag tccacgcaga tgccttactt cattttactc caatgcacaa    420
aattctcagg ctacaattac ccgatcttag gtatttggat atgcgggttg acttttcaat   480
caaaactttc tccgctgtag ctcaactttg caaagattta ggcttaaggc acccagaaga    540
attgtctctt tcgaagccac tggaacccaa tcatttaaaa tacaattata aagacctgcc    600
aaaaaaaaaa aaaaaaaaaa aaaaaaaaaa                                     630

<210> SEQ ID NO 50
<211> LENGTH: 293
<212> TYPE: DNA
```

<213> ORGANISM: Diabrotica virgifera virgifera

<400> SEQUENCE: 50

| | | | | | |
|---|---|---|---|---|---|
| attggtcaac | agaaaactaa | tagaagaaga | taacttaaca | aatttaattt | ataaaatacc | 60 |
| tagggtaaat | ttagtgggcg | caaacaaacg | gacattggca | actataaatg | aaggcatacg | 120 |
| agtaatggta | cgactgggca | agaatatgta | tgcactacaa | tgtgtaataa | tgccaaacat | 180 |
| gtcacatgac | atgatagtag | gagtggacga | attggcagaa | aaacatgtag | tggtagattt | 240 |
| taaaaataat | acgatgaaac | taacagaaaa | aaaaaaaaaa | aaaaaaaaaa | aaa | 293 |

<210> SEQ ID NO 51
<211> LENGTH: 1508
<212> TYPE: DNA
<213> ORGANISM: Diabrotica virgifera virgifera

<400> SEQUENCE: 51

| | | | | | |
|---|---|---|---|---|---|
| gggtagcaga | gaagaggaaa | ttgtatctga | tgtggtttat | gaaaaaagtt | gacggtgtag | 60 |
| gggttgaaaa | tctcggttaa | atgacacatg | gcgattgaca | caattaggac | ttctctgctt | 120 |
| ctctttaact | atttctaagt | cttcatacag | gtccaatttt | aggaagtttt | tttgtgaaat | 180 |
| attatgtaat | aacgagacat | cttctgggat | attaagggta | tgtttgtttt | ttacaagatg | 240 |
| ttgagagaaa | gtagaagtgt | tttctctttt | ggtgtgctct | aaggagcgtg | aagataagga | 300 |
| tctacaggtc | ctacctatat | atgtagcgtc | acaatcagaa | cattgtaatc | tatacacacc | 360 |
| actacgatcc | atgtagttga | tagggtcttt | ggaattggta | agacactgtc | ccagattgtt | 420 |
| gggcactttg | aaagaaatat | gagtattatc | aactgctctt | ttaagaatat | atctaatgtc | 480 |
| tccagaaaga | cgttcatgaa | gatatggtaa | ggaagcatat | gagggtttga | aggtcaagtc | 540 |
| tctagggaaa | gcagtctctc | tcaagactct | aaggtgtctc | ttttgaataa | gtttgtagac | 600 |
| aatattagga | tcgtaaccgt | tgttaacgc | tatttgacga | agaatattaa | gttctttatc | 660 |
| atagtttgat | ggtgataaag | gaatagtttc | aagtcaggaa | tagaatcaaa | aataattagt | 720 |
| aatatgtagt | taacatctgc | acttgaaccg | ttttatcagt | aacatttatt | aacaccatgt | 780 |
| accgattcaa | gtacattttt | ttaataattg | aaaaaaagga | aggatatagt | aagagtaata | 840 |
| atatacccctt | atgttttat | caccttatag | taaattgtac | actagacaaa | ttttagttta | 900 |
| atgactccta | gaatttataa | aactcaaaca | actttgaagc | tgattatctc | agaactacca | 960 |
| aaactgcact | taaacgcttt | tacgtgtggc | cccctcaatt | gtaaaccaa | atgttaatg | 1020 |
| cgggctgaat | ccccgcgaca | aatgaatcag | aagatagtcc | attctttaaa | atttagagca | 1080 |
| aaaccgtga | aagaatggac | taagagctca | aagagtgcgg | caatcactcc | tttaggagtg | 1140 |
| tagatgccat | gatgatgatg | ataccttgta | taaggatt | taattatttt | tgtgattaat | 1200 |
| tgtacacagt | cgataaaaag | aaagagtata | aatgccttt | aaatatatta | aattttactt | 1260 |
| ttccatgaaa | ctttagtgtt | tcaatatcta | atcatgaaaa | gttcaagtgt | cttcaacaga | 1320 |
| atattaactt | tcagatttgt | aatagttttg | ggattaatta | ttgtattgga | gattcgaatt | 1380 |
| taataattct | tatccaccctt | accgttaccg | tccagtccgt | ctgctgctac | tcctattgtg | 1440 |
| ataaagtat | aaattggcaa | actttatttt | tcatctacaa | aaaaaaaaa | aaaaaaaaa | 1500 |
| aaaaaaaa | | | | | | 1508 |

<210> SEQ ID NO 52
<211> LENGTH: 631
<212> TYPE: DNA
<213> ORGANISM: Diabrotica virgifera virgifera

<400> SEQUENCE: 52

```
ggggaaaaag ttattttttg ataaatttcg aactgtattt gaaaattgat tctatataat    60
aaatacataa aaagattggt tttaaataaa aatggcacac aatattaaaa aactgagtgt   120
ttcaatgagt aaagcgggaa tgccatttcc agtacctaca aagattatta gatttgttag   180
gaaaggttgt actaatagac cctttttcca catagtagtt gcagatgcta gatcagatca   240
acacgaccct tcaatagaac aacttggaac tcatgatcct ttcccaaatg aacacaatga   300
aagattaaca tccttaaact tcgaaagaat tcgatattgg ttatcgcatg gagcgattgc   360
aacaaatcct gttcttgaat tattaggtct tgcaggattc tatcctattc accccaggag   420
ttatatgact gcttggagaa acagggaaaa ggcaaaacaa gcttctgaag ctgctgaaca   480
gaccaaagag gagaaaagtt aataacatgt catttacttc tgtgttgtgt gtacatttta   540
gtatgtttaa gtagctataa gtctattatt ttgtaaaaag tcattataaa catataaacg   600
caaaaaaaaa aaaaaaaaaa aaaaaaaaaa a                                  631
```

<210> SEQ ID NO 53
<211> LENGTH: 114
<212> TYPE: DNA
<213> ORGANISM: Diabrotica virgifera virgifera

<400> SEQUENCE: 53

```
ggggatttta taaatctgtt aaacaatgag ttggtcagca taagctccaa agtgttgtag    60
caatacagaa tgagtttaaa tatctaaaaa aaaaaaaaaa aaaaaaaaaa aaaa         114
```

<210> SEQ ID NO 54
<211> LENGTH: 597
<212> TYPE: DNA
<213> ORGANISM: Diabrotica virgifera virgifera

<400> SEQUENCE: 54

```
ggggtctttt ctcagtgaag ccatcttggc aaacgttagt aacgtgaaat aaaacttaaa    60
tttttcaaa atgggtcgta tgcacgcacc aggaaaaggt attgcccagt cggcattgcc   120
atacagaagg agtgtaccaa catggttgaa agtcacacca gaagaagtaa aagaccatat   180
ttttaaactt ggcaagaaag cttgactcc atcacaaatt ggtgttatcc tcagggattc   240
atatggtgtt gcccaagtaa ggtttgtttc tggaaacaaa atcttgcgta tcatgaaagc   300
tatgggtctt gcccctgatc taccagaaga tttgtactac cttatcaaga aggcagtagc   360
tatccgcaaa catttagaac gtaacagaaa agacaaggac agcaaattcc gtttgatttt   420
ggtagaatca cgtatccacc gtttggctag gtactacaaa accaagagcg tattggcacc   480
caactggaag tacgaatcaa gcacagcatc tgctttggtc gcttaaattg tgcttttatg   540
ttaagtttat aaaataaaaa tttctattaa aaaaaaaaa aaaaaaaaa aaaaaaa       597
```

<210> SEQ ID NO 55
<211> LENGTH: 543
<212> TYPE: DNA
<213> ORGANISM: Diabrotica virgifera virgifera

<400> SEQUENCE: 55

```
ggggcctttt taacgaaaaa tcgtgtgtaa aggtagcaca cgaataatca tcttttaatt    60
ttccctataa tccttttcagg atggcaatca gaccagttta ccgtcctcaa atcatcaaaa   120
agaggacaaa gaagttcatc aggcatcagt ccgatagata tggtaaactt aagagaaact   180
```

| | |
|---|---|
| ggcgtaaacc aaagggtatt gacaacagag tcagaaggcg tttcaaggga caatatttga | 240 |
| tgccaaatat tggttatggt tccaattcta agactaggca tatgctacca acaggtttca | 300 |
| gaaaagtttt ggtacacaat gtaaagaac ttgaagttct ccttatgcaa aaccgtaaat | 360 |
| attgtgcaga aattgcacat ggagtttcgt caaagaaacg caaggatatt gtagaacgtg | 420 |
| ctcagcaatt gagtattagg gtcacaaatg gaaatgctag gttacgtagc caagaaaatg | 480 |
| aataagctat tattttgttt aataaaaaat agcaaaaaaa aaaaaaaaa aaaaaaaaa | 540 |
| aaa | 543 |

<210> SEQ ID NO 56
<211> LENGTH: 1023
<212> TYPE: DNA
<213> ORGANISM: Diabrotica virgifera virgifera

<400> SEQUENCE: 56

| | |
|---|---|
| ggggattcag tatattggga tttattaaag agatttctag cccagtgaga agaaattcaa | 60 |
| gaaagtggcg aggttcgagg gaaaattttt ttctgccgtc aataattttt tttctagttc | 120 |
| acccttggtg aaccaaatta aggacttagt tactaaacaa gtaagttcgt cagataccga | 180 |
| aatgtcacac aaagaaagtg aatctgtgga tgctacatca cctcctccaa tgctaattga | 240 |
| aaccactgag aaatccgatg gagtccctc cagatcacca tctgatgaaa ttagtaaact | 300 |
| aagaccagag gaccgctcaa gaaatcagag cttttctatc agaaatatgc aggtgtccag | 360 |
| gagccaaatg aaggaataca gagaagcctt tagactgttc gacaaagacg gtgatggcag | 420 |
| tataacaaaa gaagaattag gcaaggtgat gaggtcgtta ggacaattcg ctcgcactga | 480 |
| agagcttaaa caaatgcttc aagaaataga tatcgatggt gatggtaatg ttagttttga | 540 |
| agaattcgta gatatagctt ggtcagcaag ctcagggcgt gatcccgatc acactatgtc | 600 |
| tttggaggaa gaagaaaaag agctaagaga tgccttccgt gtatttgata acacaacag | 660 |
| aggatatatt gtctcgtcag atctccgagc cgttttgcat tgtcttggag aagacttatc | 720 |
| tgatgaagaa attgaagaaa tgattaaaga agttgatgta gacggagatg gacgaataga | 780 |
| ctttttatgaa ttcgttaatg ctttgggtga accaggcaat gaggatagct acgatgatga | 840 |
| cgacgatgat tacttatcat tttataacta gaaaacatta agatatatgg ttttttatgta | 900 |
| cctgtgtttc cagagaactt catccataat caaataagct gcctaataaa caattaacct | 960 |
| aattataaag tttaaatata cctatgcctg ctacaaaaaa aaaaaaaaaa aaaaaaaa | 1020 |
| aaa | 1023 |

<210> SEQ ID NO 57
<211> LENGTH: 1179
<212> TYPE: DNA
<213> ORGANISM: Diabrotica virgifera virgifera

<400> SEQUENCE: 57

| | |
|---|---|
| ggggctttat aatttgtcgt tgaaaaagat agggctccaa agtcctattg ccaacaaaaa | 60 |
| aacaacgcaa gacattaaac aacttttttc aagcccatct gtatttaaaa aaacagtgca | 120 |
| aaatgtttct gtgggactgg tttacgggaa tgctgggata tctaggattg tggaagaaac | 180 |
| ctggaaaact attattctta ggactggata acgcaggcaa aactacccctt ctacatatgc | 240 |
| tcaaggatga cagactggcc cagcatcttc ccacgttaca tcccacatca gaggagcttt | 300 |
| ccattggtaa catgaggttt acgacgttcg atttgggggg ccacgagcag gctaggagag | 360 |
| tgtggaggga ctactttcca gcagtcgatg ccatagtgtt ccttgttgat gccaacgaca | 420 |

```
gctcaagatt tgtagaaagc caggaacagc taaatgccct cctctcagac gaaactctat    480
caaactgtcc aatacttatc ttaggtaata aaattgatct cccaggtgct gcttcggaag    540
atgaattacg aactagattc ggcttgtttg gccaaaccac aggcaaaggc aaagtagcca    600
gaaatgatct acccggtagg cctctagaac tatttatgtg ctctatactc aaaagacaag    660
gttatggaga aggtttccgt tggttggcac aatatatcga ttaattatgt attttttccat   720 ttcgttctgt cattgagtta ggatattaat gtttgaggaa ctattggcaa cactgcaact    780
acctgattca tttcagatct taggtacttt acataaatat ctaaatatag atgttggcaa    840
tgtaattttg aacaacagta tatcattca atgtaaatta tatattttta gttaagttac     900
cttcttaaat ggtgtttgag tggctatggt actgaaatag tttgacttttt tgtgttcttc   960 gataactaaa aatgatttct tgtggaaagt tacactcaga attacatagt taacttcttt   1020
atcagcagtt gttgtcaaga tttccatttt gagacgattg ttttgtaaat taggtgggaa   1080
tttttaaaat gttggactgt tttttaacat gcctttctca acttttgtta caaataatgt   1140
tttgtccaca aaaaaaaaaa aaaaaaaaaa aaaaaaaa                            1179

<210> SEQ ID NO 58
<211> LENGTH: 453
<212> TYPE: DNA
<213> ORGANISM: Diabrotica virgifera virgifera

<400> SEQUENCE: 58 ggggaagtt cgtggtggta ttgtccgtat ccgcctgaca ttcctgccgg cttttcaatt      60
gttttccgag ttcgcgaata cattacgtgg agtggtcgtg gatttgaaaa gttttgcgtg    120
ttttaaattt tgtgagtgaa cttcgcggcg acgatacagt tggactgtgc cgctaattgt    180
tgataactgg agataacggc tttgtaataa agtggtgaca gggatctctt cgggacgctg    240
aggaaggtat ttcaatcttg gttttgtcac ttttttgaatt tcatagtaat cattttttaat  300 cgagttatga aaccttgaaa tggccatttt cgcattttcc aaattttttaa taactcgaca   360 acagtcaatt ttagagaaaa attacaaggg acctttttttg ctcagaatga cccaagttat   420
ccgaaaaaaa aaaaaaaaaa aaaaaaaaaa aaa                                  453

<210> SEQ ID NO 59
<211> LENGTH: 532
<212> TYPE: DNA
<213> ORGANISM: Diabrotica virgifera virgifera

<400> SEQUENCE: 59
ggggagtggc aagtttcata tctgtgaatt tgttgtttgt tacatttttct ccggcattac    60 agataatcgt tatgaagaag ttccccttag tgctgacatt tgttgcattt ctgtggattt    120
gggaggctaa tggatttacc gcagaacaaa taatgaaat tcgtagtatt tgtagtgaag     180
aattaaaaaa aattccacgt caaaaaggtg atatgggttt tccgggaatt ccgggtgtac    240
cagctccacc atcttttggg gcaatcggac ctccaggaaa aactatatat ggtctcccag    300
gagcacccgg aatacccggt ccaatgggag ctcccggtgc ggcaggacta cccggattgc    360
caggagttaa aggtgatgta ggttcctgta gcagaaaata atttggaagt tctgagtgaa    420
aatttaaaac tattcttact tttgacatat tatgtagata tttgctgttg tatcatccaa    480
ataagtatca ttagaacata caaaaaaaaa aaaaaaaaa aaaaaaaaaa aa             532

<210> SEQ ID NO 60
```

```
<211> LENGTH: 707
<212> TYPE: DNA
<213> ORGANISM: Diabrotica virgifera virgifera

<400> SEQUENCE: 60
ggggacagtc accactcgac ccagtcaaca taagcatcat gaactcttac agtgtggtat      60
ttgcgtttgc attggccgct gttgttgtag ccgaaccacc ttctggctac aactacaacc     120
ggcccagcgg gggtggcggc atctccttcg ggggaagcag cctctccttg ggggtggac      180
tgtccggcgg tggtggatac acggctgtat cgtctggtgg tcaaactagc gaaggagctt     240
ccgtagaccc acagcttctc gaacaagtcc gtcaaattct gctcaaagaa aacagagct      300
cttccagcgg cggtggtcat ggtggtggtg gtggataccc aggaccatct tcccaatacg     360
gtgctccatc tcctcaatac ggagtaccca gctaccaata ccgcgtcgtt ggaatcgatc     420
tagagggaat caaacaagcc atccaagttg cccagtacaa ccaaatctca cagggaccaa     480
gctttggagg ataccccagc ggacctagtt cgataccatc cgggtcttac ggagcccctt     540
actaaggctc tagaactgat ttcagtgtga ataccatctt ttaccatctc agacgggtca     600
tgatgcattc aataccatca agtttcaacc ataccatcaa agttgaatg tttgtataaa      660
gctttcgtag gttattcaaa aaaaaaaaaa aaaaaaaaaa aaaaaaa                    707

<210> SEQ ID NO 61
<211> LENGTH: 715
<212> TYPE: DNA
<213> ORGANISM: Diabrotica virgifera virgifera

<400> SEQUENCE: 61
gggacaactg tcaaatattt aactcccaac ataacctgta acctgtgtaa gatcttgatt      60
gaccaaaaaa atacaaaaat ggtcaaggct tccgagacag ggggcgtgaa gcccatgtcg     120
atagcaggtc gctttataaa cgaacgagaa cgtttactag gaatgacagc tgcagaacga     180
gactttcgca aacagtggct aaaagaccaa gaattgtccc attctgagcc gaaaaatgtc     240
cctgaaatgt ataaagctac ccataatcca atcaggaggc tctacagatt tcctctggat     300
accttaggta aaatgttgga gcctgttttg ggattacaga gtgcttctag agtgagatac     360
ttcaccggaa aatttctttt ggctgttgca ggtgcttacg ccttgaccta ctatgttaaa     420
tacaatacca atgactggac acgtaagaac ggaatgagaa tactcaagtc taacatatca     480
gtacatgaag gtgacccagg ctatcctaga gtatctcaaa ggagtaaacc atcagattat     540
ggtgatcgag gattcaatga taacaaatta aacttgtaat atatttatat gaaaatattt     600
agtgttcgtt ttaggatcat ttatttgttg cttgcaaatt ttaaccataa catctttgta     660
taataaagtg caagaactat tgtaagaaaa aaaaaaaaaa aaaaaaaaaa aaaaa          715

<210> SEQ ID NO 62
<211> LENGTH: 1242
<212> TYPE: DNA
<213> ORGANISM: Diabrotica virgifera virgifera

<400> SEQUENCE: 62
ggggacataa aatctacaag atctacagta gatacagtgt ttcgtactac aatgataaaa      60
aacaatcttt caaagagatg ttacaagaag tgctcttaaa attatgggaa ggtctagtca     120
aaaacgaagg ctcgcaaccc acccaaaaag gcaccctgta ttcgtaagac ctacgataga     180
cttcactcaa gaagaaacga ttctacagaa cctcattcca caaattcgag aagacattct     240
gaatgaatct ttagtttacc agaagaacac gccaacagtt agaggacatg tcgaaaacct     300
```

```
tattaatgat acagtcggag atcttaagcc aaaatttctc aactgtgctt taatagcgat      360
atacgcctac aagtatttta aacaggatca caccgaagaa gagttggtca aggctgggat      420
tttgggctgg tgctacaaat tgcaagacct cgccatgatt atcgttgatg acatactgga      480
tgaatcaaaa attcgttaca ataaacctcc cttgtatagg gtagtgggaa taaacaagc       540 tatcctagac tctataattt tagaatcagc cgctaacttc ctagttttaa atattttc        600 tgatcacaag catttagtta aaatccaaaa ggatctcatc ctaaacatag cgacaactac      660
gatttcacag aaacaagagc tgttaaagta tgaaatagac gaattggaag ttttgaaaa       720 tttgattaag tcttttccgc ttttaataca tgctgttaca tctgcggtgt atttggctgg      780
tatcgatgat ccaaagatcc aatccatagt gaagaagttt tgcgtggata ttgctatatt     840
tggaaaaaga tatgatgact ttacagtatt tctagaccca aaaactattg gggaaaagga     900
caacacagat atcgttagtt ttaagataac atggatggcc atccaagtct ccaaaatggg     960
aagcccccaa cagaaaaaga ctttcatgaa acactacggt cactcagatc ctgaatcagt    1020
tgctatcatt tttgatatat acagggaact caatttagtt gaacatttcg ataaatatat    1080
gatgaatttt tacgcgacga tgcttacaca aattcagaac ttgcctcctc aactgccaaa    1140 agaattttc tataatatac tagactgtgc tgtagcaaat aagatgtatg cttaataaat      1200
ttaaattatg tcgaaaaaaa aaaaaaaaaa aaaaaaaaaa aa                        1242

<210> SEQ ID NO 63
<211> LENGTH: 1950
<212> TYPE: DNA
<213> ORGANISM: Diabrotica virgifera virgifera

<400> SEQUENCE: 63 ttttttttt ttttttttt tttttttttc gcttagcaac aacactttag tttattttag        60
taatattttg tattttgaca acggcacccg atttgggcgt cgaaacgtta ataaaattat    120 tttttcatt ttaattgtgg cttatttccc atataaataa ttaatcataa aaatgccaca     180
aggaaatagc ttcagaacaa cataaagaaa cgattgttgg aaatggaaaa ttaaattaaa    240
aatggaaagt ccccactaaa atggaaaatt ttacttact ttttttggtg ttaggaccta     300
cccttcacaa tccaataggt ccccaaagcg ctcgagtgac tgcacattta gcatactttg    360
ctcccccacc attattgata gtcaagaaga gtattacaaa atgtgtatgc atacatatta    420
aaaaaaaaat actacgtacc aaagaaatca cgaagaagtg aaaagcaaca gtaatatcat    480
tctcaaaata agtttatcat ccaccttag ccctaaacat agattattat cgaactcatt    540
tagaatttag aatacatatt atgtaaaata aaaaaaccag tataataata aataatacat    600
tttactagtg aaagaacacc aatttgctgt tggtagtatg taattgttta ggaagatctg    660
tgtgttggag tggtttcttt ttgcacaaga acattcataa ataactcaac gggtcatcaa    720
tatgccatcg tggagaatta acagataagg aaaatcaatt tgcaaagcat acaaatcagt    780
caatgttaac ttacaggaca cgatgtgata ctcatatgtt cggttcttct acccactctt    840
ttttcacggc agaagtatgg tcagtaccgt attcagattg caagttact tacagtacgt     900 aaatccttca ggtggacaag ttacgtactg tataacataa atatatttta aaaggtgca    960 tttttaagaa aaataaaata tttgaatcac cctattggta aaaagtaaca atatgggtct   1020
atgaagacag aataataact taattgtgta tcatatatat tcaaaacctg taaacgagct    1080
ttttatagta taacgtatta tcaatttgtt ttaaattctt tttatagtat aacgtattat   1140
```

| | |
|---|---|
| caatttgttt taaattctta gaagattaca aggattccat ataaaaatg aagatatcaa | 1200 |
| acaagtggac aaaataaaat acttaggagt ctggatcacg gaagctttaa atccgaaatc | 1260 |
| agaaattcga tcaagaatag agcaatcaag agcagccttt ttgaatatga ggaaatttct | 1320 |
| gagtaaccaa agattcaatc tgcaaatccg atatcggatg gtaacgtgtt atatccactc | 1380 |
| tattcttctt tacggtgtcg aagcttggac tgttaatgct gacttaatga gaaagctgga | 1440 |
| agcttctgag atgtggcttt ttaggagaat attgaaaata ccatggaaaa actgtttagt | 1500 |
| tttgaaatta gtttttaaat aaaaaatatt ttaaaaatta aagacaaatt attaactcat | 1560 |
| taatcataaa ctttgttttt gatttattta tggacagcct tgctacaaaa ttccctcatt | 1620 |
| ccattcattc taacagctct attgcaccaa aaactcatac tcgaacagaa gcttcaacta | 1680 |
| acacaggtta gcgcagttgg caatatggtt gttagcatta aggggcatta accttcaaat | 1740 |
| tgacaactca tttcgactga cacaaacgtc aaaatgtgac aatgtgatag ctaaatattt | 1800 |
| tggaacacat acatagaaat gataagtagg agttattaca gctgattatg aagggtacaa | 1860 |
| ttggaagggg tcctagtgga ctacaaatat cctggctgaa aacattcgc gactggacca | 1920 |
| ggttaaacac acagacgttt ttcagagccc | 1950 |

<210> SEQ ID NO 64
<211> LENGTH: 776
<212> TYPE: DNA
<213> ORGANISM: Diabrotica virgifera virgifera

<400> SEQUENCE: 64

| | |
|---|---|
| gggtacacat aacctataaa aaaaacatta atttgattta ttttgaagtg tatatgttgc | 60 |
| agttcaagtt gattctcagt tggagttgac tccaactagt tggagtcaac tccaactgaa | 120 |
| atgagcagta aaagttgatt ttaaaaattt aaatcaactt ttactagttg gagttgactc | 180 |
| ttcctggatc gattcagtaa atgttgatta tacgagaatc gcaagtgcat ttttgatgag | 240 |
| tgtgcgtttc tttgtttgga ccgtttcaac tacttattag tatggcctgt aacgtcgccc | 300 |
| ccgttgggtg aattattctg attcgatttt ttgcacaaac ttactcaaag aaatacatcc | 360 |
| gtataacaat ccttataaca aatacacagg gtgtcacgcg gtagcgcggt cgaaaaattg | 420 |
| tttaaccaat ttttgttgac caaattcaca aaaataattt ttatctactc tatctcattt | 480 |
| atgtaaatca gcggttctca atctgtggta catgtaccac tggtggtaca aatcattatt | 540 |
| tgcggtcctg ccaaagacaa accattttca tttccaataa tgacacgagc cgtctcaccg | 600 |
| tgcctcggag agcacgttac accgtcggtc cccctgggct agtgtacatc gacactagtt | 660 |
| acttgaaaca gggttaaaga tgtaattggc gccggaactg tccgaaaggc aaaaatgcca | 720 |
| tacgatatca tatattatga aagtcggaaa aaaaaaaaa aaaaaaaaaa aaaaaa | 776 |

<210> SEQ ID NO 65
<211> LENGTH: 1191
<212> TYPE: DNA
<213> ORGANISM: Diabrotica virgifera virgifera

<400> SEQUENCE: 65

| | |
|---|---|
| ggggacaagt ttttttggat ccatcaagtg ttttcaaaat ggctacacac ctagacgtgg | 60 |
| ataaaattat tacaaaactc acctccaaag aggttcggga gagcaagaaa atcaaactaa | 120 |
| taagcatatc tgaatctgat ataaaagcgt tatgtttcaa gtctatgagc acatttatgt | 180 |
| cacaacccat gctgctcgag ctagaagcac caatcaaagt ttgcggtgat atacatggac | 240 |
| aatttctcga tttgttaaaa ctgtttggat ttggtggttt tcccccccgac tcaaattact | 300 |

```
tattcctcgg agactatgta gataggggga aacagtctgt agaagtcata tgcttattgt      360
tagcatacaa aattaaatac cccgaaaatt tcttcttact gcgaggtaat catgaagcat      420
ccgcagtatg taagatatac ggattttttg atgaatgcaa agaagatat agcactaaaa      480 tatttaaact atttaccgat gttttttaaca cattgccggt ggctgccatc atagacgaca     540
aaattttctg ctgccatgga ggcttgagcc cagatctctt acatatagga caaattcgaa      600
atattcagcg tcctattgac attcctattc aaggtttact ctgtgattta ttgtggtctg      660
atcccagtac cgagcctggt tggacggaaa atgacagagg agtgtcattc tcatttggtc      720
cagatgttat taataagttt ttaaggaaac atgactttga tttaatttgc agaggtcatc      780
aggttgttga agacggctat gaattcttcg ctcagagaaa attaataacg atattttcgg      840
ctccaaatta ttgtggtaca tttgacaacg ctggagcgct tatgtcaata aatgaaaatc      900
ttttgtgttc atttcagatt ttggagccaa caaaacatat tgaaaaaaag aagtgattta      960
aaaagtgaat tagatttatt tatggatatt aatttaagta ctaagtagtt acttattgac     1020
tgttatttaa aaacagaatc acgtaaagta acaaattaaa aaaaaaaatg taaagtattc     1080
tgctcgttac atgctttaca tgttatttgc atgacctttt acgaaattct gttcatagtt     1140
gttaatagat aataaagatg caaaaaaaaa aaaaaaaaaa aaaaaaaaa a               1191

<210> SEQ ID NO 66
<211> LENGTH: 854
<212> TYPE: DNA
<213> ORGANISM: Diabrotica virgifera virgifera

<400> SEQUENCE: 66
tttttttttt tttttttttt tttttttttt atagtgtaaa actgattttt ttattttaat       60 ataccaaa acataccaaa gcttaaaaaa taatcaatta accttcataa aatttgggca       120
attcatttcc taaaacaact cttcgttcaa taccagcttc agtgatgatc cccagtctga      180
ctacacctcc tgaagaacca tctcttgaca tggcaagtgc caatgtattt gtgacaaact      240
tcacacattc ttccttgctc atattgggct tgaagttggc atctacgtaa ccataaacat      300
aactggaacc tgatcctccg attgacactt cttgtctaac acacatccca ccaattggta      360
tggaatatac ttgtccgcct ttcttttat cccaacctgc taccagtata ccagccatta      420
gcgaatctct ataattgtag caaagttctt ggaaaatggc ggcacctact tgtactttgg      480
gttcttcacc aagttccata ccatgaaaat taagatgata agcaacaatg tctgcaattg      540
cttgtgtatc tgctgcagat cctgaacgac aacagtatat atggtcagtg actttggtga      600
gtttgtctgc tacccggttt gcaatgtagg ccccagtagt tgtgcgagaa tctgctccta      660
taacaacgcc tccatcaaac tccgcggcca aatagaggt tcctgtactg tgagcggcat      720
ctctccaatc attaggacca gtcattgcac catactcagt cataagaggc attttttaca      780
agtttaatga aaagaataca agcttagaaa aattacactt gtaatcctgc aatgcaatat      840
tttgccagtc cccc                                                        854

<210> SEQ ID NO 67
<211> LENGTH: 1162
<212> TYPE: DNA
<213> ORGANISM: Diabrotica virgifera virgifera

<400> SEQUENCE: 67
tttttttttt tttttttttt tttttttatt ataactattt atattttagt taatacatct       60
```

| | |
|---|---|
| taaatacaca gtacacatta tatacaacta ttaattcaga ttttttttcta tccagtcaac | 120 |
| aaaagtagta actctggtgt agacaccggg atatcccttt tcagcgcatc taaatccata | 180 |
| ggaaaccact ccaatcagat aatatcttat aaattcacca tcaaacttgc cccaaattaa | 240 |
| tggacctcct gaatctcctt gacatgcatc ttggcggcca tccgcccgtc ctgcacatag | 300 |
| agttctctcg tcaattgttg ctttagcccc aaaggcggca gcgcattttg atgtgtcaac | 360 |
| tactggaatc tgggctattt ggagggccga acttgaaggt ccattataat atgtggctcc | 420 |
| ccaaccagca actacagctg catattttac aaaactttgt tttctgaaat tatcgtcaat | 480 |
| tggtagacat acaggccata cccaaggatt ggtgggggct cttccaaag taagaattgc | 540 |
| gatatcactg gtgtatttca cgggactgta gtcttcgtga actttagctt tgatcaatgg | 600 |
| tatatcttct ggttctgctc catcattagg attgtttaaa tctaagtctc ctaaacgagc | 660 |
| gacatataag tctttcttgt tgtgtacaca gtgagcagct gtgagaatat gtctttctgt | 720 |
| aatgagtgtt ccgccacaca accatcttgg ctttgaaggg tccctgctat ttctataacc | 780 |
| caaattaaca atgaatggta cctcatgtaa tttggctgga attccaccta caactctaaa | 840 |
| gtttgttaca ttactaacac cacatttctc gttatttaaa acggcaccaa tgattttgt | 900 |
| atcggttgct ggttgtgtag gttctggttc tggttctggt tctgtattgt ctgttgggca | 960 |
| acaaacatat actacagctc caaatttaca tgttgaacgt tgcagatatt ggcgcgtttc | 1020 |
| ctgattattg cttcttgttt taagcaaatt gagcatgtat ttacattcgt atatactttg | 1080 |
| acaaattcca tattcattcc tagctgtgta acagggctca ccttcttcaa cagccgcgtg | 1140 |
| agcaacacta aacaaaatcc cc | 1162 |

<210> SEQ ID NO 68
<211> LENGTH: 1186
<212> TYPE: DNA
<213> ORGANISM: Diabrotica virgifera virgifera

<400> SEQUENCE: 68

| | |
|---|---|
| ggggcaaact gtaagttatt atattttgca cgattgaaag acatttacta ttagcaaaaa | 60 |
| tgtctaaaga ccgggaattg cagatgggga tgcgatgtgt gaagtacatg attttgtgg | 120 |
| cgaattttat gttcatgtta gttggattgt tgctgatatc aattggatat accattaagg | 180 |
| ctatctacac cgatttcgat gctttcctta gcagccatag ctacaaagca tccgacttag | 240 |
| ctatagctgt tgggttcgtc attctagtgg ttgctttgtt tggttgtgca ggagcaatta | 300 |
| aagaaagtgt tctactggtt aatctatacg ctttactact tcttgtaata gttatcctgg | 360 |
| aattgaccgt aagtatcatt gcttacaaat ccaggagtca cttggaagaa cactttctc | 420 |
| aggatatgtg gattagtatg gagtattaca tagccgatac tggatatatt tgggatgcaa | 480 |
| cacaatactc gttgcactgc tgtggagtac atggtccaaa cgactgggac agatttaaca | 540 |
| gttcagacta caatctcaca gtcatttata gttcacaaga cgactcaaca agttcagact | 600 |
| tgccacaaat aaaattaccca ggagtttacc aagtaccaga gagctgctgc agaaatacca | 660 |
| aatgccaaag tatcgcttct ctttacatga gaggttgctt accgaaaatc cactatataa | 720 |
| tctcgcaaag tgctcttctg cttggagttg gggctatgtg cataacattc attcagcttc | 780 |
| tcggtgctac atttgcccat cttctggcca gatctattag aaaacttaaa acacagattg | 840 |
| aagtggaaag atcaataaga agacaacaac tgtacgagtc gcttgcgaaa tctaacacac | 900 |
| aagagaaagt tagtccagtc ctatacgtgg cagagtcttc tgaagcttaa gaattcgtcg | 960 |
| tgtgttatat ataaaaataa tgatttaaat atagatttaa atatagatta aaccattgtc | 1020 |

```
catttcatta cactcatgta tattgtgtta gtgtttacag ataagttata atatatacct    1080
tttctgtttt tgtgtattct ttactaggtc tatgtatgta gattctttaa atgttaaata    1140
tagaataatt ttaactgaaa aaaaaaaaaa aaaaaaaaaa aaaaaa                   1186
```

<210> SEQ ID NO 69
<211> LENGTH: 1002
<212> TYPE: DNA
<213> ORGANISM: Diabrotica virgifera virgifera

<400> SEQUENCE: 69

```
tttttttttt tttttttttt tttttttttt ctttaataaa tagtatattt tgtaaatttt      60
tttatcttac ataatacaaa aaatatatac attagtttta tttatgtttt atttatattt     120
caattattat tctaattctt cttcttaaca tcgtcacctt ctggattttg gtgttttgta     180
aacgttagga atacctgttc tagactactt tgtcccaaag aatagtcttc aatattcaga     240
tcacttcgct tagctctttc taatatacca aacatagtgg accatgccat ggaagtgtcg     300
gttatataat aatacaatag ttcttgatgt ttctctctaa gatgagcata aggaaattta     360
tctttgatat acttctccag tgactctgta tctgcatgta ccagaccacc gctctctggc     420
aatttcttta gttttatggt taaggtgtat ccctccgcaa atttgttttt aagatgctgt     480
gtggatccaa gacatttgaa attgccgttc accataatgg ctattcgagt gcacaaagct     540
tcacattctt ccatgctgtg agaagttaaa acgatgcact tgccgttgtc tcgaattttg     600
cataatgaat cccacaggta acgtttcgtt gctggatcca tacctgttgt aggttcgtcc     660
aaaaatagta ctggcggatc ccctatcaac gacaaaacag tacttaactt cctcttattt     720
ccaccgctca tctctttaac tttcttgtcc aaatgacgat gaaaatcgaa gtctcgagac     780
aagaaattcg caattctttg ggttctttta aactctattc ctctgagtag gcagtacatg     840
ataattgttt ctcttgctgt catatcatcc agcaaagcgt cgaattgagg acagtagccg     900
atgtttcgtt gtacttgctt cagttgcgtt tttacactct ttccttcgat ccatgtatca     960
ccgtaagata cagtttcatc tccgctcatc attttaaatc cc                      1002
```

<210> SEQ ID NO 70
<211> LENGTH: 1322
<212> TYPE: DNA
<213> ORGANISM: Diabrotica virgifera virgifera

<400> SEQUENCE: 70

```
gggtatatga ccacattgtc aactattaga aagattctgt tgccaaaaat aattctagac      60
ttttagtagg tataatactg ttgtaaggta ttacaataca tagggtacta ctactgcttc     120
ttcttgtagt tccttatctt atcggaggtt ggcgatccgt accttattga cggctgctct     180
gaaaatatct actgagctgc aatctgcaat tataccactc tcttaggttt cttagccagg     240
atatttaatc ttttatctta tccttaattt taccttgcat tttactacaa cacaggtact     300
aaaatgtgta taccaaattg gatagttcct ttctgaggtg ttactctata tattactgtt     360
gaaatatagt ataaatatgg acatcttccg aaaacaacta gacagaatat gtatactaaa     420
ctcacagtaa agatgcacga gaaataaaca aaccaagaca cgtttaatgt tacgaggagc     480
actcccgaat cctgatttac atctatctat ctaattagcc tctttcggtc catctttgga     540
aatgaacctg aagaacccca atccttttc attattctct gtctgtcgct atagtcatcc     600
acctagagcc cacgtgcttc ttgatatcat ctgtccatct catttggggc ttttttctgc     660
```

```
ttagtttata ttcccatggt ctccaattta taagaatttt gttcaatcga tcttctttgt 720
gtcttatatt gtgtccggca aatctccatt tcaattttgc aacttcttgt ctaacatccc 780
taacttttgt tttcactctt acccactcgt ttcttttttt tatccattaa accttgatta 840
cacgtaacga gtattgtagc gagacagtgt tctcggccgg gtgcttgttt ggtataaaca 900
tactaacgag tacttggccg agcactcgac ccagtcatat ggcgagacag tcactcggat 960
cttgttatac atatttacta agccgagtct tcgacctccc actcttcaat cgtatactcg 1020
ccaatccact gggtatgtgt aaacaacact cgctgtgtaa ctgtacatgt taccattacc 1080
acttcatcag aggagacgac ttgtgttaat caatgttatt tgggattctc aaaaatagct 1140
aacaaatgga actcagatag gacaataaag tgtagtttaa ttctacagat aagtcacacc 1200
cgtgcttatg aaattataaa tatttggagt ataaaaataa acaaaaacgt gatgcagcat 1260
ttaaatattg ttggttttaa aacttaagga gtaaaaaaaa aaaaaaaaaa aaaaaaaaaa 1320
aa 1322

<210> SEQ ID NO 71
<211> LENGTH: 761
<212> TYPE: DNA
<213> ORGANISM: Diabrotica virgifera virgifera
<400> SEQUENCE: 71
gggggacata tggtgacata actcattcaa aatccataaa aaagtttcaa aatgagttta 60
ggagttcgta aaatattttc agtaggctca aaattagtaa gaccaagtgt ccagattgtt 120
ggtcaaagat gttgctctag cggctctaaa gatggatatt tctatgtaaa cgacaaagaa 180
cccagtatgg agtttggggc tatcacagat cgtgctgccc aaacaatgtt ctttactgaa 240
ttattcagag gatttggtgt tactttggct cacattttca aagaaccagc aactataaac 300
tatccctttg aaaagggacc tctcagtcct agattcagag gtgagcatgc cttgagaagg 360
taccccctctg gtgaagaacg ttgcatcgcc tgcaagttgt gtgaggccat ctgtcctgcc 420
caggcaatca caattgaagc agaagaacgc gcagatggct ctagaagaac cactaggtat 480
gatattgaca tgacaaaatg tatttactgt ggtttttgcc aagaggcttg tccagtcgat 540
gctatagtag aaggtcccaa ctttgagttc tctactgaga ctcatgaaga acttctctat 600
aataaagaaa agttattaaa caatggcgac aaatgggagt ctgaaatagc cagtaatatt 660
catgctgacc atttatatcg ttgaaaatat atagaaaatt gtaaaaagtt gtagaatata 720
tcttattaaa caaaaaaaaa aaaaaaaaaa aaaaaaaaaa a 761

<210> SEQ ID NO 72
<211> LENGTH: 2041
<212> TYPE: DNA
<213> ORGANISM: Diabrotica virgifera virgifera
<400> SEQUENCE: 72
ttttttttt ttttttttt ttttttttt gataacgatt tctaaagtgg aaatcgaaat 60
gtcaaaaaaa cttaatttca aagtaaagtt atggctcatt ccaaataaaa aacagtaaat 120
ttcattgtgt atataatttt gtaatgtttt tgtattcaat caaaccaaaa ataaaccact 180
aacaaaaaaa atagagtctt ttaccacctt ctccattaaa ggagattact tcactacaca 240
aatgctgatg gatgtggcga tgattgaaat gctcgaaacc gctacttgac caaatacgtg 300
tcgtttggtg ggtaaagctc gtaatcccga attacggaat attggaaacc aattattaac 360
aagatgcttt gatacatcac agagctatgc taaatagttg ctaatgttat tcagcaataa 420
```


```
cattatcgat gggatgactg aggtcgatat taccattgct taaacacagt attgaaaaat      480
ttgtttcata cattatttaa atagtaataa ttaaattgta taataatata cagtgatgag      540
cacgctcctc ctccttctcc tcctcagtcg tttcctcatt tctgagtgtc gtgattccct      600
ataatacgat caactatctc tttccgtcgg cttctgtcct gagcttccct catggattca      660
gagaatgttt ttccactggc ttcctgtact tggtccgtcc atcgagcagg tgagcgacct      720
ctacttctgc gctcttcaac cttttccgaa attataagtc tctccagatt atcatcactt      780
cttgcaatat ggccgaaaaa ttttaaggcg gtggagaggc aagtagagga aagtcgagtc      840
tgaatattaa gctcttggaa gattgagtga tttgttctct gttccgtcca tgagatccga      900
agcattcttc tccagcacca catttcaaag gcgtcaatcc tttttctgtc gtccgatttc      960
attgtccatg tttcggatcc ctaattaaat atgggaaaaa ttaatgcacg tactaatctt     1020
attttggtgt tcttcgacaa ggagcgatct ttccagattt tcgataatcg actcatagcg     1080
tttttggcaa tgcctattct cctacgtatt tctgtttcac aacatcctgt attactgatg     1140
taggatccta gataatcgaa ctcgttaacc acttcaaact ggtctaaggc ccgtgttgtc     1200
tgaagtgaat ttaatatattg ttattaagta tattcaaatg ggaaataagc cacaattta      1260 cctaaaaatg attttattaa cgtttcgacg cccaagtcgg gtgtcgttct caaaatacaa     1320
aataatacta aataaacaaa aatggtgttg cctagtaaaa aattcttcca ataatttatt     1380
taatctgact catttatatc ggcaattcag acacgtatta tacattttaa agtagacgac     1440
tttaaaatga tattgccaat attgatgagt tgcgttcctg ggactatgaa tttaaatatt     1500
ctactatcat aattttttgtt ttttgtttat tgatcttgag accacatcta ttgctttcgg    1560
cttccactag ctgcagcaga ctggacattt cttcttcgga tgcagttatt aatggtgtat     1620
catctgcata tctgagattt gagatcttct ttcctgcgat agaaataccg ccattccatt     1680
tgtcgagtgc ttttctcatt atatattccc catataataa ccatagcgcg ctaataaaca     1740
cctatatatt tctatttcta tatctatcta tctatccttt tttcagccaa cgtctgcagt     1800
ccttcctgtt ctaccattct ccatctttaa cgtctcgtct ttccatggct tcgtacactt     1860
catccctcca cgatattcgg ggtctacctc ttcttctctt tcctattggg ctccaatccg     1920
taatctttga tatccacctt gtatgatctg ctcttctcac atgtccatac caaattgaac     1980
gtttttcttc gatgtagttg attatgtctt gttctagtgc cattcttcgt tttatctccc     2040
c                                                                     2041
```

```
<210> SEQ ID NO 73
<211> LENGTH: 523
<212> TYPE: DNA
<213> ORGANISM: Diabrotica virgifera virgifera

<400> SEQUENCE: 73
gggggtgtag ctttccgcag caaaaagata ggtggttagg cattattttc taaaaaccac       60
atggatgaat tgttggcaaa ttcagcccta gaggctgaaa aatttaagcc aaccgtagta      120
aataagctta ttgatctaaa ttatgactta ggaagccttt tagcacaaga cacaaatgaa      180
tttgatacaa atttattaag gaggcagaag gaagattatt tgcttaattt agctagagat      240
aacacccaat tactattaaa tcaaatatgg gacttaacta cagaacgcct agaagaagct      300
attgtagtga aattaccact tcaaataact ttattaccta ggatgaaacc actacctaag      360
cccaaacctt taacaaagtg ggaacagttt gccaaaacga aaggtataca gaaaaagaaa      420
```
aaatccaagt tatcatggga ccagcaactc aaaaagtggg taccottata tggatttaag        480 cgagcacaag ctgaaaaaaa aaaaaaaaaa aaaaaaaaa aaa                           523

<210> SEQ ID NO 74
<211> LENGTH: 473
<212> TYPE: DNA
<213> ORGANISM: Diabrotica virgifera virgifera

<400> SEQUENCE: 74
gggaaagtga atttcactaac tatttgagta atttaaatgt caattgacct tagtttacca       60
gagctgccta tattcaccc aaggattacc gttgtgggag tgggtggtgc tggtggaaat        120
gctgtgaata acatgatcca atccatttg caaggagtaa attttgttgt agcaaatacc        180
gatgctcaag cgttagagaa gtcattatgc gataaaaaaa ttcaactggg tattaactta       240
accaagggtc ttggtgctgg tgccttgcct gatgttggca aaggtgcagc agaagaatca       300
atcgatgaaa ttatggagca tataaaagat agtcatatgc ttttcatcac agcaggaatg      360
ggcggtggta ctggaaccgg tgcagcaccg gtaattgcaa aagcagccag agaagcaaga      420
gccgcagtta aggatagagc gccaaaaaaa aaaaaaaaaa aaaaaaaaaa aaa              473

<210> SEQ ID NO 75
<211> LENGTH: 409
<212> TYPE: DNA
<213> ORGANISM: Diabrotica virgifera virgifera

<400> SEQUENCE: 75
gggagaaatg gttactttga acaagattta gtactaccaa atgttagtgt atatattatt       60
ctgcacgcat taacaattta tggatttat agaataacta ctactgaagt taaggggtca       120
gccatattat tcagtacttt tattggcatg ttggcaatat taggggtcac agctggagcc      180
catcgtcttt gggctcatag aacttacaaa gcaaaactgc cattacgagt atttttaatg      240
ttgttgcaga cagcggcct tcagaatgat ctttcattt gggttagaga tcacagaatg       300
caccacaaat atacagacac caatgctgat cctcacaact cgaacagagg attcttcttt     360
tgtcatgttg gatggctatc aaaaaaaaaa aaaaaaaaa aaaaaaaaa                   409

<210> SEQ ID NO 76
<211> LENGTH: 1532
<212> TYPE: DNA
<213> ORGANISM: Diabrotica virgifera virgifera

<400> SEQUENCE: 76
ggggaagaaa cgtcaattga atcaactaga cggtgatgtg ttcagtaatt gaatgtaaaa       60
tttaaaataa tgttgaaatt aatcaccttc atattcataa tagtgaccgt caatgcagca     120
gaaagaatca acaataattt aattataaa aatgtggata gaaccataga tttaacgtca      180
cagttagtaa aaatcaccag caccataact cttgaaaatg ccggcgcaga ccctatcaag     240
aattttctac tggcggagca accaaattta gttggacaga tagcatttaa aggtgccaaa      300
gactctgcca agcaagattt aaacgtctta acagcccaag tagaaaacca gagcgataag     360
agattccaca aagttatctt gaggcagaat ttggaaccgg gccgtactgc aacagtggtg     420
gttgaagaaa tactcattaa agtttaatt ccatatccac atagtatttc ccagaaagag      480
aagcagttag tgaggtattt tggtaatcat tatatttata caccatacac agtggttaaa     540
caaaaaactg atgttacatt aagctctaga agtattgaaa attattctaa attgaaacca     600
gttactcaga cagatagtac aatacattat ggaccatatg gagaaattgc acctttttgct    660

```
gtggatgaac tgatagttca ttacgaaaac aatgctccat ttttgacagt tgtccatcta      720
gatagaacaa ttgaaatatc tcactggggt aacattgcag tggaagagca aattgaaatt      780
aaacacacag gagctacatt aaaggggcca ttttcgagat atgattacca aagagacact      840
agtagtacac atcacagtat taaatcatac actactgttt taccagccac tgctcatagc      900
atttattaca gagacagcaa tggcaacatt tctacttcag ctgtaaaaca ccgtaaggat      960
tggatagaac ttgaactgag accaagattc ccacttttg gaggttggca aagttcttat      1020
actctcggct acagtgtccc cagttaccag tacctttca aggctgaaaa tggagataat      1080
gtattagcta tgaggctcat tgaccatgtt tttgacgata tgtatgttga agaagttgtt      1140
actaacgtag ttcttcctgt tggagtcact gatatcaaaa ttcgaccacc ctatgatgtg      1200
gagagactat cagatgatgt tacttacaaa tattggata accttgggcg taaagttata      1260
agactgaaaa agagggacct gattgaacaa cacattcaag atttggaaat tacctataaa      1320
tggcaaccac gattgttgtt acatgagcct ttgctgttat cgttggcact ctttatttg      1380 tttgtagctg taattatctg gtccgattg gacttttcac ttgcagtgcc tgagcacagc      1440
aaaagagaat aacttttgt acatctatat taacattttt tgttaaataa attatgagat      1500
tgaaaaaaaa aaaaaaaaa aaaaaaaaaaa aa                                    1532

<210> SEQ ID NO 77
<211> LENGTH: 107
<212> TYPE: DNA
<213> ORGANISM: Diabrotica virgifera virgifera

<400> SEQUENCE: 77
ggggatgact tcaatctttg gctatcgagg gccaacgagg aagaacgaga aagaggtggt       60
aaccatggtg acgtaagaaa aaaaaaaaaa aaaaaaaaa aaaaaa                     107

<210> SEQ ID NO 78
<211> LENGTH: 985
<212> TYPE: DNA
<213> ORGANISM: Diabrotica virgifera virgifera

<400> SEQUENCE: 78
ggggattgaa aggtggtacc gggactgggt gagaggctag ctagatacat acctacctca       60
tgtctctttt taactaactc ttcttgtatg tgtacgctat tttaaggctt tatgcgcaca      120
ttgatatctt gtagtgctat tataggattt tgtttatttt tcattaaaaa tgggtagaag      180
acaaaataaa taccaagatg tatccgagga tctaccggaa agaggacctg tggagagtct      240
gatctactgg cgtgatccca agaaatctgg tccagtcttt ggaggagtcc tcgtagttct      300
actcgctctc acatatttct ctctaatcag tgtggtagcg tacgtttcac tcatcgccct      360
cggcgtcact ttagctttta ggatttacaa agtattgta caagctgttc aaaagactgg      420
tgatggacat ccattcaaag aatatctgga acttagaaga ttattcttgg tcgaagattt      480
ggtagattcc atcaaattcg cagtattgtt atggactctt acctatgtgg gagcgtggtt      540
caacggaatg actctaatta ttctcgcttg ggtcgccctc ttcactcttc caaaagttta      600
cgaagtgaat aagactcaaa tcgatgccaa tttgagatt gttcggacaa aattggctga      660
aattacttca aagataaagg cagcaatacc gatgggcaag aaagccgaag aaaagaagga      720 acaaatagatt taacaacatc tatcagacta tattactata catatattaa tttattgttg      780 tttcttatt ccattaaacg ttcttatgta atgtttctaa atataattag tgtacatata      840
```

| | |
|---|---|
| taagatgtta ttttaatgtt tttttatttg aatttttga tgttatttat ttcttgtaat | 900 |
| acatagagtc gaagaagaat atagaattta acataataaa tgtgttgcag agaaataaaa | 960 |
| aaaaaaaaaa aaaaaaaaaa aaaaa | 985 |

<210> SEQ ID NO 79
<211> LENGTH: 1829
<212> TYPE: DNA
<213> ORGANISM: Diabrotica virgifera virgifera

<400> SEQUENCE: 79

| | |
|---|---|
| gggggtatat atcaatgata ttacatatcg acctacgttt cacttaatgt tttgatttga | 60 |
| cttgtttgca aataaatcat gacgtttgtg caaagatata atggaacagc tatgaaataa | 120 |
| ctaaaccaca ttcaaatagc aaattcccaa ctaaactcct ggacaaaatt aacgcaccac | 180 |
| tttaattaat ctaaatattt acaatatgaa cacaaaataa aactaagtta cactggaata | 240 |
| ataataataa acacctacaa ataagtccaa catgactttta tcatgacctt aatttgcctt | 300 |
| atgtttcttt aaaaatttgt ttttgccgga aatgcgtaaa taagctagca taactctaaa | 360 |
| ttgcaaaaag aaaaaaatca gtaaagtaac acaataaatt gcatctgggt caacaataat | 420 |
| accgtgtagg cccacctaca cggagactgc atttatgcgt caaagcatgc ttgatatcaa | 480 |
| atgttcaaca aaagcttgcg gaatattctc ccattcttca ataacggcct caatgagttg | 540 |
| gttgtgattg acaatagggg gtctacaact tctaatcttt ttttgagata gttcgataga | 600 |
| tgctctatag attgatgtcc ggactgttag gtggccactc taataataga atatcaatat | 660 |
| catgtaggta accaataaac tgtcgagcca catgaggacg agcgttgtct tgcatgaata | 720 |
| aaaaattagg tccaagaaac ggagcaaaaa gcattacatt ttcgacaata atgttgtcta | 780 |
| agtaataatg ggcattcata gacctcgtac gtatggggac caactccata cgagcttaaa | 840 |
| aacaaattcc ccccaaaaca ttttagagcc accaccaaag gtagtttagg agagatattg | 900 |
| cagctggcaa acctttctcc tcgccttcgc cagacttcgc cagcttttag gcgttgtaca | 960 |
| ggacttatat tatacataca cgtaaaattt tcttttatt aataatatag tgaaatgcat | 1020 |
| aatatatagt tattttggga taaattagga ttaattattt ttaatacaat tagtaaatta | 1080 |
| ggtctagttt ttcgtaatat tcatttcaag aagcatttac ttgacaagtt acttgatatt | 1140 |
| ttaactactg ttcattttta ttttttttga aaataaatga actttgatttt aaatacctag | 1200 |
| atagaacttt taaaaagtgt ttacgatttt tatttacata ataactattt ttaactcaat | 1260 |
| gcgagtacat atatacataa atctatttttt aacttgaacg gatcaaaatg ttatatcagg | 1320 |
| cttttatttg gcataaagta tattacattg tggttacctg accctgaaat tacgagtcag | 1380 |
| aaatacatac atcaggaatt tgctgaatag agttttacgc attacataag acataaaaaa | 1440 |
| tgactgaaat tacacactag gaaaggtgaa ttagaattta atggaattac gataatgaag | 1500 |
| aattttgaga atatattgaa ataatattat tgaaaatata agaaacgaca aacaaatcaa | 1560 |
| cgttttaaag aagaagaaag gaaaatacaa acatgatgga caagaataag tttcacggaa | 1620 |
| aatatgagtt ccgatattat gggaccgatg aatcaagatt tagagaattt tttacaaagg | 1680 |
| acaagacaaa gagaagaatc ctaaaaagga aaataaaaaa aaaacatga agataacaaa | 1740 |
| gaaaataaaa ttatttatgt acaaggatat acaagaattt ttatacaatg attttaagaa | 1800 |
| aaaaaaaaaa aaaaaaaaaa aaaaaaaa | 1829 |

<210> SEQ ID NO 80
<211> LENGTH: 1307

```
<212> TYPE: DNA
<213> ORGANISM: Diabrotica virgifera virgifera

<400> SEQUENCE: 80
gggaataaaa aatttatttt atttatattt ttatttattt taaaataata aaatatttt      60
tagtaaaagt aaagaaaaat tttatttaat gatagttaat tagtattgtg agagaatatt    120
ttattttat aaaagaaaaa tttattttt gtaccttgtg tatcagggat tattaattaa      180
taattatata tttattattt tcgaatttaa aagagctaaa aaaattaaaa ttttattgt     240
aaaataaata ttttaaataa ttttttttgta atgaaatgtt attcgttttt aaatatatct   300
aatttttaa gaaataaatt aaatttattt attaacaata tatttataat taaatatttt    360
tatattatta atattaaata tttttaggga tgagcttaaa aataaaattt tattaaaatt   420
taattttaa ataaaaatta ggattaaaaa ttttcatatt ttaaaatatg ttattattta    480
tttttatata ttattattt tatttttta taatttttta ttaaaatata aatttaaatt    540
atttaaattt agtaatgatg ataatattag tattaaaaaa ttgtatattt agtaaaaata   600
tataggttta ataaaggaat tcggcaacat ttttttcacc tgtttattaa aaacatgtct   660
ttttgtatta aatataaagt ctcgcctgcc cactgattaa tttgaatggc cgcggtattt   720
tgaccgtgct aaggtagcat aatcattagt ttttttttatt gaaagctgga atgaagggtt 780
ggatgaaaaa aaaactgtct ttatttaatt tataaagaat tttattttta agttaaaaag 840
cttaaatttt tttaaaagac gagaagaccc tatagagttt tataaaatta ttaataagtt 900
tttttagtat taaattttatt tatataataa atttatttaa ttggggtgat taaaaaataa 960
atttaacttt ttttatatta ttatattaat taataatttt ttgatccaat ttttttgatt  1020
ataagaataa attaccttag ggataacagc gtaattttat tggagagttc aaatcgataa  1080
taaagattgc gacctcgatg ttggattaaa gtttataatt ggtgtagcag ctatattatt  1140
aagtctgttc gacttttaaa attttacatg atctgagttt aaaccggtgt gagccaggtt  1200
ggtttctatc tttaatttat taatatattt tagtacgaaa ggaccaaata tataaaataa 1260
tttttatatt tagacaaaaa aaaaaaaaa aaaaaaaaa aaaaaaa                   1307

<210> SEQ ID NO 81
<211> LENGTH: 730
<212> TYPE: DNA
<213> ORGANISM: Diabrotica virgifera virgifera

<400> SEQUENCE: 81
ggggattctt ttgtgaatgt ttgcttcgcg ttctcccgtt taccgttccg tgttgacacc     60
gtagaatatt gactgatctg tagtttgaat tattttttaa aaacaatgat gtgttcatga   120
actattttct ttgttaatgt gtaaatgttg caacaagctg atctaaaata gagagcaatg  180
gaatctgcga tggaacagtg cgagaccaag cctttggaaa ctctatcaag tacattaaag 240
atgtttgaca cttttaaatc tacggaagaa gaccatgaat cagacgagga aagctttcat  300
cttccgttat taggatgtga tgatgaagcg gaaaacggca tggaaatatc tgaactaaac   360
gaagaagatg aagatgccat actaaataag ttcgacacac gcgatgaagg aatggacgtg 420
gatgaatgca gcaacaaaaa agacagcgat gtttctaaaa acaatgttgt agatgaagtt 480
aaacttagtg aagaagaggc aaagctagat ggtatagata atttaaataa agataatcgg 540
atagataatt taaatggaga tgatgaatta ttaggaaata atgagatttt agaagataaa 600
acaacagaaa gtaccccctga tgataccgaa aataaaatcg aaaatgaaat aaatgaaact 660
```

```
gagcctggtt gtgaagaaga ctcaaaagag accaatatta ccaaaaaaaa aaaaaaaaaa    720
aaaaaaaaaa                                                           730

<210> SEQ ID NO 82
<211> LENGTH: 1761
<212> TYPE: DNA
<213> ORGANISM: Diabrotica virgifera virgifera

<400> SEQUENCE: 82
ggggagtgaa tgagctttca ttcgtttcgg cgagggatta gattttgtac tcgtgaattg     60
ggtcaggtta tttggcgcca tgaatcttct tggaaaagct ctcgttttttg tattgatggg   120 taagtacaca ggaaaattgc taaagaaaat tttgagcgtt cggttgggag ttgttagact   180
gaaaatatta aacagcttac atagcaacac ttacacgact ataactatta ttttaagctt   240
tttataaatc cttaaaaacg ttcaaacata aataaaata ttggtattga taacggtata   300
ttatattttg cattttttgc tttaagctaa ttgatggaaa tagtatccat atgttttagt   360
cttttaatgc cctattatac ctgttgcata actttatata atttagaaat atcttatcgt   420
gatcattttc tgtttaatcc tgtccaggga ataaaattt tcttgggact ttcaataatg   480
caggtatctg acaacttttt tagttatgta ttgtagaccg atagaaagaa aacctgcctt   540
gtatcctgtc gagtgttcgg agctgccttt taattattac tattaacaat ttagtgcaaa   600
aaacgcgatt tttttttcgat tttaacacta aattaaaaaa atagattttc cagaatattg   660
aaaaagcttc aaaatggaga ttttttaaag tgaaaatctt ttttttgacag atacttgcat   720 tatttatttg cttgtttccc tttagtaatc accttaatat gaaatttaaa aaaacttatt   780
ttttgacgtt gttttgcaac attttcattc acctttataa aaatgttgtt tagctctta   840 cttttaactg ccgaattttg ttgcatgttt tgttgaattt tgattgtttt gtgtgaaaat   900
ttgaaacata aacgggcttt tgaatttgat gactgctggt gaagtaggta ttgagactta   960
gtttcttatt ttacacatag ctattaacaa tattggtatt gaatgataga taaaagttt   1020 tcttttttacc acagtcagat tttttataca agtgtactat tttgacggta tacaccacag   1080
tgacggtata caccatttta ccacagttag attttttata caagtgtact attttgacgg   1140
tacacatgtt catataggta tcatctttct tcttagcttt ctatagtcca tgtatgggca   1200
tggcctcctc taactgattc catcaatctg tatcctaagc aacttacttt caatttgttc   1260
tggctattgt cagagataac tagaagaaga atccgaataa cttcggcagc agtatgaaga   1320
ctgggtgttg tgttgaaaaa caaacagata tcagtataaa gaaatgata ttcaacaact   1380 agttgtattc tgccagttat gatctatgga gcggaaacta cgacacttac agagttatca   1440
gccaacagat taaaaacacc acgcagggcc ttgaaacgag ctatgtctgt gagagaacat   1500
aatatatgaa atgaggacgt gaaaagcagg gcgaatgtgc aagatgtaat tggaagaact   1560
gcccatatga actggaactg ggtaggacac ttggcatggc aaaacaacga aaggtgaacg   1620
agaaacattg tactttggag accacgcgag ttcattcaga gtagtagaag aagaccagaa   1680
aaatactggc tagacgacat caaagcaaaa gtgggagaca ctggcaccaa caaaaaaaaa   1740
aaaaaaaaaa aaaaaaaaaa a                                            1761

<210> SEQ ID NO 83
<211> LENGTH: 557
<212> TYPE: DNA
<213> ORGANISM: Diabrotica virgifera virgifera

<400> SEQUENCE: 83
```

```
ggggaggtat tctgagtttg ggtattttaa attgataaag tagctagtta agtaagaaga    60
caaaatgtat aaagtagctg ttttagtttg cttccttatt gcagcaataa atgctagccc   120
atacggaact tatgggcatc aggataaaca tgtccaacca gttcctcatg ttcctgacca   180
tccccacggc tcccatggcc atgaggaaca cggcggatat ggtcctcatc atggtggtca   240
ccaagattat acgcacggtt ctcatggtca tgaggaacac ggcgaacatg gttctcacca   300
cggtggtcac caagattata cgtacggttc tcatggtcat gagcaacacg gcgaacatgg   360
ttcacaccat ggtggtcaac atcccggtgc atacggtcct catggtcatg agcaagagca   420
ccaacatgag tctcaccata cgtacggtgg acacgcatat taataattgt tataatgtaa   480
catgtttgac tgttctttaa atttaaataa ataataatat aaattgcaaa aaaaaaaaa    540 aaaaaaaaaa aaaaaaa                                                   557

<210> SEQ ID NO 84
<211> LENGTH: 486
<212> TYPE: DNA
<213> ORGANISM: Diabrotica virgifera virgifera

<400> SEQUENCE: 84
gggataagaa attggaatta agcccaaatt ctctcgaaac aattttttgtc gtaacattat   60 gctgtaataa ctgttgaaaa gtaatggtgg aaattcggta ttttttagata tttatattaa  120 ataataattc gtaggtgaat gcaagttatt atctagaaaa tttgaaggta acaatatagt   180
ttcattagaa tcatttcagt aactcttttc gcaattttttg tcttaaaaat aattgagaaa  240
cgctgtaggg ttaaaaattt aagttacaag aagttagatt ttaggtgtag cttaatgtt   300 ttgtttttaaa tactgctctg gatggtgcag tgaagatgaa cgtaaaaaga agtaagccc   360 aaattctcaa ttgaaaaatt tttactttca tattcgctgt ggcattgagt tgatgtgaag  420
aaatggtgga ataaaatttt ataattgtat atatacaaaa aaaaaaaaaa aaaaaaaaaa  480
aaaaaa                                                             486

<210> SEQ ID NO 85
<211> LENGTH: 492
<212> TYPE: DNA
<213> ORGANISM: Diabrotica virgifera virgifera

<400> SEQUENCE: 85 gggggatttttt tagacatttt gatattttgt cggtatacac gtttcgtgtc tcaagactta  60
aaaatgcgtt acgtggctgc ttacttattg gccgttttgg gcggcaaagc ctctcccaat  120
gctgcagatc ttgaaaaaat cttgggatct gtaggtgttg aagctgaagg agaaagagta  180
aagaaagtca tcagcgagct cagtggcaag tctgttgaag aactcattgc tcaaggtcgt  240
gaaaagttga gctccatgcc agttggtggt ggtgccccag ctgctgccgg aggtgccgct  300
gctgctgctc cagctgctga agaaaagaaa gaggccaaga aggaagaaaa gaaggttgaa  360
tctgaatcag aagacgacga catgggcttt gctctattcg actagactca ttagttgtaa  420
gatcaacctt gttttgtacc ttaatatata tttttttaagt caaaaaaaaa aaaaaaaaa   480 aaaaaaaaaa aa                                                      492

<210> SEQ ID NO 86
<211> LENGTH: 444
<212> TYPE: DNA
<213> ORGANISM: Diabrotica virgifera virgifera
```

<400> SEQUENCE: 86

```
gggagcactg ataaaaaaga tggtgtcgtc acttcgctta acatgaaatt ctgtctattt      60
taatatagaa gtctatggga agaacctgga caagagatta tgtccagcag tgaattaaaa     120
tgaccatatt aattactgac agttttttta agaaatgttt ttttagtagt agtgtttata     180
atttaaatgt ctttggtgtt tggaaattgg cctacacatt gtcccatgta cctatgtgaa     240
acccacgata aaaatatcc catatgtttt tgtacaaatt acaactgtag ctataattct      300
tctatttgac tgatcacatc ctttgacata agaaaaaac ttaaccttga ttatgatcta      360
ttcttaaacg aagcaacatt atttatttat acctatcgct tcttatagtc ttacaaaaaa     420
aaaaaaaaaa aaaaaaaaaa aaaa                                            444
```

<210> SEQ ID NO 87
<211> LENGTH: 340
<212> TYPE: DNA
<213> ORGANISM: Diabrotica virgifera virgifera

<400> SEQUENCE: 87

```
gggcattcac aaaattaggc ataacgtata tgttactagg tctcaaattg cacctaaatt      60
tcctaaaaac attagtgaat tccatacgtt attaaattct gaagaaataa aaactaatag     120
ggggaacgtt ttcttataaa aaatgacgat aataatcaga tcatgttctc gtgtgaaagc     180
aattttttgg atttaagaca aatatcgaca ttttatattg acggcacttt tgaatactgt     240
ctaagacagc gattctcaat ctgtggtaca tgtacaactg gtggtacaat tcattacttg     300
cggtggtaca caaaaaaaaa aaaaaaaaaa aaaaaaaaaa                            340
```

<210> SEQ ID NO 88
<211> LENGTH: 1447
<212> TYPE: DNA
<213> ORGANISM: Diabrotica virgifera virgifera

<400> SEQUENCE: 88

```
tttttttttt tttttttttt tttttttttt cttagtacta gataggattt atttatctgc      60
ccagttacaa atagttata gtaagtaaat ataacaaata ataataatt ataaggtgtt      120
ataagatctt aaaagtctgt ctggcagtta caaccacggt cgcatattat ttaagaactg     180
caaagatgta aacacagtac aaacaacatg aaaaatagct tattaggtat gaattgatta     240
aatagcttag aagcacttgc ggtggacaat tcctgggccg gattcgtcgt attcttgttt     300
ggagatccac atctgttgga aggtggagag ggaggccaag atggatccac cgatccagac     360
ggagtatttc ctttctgggg gagcgatgat cttgatcttg atggtggatg gagcaagggc     420
ggtgatttcc ttttgcattc tgtcggcaat acctgggtac atggtggtac ctccggagag     480
aacagtgttg gcgtacaagt ccttacggat atcaacgtcg cacttcatga tggagttgta     540
tacggtttcg tggataccgc aagattccat acccaagaag gaaggttgga agagggcttc     600
tgggcaacgg aatctttcgt taccaatggt gatgacttgt ccatcaggca attcgtagct     660
ctttttcgagg gaggtggaag cagcagcggt ggccatttcc tgttcgaagt cgagggcgac     720
atagcagagt ttttctttga tgtcacggac aatttccctt tcagcggtgg tggtgaatga     780
gtaacctctt tcagtaagaa tcttcatgag gtagtcggtc aagtcacgac cggccaagtc     840
caaacgagg atggcgtggg gaagagcgta accttcgtag attgggacgg tgtgggtgac     900
accatctccg gagtccaata caataccagt ggtacgacca gaagcgtaca aggagagtac     960
ggcttggatg gctacataca tggcgggtgt gttgaaggtt tcaaacatga tttgggtcat    1020
```

```
cttttctctg tttgccttgg ggttgagtgg agcttcagtg aggaggactg ggtgttcttc    1080
tggagctaca cggagttcat tgtagaaggt gtgatgccag atttttttcca tatcatccca    1140 gttggtgatg ataccgtgtt caatggggta tttcaatgtg aggataccte ttttgctttg    1200 ggcttcatct cctacgtatg agtcttttg tcccatacca accatgacac cttgatgcct    1260
tgggcgaccg acgattgagg gaagacggc acggggtgcg tcatctccgg cgaatccagc    1320
tttgcacata ccggatccat tgtcaacgac aagagccgca acatcgtcgt cacacatgtt    1380
gtcttttgtg gttgatcact gctcactaga cagaaaaaca cagctaataa gcttgaatgc    1440
gacccc                                                                1447

<210> SEQ ID NO 89
<211> LENGTH: 1444
<212> TYPE: DNA
<213> ORGANISM: Diabrotica virgifera virgifera

<400> SEQUENCE: 89
gggagtcgca ttcaagctta ttagctgtgt ttttctgtct agtgagcagt gatcaaccac      60
aaaagacaac atgtgtgacg acgatgttgc ggctcttgtc gttgacaatg gatccggtat     120
gtgcaaagct ggattcgccg gagatgacgc accccgtgcc gtcttcccct caatcgtcgg     180
tcgcccaagg catcaaggtg tcatggttgg tatgggacaa aaagactcat acgtaggaga     240
tgaagcccaa agcaaaagag gtatcctcac attgaaatac cccattgaac acggtatcat     300
caccaactgg gatgatatgg aaaaaatctg gcatcacacc ttctacaatg aactccgtgt     360
agctccagaa gaacacccag tcctcctcac tgaagctcca ctcaaccca aggcaaacag     420 agaaaagatg acccaaatca tgtttgaaac cttcaacaca cccgccatgt atgtagccat     480
ccaagccgta ctctccttgt acgcttctgg tcgtaccact ggtattgtat tggactccgg     540
agatggtgtc acccacaccg tcccaatcta cgaaggttac gctcttcccc acgccatcct     600
ccgtttggac ttggccggtc gtgacttgac cgactacctc atgaagattc ttactgaaag     660
aggttactca ttcaccacca ccgctgaaag ggaaatcgtc cgtgacatca agaaaaaact     720
ctgctatgtc gccctcgact tcgaacagga aatggccacc gctgctgctt ccacctccct     780
cgaaaagagc tacgaattgc ctgatggaca agtcatcacc attggtaacg aaagattccg     840
ttgcccagaa gccctcttcc aaccttcctt cttgggtatg gaatcttgcg gtatccacga     900
aaccgtatac aactccatca tgaagtgcga cgttgatatc cgtaaggact tgtacgccaa     960
cactgttctc tccggaggta ccaccatgta cccaggtatt gccgacagaa tgcaaaagga    1020
aatcaccgcc cttgctccat ccaccatcaa gatcaggatc atcgctcccc cagaaaggaa    1080
atattccgtc tggatcggtg gatccatctt ggcctccctc tccaccttcc aacagatgtg    1140
gatctccaaa caagaatacg acgaatccgg cccaggaatt gtccaccgca agtgcttcta    1200
agctatttaa tcaattcata cctaataagc tattttttcat gttgtttgta ctgtgtttac    1260
atctttgcag ttcttaaata atatgcgacc gtggttgtaa ctgccagaca gacttttaag    1320
atcttataac accttataat tatttattat ttgttatatt tacttactat aactatttg    1380 taactgggca ggtaaataaa tcctatctag tacgcaaaaa aaaaaaaaaa aaaaaaaaa    1440 aaaa                                                                 1444

<210> SEQ ID NO 90
<211> LENGTH: 993
<212> TYPE: DNA
```

<213> ORGANISM: Diabrotica virgifera virgifera

<400> SEQUENCE: 90

```
ggggagttcc tgtctagttt tgttgctgaa tgttatactc gtagaattga ttgaatcgaa      60
aaaaatattt aaaatgaaat ttaaattttc cgctgatgat gtaattgctg agaaaagaac     120
aacacaagga aatataaatc ttattaaacg atggctgttt gcagccgatg aaaaatatgt     180
accatctaaa ttatcagatg aattcatagt tctgtttcta ttgtcttgta acaatgacat     240
tgatgtgact aaaaagacta ttactgccta ctataaatta aggaaagacg cacctgaact     300
gtttgatgac agaacttccg agagagaaga tattcagaaa gccttaaaca cactgagaat     360
ggtaagcata ccaaatcgga cagacgaaaa ctatcaagta gtgtatctta gtctaaaaga     420
tacagatagc agtaactttg aactgaatcc cgttatgaaa gcctcattaa tgctaataga     480
tatagaacac cacaatagcc caccagatgg agttatgttt ctagctgata tgaaagggtt     540
cgggttttta cacgcgttta aattgaatcc aatctcgtta aagaaatatt tcaattatct     600
tggagaagga ataccaactc agttcaaagg aatgcattta atgaacggaa attatttcgt     660
ggatcaattg ttgagcattc ttaaggtgtt tatggcttca gaccttataa agagggtaat     720
catccatcaa gtaggctgga atccggaaga agcattccca aaaaaatgtt taccaaaaga     780
acttggagga gacctagaat cagaagacgt actttgtgaa cggacattac cgctgttcaa     840
ggatcgggaa tattttggaa aggcggaaga ggaactaagg aaaagtgtac ttaaataaaa     900
atgcgttaca tgtaatagta ttaaggaatt acaattattt ttggaataaa tatttatagt     960
gccaaaaaaa aaaaaaaaa aaaaaaaaaa aaa                                   993
```

<210> SEQ ID NO 91
<211> LENGTH: 989
<212> TYPE: DNA
<213> ORGANISM: Diabrotica virgifera virgifera

<400> SEQUENCE: 91

```
tttttttttt tttttttttt tttttttttt ctccttccgt attaaatcga tcagttcttt      60
agctctcctt acttttttctt cccctgacag ttctgcttct gcctcttctt tagtgtctgt    120
agtttctttt tctgttttaa cttcttcaga ttctgtatct actttaactt ctttatcctc    180
cttattttcc tcggctaccg taacttcttt acctttcgta cttctgcgt tctcttcttt      240
tgctggttct tcttcttttg ctggttctgt atgcgtttct gacggactcg gttgctcttc    300
ggggggttta tcttcggatg attttttcaat ttctgtttcg gaggggctca attcttcttc   360
ggggggactt tcttcggacg tattcagagc attattatca ctttcgactc gtggtgtctc    420
accagcttgt tcatgtgcca ggaagttttc tgattcagct gaaatagaat gaactggggc    480
tgtactgaat cctgccctgt tcaagacatc atccacttta gcagaaactg tttctaaatt    540
agtacttcct gtaatgatat ctaaaggaac acccttctga ccaataaaat atatcgaggg    600
tacactcggt tctttataaa tttcgctaaa ctgctggtga gctgtagagc ccgcaattac    660
tttgatagct acaaagtgat cttgttccag ttttttctcca aggtcgccat tattgatgag   720
gtctgttatt ttttgtgact tttcgtcagt accttcaata tacactacaa aaacggctcc    780
tttcgattta gaaaaagcaa ccgcatcggc tatttctcca ctgtaccact tcattttaaa    840
aaaaaataag ttagtttaga cttttacaac aataaaatac tagcagactt ctaacaatta   900
aaaaagtaca catcagttat cgcaactaca aacacaaaat acaattttaa acgtcaccgt    960
caccggtcac aatctgtcat gtactcccc                                      989
```

<210> SEQ ID NO 92
<211> LENGTH: 817
<212> TYPE: DNA
<213> ORGANISM: Diabrotica virgifera virgifera

<400> SEQUENCE: 92

```
ggggatggcc ttttccggtt cacgccgtcg ttcagcaaga gcttgcgatt tttatttttg    60
aaaaatagag agtattctct aatatttaag gacagcatgg aagacgattg ggctgtggat   120
aatcagagtg gtggagttgt cgccccaaaa attgcagaac tacctgaaat taagttgttc   180
gctagatgga actgcgatga tgtccaagtt tcagacatgt cccttcagga ctacattgca   240
gtgaaagaaa aaaatgcaaa gtatttaccc aattcagctg gtagatatgc tgcaaaaggg   300
ttccgtaaag cacaatgccc aatcgttgag aggttaacaa actctctaat gatgcatgga   360
cgtaacaatg gtaaaaaatt gatggctgtc agaattgtta acatgctttt gaaattatc    420
catttactaa ctggagaaaa tccattacag attttagttt ctgctattat caattcagga   480
cctagagaag attctactcg tattggtaga gctggtactg taagaagaca agctgttgat   540
gtgtcaccct tgagaagggt taaccaagca atttggttgc tctgcacagg tgctagggaa   600
gcagcattcc gtaatattaa aactattgct gaatgtttgg ctgatgaatt aatcaatgct   660
gccaagggat catcaaattc atatgctatc aaaaagaagg atgaacttga acgtgtagcc   720
aaatccaacc gttaaattta tttctcattt tatattttat ttccaataat aaatatggat   780
aaaacacaaa aaaaaaaaa aaaaaaaaaa aaaaaaa                             817
```

<210> SEQ ID NO 93
<211> LENGTH: 1186
<212> TYPE: DNA
<213> ORGANISM: Diabrotica virgifera virgifera

<400> SEQUENCE: 93

```
tttttttttt tttttttttt ttttttttc gcaatgcgga gacaaattta taaaagagg     60
acttgtgcaa atattgctg aacatgtcaa aagaaccaac agaaattgtg ccatccactc    120
cctatattaa ccaaaacagc agtacaaaga aattaacgtt tatttaaata atatctaagg   180
attttttctta ataaaatgac aacacagtgt caaatctata agcgctaata tattttataa   240
cttttttctaa gtttggaccc aaaagtgtat actgtaaatg tttatgttta tatacagtgt   300
gtcatttaaa gtagaaacat ccctgtaaca tttgaaatcc ttaaacattt caagagtttt   360
tttaataccg tgtgttact tttaaattag atatagatag gaatacatcc aatacatggc    420
aacactgctt cctcgtttcc cacacctgag tcgcgccaat tgactcagtc attcgtcgat   480
tctacagtag caatgcaact tattctcata aaaaatgttg ccgattttag cgattccttt   540
agtctcctat ccctaatcga aaactaaacg tatggtaaag taataaaaga ggtaattcgg   600
gacaacattt aaagggttca tttaaagtac catatcataa tcatcatcat cagcctgttt   660
taaatccagt gcaggacata agcctctcct gtttgtatcc agaggccgtg cctctcctgt   720
acggttttgt gtagtatgga tccaattttt cgttatcttt catcatcttc caatcgtgta   780
ggtggtcttc ctctctttcg gttatctgtt cttggtatcc attcagttaa cttgcgtgtt   840
caccttctat ctttcatcct tgccatgtgg ccagtccatc tccattttag tctgcaagct   900
ctctccacaa aatctgtaac tctagttttg tttcgtagat cttcatttgt gatcttgtct   960
tttatttttta ctcctatcat tgaacgattc atttttcttg tgctattctt agttttaaag  1020
```

```
cattcttttt gcagacagag tttctggatc ataggtcatt actggcagaa cagactgatc    1080
gaagactttt actctttaga ttaatcggta cattgctgcc tttaaatacg tttttaacag    1140
ctccatatgc tgcccatcca tgtgctattc ttcttgatac atcccc                   1186

<210> SEQ ID NO 94
<211> LENGTH: 1033
<212> TYPE: DNA
<213> ORGANISM: Diabrotica virgifera virgifera

<400> SEQUENCE: 94
tttttttttt tttttttttt ttttttttttg cgtagtctga cattgcgacc aggttttgta     60
gacgtcttga actattttg ttattttta attgttgaaa tctaaataga gcggattgaa      120
tattatcatt tactaccctg tgacaataat attattattg tcacaaaaca gtaaacaata     180
atattctcat tccaatgttc gaacaacaat gaatgttaat atagaccagg actaatctgt    240
aaaaattcgg atggcattaa aattttttgca gataaagtta ggtgacacct ttagtaataa    300
taattgaccc atgctccctc tcaaacataa ccggaacatt aataaaaaat caaaatattt    360
aaaaattcag aaaagatcc atttttttct gctttctttg cttatagctt taaaacggtt    420
cgttctggaa caaatccgta cagaaacaaa acagagacaa ttgaatcatg tatgatgtac     480
gaccggtcaa aaatgtctta aggtattacc ttttctgcaa aatagcaata aacacaaaat    540 aaggggggcaa aacacgcgtg ttgttattca atgtctctta accactttgg tggcagttag     600
aaccttagta atccgcttag aaaattctta tagcttagtt aaatggtcta ccaaatttca     660
ctaaaatcga cctaacagat tctgcataat aaatttgcaa tataaatgtt tttaaaaaag    720
ttcaaatttc aaaatctttc tgaacaaaaa gtagacaatt tagtagttgg ctaattttc     780 cacatacaaa aaggcactcc acccatctaa tacaccccac agcatcaaaa tcggaccatc    840
taaggggcct cagcaatgtt tcaaaaatac taacaacttt ccggctcata aacaaatagc     900
tttgtttaat aataaaaaaa taataatttt tagcaacgca aataattaat accggtatag    960
tttgacttaa tcttttaaat gctgtcagca gaattgctat tttattttt aatcaaaagt    1020 tatcctcgtt ccc                                                       1033

<210> SEQ ID NO 95
<211> LENGTH: 551
<212> TYPE: DNA
<213> ORGANISM: Diabrotica virgifera virgifera

<400> SEQUENCE: 95
ggggacatta atttcaagcc taggttctgg agaatattaa ttaacatttc ctgcggtatt     60
gttggatgaa cattagataa gagaagacgt tccgatggag tgactaatct acgtgttaga    120
agtacttcat tatttatttt tatggatcct accttattta gaaagtcatc aactacagct    180
ttacttgaaa gataaacgca tactcggtta ttagagattc ttgatgaata aataatatttt    240 tctggttgga cgagtggtcc tagttgcaaa agataatctt gcaattttgc gccattaatt    300
gaactgaaga tgatggcttg ttctttcact ggtaattttg gagtagtttg ttgagatgca    360
atagtagagt acattagagt gttttgagaa gtggtaggag tttccattgt tgataaagta    420
ttattcatca tttaatgtta cttgaacgat ttattataaa catatttagt tagggttata    480
atatgtatgt tgtgactggc tgaatcacta atgtgtatgc caaaaaaaaa aaaaaaaaaa    540
aaaaaaaaaa a                                                        551
```

<210> SEQ ID NO 96
<211> LENGTH: 1050
<212> TYPE: DNA
<213> ORGANISM: Diabrotica virgifera virgifera

<400> SEQUENCE: 96

| | | | | | |
|---|---|---|---|---|---|
| ggggagaatt | tatgaatata | ggtaagcctt | aatacactaa | tttaagagtt | taataattgt | 60 |
| atattatttt | caaaaatgtt | ttaagtgtgt | gactttgtag | agatattgtt | ctgtgatctg | 120 |
| agcaggtttt | gcacttgact | ttttgagaat | tgctacaaag | gtcgattgca | gcaattgtca | 180 |
| ggcgattgtg | aagtctgat | atgataaatt | aggagttcaa | ccattacata | aatatcatct | 240 |
| tcatcaatga | gttttaataa | ttcgatgtgc | acatcttctg | gtccagtaac | tttgctatct | 300 |
| ttagtgttct | tgatgacata | gatgacttct | tctcgtaata | atggtggttg | atatcctcta | 360 |
| tggtttctag | tgacagtttt | tctctttcct | cattaattaa | ttcttgaatg | taattgatcc | 420 |
| agtgacacat | tctctccaat | tatatcagta | ataattcatc | atataacaat | tcatcatatt | 480 |
| tccttcatca | tttttgatgt | tatttctatt | aaaaatgtcc | gtacctacat | tatcctcctc | 540 |
| ctcctcccct | atcctttatc | cttcgtaagg | atgtggtgac | gttatggtat | tgacgaatg | 600 |
| gtttctatcc | attcttctct | ctcttgggcg | cggtgtgctg | cctcagacag | agagtaaccg | 660 |
| gtggcgcatt | ttatttggtc | tgaccatcgg | agtggctatc | ttcctcgagt | tcttttaccc | 720 |
| tctaccttgc | cttcaaccac | caacctctcc | atgccttctc | ttcgtctggt | aatgtgtcca | 780 |
| aagtacctca | atatattttg | gttgatgatg | gtggtaagcc | tagtgttgat | gtcgagttct | 840 |
| gataatattg | agatatttgt | gcgatgtgct | acattatcca | tattcacctt | aattaaatgc | 900 |
| acttttaaaa | catttttttt | tataataatt | atgtaggtcg | ttttttttaat | ttatcattaa | 960 |
| gctctaatca | agttgagaga | agccgaacct | cagctatgta | tctaatatta | tacagtatgg | 1020 |
| tacaaaaaaa | aaaaaaaaaa | aaaaaaaaaa | | | | 1050 |

<210> SEQ ID NO 97
<211> LENGTH: 1391
<212> TYPE: DNA
<213> ORGANISM: Diabrotica virgifera virgifera

<400> SEQUENCE: 97

| | | | | | |
|---|---|---|---|---|---|
| gggggaaaaa | atgtttggat | acaatgtatg | tatacaagtg | ggctttgatg | atgtgttatt | 60 |
| gtgttttaag | tgctaaaaat | attttttttat | attatgttca | caaaaaaaag | catgtgtgtt | 120 |
| ggtgacattg | ttaatcctcc | tgtcagttaa | gtcctttatt | catcttaaac | aataaacttt | 180 |
| taaaacatga | gcttcaaaaa | agagcataaa | tgattattat | tttaatgctt | ttcaaaatgg | 240 |
| ggttttagat | gtacacgata | tatattatgt | tttgcataaa | tgatacttt | attatattt | 300 |
| tattatttgg | tcttacttta | ttgtagttat | tttttttgata | tttttttgtt | cttactttgt | 360 |
| tatttttttg | tagattgtta | atttgcaact | aaacgatcta | cttataatag | cgttagtaca | 420 |
| aattaacaaa | acgaaaccta | atatctacca | cgagttactc | ggttaagacc | atacagaaat | 480 |
| aaataaattg | cttaattgca | attaaaacag | ccgtcaaaaa | tgataagaaa | attaagaaaa | 540 |
| acaatatttt | ttctaataat | aaagtaataa | aggcagtttt | tgttttttatt | ctattcagag | 600 |
| ttggaccacc | atctccatat | agctatttca | gcatcccatg | catctttagt | gaagctatgc | 660 |
| agtcacaact | ctgaagcgaa | tattaacaac | cctgaatatt | taagggaaac | catcgcgata | 720 |
| caatgattcc | accttttgag | acgcaatcta | gcgacatctc | tcgcaaaacg | aggaaaacaa | 780 |
| cgaaaagccc | tagatacaaa | gtttactact | ttttaaacaa | ttagaataat | tgaaataaaa | 840 |

| | |
|---|---|
| ataataataaa caatatttta aatccacgaa tttcgttaat aaactgcttt ctggctgcat | 900 |
| cctgtatatc tggctatta tatttagctt aatatttttt ctcttttaat atttggttca | 960 |
| agatatagag tgtttagaaa caaaattaca ctaagggcgc tcgcaaacac agccacttgt | 1020 |
| ggccgccacc ggtggcagtg ctgactgagg tttgtatgta ttttaaatgg attcggccca | 1080 |
| cacactatgt ttccggtgat cttcgagcga caagccacga caagctatgg cggtggccgt | 1140 |
| ttctggctac atgaagtcgg tggcgatcac aaaacagcca ttcgtccaga gagagaaaga | 1200 |
| gttaaaacaa catcataaga aagagcttgg atacaaaaat aggctaccag aatatatgaa | 1260 |
| ataaatagtc ggtctgttta gccatgaaga ggaaatggat gaagaacaac tacgaaaaca | 1320 |
| aactgtaact cctaacttca aaattaaaac accatgtatt gaaaaaaaaa aaaaaaaaa | 1380 |
| aaaaaaaaaa a | 1391 |

<210> SEQ ID NO 98
<211> LENGTH: 515
<212> TYPE: DNA
<213> ORGANISM: Diabrotica virgifera virgifera

<400> SEQUENCE: 98

| | |
|---|---|
| ggggcttact tacctgtaaa cgaatcattc ggtttcactg ctgatttacg ttccaacact | 60 |
| ggaggtcagg ccttcccaca atcagtcttc gatcactggc aaatcttacc tggtggccca | 120 |
| atggaaccca gtaccaaacc ctatggaatt gtgcaggaca cacgtaaaag aaagggtctt | 180 |
| aaagaaggac ttccagacct ggcacaatat ctggataaat tataaacaac taagaaactt | 240 |
| aatttatgta cagattattt aataaaatta tttcaattta ctcaacggtt tttatagtta | 300 |
| attgtatttt tgatattttt attctgataa gttttcagtt ctctcaaatt gatggcaaca | 360 |
| ctagaaatga aataaactaa ataatctgac taatatttta tgtttgctat atatatttt | 420 |
| gttaacagtc cagatatttg tatatttatt aatttgacat caaaagtaaa tctgatgaaa | 480 |
| cattgaaaaa aaaaaaaaaa aaaaaaaaaa aaaaa | 515 |

<210> SEQ ID NO 99
<211> LENGTH: 580
<212> TYPE: DNA
<213> ORGANISM: Diabrotica virgifera virgifera

<400> SEQUENCE: 99

| | |
|---|---|
| ggggatgtta tacattactg aatattgttt gcttaagtaa taataataat acaaaagagt | 60 |
| catcatgaag ttcttggttt tcagcttggt ctttgctgtt tactatgcaa atgcagctat | 120 |
| tactcccgaa caagctgaga agatcaaaag tttccacaaa gaatgtcttc cagaatccgg | 180 |
| agttaatccc gaattggttc aaaaggcaag acaaggagat tcgccaatg acgacaagct | 240 |
| aaaagcacat atcttctgcg tctccaagaa gatcggtttc caaaacgatg ccggtgaaat | 300 |
| tcaagtggaa gttctcaaag ccaaagtggg tgctgcctta aagatccag ctcttgctgc | 360 |
| ccaattgatc ggcacctgtg ctaagcaaca agcaaatgga cccgaaacag cctttgaaac | 420 |
| cataaaatgc tatcacgaaa agacaccaat tcatcttagt attatttaaa tattttgatt | 480 |
| ttgttataat ataaaaaact tctttttgaa gagttgttat aaaataaatt ttttatcatt | 540 |
| atatgtacag aaaaaaaaaa aaaaaaaaaa aaaaaaaaa | 580 |

<210> SEQ ID NO 100
<211> LENGTH: 913
<212> TYPE: DNA
<213> ORGANISM: Diabrotica virgifera virgifera

```
<400> SEQUENCE: 100
ggggagtgtc aacaatgatt tatagcagat atctgtggat tgtgtgtgta gtgttatcac    60
tattttatca gacaaattgt gaatgccta  aaatatatac tcgcaatgaa tggagcgctc   120
gaaaagcatt aagtaccaga ccgttaagag aagatcctcc accatatgtg gttgtccatc   180
attcggccac tcgctcatgt ttttcagttg aagattgttc aaaacttgta aaaagcatcc   240
aagattacca tatagatcac aatggatggg atgatattgg ttacaacttt ttgattggtg   300
gtgatggaac tatatacgaa ggtagaggat atggtttaca tggtgcgcat tctattccat   360
acaacgcaag aagcttaggg gtttgccttt taggaagttt aaagatacg  aatcctccta   420 atgtacaact gaaagcattg gaagactttt tgtcttgtgc agcagctgat cacaaaatta   480
ttgcagatta tcaccttatc ggacatcggc aagctgataa aacagaatgt cccggggatc   540
gagtgcatgc agttatcgaa aaatggcctc attttgaagc caatccacaa gatgcttccc   600
caaagaaact gtaaacatag cgaagttacc ttttctctta tggaataaac acctctctat   660
cgcaatgttt ttagattaca attattaata catgtaaata tttaaaagac tgtatatcta   720
ctcatacttt aaagatgtgc gaaaatatat cactatcttt aaaaaaaaaa aaaaaaaaaa   780
aaaaaaaaaa aaaaaaaaaa aaaaaaaaaa aaaaaaaaaa aaaaaaaaaa aaaaaaaaaa   840
aaaaaaaaaa aaaaaaaaaa aaaaaaaaaa aaaaaaaaaa aaaaaaaaaa aaaaaaaaaa   900
aaaaaaaaaa aaa                                                      913

<210> SEQ ID NO 101
<211> LENGTH: 569
<212> TYPE: DNA
<213> ORGANISM: Diabrotica virgifera virgifera

<400> SEQUENCE: 101
ggggaggcgg tcgacatgtt ttttttttt  ttttttttt  ttttacattt atccacattt    60
tattctcaaa ataaaaagtg tacaattata aaattaaatc tacagcctag aacctcaatt   120
tttggaagaa ccatttgttc tttccttgct tataccttcc ctcaaatttg acacgggtct   180
ggaatctagc cttcttcctc ttcatggcat cttttgaggtc cttgggtaca actttcaagt   240
ctgatgccaa atctacagag tatctagtgg gcatgagatg ttgtagttc  aatactttga   300 taaaaggctt gatcttggac ctcttgtgca ttttgccttt gcccatgcgt tgtggattt    360 tccttgggta cctatcaatt ccagctacta aggcatgtcc gtattgttta tctgatgtac   420
cttcatcgta ggttttgacg actacggctt tcggccggc  gtatcggccc ccgaggacca   480
atacgacttt tcctgatttc attattttac ccattgtggc agtgctttga caactgctga   540
aaaaaaaaaa aaaaaaaaaa aaaaaaaaa                                     569

<210> SEQ ID NO 102
<211> LENGTH: 1350
<212> TYPE: DNA
<213> ORGANISM: Diabrotica virgifera virgifera

<400> SEQUENCE: 102
tttttttttt tttttttttt tttttttttt gaactaaaaa tgaaaataca ttttgggct    60 acgtaatatt cctatcagct cttttacagc tggaatgttg tatgtgctgc tcattattac   120
tgcgttcagc ggttttttat tcttgtcaat ttaatacatg atatttaaaa aaaaaagta   180 tatttacaaa cctagggggtt ttggaaaata atatgtacag tagatattac tctatgggca   240
```

```
gtaagttgcc atatatgaaa gtcatggata tttacaatat ctggaaagtg attcaataac    300
tggatcttca gtgtgtcgat gtctatcgtg tcaggcacag tctgtagaag aatcaggcag    360
ctttctttca tatatggata acttaagaac attatcaaag ttgaagatat tatcgccatg    420
ataggatcta tatattttgc agtatctttg tcagtaaaat atactaggag agcgcatatt    480
acaaccaaaa tacaaccgtt tacatctctg gccatttccc aaaatccctg cctttgtttt    540
tgatggccga tcataggatg gatagttttg cttctggata atcgtcttgc gccttgctgc    600
aaagactggt caactactat tttacttaaa actacatttc cgctttctgt tacataaaga    660
aaacttcctt ggtggaatgt atatccacca atcaacaggt agcatactcc gttgagtaat    720
aaaccacatg ctcctaaaca taaaacagat atggaatgat gcatctcgtc atgatggtcg    780
atatgaacca atgtctgaca tgcttcaaca aaaatagaaa aacttaacga agctaagaac    840
acacaacata ttaacataaa tatgcatcta gttctggccc agccaaatgt atttttagc    900 ttcttttctt ggttggacct ggttacggac gctttcgtct tcttatggtc atggcacttg    960
gccgggttgg atgttaactc ttctcctata cttcgctt cgcttggtgc cttttcatt   1020 tcgaatactt gtttcggagt atcttttcca tacttaatag ttaaaataca tcctcccaat   1080
gccataatat tacacaaagt gtggtaagag tccattaata gtgtcagagc atgagtgggg   1140
tgacttacaa ttagttctaa taagaaaaag gcgatggtca agcctagtac cacgtacagc   1200
tgaaaaggtt gcatccttct tacccattct ttcattgcca tggttgaact attcagagca   1260
cacgtctgaa cgctaggaat atcttaattg aatattttcc actgaacact gcaactatac   1320
tgtagaaact gtcaggtgtc gactgtcccc                                   1350

<210> SEQ ID NO 103
<211> LENGTH: 991
<212> TYPE: DNA
<213> ORGANISM: Diabrotica virgifera virgifera

<400> SEQUENCE: 103
tttttttttt tttttttttt ttttttttc ttaattacaa atatttacta attttcttat     60
tattatcagt caaattacaa aacaaattct attttgctc atcaatgggc ttaaagtgat    120
ttagtaaatt tacggtccaa tctccttcaa ccccttttgt aaattctctg ataaatctat    180
agttgcaaat cgaaattttt tgttgatatt caggtagcat tcccatattt aagggaggtt    240
cttcacctct agatctcatt ccagctaaac cttcaaaga atggtaaacc atggttattt    300
cgacgaatcg ttttgttct ttgccttctt cttcgttaaa tataacacca acctgatatg    360
gaaatgaaaa atatatgtca tctacactag ttgctatctg ctcccttga ctcatggaca    420 tcatagatat tgcttttgt agactaccga taatgtcatt tgttactaga ccgtctaatg    480
atttaatatc accttcagac aatttatgtg atactacctc cactgctttt ttagaagcac    540
ttacaaaatc tggaagatta aattcttgat ctaaataggg cctaatgata aaggtagcaa    600
gaataaaatt tctatagtt ttaaataaag aaggccaaac aaatatggga gagtctggca    660
gtaatggagg taatttgttt gaaggagaac ttggatcatc tgaataccat cttctttgat    720
taaggcctga atttaaggat ttgttattta aaaaatatga aggctgcttg gtacaaaaac    780
ttgcatgttt acataagaaa tgatttgtta ttgtactatt aaatttacac aaatttaaat    840
tactataatt tcgcacattt ctgaacaaaa cgttaatatt catttatca ttttaatata    900 aatcaacaaa gtcaaaagta ctaaaatatt ctaaaatttt agatttttta ggttctgtcc    960
tgtcacggtt ctgtcctgtc acctactccc c                                  991
```

<210> SEQ ID NO 104
<211> LENGTH: 445
<212> TYPE: DNA
<213> ORGANISM: Diabrotica virgifera virgifera

<400> SEQUENCE: 104

```
ggggagtatt cacttgatct tcaaggtaga ttaacgcaag tagaaatcta aaacatgtct      60
ggacgtggta agggaggcaa agttaaggga aaagcaaagt cccgatcaaa tcgtgctggt     120
ttacaatttc ctgtaggtcg tattcatcgt ttattgagaa aggaaatta tgccgaaaga      180
gttggtgctg gagctcctgt atacttggca gctgttatgg aatatttagc tgctgaagtt    240
ttggaattgg caggaaatgc agctagagat aacaaaaaga cccgtataat tcctagacat    300
ttacaattgg ccataagaaa tgacgaggaa ttgaacaaat tactgtcagg agttaccatc    360
gcccaaggtg gagtattgcc taatatacaa gcagtacttt tacctaaaaa gacccaaaaa    420
aaaaaaaaaa aaaaaaaaaa aaaaa                                          445
```

<210> SEQ ID NO 105
<211> LENGTH: 2235
<212> TYPE: DNA
<213> ORGANISM: Diabrotica virgifera virgifera

<400> SEQUENCE: 105

```
ggggcagtgc tttagaggcc acgaagcaat ttctaggata gacgaacgac gctcgcgacg     60
acgcgctgcg acgcacacga caaaaaaata cacaatacga caccacgcgc cattttgcca    120
ttttctgtgt gtgcagtgaa gtgaagtgct actaaaatct tcaaaattca acccttctaa    180
gaaggccgat ttcatgtgtt ctatatcgaa gtaaaagagc aatagcatgg gagtggcaga    240
ggatttcgct cccagcttca cgcaaaagcc tcaattgagg caggaggacg atggaaacaa    300
actcattttc gaatgccagt tactggctgc tccgaaaccg gaaatcgaat ggtttcgaag    360
cgatatacca ctttcagaag acagtaggac taattttaaa attcaatcca taggcaccaa    420
caaatttta gtagtactcg aattagatga tgttattgaa accgacgctg gcctttacaa     480
ggtcaaagcg aaaaatacca tgggggaaat agcagcctcc atcaatctca acttcagccc    540
catggacgaa ccaaaagaaa aacaaataga cggcctagca cccacttttg cgaagaaacc    600
agctattcgc caagaagatg atggcaaaaa attattattc gaatgtagga tacaggccga    660
tccccgtcca acggtcagtt ggtcccacaa tggcaacgct gttagcgaag gtccacgtca    720
caagttgagg atagataaag atggccattc atattttgcg acccttgaaa taatcgatgt    780
cacggtagag gatgctggca aatacaaggt gaccgcaaaa aatgacttgg gagaaagtaa    840
cgccacaatc agcctaaact ttgacagtgg agatagcgct gatggctttg cgccttcttt    900
ccttgagaaa cccaaaatca tacctaatga gagtggcact cttattacta tgaaatgtaa    960
atgcaaagct aaacctaaac ctgacgtcac gtggttccgc ggaaccacag ccgtcaagga    1020
atcttccaaa attaaaatcc agatcgttga tctcgaagaa gacaaattcg aactgtcctt    1080
agaaatcaag gatccatcgg cagctgatgg gggtacttac agatgccatg tgaagaacga    1140
atacggagaa agtaatgcaa atctgaacct aaatatcgaa gcagaaccag aaccagaagg    1200
agaaggacca acgttcgtcg aaaaacccag gataacctct cacgatggag gcaaactcgt    1260
tgtcatggag tgtaaagttc gtgctaatcc taaaccccact atagtttggt acagagaaag    1320
caaagaagtc acagaatcat ccaaaattaa gatcagtatt aaacaaacag aagaagatat    1380
```

```
atattacgtc aaattggaac tcaatgatcc ggggattgat gactctggct tgtacaaatg    1440
caatataagg aacacacttg gtgaactcaa cgccaacctc accttaaaca tcgagattat    1500
tcctgttatc aaagaaaaac ccaaagttat taaaatcatt aagaagaaaa ctgttattgt    1560
tgaatgtaaa gttctcagca agtttgcacc tgattgtaca tggtttaagg aaagcgatgc    1620
cgttaaagaa gattcaagac atactgttca cgttgaccaa gttaaagacg gcgaatttac    1680
tgttaaactc gaaattaatg aagttgagaa aaaagacaaa ggtatgtaca aattggttgc    1740
taaaaacgaa aagggtgagg caacttcaca agtcgttgaa gtcactgagt tacctccaga    1800
ggagaaaccc aaaggagaca agccgaaact gaccaaacta accaatatcg ttactgacga    1860
aggaaaatca gttgatttta taacttctct caaaatcgaa gacaaaacag tcaaaatcac    1920
atggtacaag aacaccactg tgataaccga atcttcagaa atcaaaatct cttttgatgg    1980
cactgtgacg cgacttagca ttagtaaatg taaagtatca cattccgcta catacaagtg    2040
cgttgccaaa aacgaatttg gcgaagacga aataagcgct acacttaaag taaacgaagc    2100
taaagaggaa gatgaagaag aagaagaatc cgaagaggag gttatcgaag aaaagaaaga    2160
ggaaagaaaa gtagaaaaga aagaagaaaa acaggaaaag aaagcaaaaa aaaaaaaaaa    2220
aaaaaaaaaa aaaaa                                                     2235

<210> SEQ ID NO 106
<211> LENGTH: 1148
<212> TYPE: DNA
<213> ORGANISM: Diabrotica virgifera virgifera

<400> SEQUENCE: 106
ggggagagta gatagtaagt aagtgaatgt acgttgtgaa tgacggaagc cggtttgtta     60
cagagaggag gatggagtcc aacacgataa cgttgacgag attttcttg gcggaacaac    120 aaaaatttcc agaagccaca ggtgaattga cccagctgct gacttctatt caaacagctg    180
ttaaggttat cagtagcgcc gttagaagag ctggtattac caaattgttt ggtaccgtag    240
gtgaaacaaa tgtacaggga gaagaagtta aaaagttgga cgtattggcc aacgaattat    300
ttatcaatat gcttaagtca tcttatacag tagcattgct tatatctgaa gaaaatgaaa    360
caattttgga ggtagagact gaacaccgag gaaagtatat agtagccttc gatccattag    420
atggttcctc gaatatcgac tgtctggtat cgataggttc aattttcgcc atttacagaa    480
aatccgacaa cacagttcca gccctcgatg acacactaat gtccggaagg aatgtagtag    540
cagccggata tgcgctttat ggcagtgcaa ctatgctggt catatcttct ggatctggtg    600
tgcatggttt catgctggat gccaccatag gagaatttgt tttgactgaa cacaacatgc    660
ggattccgaa aaaaggaaaa aatctactct ataaacgaag ggtactacca cgaatgggat    720
gatgccataa gagaatacgt cgatgccaag aaagatcctt ctaaggggaa agcctatggt    780
gccaggtacg taggttctat ggtcgcagat gttcacagaa ctattaaata tggaggaatc    840
tttttatacc ctgcaacgaa gtcttcccct aagggcaagc ttagactgat gtacgaatgt    900
gttccgatgg ccttttttgct cgaccaagca ggaggattag ctactgatgg caagattaat    960
atattagata tcaaacctac taaccaccat cagagaagtc ctattttctc tggggtctata   1020 gaagatgtag aggaggttca aagttatatc aataaacatt gtgaatgtaa aaaataggtt   1080
aagagatttg tttcaataaa gtttattatt agttatacaa aaaaaaaaaa aaaaaaaaa    1140 aaaaaaaa                                                             1148
```

<210> SEQ ID NO 107
<211> LENGTH: 574
<212> TYPE: DNA
<213> ORGANISM: Diabrotica virgifera virgifera

<400> SEQUENCE: 107

```
ggggagttat ttttgattat ttttacgtat attatacagt cttaaagttt ggcttcaccc      60
tgtagtagta gttttcccta attctgacct gttttttta ttgtttctaa attcccaatt     120
ttgtgtcagt gacactttc cacaaatctt tttacataaa agaccttatt aacaagaatt     180
tatattaact ataaacgaaa ataagatttt tttctgatac aatgtttgtt gttttgtttc    240
ttttttgcaac acgttttatt ctttgctata acttaaaaat gggctattca ttagatacca   300
attttttcat ttaagtccct ttttttatttt tcatatcaat gatttgttat tgcgaaaata  360
ttcttagaaa tgaattatat aataaaaaaa acaataaaac taatgttaac cgtcttgatt   420
ttcgcaaaaa tatgggttca tcattttatc tttcggaagg actaaccgaa aaattataca  480
tctactttgc attcggagta ttgtaagaaa aacatgcatt cgttacagta gtaccagcta  540
tacaagagat tcattatgat tcagctctgc gggg                               574
```

<210> SEQ ID NO 108
<211> LENGTH: 725
<212> TYPE: DNA
<213> ORGANISM: Diabrotica virgifera virgifera

<400> SEQUENCE: 108

```
gggagtgagg cttattgtta acaaactggc aaaaaaataa ttaaaactaa acaaatttga    60
tgaaaaatgt tcataaaagg tatatttcgt tgattgggaa gaatagtatg atatttcaaa   120
aacatcaagt ttacagaaaa gacaattaaa gattgagatg ggttacaaga ttggattact  180
taagcaatac aatattaaat atgcttttca tcagaataat taaaacatac agtattaact  240
gacaatatgg gtgttacatc caattcatac accaccccca actcatattt ttcatcccca  300
ttttgagtta taatactttt ctctataaaa attttgtact atttcacaat tataaggtta   360
ttagggacaa taaaacgaaa cagtttaaat gttttattag agtttaaata acaatgaatg   420
aaaaaaatcg cagttatagt acaataacaa tataaaaaaa attaaaaatt tgggcccgcc   480
taaaaaaaaa ggttctacaa gttacaaccg ctacattttt ttttcttttc aaaaagagag   540
agcaggccag ctttcttttt ttcacttatt cccactttct tcttgtaagc ttgttttaga   600
gtaacgtcac gtgctgatgg aagtttgctt tgaagaacgt ttatggtgtt aaattcctgt   660
tctttgtatg acttatatag taggtgacta gggattagat tacatctttt ttcccgattt   720
ttatc                                                                725
```

<210> SEQ ID NO 109
<211> LENGTH: 725
<212> TYPE: DNA
<213> ORGANISM: Diabrotica virgifera virgifera

<400> SEQUENCE: 109

```
ggggagtgtg ccacgggatc ggattgaggg tgattgtact gtttgtgtag aacattagtt    60
taataaaatg gcagccgtag taaacttgta caattatttt tataacttag cagatcccag   120
agtgaaaaac tggtttatga tggaaaatcc cttcccaact ttaggaataa ttggagtata   180
cctattatta gtcctgcaaa tcctgccaaa ctttatgaaa aataggaaac ccttcgaact   240
aacgaagata attagattat ataatatatt tcaagtagtg gcctgtattg gtataatgta   300
```

| | | |
|---|---|---|
| cagtatcctg acgtcaggct ggattcaagg agaatataat attggttgtt ctccaattga | 360 | |
| ttactccaac aaaccaaatc ccgtcaaact cctgggtgca ttctactggc tctatttgtt | 420 | |
| aaaaggtgta gaactgatcg agactatatt cttcgctcta cgaaagaaaa acaaccagat | 480 | |
| aacaggcctc cacatctacc accatggatc tacgttcttt ttggcatgga ttgggtgcaa | 540 | |
| attcattgga ggtggtatgg cttctattcc tcccttcgtt aactcattca tacatgtact | 600 | |
| aatgtacaca tattactact tgtcttcttt gggacctgaa tggcaaaaga agctgcaacc | 660 | |
| atggaaacca aggcttacta tgttgcaaat gatacaattc accctcctca taattcactc | 720 | |
| tctga | 725 | |

<210> SEQ ID NO 110
<211> LENGTH: 508
<212> TYPE: DNA
<213> ORGANISM: Diabrotica virgifera virgifera
<220> FEATURE:
<221> NAME/KEY: misc_feature
<222> LOCATION: 439
<223> OTHER INFORMATION: n = A,T,C or G

<400> SEQUENCE: 110

| | | |
|---|---|---|
| ggggagtgtt acgacgcgaa cggtgccaag cgctgctgta aagttgcgtg cttttctgaa | 60 | |
| aaaactttcg atttgcgtgc cgcgaaaaag cgagttgtca cagacaattt tgttttgtgg | 120 | |
| tgaatattcg gcggattgcg taatttgtcg attggttttt ggtgtttttt tgtgtgtgcg | 180 | |
| acagagtaac tattttattg gattgtgttt tgaagattac tcagctttat cggaacctct | 240 | |
| gagaggaaag tctagtattc gagcaggtcg aatggagttc ttctacaccg aaaaaaacca | 300 | |
| gtgaattgtg ttttaaagtg tgcgtttttg tcgatttcca atttcctctg cggcgtataa | 360 | |
| tttctattgg ctacattatc tatacagttt gtgtttgtgc tttgtaccag atttccaatc | 420 | |
| acttagccat gtttggagng gaataattaa aaggtgagtt tgaattttt ttacattatc | 480 | |
| tcttctacaa aaggaacaat agaagctc | 508 | |

<210> SEQ ID NO 111
<211> LENGTH: 623
<212> TYPE: DNA
<213> ORGANISM: Diabrotica virgifera virgifera

<400> SEQUENCE: 111

| | | |
|---|---|---|
| ggggatatca aacgccaaaa gacgtttata aacatattta atgcataaat acatcctact | 60 | |
| aaactatatt ttccataaaa tctacaataa ataagttata taaactttac acgcccatct | 120 | |
| gcttcttcca agatgacgtc accatctttt tcactcacaa aaatatcaca atctacaaat | 180 | |
| caccaaacat ctccaaaata tcggttttat ccaaactatt tctgatattt catatcgtat | 240 | |
| atttcagtta tcgcaagtgt tgagaacctc aatagcaaaa tagatttgcg ggccttattt | 300 | |
| ttcacttcaa aatgtctgct aaccagtata ctattagaga gattgtggac tatcagtcta | 360 | |
| cccataatgc aagtagtgcc gatgacgaaa atgacaccgc atcggacgaa gaacaagtac | 420 | |
| ccattatgta ccaatacgaa atggtgggcc cattggaaag gacagtaaag cgacgaggcc | 480 | |
| atcttcctaa agaagcggtt aaaattctaa aaaattggtt atacgaacac agattcaatg | 540 | |
| catatcctac ggaaattgaa aaacagattt tgtcacaaga aacgaacctg acggttcttc | 600 | |
| aaatcagcaa ttggttata aac | 623 | |

<210> SEQ ID NO 112
<211> LENGTH: 625

<212> TYPE: DNA
<213> ORGANISM: Diabrotica virgifera virgifera

<400> SEQUENCE: 112

```
gggtttgttt gaattttttcc gaaacaatgc atgttttcgt tctaattgca ctcccctaca      60
tagttacagg ttattgaagc gctattatag tcgaggcaat aaagcagtaa aaagatcaaa     120
acccgccaaa tttttgcagt tggatgaatc tcaatgaaat attttgcatt cgattcgtaa     180
gagacttagg aaacttcgta aacaaaaatg atgatgaccg aatgtaaatt gcataattga     240
tttgcaaaaa tgtaaacata atgtgtataa gtcgtatttt ataatgaata acgtcataat     300
tgggaggaca aaaactgaaa cgatttacaa tataccgctc caagttgtaa atcctcatag     360
ttaacattgt atttgtgttt gactagatca ttaacgaata cggaaataat caaataaaca     420
acttgtttcg aacatggtaa atgttatgtg taaaattatc attttactta aatttttta     480
aacctaatgt gcatcagcgg tattttaaa tttataacgt cataattgga gtaaaaaaaa     540
tgcaacatgt taaatataca gcaccaggta gtacaaattt tgtctagacc ttatagacct     600
tatattatag accttagcat agtta                                          625
```

<210> SEQ ID NO 113
<211> LENGTH: 664
<212> TYPE: DNA
<213> ORGANISM: Diabrotica virgifera virgifera

<400> SEQUENCE: 113

```
gaggagttca ctttgggatt gtattcctga atattaaccg gtagtgccag gtgacagtgt      60
ttaattaaat atccagaaaa aatgccaggc ccttcaagac ctctgtggca agtagccgga     120
aagcgtgatc cagaacaaga acgcgaagct caagcatgga tcgaagctgt cacaggaatg     180
aggtttcctc caggagttcc atacgaagat tgtcttaggg acggtattct cctttgcaca     240
ttgatgaacc gtttggcacc tggaatcatc caaaaaatca acacatctgg tggagactat     300
aaaatgatgg ataacttgaa ccaattccaa aaagcttgtg tgaaatacgg tgttcccgat     360
gtagatcttt tccaaacaac tgacctgtgg gacaggaaaa gcatcgtttt agtcacaact     420
accattttttg ctctaggtcg cacctgttac aaacaccctg aatggcgcgg tcctttcttg     480
ggacccagac catctgaaga aaacaggaga gacttcagcg acgaacaatt aagagctggt     540
gaagctatta ttggactcca agctggccaa acagaggtg ccactcaagc tgggcagaac     600
tttggtgctt ctagaaaaat cattttggga aaataaacaa acattcgaag agacatattg     660
aatc                                                                 664
```

<210> SEQ ID NO 114
<211> LENGTH: 656
<212> TYPE: DNA
<213> ORGANISM: Diabrotica virgifera virgifera

<400> SEQUENCE: 114

```
gggtaagaat gcagcagcta gcaataaggg cgaagtagtc tgcagaagca ttttctttc       60
tagagctcct taaacatca ttcacgattc attaatacca gttttcattt tttttttaaat    120
atgtagtctt tttattgaaa cattttcaaa tcaaatttc tagaaaacgg tgtgttttac     180
tgacttaatc aagagtacct tctaatacta gaataccgca caatttaata atccagtgtt     240
agaaatgttt aaaaattaaa gacaaaaaaa ttatccgata aaattacagt tatcctacca     300
aaaacggacg cctacgatcg gtactaggaa ttcacagtag ggcttttcat tcacagaagc     360
```

```
tcgaaacaaa tgacaatcga tgaaaagcct tattaatgga atcaatttat ctccgggaga    420
taaacaggca taccagtttt ccattttca aaatagaagc gttctggagg tattaaagat     480
aactagttat aagacgccaa cgtccaagag ctctagttcc cttaggaagc aatttcgaac    540
tacttgaatt aggttaaaaa caggagagtt tctggacacc ctgtataaga aagacaccag    600
gaatattttc acgaatacga caaccagtgg agctaagagt tgaatctttt gtcacg       656
```

<210> SEQ ID NO 115
<211> LENGTH: 185
<212> TYPE: DNA
<213> ORGANISM: Diabrotica virgifera virgifera

<400> SEQUENCE: 115

```
gggatgtcaa atcataaaaa tcatccttat catttagtag atattagacc atgacctta     60 ttaggagctt ttagagcaat attaacaata ttaggaataa ttaaatgatt tcatttatat    120
aataataatt tactaataat tggattatta attacaagat taattatata tcaatgatga    180
cgaga                                                                185
```

<210> SEQ ID NO 116
<211> LENGTH: 661
<212> TYPE: DNA
<213> ORGANISM: Diabrotica virgifera virgifera

<400> SEQUENCE: 116

```
ggggaattgt caacctggaa aacgacttgt cgaagtcgca tagttttat aagttaaat      60 aaactaaatt aaatataaat acttcgagaa tgcaataatt attattcttt aactagaccc    120
acagcttatt aattagcaga agtagtagca gacttatact aactagcata aggagaaaca    180
tattaacata gcatggcaga cttcatgat tctgaagcag aagaaagtag tgaggaggag     240
gaattagatc atagggatcg taaaaaagcc caaaaagcca agttgtaga tagttcagat     300 gaagatgatg aagatgatga cgaaagactg agagaggaat taaggattt gattgatgat     360 aatcctattg aagaaagtga tgctgagtct gatgcttcag aagggaaaa acgtaagaaa     420 tctgacgacg aggatttgga tgatcgactg aagatgaag attatgattt gcttgaagaa    480
aatttgggtg ttaaagttga aagaaggaaa ttcaagcgac tgcggcgttt tgaagatgaa    540
gaaagtgaag gagaagaaga acatgatcct gaacaagata gggaacaaat tgctatggat    600 atatttcag atgatgacga tgaaagacga tcagaacgaa gtcacaggcc tgccgtcgaa     660
c                                                                    661
```

<210> SEQ ID NO 117
<211> LENGTH: 488
<212> TYPE: DNA
<213> ORGANISM: Diabrotica virgifera virgifera

<400> SEQUENCE: 117

```
ggggccactt gatttttgt tttagaaaaa ggcacgaaaa tggctggaga ctcagttgat     60
gcttcaaagt taaccggtat gagcaaaatt ttcaatggct ctaccatgag aggaagggca    120
aatgttgcct tagccacata tgccagtgtt ggactcctaa tcgcctattt ctcactgaaa    180
ccatcaaaac ccaaggcacc aaaaaattag tctagtagtc tattccgtaa tgttactcta    240
taactatgta catgtttaat aaaacttaaa atctcaatgc ttaataagtt ttttagata     300 caatgttttt tgtagacata tgtaatgact caataaaatt gatgttgtat acaagggcaa    360
gatgaaaagt tctttgcctg gtagtgaaaa gtgagttttt tattcaaaac atgcctttat    420
```

```
ttacagtgca atctcacttt attgtaatat tatttgatat attttttccag taaagagatt      480 ccaccatc                                                                488

<210> SEQ ID NO 118
<211> LENGTH: 616
<212> TYPE: DNA
<213> ORGANISM: Diabrotica virgifera virgifera

<400> SEQUENCE: 118
ggggattgtc aaatagttgt cagcgttaca cagcgaatat tttcctcatc agttcaatat       60
taacaataaa ttgttttgtt gaaattgaaa tcacaaatta ctttataaaa tggtaactct      120
agaagacgtt gaaatgaaaa atgcagacag tcctccagga ttagaagctg gtgatacaaa     180
gaaagatacc gacctacaaa gtgtaataga gattcgtgaa catgcaagac aaatagaaaa     240
atcagtcaca agtaaagaaa accgtttcat cttacgagtt ttacgttgct tgcccaacac     300
tagaaggaag cttaatggac tggtgctgag aagcctcatt actcaaatat atcctgtagc     360
tgaacgtgat gccctcctta gtttcgtcga ggaagcttct ggagaactcg acgccaccca     420
gtcacgagca agatcagctg ttaagtcgcc tgttcccgag gtggatacat atataaatct     480
tttaatacta gtacgtttaa ttgataccaa taagttagtt gaagcagagc gctgttctca     540
agctcttatg aataaaataa ctaaccaaaa cagacgtact atagatcata ttgctgccaa     600
gtgttatttc tatcac                                                      616

<210> SEQ ID NO 119
<211> LENGTH: 609
<212> TYPE: DNA
<213> ORGANISM: Diabrotica virgifera virgifera

<400> SEQUENCE: 119
gggggacaag attttgcaat ggcggatgta gtagacgagg tgattatgga ctctgatgaa       60
aatgaggaaa tactatcaaa aagcccagaa gagatggctg aactcaaaaa ggaaaacggt      120
aaccagttat acaaaaccaa acagtacaga tctgcactcc ctctctatag cgaagccatc      180
aatctttgtc caaatgtagc cccttattat ggaaatagag ctgcctgcta catgatgctt      240
tacaggttta cagaagcttt ggaagatgtc aggaaaagtg tgcagctgga tccagaattc      300
gttaaaggat acatcagaat gttaaagtgt gctatagcaa tgggtgacac cactacagct      360
gattttgcca ttaagaagct tcaggacttg aaagttgacc aacaaacatt gcaaatgaa      420 ttaaaatcgg ttcagcaatt gaagcagtac gagtcagatg gaaccaaagc gtacgataaa     480
aaagattatc gtttggttgt tttctgtatg gacagatgtc tcgataatgc ccctacttgc     540
taccgataca aaattgccaa agcagaatgc ctcacatatc tcggccgtta ccaagaagct     600
caggaaatt                                                              609

<210> SEQ ID NO 120
<211> LENGTH: 517
<212> TYPE: DNA
<213> ORGANISM: Diabrotica virgifera virgifera

<400> SEQUENCE: 120
ggggtcttga aggtggctcg ttgtagcaga tttgttgaaa accatggaaa tcgttcaaga       60
attatccagc caatatgttc tgtatattcc tgtagcttta gtaatcgttg gagctatttt      120
ggtgttcact tttggtttta aatctgcaga acaaccaccc ttcgacaaat tatcatttga      180
```

| | | |
|---|---|---|
| cgatagaaaa tctgctggga aaaagcgtaa aactaaggaa aagaaaccta ctgctaatgg | 240 | |
| tcacatcagc aatgtagaaa aatctgataa atccccatca aaggactcca agaagtcccc | 300 | |
| ccagaaagaa gctgttgaag caaaacaaga aaagaaggag aagaaactag acaaacaaaa | 360 | |
| tgaaaagcct aaaaaacagg aaatcaaaaa gacagaggaa atcaaaaata agaaaaattt | 420 | |
| aaacaaagtg tcagagaagc cagtagattt tgatgatggc aactgggaga cagtacctct | 480 | |
| taaatctgat aagaagaaga aagaccaatc gccagtt | 517 | |

<210> SEQ ID NO 121
<211> LENGTH: 607
<212> TYPE: DNA
<213> ORGANISM: Diabrotica virgifera virgifera

<400> SEQUENCE: 121

| | | |
|---|---|---|
| ggggacagcg tgaaatctgt gcgcggacaa aaaaaacttg ttatcgccga tttattataa | 60 | |
| tttatattta tgaagtgact gtgtcggtac ttaatagctt tatgtatatt gtgtttgttt | 120 | |
| tcatttaaat tttaaatttc ataccaaag atatgagccg gttgaacata ttcagttttt | 180 | |
| tgaaaatgct tcaagcattg tgttgtgtac tgggagttac atcagcatct tcagacccag | 240 | |
| ttatagtctc cagagaagaa tgggggggccc gcgctcctaa aaacatagaa aatatggcga | 300 | |
| acccagtacc ttacgtcgtt atccaccaca gttatctacc accagcttgt tacaatttaa | 360 | |
| ccgattgttt caaagccatg cgttggatgc aagaccttca ccaagacacc aacggttggg | 420 | |
| cggatattgg ctacaacttt ggtgttggcg gagatggtag agcctacgaa ggaaggggat | 480 | |
| ggtccagagt tggtgctcat gctccctatt acaacagcag aagtattgga atatgtataa | 540 | |
| ttggagattg gacagttgaa cttccaccag aaaatcagct agcgacagtt catgagctaa | 600 | |
| tacaaaa | 607 | |

<210> SEQ ID NO 122
<211> LENGTH: 590
<212> TYPE: DNA
<213> ORGANISM: Diabrotica virgifera virgifera

<400> SEQUENCE: 122

| | | |
|---|---|---|
| gggggttgcc caatttgttt caatattgtt ctgattttat ttaaaagcgg cacttaaaca | 60 | |
| tagtatataa ccatggttga gaacagtaca ttaactatag atgaaaaatt tcacctaata | 120 | |
| tccagaaacc tgcaggaaat attaggtgaa gatagaatta aagcagtatt gaaagaacgt | 180 | |
| gatttgaagt tgtattgggg cacagctaca acgggtaaac ctcacattgc ctacttcgtt | 240 | |
| ccaatgtcca aggtagcaga ctttctcaga gctggtgtag aagttactat tcttttttgct | 300 | |
| gatcttcatg cgtatttgga taatatgaag gcaccctggg aacttctagc gcttagagtt | 360 | |
| cagtattacg aacattgcat taaagctatg cttcaatcta ttggagttcc tttggacaaa | 420 | |
| cttaaatttg tgaagggaac agattatgaa ttgtctaaag aatacacact agatgtttac | 480 | |
| aaaatgactt cagttgttac tgaacatgat gcaagaagg ctggagctga agttgttaaa | 540 | |
| caagtagaaa atccttact aagtggtctt ctatatccta gtttgcaagc | 590 | |

<210> SEQ ID NO 123
<211> LENGTH: 103
<212> TYPE: DNA
<213> ORGANISM: Diabrotica virgifera virgifera

<400> SEQUENCE: 123

| | | |
|---|---|---|
| gactcttacg aactcagata cttccagatt gacagtcaag aagacgatga tgaagaagat | 60 | | aatgaataat ttattcagtt atttttttta ttaaatagat tat        103

<210> SEQ ID NO 124
<211> LENGTH: 381
<212> TYPE: DNA
<213> ORGANISM: Diabrotica virgifera virgifera

<400> SEQUENCE: 124
gggaactata aaatgcggtt acaacgttgt tccagcttag cattctagta tagatttcca        60
tttcagcata tcaagaacga tcacaattta gtgaaagtgt acatgggaat aacaacaact       120
ctatattgaa atattgttta atatttaata tgctaagtaa tattcagtta gaatattatc       180
atggatcatg gatgggtgaa atatcacagt tttaacaaaa aaaaaaagaa tgtgttgtat       240
tttgtacgcg cctaagaagt tatacttcta ttatgtgatt tcaatgaaat aaacatattt       300
taaacagttt atttgtattt tatttaaata ttaaactaat tttaatacct atttcttacc       360
aaatttgttt attaaaatag c                                                 381

<210> SEQ ID NO 125
<211> LENGTH: 627
<212> TYPE: DNA
<213> ORGANISM: Diabrotica virgifera virgifera

<400> SEQUENCE: 125
ggggaacagt ttaattgcta gagttgtata gtcagtgtct ccagttgttt attatcaaac        60
aaaaatgtct ctgacaatga ttggtggtgt aaagatcccc atagtggggc taggaacatg       120
gcaggctacc aatgaagaag aattggaagg tgccgttgag gcagctctgg aaactggata       180
ccgccacata gatactgcat ctgcatacca aaacgagcat gtcatcggca agttctaaa        240
taaatggttg gcgtctggca aacttaagag agaagatatt ttcattacta ccaagcttcc       300
aatgacacac atccatcccg atctcgtcga aacagctctt aaagaatcct tacagaagct       360
tcagctggac tatgttgatt tgtacttggt gcattctccc atatacatga aatttgttga       420
agctggaaag ccaatggaac ctctacctac tgaccatctg gctgtttgga agaaaatgga       480
agagcaagta gatgcgaaaa gaaccagaac catcggtctc tccaacttca acgtaaacca       540
gatcgacaga atagtgaaga attgtagaat tcaaccagcc aacactcaag tggaactgca       600
cgtttactac cagcagaaaa aacttag                                          627

<210> SEQ ID NO 126
<211> LENGTH: 640
<212> TYPE: DNA
<213> ORGANISM: Diabrotica virgifera virgifera

<400> SEQUENCE: 126
ggggattgta ttttagtatt ttacaattct ttgaattgca gattatttag cggtttagta        60
caaaaacctg aagtaaattc tataacggaa agtgcttaaa ttttaatggt aaaatgtcca       120
ttctagctta caatggtggt gctatggtgg cgatgaaggg agaaaactgt gtagcaattg       180
cagcagatag gcggtttggt attcaagccc aaacagtagc tacaaatttc caaaaaatct       240
ttgaaatggg accacattta tatgtgggtc ttccaggatt agccacagat acccaaacag       300
ttatggaaaa actccgtttc cgaaaaaact tgtacgaact taaggaaaat cgaaaaatat       360
ctccaaaagt atttgcctct atgatatcaa atatgttgta tgaaaaagaa tttgggccat       420
tttttgtaga acctgtagta gctggacttc tacctaatac ttatgaaccc tttatctgta       480

```
atatggattt aattggttgt ataaaccaac cttcagactt tgttgttggt ggaacagcgt      540
cagcacagtt gtatggtatg tgtgaagcac tttgggggcc taacctagga cctgaggatc      600
tttttgaaac catctctcaa gctctcatca atgcctttga                            640

<210> SEQ ID NO 127
<211> LENGTH: 591
<212> TYPE: DNA
<213> ORGANISM: Diabrotica virgifera virgifera
<220> FEATURE:
<221> NAME/KEY: misc_feature
<222> LOCATION: 156, 241, 244
<223> OTHER INFORMATION: n = A,T,C or G

<400> SEQUENCE: 127
gtacattaaa atcgctaaaa acataaaaaa atacaatatg ggtacttgta tgtgataatg       60
ttacctgtta gttactaaat ttaaaacggt tgatattttg tatacttata tttagacatg      120
gcggtaaatg tttattccac gaacgttaca tctganaatc tatcccgtca tgatatgcta      180
gcatgggtga acgaatgttt gcagagtagt tttgcaaaaa ttgaagaatt atgtacaggc      240
nccngcatat tgccagttta tggacatgct ttttcctgga tctgtgcaat taaagagagt      300
taaatttaga accaatttgg aacatgagta catacaaaat ttcaagattc ttcaagctag      360
ttttaagaaa atgcaagtag ataagatcgt ccccatagat agactggtga aaggtagatt      420
ccaggataat tttgagttcc tacagtggtt caagaagttt tttgatgcca attacaaagg      480
gacggactac gatgcgctgg gagcacgtgc cggagagcaa ttggggcaag gaggatctaa      540
cgcccctaga ggtcaatctt tgatgttacg tcggccgaac gcgacgccct c              591

<210> SEQ ID NO 128
<211> LENGTH: 614
<212> TYPE: DNA
<213> ORGANISM: Diabrotica virgifera virgifera

<400> SEQUENCE: 128
gggggaggag gttaagttaa acttcgtttg gtttggtttg gttgaccgag tgattttcca       60
gggtggagtt ttttttgtgat gctaatttat ttatggccat ttcgcgttct ctgataaatg     120
aactataaag tattaaagca cataaattaa taatctttga ataacttaca ttgatattgc      180
gatcaacaag gttttctaa acaaatattt agttaaaagt gcacaagttt ttatgcaggt       240
tgtcttgtaa ttgttttcaa ctgcttagag cttctatctc caccatgggc gatcaggttg      300
aaaattcgaa caataaagtg accgaaaatg atccacagcc caacagggac gaaatgataa      360
tggctcagca gaggcaaatt gaacaagagt atattgatgt cctcagaaga ctaaaagata      420
tagataatat tgatgaagcg cttaaagaat tatatagtgt atttaatgat caaggttttct     480 cagattattt ggtggtctac ctcagattgt taaccagtgg ccagttacaa aaggaacacg      540
aattttacag ttgtttcata gaaggtgata gaacggtagc tgattttttgt caccaggaag     600 tagagcctat gtat                                                        614

<210> SEQ ID NO 129
<211> LENGTH: 639
<212> TYPE: DNA
<213> ORGANISM: Diabrotica virgifera virgifera

<400> SEQUENCE: 129
ggggagtcga aaatatggc agcgtttcta aggcatggcg ttttcaaaac aggacgagtt        60
gtctcttcaa aaaacgtact tttgaggtcc tttgccacga aggctgagaa gaggaaagga      120
```

```
atcgacagaa aagttggccc aaaaatagac tccacagctc aatctttagc ttcaaaaggg      180
tttctgaggc aacaaagaga ttattctcca cctgaagatg ttaattccaa gttagaagca      240
atcttccaga ccgtcgtcgg tagttcagat atatctaccg aactcacaga tctgaatcaa      300
aagtttactt tattcatgca gtgtgaacag caactaggcc atagtattcc taattcgtta      360
cttcatcaca tgaaaacatt gaaggacgtt caaatattct ataacatgcc cgtagataca      420
agaacgccac tggaaagaat gaaatccatg gacttgccgg aaaatttaca tgttcagtac      480
gaatataaac gatttaatgc tgatactgat acgatgtttg gaggaaaaac agcattccct      540
aagagttcta caattgttac aggattaaaa tacaaagata agtacaaagg acaaaagcaa      600
ccattacctg atttctagtg tttttttcta gaaaataaa                             639

<210> SEQ ID NO 130
<211> LENGTH: 651
<212> TYPE: DNA
<213> ORGANISM: Diabrotica virgifera virgifera

<400> SEQUENCE: 130
ggggatgttt taaaaggcgc tttaagttta agattcacac attgcataaa ataatttat       60 aactaaacta aatcatgggg aagaataaga agacaagaa aagggaaaa ggggccgaga       120 aaacaacagc aaaaacagaa aagaaactgt caaacaaaat gaagaaagaa ctgcaagcta      180
agggagagga tgatatagaa tctatttat  tacaaattga aaggaagag aagaaaaggt      240 tgactgttac tgaagctata atcagtccac cttcaagaag attaaatttc acctttatgg      300
cccatccaga aaaagaacag cttattttgt atggggagaa attttttcaat ggacaaaaga    360 cttttgtgta tggtgactta ttttttctaca atataccaaa taacaaatgg acagtagtta    420
aggctcctaa tggcccaccc cctagatgtg gacatcaaat ggttgtctct tcagcaaata    480
aaggtcaatt atgggtgttt ggaggagagt ttactacacc cacacaatca caattttatc    540
actacagaga tctttgggtc ttccatttag ctactaaaca gtgggaaaaa attactgctc    600
cgaatggacc atcagcgaga agcgggcaca gaatggtatt aataaagaag c              651

<210> SEQ ID NO 131
<211> LENGTH: 652
<212> TYPE: DNA
<213> ORGANISM: Diabrotica virgifera virgifera

<400> SEQUENCE: 131
gggggaccta aatatccaga tatttaaat ccttgctgag caagacaatc ttcaacttca       60
taacattgaa tatttcttaa ttagttatct ggataactgc tgattcaata tcctccagga     120
gtttcatagg acaacacttg tcctcatgaa gtgtaaatca aaagtgatcg atatttaata     180
caccattcta cattcatgaa ccattctaca aaaatttgtc caaattgctc ttctttctta     240
gatatcttca tacattttgt tctcttaatg ttttgtgaaa gttcatatct cttagactta     300
cttctatgat tctatttggc tccccacgtt gggcgccaaa tgttactctt cgccgatgtt     360
accagttttt ctataaggta tgcgaaggta attaactact tttatttct aacaaacgaa      420 agagaataat aataagaaat caaaaaaatc ggagaatcat acactattta ttcttattaa    480
ccaaaattat aaaatttata ttaatcttaa ttgaagatat aaaaaaacca aaagaaaaag    540
gtaaaaagct taaataaagt ttatgcttgc ctctaagaat attcttttca gcgtacacac    600
atattaaaat tcttaaaact atgtaatatt atatttaggt actatttaca ag              652
```

<210> SEQ ID NO 132
<211> LENGTH: 658
<212> TYPE: DNA
<213> ORGANISM: Diabrotica virgifera virgifera

<400> SEQUENCE: 132

```
ggggacatta ttattccaag tatctttaag cagtgacatc gagtgttagg cttcaaagat      60
gaaggttttt ctaagtatta gtattggact ttttgtactt tgttcaatag aatcaaggtc     120
tctaaatagc aagctttcta aaaagccaat atttaaagac ttttacggaa agctaaacat     180
agaagtaaga ggaaaccctg gagagccact gatattaact gacttgatta aagcagggaa     240
gctggatgaa gctcagaacc aatcactcgt gcaaggattg gacacagagg ttaaaagtta     300
ttccggctat ttcactgtag ataaaaagca tgattctaat atcttcttct ggttttttccc     360
ttcacaaagt gatcccagtt cggatccggt tgttctatgg ctccaaggag gaccaggatc     420
tacatccatg tttggacttt ttcaagaaaa tggacctctt acagtaaaag atggtgagct     480
gggtattaga ccaacgtctt ggaataggaa tcactcagtt atctacatcg atcagccagc     540
tggaactgga tggagttata ctaacggagg atacgccaag gatcaacata agtagccac      600
tgatttgtac gaagccttgc agcaattttt caccctcttc tatcaatacc aggagaga      658
```

<210> SEQ ID NO 133
<211> LENGTH: 638
<212> TYPE: DNA
<213> ORGANISM: Diabrotica virgifera virgifera

<400> SEQUENCE: 133

```
ggggatattg acattcgaca actttttttgg gaggacaggt gaatgttgta gcgttttttca     60
aagtgtaagg tgtttatttt caaaaagttt ataaaataag caatcactat gggtaatgtg    120
tttgcaaatt tattcaaagg cctctctggc aaaaaggaaa tgaggatatt gatggtagga    180
ctcgatgcag ctggtaaaac cacaatttta tataaactta aattaggaga aattgtaaca    240
actattccaa caattggatt taatgtggag actgtagaat ataagaacat tagttttaca    300
gtatgggatt taggtggtca agataaaaatt aggccattgt ggagcactta tttccaaaac    360
acacaaggcc taatttttcgt agtagacagt aacgacaggg aacgtatcac tgaggctaaa    420
gatgaattaa tgcgtatgtt ggccgaagat gaacttagag atgccgtact tctcattttc    480
gccaacaaac aagatttgcc caatgcaatg aacgctgcag aaatcaccga caaactcggt    540
ctccattcac tacgcaaccg caactggtac attcaagcta cctgtgcaac tagcggagat    600
ggtctctatg aaggtctgga ctggttgtcc aatcaatt                           638
```

<210> SEQ ID NO 134
<211> LENGTH: 192
<212> TYPE: DNA
<213> ORGANISM: Diabrotica virgifera virgifera

<400> SEQUENCE: 134

```
ggggaaaata cgtcaagctg tcattaatgt cgctatcctt tccttccttt tccttttttaa     60
cttaacacac gtttgcatag gtaggtcaaa atgaccaaag gtacctcaag ttttggtaaa    120
cgtcgcaata agacccacac cctatgcagg aggtgcggta gatcttcata ccacatccaa    180
aagtcacaat gc                                                        192
```

<210> SEQ ID NO 135
<211> LENGTH: 576

```
<212> TYPE: DNA
<213> ORGANISM: Diabrotica virgifera virgifera

<400> SEQUENCE: 135
ggggattttt atttacttta acctaaattt atttttagttg atcaacaatt tttttagttt      60
atttgacaaa ctttgtaatt ttaaattatg ccgaactgga atcagatcca ggctcaacta     120
aggcatccag ctaatcctgt agtattcttt gatgtatcag taggaactac agaaatcggt     180
aggatgatat ttgaactttt tgccgatgta gttcccaaaa ccagtgaaaa ttttcgacag     240
ttttgtacag gagaatttag aaaagatgca gtacctcttg gttacaaagg agctagcttt     300
caccgtgtta ttaaagactt tatgatacaa gggggagatt ttgtgaatgg tgatggaacg     360
ggtgtgatga gtatctatgg aggaagtaca tttgccgatg aaaactttag ttttaaaaca     420
tgatacacca ggactgttat ccatggcaaa tagtggaaaa gacacaaatg gttgtcagtt     480
ttttataact tgtgcaaaat gtaattttct tgatggaaaa catgttgttt ttgggagagt     540
tattgatgga cttttagtta tgagaaaaat tgaaaa                                576

<210> SEQ ID NO 136
<211> LENGTH: 618
<212> TYPE: DNA
<213> ORGANISM: Diabrotica virgifera virgifera

<400> SEQUENCE: 136
ggggaatatt tattttatt taaacaagtt aactgatagt tatttaaac atttttatat       60 tcagcaacaa tggtgaaggt aaaaaaacaa aaaggcagta tcatctgagc gtgttcatgt    120 taaaaagaa ccgaaaaaaa tgaaccccctt cgaggttcat gtaaatagggg aaaaactaca    180 agtgataggc aagaagcaaa agaatgcag aggtcttcca ggtgtctcca gagctaaagc     240
catcaaaaaa cgaaaatcta cgttactgga agaatacaag gtacaaaaca aaaacaataa   300
attcgttgac agaagaattg gcgagaaagc tcacatggac agtgaagaaa agctttggc     360 gaggtataca gctctaaaag taaaggccca taacagaaag agcattttca atcttgcaga    420
tgatgaaatt ttaactcata aaggtcaaac actgaacgaa atagaaaat ttgatgatcc     480 tagatcggat gatgaagact tcgatgatag cgaaacaaag actggaaatt tggagtcaaa    540
ttttatagga gaagcacatt ttggcggagg attatttaca aacacaggaa agaaggtgc    600 tatgactcac aaagatt                                                    618

<210> SEQ ID NO 137
<211> LENGTH: 421
<212> TYPE: DNA
<213> ORGANISM: Diabrotica virgifera virgifera

<400> SEQUENCE: 137
ggggtaaaaa cgatgggaaa tgaaatatct ttggataaag aaattattac aggaaatgaa     60
tcaaaaaaat ctgtgtctct gtatcaaaca aattataaat gttatatatg ttctaaatac    120
ttttcagatg aatatatgtt gcgaaggcat attacgacag tgcataatga agaaaattg     180 tttaagtgtg aagaatgtgg caaagttta aaaactcgta actcattcag aaagcacatg     240
cgaacacata ccgaagaaga aatgtttgaa tgtaaagtat gttctaaaaa atttagagaa    300
aagtatgtgc acaatgatca tatgcggact catacaggag aaaaccatta tacatgtagc    360
ctttgttcag caacgtttag aaacaggacc ttgctaagaa atcatattgc atcaagtcac    420
g                                                                     421
```

<210> SEQ ID NO 138
<211> LENGTH: 508
<212> TYPE: DNA
<213> ORGANISM: Diabrotica virgifera virgifera

<400> SEQUENCE: 138

```
ggggttcacg aagacaaaaa tcgggtaccc ttcgtcaaag gggcaactga aaggtttgtc      60
tcaagccccg aagaagtatt cgaagctata gaagaaggaa atctaatag gcacatcgct     120
gtaacaaata tgaacgaaca ttcgtctagg tctcattcag tattttaat aaatgttaaa     180
caagaaaatt tagaaaacca aaagaaacta tcagggaaac tttatttagt agatttggct     240
ggttccgaaa aagtgtcgaa aacaggcgcc gaaggtactg ttttggacga agctaaaaat     300
attaacaagt ctctgtcggc tttaggaaac gtaattagtg cattagcgga tggtaacaaa     360
actcacattc cttacagaga ctctaaacta accagaatcc ttcaggaatc gctcggagga     420
aacgccagga cgacgatcgt tatttgttgt tctcctgcta gctttaacga atctgaaact     480
aaatcgacgt tagaatttgg taaagagc                                        508
```

<210> SEQ ID NO 139
<211> LENGTH: 517
<212> TYPE: DNA
<213> ORGANISM: Diabrotica virgifera virgifera

<400> SEQUENCE: 139

```
gggtcagccc gatattccca aatttccttg gtacaagtct tgtagggctt ctagaaagta      60
cataacttct attattagag tacgattcgg gcacgcatgt tatccaaagc atttatttaa     120
aatacaggtt ttggataatg ataaatgtga gcattgtgaa gaggaaagtg atttagatca     180
tatatttttt ggttgttcta aaaatacaat ttactcatct aaattaatga atgatttatt     240
aaaatgtaaa gtagcaactc cttggaatat actatattta ttatcacttg gttctgcaga     300
tgtataaaac tctttaatta acttttaaa agacagcaaa tcatcattat aattccctta     360
aacatttta attaatgcct tggtagtta gttgtttag ctgttaagct tagtgttact     420
taataccttt tagttgttat ctttgttta aacctgtttt gtataacttg ataacttgta     480
ttccttatgt gtctggcagt atgacggtaa gtctaag                              517
```

<210> SEQ ID NO 140
<211> LENGTH: 585
<212> TYPE: DNA
<213> ORGANISM: Diabrotica virgifera virgifera

<400> SEQUENCE: 140

```
gggggtcggt aaaaagtatg tcaagtaaat gatttatcca atccaaaagt ccaatctgat      60
taaatacttt cctgtttggc tgagttgtga atctggtcga gcaggatta caaggaagaa     120
tagaacacta gttttattct cactatctcg ctactcttat ttcagatgta tcggtcgcca     180
tcgcatgata gaacgcacaa gagatgataa agtttcttcc tacctatagg cttagcgaat     240
acaagtgaac aaagccaaag ttaattaagt aatagatatg attatcagag acagagtacg     300
ttaaataaa ttgccatgtt accggcggct cacagtggtt ccaaatgctg aaaacgtggt     360
catgagatgt catattctcc ctaaaattgg ataatactta atacaaaaaa agtgataata     420
tggtaagaaa tcagcttcta tggtatgacg gtgtgttgcg ttctcaccac tggcaaagag     480
agtttcatct tcattggtaa gataaaatgg gaaatagtac taaccatgca ttaagatata     540
acgcagaatt tcgactacgt cttctggttt ggcgatttaa acttt                     585
```

<210> SEQ ID NO 141
<211> LENGTH: 383
<212> TYPE: DNA
<213> ORGANISM: Diabrotica virgifera virgifera

<400> SEQUENCE: 141

| | | |
|---|---|---|
| gggtatatac ggatataaaa atttatattt ttaaatttaa gcggaagttc ggacacaatt | 60 |
| ctaactttaa agtgaactcg tttaagatag tgtacacaca agtgttcaat tgttattata | 120 |
| acagtgtgac atgttttga atttgtaccc tttgaatgga gactatggaa tgaagaccgt | 180 |
| gatgcttgca gagttgtcag ccattagatt aacacaaaaa tgccacagat gacacccaca | 240 |
| aaaaaaagaa tgtgtgtgta ctttgtacgc acgtaagaag ttatacttct attatatgat | 300 |
| ttcttaaaaa taaatatact ttaaacagtt tgttttaatt ttttttttta acaccaaact | 360 |
| aattttgtgc ttaccgcctc cag | 383 |

<210> SEQ ID NO 142
<211> LENGTH: 616
<212> TYPE: DNA
<213> ORGANISM: Diabrotica virgifera virgifera

<400> SEQUENCE: 142

| | | |
|---|---|---|
| gggggccata attatatctt aagccaagaa gttaattta attatgaaaa taatttagt | 60 |
| agttttggtg attgtagctg cagctacagc atctacggac gaagaaaaat ggagacaatt | 120 |
| taagattacc cacaacagag tatataacaa tattgaagag cataaacatc gatttgaaat | 180 |
| ctttaagaaa aatctgattc gtattaaaga gcaaaacgaa aaatacgaaa aagggggaatc | 240 |
| aactttaac ttcggaatca ctcaatttgc agaccttacc gaagaagagt tccttagtcg | 300 |
| ttttaaactc gctggtagtt ctaagttaag caaaattaat agcaatgtct cttcttctaa | 360 |
| aagtagaagt aaaacctccg gtggatcaga tgatttgcca gaacaatatg actgggtccg | 420 |
| cactggtgca gtaacatctg taagagatgt tgcagattgt ggtgattgca cagctgaaag | 480 |
| cgtggtagcc gcagtagaag gcgctgagtt tataaaaact ggaaatctaa tacagcgaag | 540 |
| tcccaagcag ctagaagact gcattccttt taacccagat gaatgttgga tatgttatga | 600 |
| gaaggtcctt aattac | 616 |

<210> SEQ ID NO 143
<211> LENGTH: 174
<212> TYPE: DNA
<213> ORGANISM: Diabrotica virgifera virgifera

<400> SEQUENCE: 143

| | | |
|---|---|---|
| gggttgataa gaacatgttt agttgttaaa gtccctaact ttttttatta cacaacatag | 60 |
| gcgaatgaat ggaaagcaga atgttaagaa aatatagcct gaggctatag ttgggtttta | 120 |
| atttcaatat tttataaatg ctagaatatt cctcagggtg ttgtgaaagt tgag | 174 |

<210> SEQ ID NO 144
<211> LENGTH: 619
<212> TYPE: DNA
<213> ORGANISM: Diabrotica virgifera virgifera

<400> SEQUENCE: 144

| | | |
|---|---|---|
| ggggctacta cttcagttca gtgtgtaagt aagagagacg agaattcatg ctttcgtct | 60 |
| ctatgtatgt ttggaattgg aatttcatgt gggctgcgac acgacacgat attgctgtgg | 120 |

```
tggtagggaa aggtgttgac gtttaaagtt cttacagcaa cagtgtggaa tttgtgatta      180
aacggcccaa tgggcgaact tttgtgaaat atcagaactg acaggcaata cttatcaaca      240
atgaagctca gcactcagga aaaacgggaa ttggataaat ttacaaaatt tttggcttta      300
aaatgtactc agatcatcgt acagtccaga cttggagaaa aagtaacaag caactgcaga      360
tcacaaacca caagcacgga ttggttcaac ttgaacatca gtgatctccc ggaagtcctt      420
gcggaaacga aaagagttct caacggcgaa atcctatcct caaatctgcc cttatgtgtc      480
gaaatttctt tgcgtacggt cgagggtgac catatggtcc tcgaaaattg gtgtctgggc      540
atgttgcccg aacaacagtg tgatcctacc acaagaatag tgcatacaat ctataatcgt      600
atggggactc tgctaaaat                                                   619
```

<210> SEQ ID NO 145
<211> LENGTH: 612
<212> TYPE: DNA
<213> ORGANISM: Diabrotica virgifera virgifera

<400> SEQUENCE: 145

```
ggggaacatt ttgcgattta aatagttttt gtcagttttg tttattatag atttaaatag       60
attataaatg ggtacattgc ttacatttga ttattttcat taacatatgt attttctaat      120
agtgtggcgc aattatataa ttatcaaaag tacgatttat ttggaaaata gtaaatccaa      180
acaccaaata gcaaagatgc ctcatgaaca tattaaatac acaaattctg tatcttcggt      240
aaataattca gatgaagaag aagatgtgga agtaagact tctcccatga gctacaaaga      300
acgcaggaga gaagctcata cacaggccga acaaaaaga cgtgatgcaa ttaaaaaagg      360
atatgataca ttacaagaac tggttccaac ttgccaacag cctgatgttt ctggctacaa      420
attgagtaaa gctactgtct tacaaaaatc catagactat attcagtatc tccaaatgca      480
aaagaagaag caagaggagg aacgaaatgc tttaagaaaa gaggtagtag cgttaagaat      540
aatgcagacc aactatgaac aaattgttaa ggcacaacaa tcacaaccgg acacactgg      600 aactagaatt tc                                                         612
```

<210> SEQ ID NO 146
<211> LENGTH: 434
<212> TYPE: DNA
<213> ORGANISM: Diabrotica virgifera virgifera

<400> SEQUENCE: 146

```
gggtaataat aaaataaaat acactgcgaa tctcaacgca aagaaaataa acaacggctg       60
tgaactctga gcggcttgac gaaaacaagt agaatggtgg tgcgtggccg gattatctat      120
caccatcacc accaccacca tgtgattgtg cttgtgctac gacgttgccg gttgcattca      180
aaaggcgcgt aggttcgtag gtattcgacg tattatattt aatatcttag accatggtct      240
aagtttaata taatattatc tccataattt tgttttggt ttatatactt gtataatata       300
ccttttatgt caacgtaaag gtattaactt tttaggtttg agtacagaaa aatatacaaa      360
atagtaaaat ctcaggggg gccacgaccc ccccctggcc cctctctgcg ggcgcccatg      420
gatggaaaga acac                                                       434
```

<210> SEQ ID NO 147
<211> LENGTH: 590
<212> TYPE: DNA
<213> ORGANISM: Diabrotica virgifera virgifera

<400> SEQUENCE: 147

```
gggaagcagt ggtatcaacg cagagtggtc attacggccg ggatattgat acctacgaaa      60
gcctcctgaa ttgtaaaaat ggtcttcgag ggggctgcgc gtcgcatcta agctatttga     120
ttatctgatt ttgttgtacc cacttcatta tttaggattc tgggggctca acaatcctat     180
atgtataatg tagttatgga gcgctgaaaa ctacacctgc atattttagg ccaattgtgg     240
gatgcaacac tctttgtatg aggtatcaga taatcaaata gcttagatgt gacgagaaga     300
caattttcac gatttgggcg cctttcgtag gtataaataa cccatatttc tagtataata     360
tcataataat agaaccagtg gaaattgcta cccacaaagc aaaggcgctc gagtcgtaaa     420
aagtcgaaaa tttattataa cggaaacagc ggatattgat acctacgaaa ggtgccagaa     480
tggtaaaaat ggtcttcgag ggcgccgcgc gtcctcggag cggatattga tacccacgac     540
gaaaggcgct cgaatcctaa aaaatctacg acggcgcaca gtggtccaaa                590
```

<210> SEQ ID NO 148
<211> LENGTH: 149
<212> TYPE: DNA
<213> ORGANISM: Diabrotica virgifera virgifera

<400> SEQUENCE: 148

```
ggggtgcggc gcgctccatt tcaaaaatct cctattttca tccgaaaaat attttttata      60
gattctttgg gacattctaa ataaaataag tttcttgaca ttttctcaa aagttaatag      120 ttttcaagtt ataagcgatt gaaaatccg                                        149
```

<210> SEQ ID NO 149
<211> LENGTH: 625
<212> TYPE: DNA
<213> ORGANISM: Diabrotica virgifera virgifera
<220> FEATURE:
<221> NAME/KEY: misc_feature
<222> LOCATION: 498, 499, 500
<223> OTHER INFORMATION: n = A,T,C or G

<400> SEQUENCE: 149

```
ggggaagata aataatttc ctgaaataaa gtattgccgt tgaaaaatat ctacaaaacc       60
actttggggg gtgttcaaaa tggacgtcat tcttcatatt cgctaattgc cggtgaaaaa     120
tattgtctag agttaaaatg gaaacagtaa attcacagtt gttgaccaaa gccataaact     180
ttcatggtca acagctgcag aagttgtggg aaggagaatt tggagaaaat gatttgacaa     240
gaaaaaatgt caaagatttg aattacaatg tgtatagtca acgccagaag aacctatctt     300
ttcaagatag aggtaaacgg ttgaaactcc aacagttttt gataaagaag gctaatttta     360
tctatagttt ggaacccacg aagcaaaaga acaatgagaa agcgattact gaagatatgt     420
atgctgttat gcctccttt gaaacttaca ccagtgtaga caaacaaaaa agagtggcat     480
tcttcatgga gaatgtgnnn taggtaatct aatcctgggc accattgtga gcagacaaca     540
atcaggaatg atgttgaaag tgttgtgtac tactggaaat ggtaacactt gtttatatgc     600
tgctgatatc aacgtcaagg cattc                                           625
```

<210> SEQ ID NO 150
<211> LENGTH: 594
<212> TYPE: DNA
<213> ORGANISM: Diabrotica virgifera virgifera

<400> SEQUENCE: 150

```
gggggggtatg aggatgcagc acaatttgga gcaacagata caagcgagaa accagtccgg     60
```

```
tgtgagcgag gatgccctaa aagagttctc catgatgttc aagcacttcg acaagaaaa      120 atccggaaaa ctcaaccatc aagagttcaa gagttgtcct cgagctcttg gatacgactt     180
acctatggtg gaagaaggcc aacctgatcc agagtttgat gctatactgg atgtagtgga    240
tccgaatagg gatggtcacg tttctctaca ggaatacatg gcctttatga taagcaaaga    300
aactgagaac gtccagagtt ccgaggaaat agaaaaggcg ttcagggcaa taacggcagg    360
agatcgtcca tatgtcacca aagaagaatt atatgccaat cttaccaagg aaatggcgga    420
ctactgcgtg gcgaggatga agccttacgt agagccgaag acagaacggc ccatccaggg    480
cgctttggac tatatcgagt tcacacgcac acttttcaa aattagttag gttaggttcc      540
gcattagtcg cttactcttg ctaaacgtta gatagacagt ataatattat tatt           594
```

```
<210> SEQ ID NO 151
<211> LENGTH: 627
<212> TYPE: DNA
<213> ORGANISM: Diabrotica virgifera virgifera

<400> SEQUENCE: 151
ggggttaagt ttgtaatcga agtcgtttcg ttttcgtttt gtcgtttgta ctttattttg      60
cactttattt gtgataattg ataataaaga caaattaata caaaatgaa acaatttgg      120 aacaacagcg tcgttaccat gaagaaaaag aacgtttaat tgatgccatg gtaaagaaa    180 tgcttcacaa aagacaact ttcagagaag caataaactc agaccaccga caaagtacc     240 tgctggatag atatatggct tcaacagaaa gactaataga tctttatgat gatagagacg    300
gacagcgtaa ggctgaagta gccgctctta cgggccccaa cgagttccaa gaattctaca    360
gtaggttaaa attaatcaaa gacttttaca gaaggcatcc aaacgaaatc agtgttccta    420
tgtcagtgga atttgatgag tttgccaaag ccagggaaaa tcctaacgag gatatggcta    480
actttgtaga atttacagat gaggagggct acgggaagta tttggattta catgaatgtt    540 acgaaagta tataaactta aaaggcatag aaaaggtaga ttacattacc tatttgggta     600
tgtttgacca actatacgat attccga                                         627
```

```
<210> SEQ ID NO 152
<211> LENGTH: 526
<212> TYPE: DNA
<213> ORGANISM: Diabrotica virgifera virgifera

<400> SEQUENCE: 152 gggggggcatt gtcttttata aatcgttatc taaaagtttt cagtatgaag gtcgctttac      60
ttttactagt ttttatctgc tttgtaaata ggacctattc ccgaccaaat attttttaaat    120 tcaaagacgc caaacgaatc catgccgtat gtcaagcaaa ctcggaaaca catgtcaacg    180
agtaccttga aaggcttcaa gaatttggca agattgaagt tccaaatatg gcgaagcata    240
cactctgtat gaacattaat gccggactac aatacgaaaa cggtgatatt gcagttgaga    300
gattaagaag cgacttggaa gaagtttcaa acaacgaaaa taaaatcaaa gaaattgttg    360
atacttgtgg tgttcgagcc cctggaagcc ctgaagatgc agctatggct tttggcaaat    420
gtctatgcag tcaatggcct caacatgcag tatgtgtttg cagcacatag tagcagcgaa    480
aaatagtttt tatataaata tatatcaata aataaatttt atcttc                    526
```

```
<210> SEQ ID NO 153
<211> LENGTH: 601
<212> TYPE: DNA
<213> ORGANISM: Diabrotica virgifera virgifera
```

<400> SEQUENCE: 153

```
acttttagt cttacacttt tcaaacaata aatatatcg ccatgtttat taaaatatat       60
gtataaaaca tatgatgtac aaacatgaaa agtagtcgga accggcaaaa aatttaaaac    120
tttttttgttt atttgtgaag cataacgtaa acaattaacg taaaaagtct tatttttaaa   180
aattcttgta gttgatgcac taacaaaaaa tgacatgtga aattatcaac aaaaaaaaaa   240
aagaatctag aaacataaaa ttgtaatatt tttcgatata aaaaaatttg ggaggtacac   300
ccaattttt caaggtatac accaacaact ccaaaaaaca aaccaaataa gattttgttt    360
aaaatttatc atcaaacttc ggagatatgt ttatatacac atttgtcaaa aaaaaaaacg   420
ataaatcgat attttttgat atattttcgc ttaaacataa aatatttaca catatgattg    480
aagggtttca aaaaaacaaa atgagacttt ctaaattaaa atgaaaaaag tttatgccat    540
aattacaggg gaatagcgct actaaacgtt gcgtataaaa tacttgcagt acatataaaa    600
g                                                                   601
```

<210> SEQ ID NO 154
<211> LENGTH: 95
<212> TYPE: DNA
<213> ORGANISM: Diabrotica virgifera virgifera

<400> SEQUENCE: 154

```
aatgtgaaag ggcgcacttg atgaaaagga acccccgtaa agtaacatgg actgtcttgt    60
acagacgtaa acataagaag ggtcaggagg aagaa                               95
```

<210> SEQ ID NO 155
<211> LENGTH: 635
<212> TYPE: DNA
<213> ORGANISM: Diabrotica virgifera virgifera

<400> SEQUENCE: 155

```
ggggattctc gcgtcctttt ccccaagaga tcgtgacgaa aataactgtt tgttgaattt     60
ctccaattat ttgtgtaatt ttgccattaa tcgcgtttaa aatggcaacc cgagtgtttg    120
tgggtggtct tacttacaaa attcgcgaac gtgacttaga aaagttcttc agaaagtatg   180
gaagaatcaa ggaggtttcc atgaagaatg gttatgcatt tgtggaattc gacgatcgca   240
gagacgccga cgacgcttgc tatgagctaa acggtaagga cttaatgggg gaaagaatta   300
ctgtagaaag agcccgtggt acgccccgcg gaagtgatca atggcgggga agcggtcgag    360
atagaggtta ttcaggttat agcggtccac gcggtagaaa cgataattct agagctcgtg   420
acaaatatgg gccccgacg cgtacagaat acagagttat tgttgaaaac ttgtctagcc    480
gttgtagctg gcaagatttg aaggattaca tgcgtaaagc cggtgaggta acctttgctg   540
atgctcataa actagttcca aacgagggag tcgtcgaatt tgtttcatac agcgatatga    600
aaaatgctat tgaaaagctt gatgatactg aaatt                              635
```

<210> SEQ ID NO 156
<211> LENGTH: 599
<212> TYPE: DNA
<213> ORGANISM: Diabrotica virgifera virgifera

<400> SEQUENCE: 156

```
gggggacctt ttctggttgc acctccaagg cttctaaaat ttgcaagcca taacggatgc    60
tgagactaaa aaagatgagg gaattttaca atttataatt cacgtctcat ctgctcagcg   120
```

```
cggtaaagtt ccaacgagaa tggttccctt agtactccaa tcagagtaaa catgttaatc      180
aaaaattaat aaccattttc aatttcgttg caacactaca gccgcatcat attctagttc      240
aatcagaggc cgcatcatat tctagttcaa tcagagagtg cagcaagcac ctctaccggt      300
ttcgaaactt attagtctct catcaggagg cacatctgct gctctctctg acccaaccag      360
gacaaaccct ggcgtgcagg tacgcattgc aacgaacgaa atggcaggga tgctctagcg      420
gcaactgcta gcaagagact aagttttcaa actaatagca cataaaataa tatcaaaaaa      480
attactctac atcccaccag attgaaaaca atgagaacct tctctgatta cacatacgag      540
gcttctaaaa tttgcaagcc ataacggatg ctgagactaa agaagatgag ggaattttta      599
```

<210> SEQ ID NO 157
<211> LENGTH: 167
<212> TYPE: DNA
<213> ORGANISM: Diabrotica virgifera virgifera
<220> FEATURE:
<221> NAME/KEY: misc_feature
<222> LOCATION: 85
<223> OTHER INFORMATION: n = A,T,C or G

<400> SEQUENCE: 157

```
agagtacgga atcaagtaga tgaaaagagg cgaatatttc aagcaatatc tgcgaatgtt       60
agttctgaag gtcagagatt gttcntagct atagctaaaa caattagtga ggttaggtgg      120
aacgattcgg aaattgtggt ttttaatcga gatgttataa ttagtcc                   167
```

<210> SEQ ID NO 158
<211> LENGTH: 650
<212> TYPE: DNA
<213> ORGANISM: Diabrotica virgifera virgifera

<400> SEQUENCE: 158

```
ggggaaatat gttagtatgt ggaaattact tgataaataa ataaatatt gcaaaaagga       60 gcctaaaccg ccattaagaa agacaaaaaa atacactttta ttcaaataaa ctttttttatc    120 ccacgcctag attttgtgtc acattggatc tactaaaaat cgattttcta taacaagaaa     180
tcgaacgtga ctgactcggc aacatttcgc gcctatgagt ataaaaatta ttgttttttga    240 tagtataaaa atgtcattgt cagtgtcgaa ttaccgacgc actgttgcct cactgttgaa     300
agttcgcaga acttttcgaaa aacaagaata ttgatgacgc gctactgttt actcttaata    360
ttaaatttgt aattctcttt tagcgttcct caataccttc ctctatgctt ggtgtccgct     420 caatttttttg ttctagtatg ctggtcattt cttgttttac aatatcacat accatttctt    480
ctctatcaat aataactatt tgctttgtca cccatataat cttgtttaat ctcaatctga    540
tttttcctac aaaatatgg tctccttgtt gccaatcctt aaatagtgca tgtcttctca    600
gttggttttg agttttggag atattattta caccaattgt aatttcaact                650
```

<210> SEQ ID NO 159
<211> LENGTH: 584
<212> TYPE: DNA
<213> ORGANISM: Diabrotica virgifera virgifera

<400> SEQUENCE: 159

```
ccactgaaaa ataaaaaaaa aaactttag taaggggcta ttctggacta cggggcaatt       60
ctggacagtc aaaaaaatgc ctgtccagaa tggccccggt tgacaaatat acttataact     120
tttttttggc tagaacaaaa aacacaacct caagggtcaa taataacaag ccatgtaaca     180
ttttgttaag gtgaaaaaca ttaccattac ttacttggaa atgagtgcag cacagaaagc     240
```

```
ttgaccgcta tatttttta acggttttc cacgaaattt tgtttgcgcg ccaaaaggtg      300
aaaatgccca gcgcggacct tccaacagtt atcaaccaac tggctgaatt tctcgcgaaa      360
agttgtgaat atcacgccac ccgcaagtgc aggctttcgg cgcggttgcc acgtttacct      420
gagaaaacgc gttgtccaga attacccgc atgtccggat taaccccgtt atacggtacg      480
tttttactta aaacttacgt aaaagttttc aaaaattgca ttttgcgtc atatcatttg      540 aattaaattt ttggcatttt tttgaatgaa acattgttta gtaa                       584

<210> SEQ ID NO 160
<211> LENGTH: 508
<212> TYPE: DNA
<213> ORGANISM: Diabrotica virgifera virgifera

<400> SEQUENCE: 160
ggggacattt gaattttttt ttggagaaga ctggactttg agaaattcag gttagttgag       60
gacaaatttt gcggacttac cttctagtga actagtcaaa ttgtcggtaa ggagtgttct      120
agggcggtac acagtggttc caaatgctga aaacgtggtc atgaggtaaa agagtgtggg      180
tacttatgta caattgtaca gctcccagaa agaatcatgg ccgatgacaa acgctgtcgt      240
cggtcgtaca cccacctaaa ctttagcaga gaggatttct ctcgttggtc atggttcgct      300
ccgggagctg tacacacgta acaagttata cttctttggc gtcattaaaa agtagttttt      360
gattatatta tgtaaataat tacaataaaa taataaaagt actggaaaac gatagtcaaa      420
gttcagttta aatttgaaaa attaaatatt taaatatttt tttatttatg tataaaattc      480
gttaatatac cagaaataaa acgaaaag                                          508

<210> SEQ ID NO 161
<211> LENGTH: 644
<212> TYPE: DNA
<213> ORGANISM: Diabrotica virgifera virgifera

<400> SEQUENCE: 161
gggttctgag aaatgttaat tggtttataa caatttttt aaacatttaa agattatgca       60
aaaaactgaa aaatttatat tttgtcgaca aaatattaaa taggcatcac acctttatca      120 tcttctaag tttgatcaat gtctcatgat tattttggtt gttattgcga ctgtaaattg      180
ttaattaaca attgaattgt tgctaaagta ttcgtttcat tttcaccggc ttctgaattt      240
ataatctata ccaagaaaga tttatttct ccaagctata tactgataaa taattactgg      300
cccaaaaaaa ttatttgaaa attcgagatt tgttgggga acccacatt ttccgaggaa      360 aattttcgtc ggagcaaatc gggaaaaaca tgcctctatg tagaattaaa ttggggtgaa      420
tttttatttg agtgttttg gtgtaaagtt aaaatcttcg gagttataga gcaataattg      480
aaaaaaatac gatttgtcgg cgcaatttg tttataaaaa agtagcacac tatctgcgga      540
cttttcaaac ctatattaat aatatatagg atcttataat tagattccag caataaaatg      600
gctggtaaat aacctttctt tgtacttaac taattagacc agcg                        644

<210> SEQ ID NO 162
<211> LENGTH: 659
<212> TYPE: DNA
<213> ORGANISM: Diabrotica virgifera virgifera

<400> SEQUENCE: 162
ggggcgtgta tatgtatata tttttatatt catgtaacgc cttggaaatc tcaatattta       60
```

```
attttattttt ataatctctt ggtattaaaa tttttggtat cggaactaat aaaagatagc    120
ggcttataca taattttgtc acgttttatc cttgatacat aacaagggtt ccaaaatctg    180
ccagtttata tcactaggta aaaagtttta gttcgacggt ccttctcact tttgttgtaa    240
aagccgtgaa tacctgtgtt ccagaggcgt gcggtccatg gaagcggggg aagcaccgct    300
tctctattat atacttcgat ataacaaaat atattattaa ctaatattta attatcaaaa    360
attttcccca atcccagtaa tctacatatt attacctagg caataggcat tgaaaaatat    420
taaaaattaa tcgcatagga aggaactcaa tatgcactat gcacacaatt caactattcg    480
gtccacccct gacagaagcg catctcaaaa tcgccgcttg tcatgcagtt gtcctgtata    540
aaaattggtc agggttcaat aaccgcaccc actagtcgcg cgaattttgg taccctgtag    600
aagcgattgt tcgatcgcct tccaagagtg ggatcatctg actgttactg cttctaagg    659

<210> SEQ ID NO 163
<211> LENGTH: 598
<212> TYPE: DNA
<213> ORGANISM: Diabrotica virgifera virgifera

<400> SEQUENCE: 163
gggggaagtt gcgctgtgct gtgagttaca accacgaatc tctcggccag gatgctggca     60
atttggtttt tatttgttgc tgtttcatcc tcaaatcaat ttgtcgttga taccgtgacg    120
gccaatgaag tctggcaagc tcctggttgc cataaagtgg gtcatactag aaaagtcagt    180
attccaaact gcgtagaatt cgtgataaca acaaacgctt gtcgcggatt ttgtgaaagt    240
tgggctatac cgtcattaat aaaaggatcc actatccaac cgataacatc cgttggccaa    300
tgctgcaata taatggagac agaaaatgtg ttagcaaagg ttatgtgcgt tgaaggaatg    360
aaagtattca cgttcaaatc ggccgtcaca tgttcttgtt accactgtaa gaaagattag    420
agcgactgct ggaaaggacc aaggcgagtt tattcaaaat ttatatgtaa catacttaaa    480
gttcattgat tatatttagg cgtaagtaaa aattacaata tactttctta attactgtat    540
atattgtact gactgactga ctgattgtag gaattatgtt cattaaattt tgtttccc     598

<210> SEQ ID NO 164
<211> LENGTH: 410
<212> TYPE: DNA
<213> ORGANISM: Diabrotica virgifera virgifera

<400> SEQUENCE: 164
gggagacagg taatagcaga gataaataga aaaagggtag aataagagaa taatatataa     60
aggtaatgac acacagatag gagaagctat gctctaagtg aataaaatat atcttgaaaa    120
gctagaataa atggaatatg gagagaagta gaaagttgag agatatgtga agaaaattta    180
ttgaaaaagt tacttaaata cgaatgaaga acggtaggag attcatacag aaaacacaga    240
aacagcgtaa aaagactaat aagtgaaaca cagagaataa taattaaatg acagtttgga    300
aaataataat acatagttct gactatgaac tacaagattt aaagaaagga aaaagtcgag    360
gtaatagcac ctatacaaaa aattacagta attacaaata aaagcaacac                410

<210> SEQ ID NO 165
<211> LENGTH: 646
<212> TYPE: DNA
<213> ORGANISM: Diabrotica virgifera virgifera

<400> SEQUENCE: 165
aaaaaatctt tacctaaaat aagagaatca agaagatttt ccccagtaga aatcagtaca     60
```

```
tttatcgaag aagaaagatc cgctatatta aaggaaaatg atcatgtcgt tgatagttct    120
tgggtcgtaa tagaagagga agaacttagt tatataccag aagtaatacc acctgtcatt    180
gttgaaccag aaaaaatgga tgcagatact actgaaaaag atgaacctat tcaagttaaa    240
cctgaagata gtttacctga agatcaaatt gaacatacag agtctatcaa aaagccaaga    300
aatcggtcta agtcaaaacg ccaaaaaacc cctaaagaac aggaattgtc tgaaactatt    360
gagcattcgc cacgtgtatt accagctata gctactgtcc aatctaacga acagtttgaa    420
gttaaatcaa ggtcccctag tagaacctac gcatcagttg tgaagtcgca tatagaagga    480
gttactcctg aatacattca gtatacccaa gttattactt ctatcgataa taaaccccag    540
accgttgaaa gcattactga ttcaacagtc gaagaaacta cagaagagat aatatcagaa    600
aaagtagtgg agcaacccac agtgcaagaa ttgcaaacaa cagaga                  646

<210> SEQ ID NO 166
<211> LENGTH: 277
<212> TYPE: DNA
<213> ORGANISM: Diabrotica virgifera virgifera

<400> SEQUENCE: 166
gggggcctgg tacttactta tataatgtta agcttcttta aagtaacttt ttctacaacc     60
gtgttaaaaa tgcaattttt agcactccat acgagcgtta aaaatgctac tttaaggcac    120
tagtgcttta aaaaatttaa ggcagtgcag ttcatattga ccgtatacgc tgtgagctcg    180
tacgtagagg ggatgtttac aaattcgcga gcgccagtag tgacaagtcg gtaaacgttt    240
accggaaatt tgacataaat gtcaaagtgg ttaattc                             277

<210> SEQ ID NO 167
<211> LENGTH: 659
<212> TYPE: DNA
<213> ORGANISM: Diabrotica virgifera virgifera

<400> SEQUENCE: 167
gggagtgatg aagttttatt cagactggtt attcatccta tatttttttt gtaataatta     60
tggcgacatc aaaattaatg gtgtatctga agaaaaagta tcacaatcct gatgtagctt    120
atagagaaat aatcaacatc accacacaat acagaggttt acatccagaa cagagtgtct    180
acaccttcaa cgatggcaca agaatggatc tcattaactt aactggtaca attcctgtgc    240
gttacaaagg caatatttat aatattccaa tttgtatatg gttaattgac acgcatccag    300
agaatgctcc catttgctat gttaaaccga cttccgacat gtccataaaa gtttccatgt    360
ttgtagatca aaatggaaaa gtttatctgc catatttgca cgattgggtg ccgaatgaat    420
cagatttgct aggattaatc caagttatga ttgttacatt tggcgaacaa cctccagtgt    480
ttgctagggc caaagacaat gaatcgtatc cgtcaaattc attcatgcct caaccatctg    540
gtggttacat gcctccgtat cctaccccct acccaccagc atcaggaggt ttcggcgggt    600
accctccata tcctccaacc agcaacaatt ctttccaagg atatccaccc tacccttct    659

<210> SEQ ID NO 168
<211> LENGTH: 409
<212> TYPE: DNA
<213> ORGANISM: Diabrotica virgifera virgifera

<400> SEQUENCE: 168
ggggaggtta aggttaaact tatgtcaaat caaattttaa atttgaacat gtggcctgtt     60
```

```
atatacacag cactcagaac atatgcaccc tatgtaactc ttcctgttgc tgctcttgta      120
ggagtcatag gttacaatct agaaagttgg atctctaata gatatacacc atacaacaaa      180
tctattaaag aacaacgaga agataggcta ttagttgaag caaaacttaa agaatctgat      240
aaagtagaga agttaaaata taaggctaat attctagaca caaatttatc tccttcctta      300
acttgaacat tagaatggtg cattggtata cacttaaatg ttaaataact ttaataaatt      360
ggagtatgta ttgttttagt tctctatatt aataaaaagt tgtgatatt               409

<210> SEQ ID NO 169
<211> LENGTH: 253
<212> TYPE: DNA
<213> ORGANISM: Diabrotica virgifera virgifera

<400> SEQUENCE: 169
ggggacaaaa tatggagaaa taaaatatcg gaaagaaat aaaaggcaga atttacaaaa       60
cagtcatcag accaataatg acatacgcgg cagaaatacg acccgacaca gagaggacca     120
aaagattgct cgaaacagag gagatgaaaa ccctaatata atcgacaagc tcatccggaa     180
aagagaatcc aatcgtcttc agcaactagc ttacaattca aacccagtca tcacaccaat     240
ctataggtcc ctc                                                       253

<210> SEQ ID NO 170
<211> LENGTH: 633
<212> TYPE: DNA
<213> ORGANISM: Diabrotica virgifera virgifera

<400> SEQUENCE: 170
ggggaaatac gaatatgaaa acatttcacc acatcaacac gtgaattaat attcgaaaat      60
ggagtacgaa aatacacaac aaaatataaa cttcgtaccg tgtgtaagat gggttaaacg     120
aggagtggcc aattcaagcc cagtaaaatt gcaactgtcg aaaaacgagc tggctcaaat     180
tattaatgac accaagatta aattacaaga atccaatgaa aatgaagatg agcctatgga     240
agaaggtgaa acgtctcaaa cagatgagtt tgccttagag gattacgata agaagacga      300 aaatgaggac actgcaaatg ctttaggaat tggatcattg gcagaactcg ataatgatgc     360
tgcagacaat ttttctgagt cagacgattc tgaaaaagaa gatgataaaa tcaaaccatc     420
tgacaatctc atactagtag gacatgtaga aggggatgca agtctattgg aagtctacat     480
atacaatgaa caagaagagt cattgtatgt tcatcatgat attatgttat catcctttcc     540
tctgtgttta gaaccgctaa actatgaacc gaagatgccc aaaggaaatt attgtgcagt     600
gggatcaatg tcacctgtta tagaggtctg gga                                 633

<210> SEQ ID NO 171
<211> LENGTH: 640
<212> TYPE: DNA
<213> ORGANISM: Diabrotica virgifera virgifera

<400> SEQUENCE: 171
gggccctgta tatacctcga tggcaataat ggacctgacg gatgtgctat ttttatgaga     60
aaggacaaat tcgaattact tgaggcacag accaaaattt tggagatatg gaaggttcaa    120
agtaatcagg tcgttctact gacaatctta agatgaaag aaacaggcca aaaaatctgc     180
gtcaccacaa cccacctcaa ggccaaaaaa ggagctctac tatccactct tcgcaacgaa    240
caaggtaaag atcctctcca gtttgtgaaa gcaaacagcc aggatcttcc tttgattcta    300
gccggagatt tcaacgcaga acctactgaa cctatctact caaccgtact cgacaatcct    360
```

```
ctgaagctgg gtagtgctta tgctgactgt gatattgatc ctacgatttc ctcagctgaa    420
agggaacctt cgtacacgac gtggaagatc agaggtgaag gagaggtctg ccataccata    480
gattacgtgt tttattccaa gaataagcta gaactagagg ccgtattaga tatgccgacg    540
ggagaggaaa ttggagagaa cagagtaccc agcttttctt acccatcgga tcactttcc    600 ttagtgtgtg atttcaaaat aggccatagt taagtttagg                          640
```

<210> SEQ ID NO 172
<211> LENGTH: 651
<212> TYPE: DNA
<213> ORGANISM: Diabrotica virgifera virgifera

<400> SEQUENCE: 172

```
gggggacaaa ttgatgaaag aatgatggtt ggtgcttttt tcaagtctat accaatggca     60
gcttttgcgc actgtagcga tctgaaataa gaaaaaaagt ttttttcgaa ccaccctatt    120
aagcagacaa attaataatt gtatcagaat catttattca ttgggagtta gtaaatatct    180
ctgctcataa tttaaaataa aatatttaaa aaatatcccg ggaagtcttg aagaattctc    240
ggtaatcggg atttcattt tttactgatt tcccgagaaa tttgtcccgg gaatgcagct     300
ctatttgtag gtactctact ggatgattga aaaaaacaa cactaaaaag cttattgtaa    360
aaagttatga ccgagaaaat aaggccgact taaaagtacc attgggaagc aactgtcaaa    420
aaaaatctaa atgtgctgag agactaaggg ttaattatga tatacagatg tcgttttcct    480
cctcacaact ttttctgttg tccctttggt ctactagctg ataactttgt aggttccttt    540
aaattcatgt gtaactggag tagttgaatt tggtttcact tctctttagt tcatataggt    600
cttgatcatt atcatcattc aatgatgatc ttgatcatca atcagttttg a             651
```

<210> SEQ ID NO 173
<211> LENGTH: 667
<212> TYPE: DNA
<213> ORGANISM: Diabrotica virgifera virgifera

<400> SEQUENCE: 173

```
ggggcctttt ccaaagtttc atataatttt taagatgagt actgttatta aaatcgtttt     60
aaaatggaac ggaaaagaat ttaatttaga atcatcggaa gatgacactg tatctgattt    120
aaagaaaacc atagaaaatg taacctcagt aaaatgtgga agacaaaagt tgttaaattt    180
aaaatacaaa gggaaaacgc ctgaagatga ttgtactctt ggtctttttga aacttaaacc    240 caactttaaa ctcatgatga tgggttcact tgaagaagac atagcagaag caaatactgc    300
acctgaaaac cttcctgatg ttgtcaatga tttagatata gaggaagagg aagttgccat    360
tgaaaatcag gatgtatatc ttgcaaaagt ggaaaaacgt atcaaagatt ataaaataaa    420
tatgttaaat gatctccggc ctgaaaaaaa gttgctagta ttagatatag attacacact    480
ttttgatcac agatctaccg cccaatctgg agcagaatta atgaggcctt atttacatga    540 gttttaact acttcttatg aacactatga tattgttatt tggtctgcta caggaatgaa    600
atggatcgag gagaaaatga agctattagg tgtttctacg catcctgatt acaagattgc    660
ctttat                                                                667
```

<210> SEQ ID NO 174
<211> LENGTH: 623
<212> TYPE: DNA
<213> ORGANISM: Diabrotica virgifera virgifera

<400> SEQUENCE: 174

```
gggggagtctt gtgaaaaaag tcacagcgct cactggcgtt ttattaagat caaaatgcca      60
tcttcaccgg aggaaacaac ttttcctcaa agactgcagt caagcaacaa cttaggcgaa     120
caaaattcaa aagaccaaat aaaaaaaaat ggttatttcg agcaagattt ggtatggagg     180
aatgtaatta tatatatagt actccattat ctgttaattt ttgcaatatg gagacttttg     240
accggtcaaa tgaagcttgg aacttttatt tttcattgta tttacgctac ggcttctgtc     300
cttggtatca cagctggaaa tcgtcgtctc tgggctcata gaacctacaa agcaaaactg     360
ccattgcgaa tatttttaat gttaatgcaa acaacgacca tccagaataa tatttacgtt     420
tgggccagag accatagact acatcacaaa tacacggaca ctgcagctga tcctcacaac     480
tcgaatagag gattcttctt ctctcacgtt ggatggctat taatgaagaa gaaccctgaa     540
gttaaaaaac aaaggaaaga atattgatat gagcgatgta gcagctgacc ctgtggttca     600
atttcagatc aagtattatg gaa                                             623
```

<210> SEQ ID NO 175
<211> LENGTH: 406
<212> TYPE: DNA
<213> ORGANISM: Diabrotica virgifera virgifera

<400> SEQUENCE: 175

```
gggatatgca gaagacataa ttcttatagg cagatacaag gaaagataaa acaagcagt      60
aacaatcctg gcaaatcaag tatgggaaag aggtctaaag gttaacgaaa taaaaacaaa    120
atatctactc tgctctagaa gagaagataa aaagacgaga gaaatcaaga tagaaaacta    180
cacttttgaa agggttcaat aatttaaata tttgggagta attgtaaatg caaaaataa    240
gaaaagtgaa gaagtaatgg agcgaatact agcaggcaac gaaaatactg gagatatcat    300
aggctaatga aggaccagca cttatccaga aatacaaaac tgaaaatata cagatttgca    360
atcagaccag tatttacata cgcagctgag acaatgtgcc tcacag                   406
```

<210> SEQ ID NO 176
<211> LENGTH: 660
<212> TYPE: DNA
<213> ORGANISM: Diabrotica virgifera virgifera

<400> SEQUENCE: 176

```
gggggggaaga atttgtaggt taagaataaa ctgcatgttt ttgttttaat ttaaattttt     60
gaaagatcag taatacaaaa tggaaacaca ttcatctgaa agttcacaaa aagaaataa    120
cagaaaaagg aagaagtctt ttctaaaaaa tgcaagaaaa tatgccaaaa aaggacattt    180
tggaagaggt tcccaattgg attctgatac atatcattat ttcgtaaaaa tattagaaac    240
atataaagaa ggttttgata cagatgaaga taaacaagtt tttgctaata atgtgtttgc    300
acaaccgaaa gatcaagaag tgaattgttc ttgtaaccaa gtaggatgca gagttgtgga    360
aatgctatta cctttttgcca atgatgacat attgaagaaa ttcatggttg cctttagtga    420
agatatgagg cctctaatca gtgatagatt tgcaagccat gtattagaat gtcttgtttc    480
ggaaagttgt aaaaggactt taaataacaa agtgccagaa gaatcaagaa cagagtatca    540
gaaatttgct attaaagtta gcaagttctt gttaaacaat ctagaggatt atatttggga    600
tacttatggg aatcatgtta tacgaagttg tcttacacat ttaatacaga tgcctgttga    660
```

<210> SEQ ID NO 177
<211> LENGTH: 578

```
<212> TYPE: DNA
<213> ORGANISM: Diabrotica virgifera virgifera
<220> FEATURE:
<221> NAME/KEY: misc_feature
<222> LOCATION: 284
<223> OTHER INFORMATION: n = A,T,C or G

<400> SEQUENCE: 177
ggggcatgct ttgagcgtac agttgaactt ctctacaaat atgtagtacc taaaccacgt      60
gctgactgca ctaaaggcga acaattgatt gttacatttg ctgctggtta cattgcaggt     120
gtattctgtg ctattgtatc acatcctgct gatactgtcg tcagtaaatt gaaccaagaa     180
aagggatcaa ctgctctcga ggctgctaag aaattgggaa tggctggatt atggaaggga     240
ttgactccta ggattgtgat gattggtaca ttaactgctt tgcngtggtt catctatgat     300
gccttcaagg ttgccatgag aatgccacga ccaccaccac cagaaatgcc agaatcatta     360
aagaggaagt tggagggcaa atagagaatt aatttattaa cactaatatg taatttatga     420
ctttatttcc agaaaaacga aatcgcagta tttccattag ttcgttatag ttattgattg     480
tcatcaactt tgcgaatttt gatgttttta agttcatacc agttatgtcc gatattttag     540
attgtaaata gataatcatc aatatacaac tggaactc                             578

<210> SEQ ID NO 178
<211> LENGTH: 678
<212> TYPE: DNA
<213> ORGANISM: Diabrotica virgifera virgifera

<400> SEQUENCE: 178
ggggagaatc aaattagaat ataaatttca atgttttca aattttcaaa tatgaattat       60
taaataaat agaaatgatt ttgttaata acttctttct tcgacacgta ataagttaa        120
taaaacaagc atactgtaca aatataagta gtttgtcaaa agttgaaaga attaaattcc     180
taaggaaaat ggcccgtcct aacgcaaggg aaaaccccggt gataatgaaa ctaaactcac    240
aagaattcca ctctatattc aacgaggaat tgcgaacttt agtatcctta tttaaagagt     300
atggctatga aattcgaatt gcaggtggag cagtaagaga tcttttaatg gaatgcaac      360
ccaaagattt agattttgcc actacagcta ctccaaccca gatgaaagaa atgttcatat    420
cggaaaatgt tcgaatgata aatgccaatg gagaaaaaca tggcactatc acacccagaa    480
taaatgataa agaaaatttc gaggtaacta ctttaaggat agatgtggta actgacggta    540
ggcatgcaga gtacagtttt acaacagatt ggctactaga tgcactgaga agagacttga    600
caatcaattc aatgttccta ggtctggatg gttctgttta tgattacttt tatggacatg    660
atgatcttca aaaacgaa                                                  678

<210> SEQ ID NO 179
<211> LENGTH: 647
<212> TYPE: DNA
<213> ORGANISM: Diabrotica virgifera virgifera

<400> SEQUENCE: 179
ggggctctgt cattttaaaa tgggtagtgc aagaactctt tttggaattt taggctcaaa      60
acagatatta ctatgttcaa attcccagtt tactactaaa atttcaagaa catttcttca    120
tcaatgcttt agatgtcata aatctctact gctaaatacc tggtcagcta ataatttaac   180
tcaaaattct ttactccata aaagaacgtt tcataagtca cacagtttca atgccgcaag    240
acgggattat tatgaattat taggagtagg taaaaatgct tcaaactctg atattaagaa    300
```

```
agcttattac aaattggcca aaaagtatca tccagatgta aataagaatg atccagaagc    360
atctaaaaag tttcaagaag tttctgaagc ctatgaaatt cttggagatg aaaataaaag    420
aaagcaatat gacacttggg gtgcaacagc tgatcaaatg ggaggcatgg gtggtggagg    480
aggccattca aaaggtccac aaggattcag tcagcaatgg caatatcaat caacaattga    540
tccagaagaa ttgtttagga aaattttcgg agatgctttt actcgaggct cttctcattt    600
tgaagatttt gcagaatcaa actatggatt tggcgaagct caagaga                 647

<210> SEQ ID NO 180
<211> LENGTH: 204
<212> TYPE: DNA
<213> ORGANISM: Diabrotica virgifera virgifera

<400> SEQUENCE: 180
gggttgttag ataaattgaa aaaaaatgta cccacgaata tattcaacaa acattacatt     60
ttctcgagaa tgggcgggca tgatgacgta atcgatgatt tttattaaat gataatagga    120
ttcgtgtgat atctcactcg aaagtttatt caatgctcta ttcactaata taaacattta    180
tataattatt tataaagggt gccc                                           204

<210> SEQ ID NO 181
<211> LENGTH: 98
<212> TYPE: DNA
<213> ORGANISM: Diabrotica virgifera virgifera
<220> FEATURE:
<221> NAME/KEY: misc_feature
<222> LOCATION: 73
<223> OTHER INFORMATION: n = A,T,C or G

<400> SEQUENCE: 181
gtttggacag tctggagctg gaaacaactg ggccaaggga cattacacag aaggtgctga     60
attagttgat tcngtattag atgttgtaag gaaagaag                             98

<210> SEQ ID NO 182
<211> LENGTH: 174
<212> TYPE: DNA
<213> ORGANISM: Diabrotica virgifera virgifera

<400> SEQUENCE: 182
gtaaaattaa ctactctgt gaaaacattt atgaaattat gtaagtagtc gttttatat       60 tatattggta ttaagattat aataatattt ataaattagt attaaaaata gatggatgca    120
acaaaatgta ctcgtacagt gcgctggagt aagtgttagt gttaccccc cccc            174

<210> SEQ ID NO 183
<211> LENGTH: 577
<212> TYPE: DNA
<213> ORGANISM: Diabrotica virgifera virgifera

<400> SEQUENCE: 183
ggggagtagc tgataagcat ggatcataca cctattcaac agttttatag ggatgccaac     60
gtatttatca ctggagggac gggatttatg ggaaaaattc tcgtggaaaa gctgctgagg    120
tcaacggagg tgggaacttt gtatttgctt gtacagaaaa agaaagggaa gcacaaggat    180
gacagaatca cggaaatatt cgacgatgtg gtttttaaaa gacttaaatc agaaaaatcc    240
aaattcagac atcgagtaca agctatatcc ggagacttaa tgctaccgca tttgggatta    300
tcagagtcag atagacagct tttaatttca aaagttaacg taattatcca catgggagca    360
acaatcaaat tcaatgaaag catcatcagt gcattacatg ccaatgtata tagtaccaaa    420
```

```
ttagttatag acttagccaa agaaatgaaa catataaaat cgattgttta tgtatccact    480
gcctattcaa attgcacacg aagcgaagta gaggaaaggc tgtatgatcc accgatatcc    540
tatgagaaat cagtagagtt aatagaaaag ttgtcaa                             577

<210> SEQ ID NO 184
<211> LENGTH: 473
<212> TYPE: DNA
<213> ORGANISM: Diabrotica virgifera virgifera

<400> SEQUENCE: 184
gggattcctg aagttgattc cgttgtagaa cgatcagaca aaagtcgaag aacagccatg     60
ttgggtagtg tcggcgaaaa aagtgtatgt tcctagagaa aaactcgcag attttttgtgc   120 ttgtgttgtg caatttgtta agtgtttgac ataatttgga ttatgaccgc cgtagcggag    180
aacctcaact ggggcaccga gctctgggac cagtatgaca acttgtccct gcacacgttg    240
aaaggaatag acttttttgga aaaatatgga cagtttgtta gggatcgagc tagtatagaa   300
tgtgaatatg ctacaaaatt aaggagacta gtcaaaagtt atcagcctaa gaaaaaggac    360
gaagatgatt accaatttac ttcctgtaag gcatttcgag ccttaatgaa cgaagtaaac    420
gacttggcag gccagcatga gttagttgct gaagatttac aagcgaatgt gat           473

<210> SEQ ID NO 185
<211> LENGTH: 683
<212> TYPE: DNA
<213> ORGANISM: Diabrotica virgifera virgifera

<400> SEQUENCE: 185 gggggggattt tcaaaggtgt ttacaaattc aaattgttta ttacaagttt attacaatga    60
gagtgtatct ttgaaactgg aaatggcata gtccaagaag aaaaaggatt tttgaaaaac   120
gccggtacaa aggaagaagc tcaagtcgct caaggttttt cctcatatac ttccccccgaa   180 ggagtaaaaa tagaactccg gtacatcgca gacgaaaacg gtttccagcc aatcggagac    240
cacctaccga ctccgccacc aatccctgag gctattttac gagcgctaag tgtactgaaa    300
cagttgggta atttgaatga agaccaagaa gaaaataaca acattagatg aagagagagt    360
gtgatcaaat cgttattttg gataagtccc ttcatatttc aaaatggtac catactaact    420
atgaaatact tcaaagaatt aagatctttt taaaatacgt caacacttta gagtaggaaa    480
cagcggtgga acctcgcaaa atgtacacaa gttcggtttt attttttttgc aggaaaatca    540 aggggtgctt ataatgaaac taacattttc ttaaaaaatt tcgcccctga acccccctt     600 ttatcccttt aagggggta tttgtggttt ttgcgaaacg aggcccttcc tgtatacgtt     660
ttgcaaagaa atgtacttaa tgg                                            683

<210> SEQ ID NO 186
<211> LENGTH: 446
<212> TYPE: DNA
<213> ORGANISM: Diabrotica virgifera virgifera

<400> SEQUENCE: 186
gggttatttt agtatttgca cgaatctgcc gcacatgggt gcatgtgaag gtgagttgtg     60
catttattac atggtggttg acatagctaa aatgttttaaa atgtttccta aaaaatgttt   120
ttgcgctctt ttcaatggcg gtattaactt ttttaaaaat taatacatac agggtgaaag    180
aattaaaaaa aaaacaacat attttttacat tctaggaaaa acacaacttc tggtaaaccg    240
```

```
attcttccgg ttcgacacct tgatcttaca cattaaataa agaacctata taccaaattt      300
ggtttgaata tgacgtctca ataaagaagt tatcgtgcta ttagtcacat atgtatagtc      360
agggccctcg ctacaatatg tgcaaagtgt gaaatgcaca cgggctccgt tctttagggg      420
cgccacaacc gagggtcaaa aagtac                                           446

<210> SEQ ID NO 187
<211> LENGTH: 148
<212> TYPE: DNA
<213> ORGANISM: Diabrotica virgifera virgifera

<400> SEQUENCE: 187
gggctgttct tcattcttgt tgctttactt aacacatctt caaattacaa agaccggatt       60
tctgtaactt tgaaacgct cattttacc accgttaaaa atggtttatt ccatttttcc        120
atgttgagat tgttgtttta tctacgtc                                         148

<210> SEQ ID NO 188
<211> LENGTH: 517
<212> TYPE: DNA
<213> ORGANISM: Diabrotica virgifera virgifera

<400> SEQUENCE: 188
gggggtttcg tttcatcatc atttgttgta attttttgtag taaagcacat taaaaaaaaa       60
atctgtttta aagccatggc tgatgaagaa tttgacgaaa atgatgtagc agatgatttc      120
gatgacgacg tagaggatga taatatcgaa gaactcgaac aacccgagga agatggagat      180
aacatcgata tccttgctcc aggacaagca ggaggtggtg taccaaaaaa caagaggata      240
acaactaaat atatgaccaa atatgagaga gccagagtat taggtactag agccttgcaa      300
atagccatgt gtgccccagt tatggttgaa ctagatggtg aaactgatcc tctgcaaatt      360
gccatgaagg aattaaaaca gagaaagatt ccaattatta ttagaagata tttacctgac      420
cattcctatg aagattgggg aatagacgag ctcattatta tagatcacta gattgtaatt      480
tttatgtgga tattatttaa tacataggtt tttataa                               517

<210> SEQ ID NO 189
<211> LENGTH: 654
<212> TYPE: DNA
<213> ORGANISM: Diabrotica virgifera virgifera

<400> SEQUENCE: 189
ggggacatac gtggaactta gctataagtt gtagttttgt agggtaaatt cgtaggtttt       60
agtgaaagaa aatgtcgtcg aaaagaaaaa gtaaagaaag cataattgct agggtgaatt      120
tcccactata tactcttcag atgttaacgt caaggcatgt aatcgttggt ggtgagggag      180
ggacatccaa aactggtgta cacaatggtt ttgaaatatt tgagattttt catgacggca      240
cacgctttgc agcaaaagaa gtaaccagac acgaaactgg aggcaatgtt gttatgaact      300
gttctgttta cagtgataga aaatattctc ttttggtagc tggacaagaa agtgagtgtc      360
aattgtacaa actgaatcct aaactagtcg aggaagtgga aaatatcggt aataatactc      420
atctcaggca acgaatacaa aaaacaaag aagttacaga tgcaacaaa aacgtgacaa       480 aagagttata ttttgatgtt aatgcaatag aaaatgttca aactgacttt aatgggagtg      540
aaccattatc gagggtggta aaaattaatc atgatggtac attattagct acaggtggta      600
cagatggaga tgtacgaata tggaagtttc ctagtatgca acctctattt attc            654
```

<210> SEQ ID NO 190
<211> LENGTH: 433
<212> TYPE: DNA
<213> ORGANISM: Diabrotica virgifera virgifera

<400> SEQUENCE: 190

| | | | |
|---|---|---|---|
| gggccacgtc acaatagaag acgcgtgtaa cggcgggtta acgaactccc ttacattaag | 60 |
| agccaatata tggtagaggt acattttcag ggtacaaggt ttctccccat gtaataatct | 120 |
| gacgcgctcg agtaactgca aaaatccccg cttgggctcc cctactatat tgaatgtagc | 180 |
| aaatatttat tgaaatcttt tattttcaca aaatatttat ttagtattga tattttcaga | 240 |
| tagaaaatgt tctgtcagac atactgcata ataatataaa attgaggtat aggctgttga | 300 |
| ttatgtactt tagaaaggga ctacaatgtc aaggtgttt tattgtttca tatagtcaaa | 360 |
| gggtccccaa atataaaaaa accgcggagt gctattactt aaagggctac gtttctaagg | 420 |
| aaagggtgaa tta | 433 |

<210> SEQ ID NO 191
<211> LENGTH: 316
<212> TYPE: DNA
<213> ORGANISM: Diabrotica virgifera virgifera

<400> SEQUENCE: 191

| | |
|---|---|
| tttaatactt cagaaagttg catttcagta tttctttaat ttaattttaa taaaattaat | 60 |
| tcacattgta ttcatttaaa tccttagaag caaaaatcca ataatggccc tatcaccatg | 120 |
| gttgaagtcc ccttttacag acttaacggg atctctagta aatcaccagt ggtacggaga | 180 |
| atgtgctgat atggaattaa aagttttaga ctgtctagat gcctatggat tggacagggg | 240 |
| cttaaaaaaa tgtgatgatc tgattgaaga cttcagagag tgtgctttaa aaacaaaaca | 300 |
| gttcaaaaga atgtac | 316 |

<210> SEQ ID NO 192
<211> LENGTH: 673
<212> TYPE: DNA
<213> ORGANISM: Diabrotica virgifera virgifera
<220> FEATURE:
<221> NAME/KEY: misc_feature
<222> LOCATION: 654
<223> OTHER INFORMATION: n = A,T,C or G

<400> SEQUENCE: 192

| | |
|---|---|
| gggggagcga cgtggtggcg acgtcagctg attatttcta tttccctatt tctatttctt | 60 |
| acccgttttg tagtttataa atttataaaa acaacgaatt tagaatgtag ttttctgtag | 120 |
| gtaggaacca taaacataaa aatcatatta tttgattttg cttttggat gtaaacgtaa | 180 |
| aactgaaata cctctacaat aacgatctat ttatacataa atttatttta aaaatcaaat | 240 |
| atggaaataa atcgagaagc tagtgaaaaa actgttgaaa taaaagtaga aaacgaagac | 300 |
| acctgtgttg gtcccttgga tgctttcaaa attgaaatta cagaagaacc caagagagaa | 360 |
| cccagagaac ccgcatacga ggcatttggt tctttagact caaataaatt tctgttaaac | 420 |
| actgaagtaa aacaagacga atataaattt gcaccatttc aagaaaagca aagaacagat | 480 |
| gaagaaaaat atattataca agttctaact actctatact gaaatcataa tgaagatgca | 540 |
| ctagaaataa acaaaccaat atttatttat taagcgcaaa aggccttgta ggcctagggc | 600 |
| taaaatgttt acatttctga ttacataaat aatataataa ataacttagt atancttaca | 660 |
| taacttataa aag | 673 |

<210> SEQ ID NO 193
<211> LENGTH: 614
<212> TYPE: DNA
<213> ORGANISM: Diabrotica virgifera virgifera

<400> SEQUENCE: 193

```
ggggtcatca agttcttgtt ttgtctcgag gagttgattc gttttgttgg cagtacattt      60
tataattatt ggagtcggaa tatttaatta atgtgattag aaagtgtata gttttagaac     120
tagccatcac ttacttaaat ttctttaata gactcattgt tttaatatag tttggtcagt     180
tagttaataa agtgtaatta aaaatgagtg accccacaaa tcctactgga ctacctagaa     240
gtttaaatta tgaagcatta aaggctcata taatatcgca caaataaat tgcggcctat      300
ggttaattag ggtcataggc attctctgct ccatagctta cttcattcca attttggaa      360
atccttacaa ctactattac aaagtactcc tagcaaatgc agctatcagc gcattgagat     420
tacatcaaag gataggcaga gtgcaattca cgagacaatt tgctgcagaa ttactttcag     480
aagatagttg tcactatctt ttctattcgt tgatattttt atacgtatcg ccagtatcat     540
tggtactcgt accaattatc ctcttctgcg tactccattc agctagttat tcactcacat     600
tgttagatac atta                                                        614
```

<210> SEQ ID NO 194
<211> LENGTH: 396
<212> TYPE: DNA
<213> ORGANISM: Diabrotica virgifera virgifera

<400> SEQUENCE: 194

```
gggataatca ttagttttt tattgaaagc tggaatgaag ggttggatga aaaaaaaaac      60
tgtctttatt taatttataa agaattttat ttttaagtta aaaagcttaa attttttaa      120
aagacgagaa gaccctatag agttttataa aattattaat aagttttttt agtattaaat     180
ttatttatat aataaattta tttaattggg gtgattaaaa aataaattta acttttttta     240
tattattata ttaattaata attttttgat ccaattttt tgattataag aataaattac     300
cttagggata acagcgtaat tttattggag agttcaaatc ggtaataaag attgcgacct     360
cgatgttgga ttaaagttta taattggtgt agcagc                                396
```

<210> SEQ ID NO 195
<211> LENGTH: 533
<212> TYPE: DNA
<213> ORGANISM: Diabrotica virgifera virgifera

<400> SEQUENCE: 195

```
ggggaggtta taaatatttt gatttttgct ttttgcaacg gggattttg atttattatt      60
tatttataat tcataggatt tatttgaggg aaaatttgaa aatttggcac agatttgggg     120
atgcctgttg tgttaagtgt tggtagagag taatcagtta ctatttatca tgggaaaagt     180
aaagaaacca aaagcgaaag cgctaggtgc gtttgaatcc aaaaataata gtgctccaat     240
aaaggaatcc atttcagcca actttgattt tagtataaaa caaggaaaat cagttgtggc     300
agatgatgta aaagtgttc tttcatataa atccattaag tcccataatc caattaacag     360
gattataaag aaaaagaaa aagtgaattt aaaacgaaag ttactgatga aaaaaattga     420
tttaggcaat gtactaaaga aagaacaaaa gatcagggac aagagaaaaa atacatcact     480
tattggtgac actaatgcac tgcatgatgc tttaccttca ctggattcat tat           533
```

<210> SEQ ID NO 196
<211> LENGTH: 655
<212> TYPE: DNA
<213> ORGANISM: Diabrotica virgifera virgifera

<400> SEQUENCE: 196

```
ggggatttgt aattgagata tctgttggta tgtgttggtt ttctatacac ttgagtctca      60
tatccagtat ccttctttaa gactaaagca tcgaggaaag gcagggtgtt attatattcc     120
ttttccattg taaattttat tgtctctttt atttattta ttgtctattc tattatctct     180
aacgcgagag ttttagtgtc accgttgcat gtggttgtct ttttgaagac agatcgcatg     240
ctatgatttt ttttgtgac ggatgttctt gagttgggt tgatttcatg tggtcgagtg      300
agctatcttt cagtggagtc gtcccaggaa cgcgactcat aaatgttggc agtatcattt     360
taaagtcttc tactttggaa tgtgtcatat gtatctgaat tgccgatgtg aatgagtcgg     420
attaagtaaa ttattggaag aattttttac taagcaacaa cattttttgtt tatattagtg     480
gtattttgta ttttgacagc ggcgcccgat ttgggcgtcg aaacgttagt aaaaatcatt     540
ttttaatgat attgtggttt atttcccatt ctaaatagtt aaaaatgatt tctttgattt     600
gtgtctgatg aataattatt taggtattt taaatgctac ttaaattata ttttt          655
```

<210> SEQ ID NO 197
<211> LENGTH: 602
<212> TYPE: DNA
<213> ORGANISM: Diabrotica virgifera virgifera

<400> SEQUENCE: 197

```
gggtattcgc tttaaactcc agttttttta aaaactaatc attctaagcc agtcaaactt      60
ctagaatcta ttaataatac ataaataaag aagaataaat aagtccaatg actgaaaaca     120
ccgccaactt acattattat gcttccaatt ggatttctct tttttttttc aaaaaaatat     180
attgattttt taaccgtaac ttttaaatt tttatcttag aaagtcgtt aaataagaat      240
tttgtaggtt tttacaaggt ttataatgct attaacatta aatccttta aaattctcag      300
tcacaaaaag aggtggcatt gaaaggtttg gtaaaggtgg ttttgcgtg atattacaag     360
ttttaattgt caatagctca ctcaattttt gtcgtaaaaa aattttgca aactaaattc     420
ttgggaatta aataagttac aatttcatat ttaaatattt tttttcgta tctctgatgc     480
tactctttct attctgaaga aaaggcattt tttaacaaac tacaaaaact cgttattcgc     540
ttttaactca attttttaa aagctgatca ttcgaagccg atcaaacttc tagaacctat     600
ta                                                                   602
```

<210> SEQ ID NO 198
<211> LENGTH: 557
<212> TYPE: DNA
<213> ORGANISM: Diabrotica virgifera virgifera

<400> SEQUENCE: 198

```
gggacatggc ttgctgtatg ttgtacagag gggatgttgt accaaaggat gtaaatgctg      60
ctattgcaac cattaagacc aaacgtacca tccaattcgt agactggtgt ccaactggtt     120
tcaaagtagg tatcaactac caaccaccaa ctgttgtacc tggaggtgat ttggctaaag     180
tacaacgtgc cgtatgcatg ttgtccaaca ctacagctat tgctgaagcc tgggcaagat     240
tggaccacaa attcgatctt atgtatgcca agagagcttt cgtccactgg tatgtaggag     300
agggtatgga agaaggtgaa ttctctgaag ctcgtgaaga tttggctgct ttggagaaag     360
```

```
attatgaaga agttggtatg gactccggag aaggtgaggg tgaaggagct gaagaatatt    420
aaatttgatt ccaaacatga caaatcactt gtttttaaga caaaaaattc ctttcaattt    480
ttttacactt tttcattact tttctgtgaa acgattattt aaagtctgat ttaacttaat    540
acagaatttt ttacgag                                                   557
```

```
<210> SEQ ID NO 199
<211> LENGTH: 630
<212> TYPE: DNA
<213> ORGANISM: Diabrotica virgifera virgifera

<400> SEQUENCE: 199
gggagttact cggtattcgg tatcaataat gttattaaca gactcgttta atattttatc     60
agttttctcc tcgacaatga gcagctagta tggtcgttcg gaaatacttg tatataaact    120
ttttgatatt aatggagttg tcctatttct acgcgacttt ctgaacgtgt tagagaatat    180
agttgatcta acatttggta atagtatttt ttagagtgtt tattagtgtg ttcaagatgg    240
ttaactttac gaagagacag tggtcaacgt tgatcgttat tggtattgct gattttgta     300 acgctgtttg tgtgtcgctg caagctccat tttatccaca agttgccgaa agtaagcatt    360
gcacagcgac ggagtatgga ttggtgtttg gaatttttga atttgttgtg ttcttgatta    420
gtcctatata tggagcaaac ctgaatagaa ttggacctaa actcatgttt aatgttggag    480
gctacactat tggtgtgtgt gctatattgt ttggagctga gacaaaaact gagcatcgga    540
atctgaagct agcggggttt aatgtaagtt ccaataaata attttagaca atagattgta    600
ttttagttga gtgattgctg aataaatagt                                     630
```

```
<210> SEQ ID NO 200
<211> LENGTH: 615
<212> TYPE: DNA
<213> ORGANISM: Diabrotica virgifera virgifera

<400> SEQUENCE: 200
ggggagtgaa aacccctcac cacaacgcac cgacaccgag tatgattcaa cttcaacaag     60
agtgcaacca ttcgatatag aatcacaatc tcatatcgat tttgcaccag taaataatca    120
gaatcagaac aactgtgata gtttagacgc gaaagaaatg agtgcaacga agaacaaca     180 aagtacattg gggggagccg ataaagtgaa aaaacacaag aaaggccctc gacctccgcc    240 tcccccctgga ttaaaagatg atctaacaac aattgcacat gtttctgtgg tgattttcgt    300
agggcttatc ttgtatttat gttttgcacg gccgtttgaa ttcttcacgt ggcatccttt    360
gttgatgtct gtagggtaga tgcttatgat gatagaaggc gttctcttca tatccaaaga    420
aaacccgata ggaagaagac taaacttggg ccgccttttta aaagttcgtt tccattggat    480
agctttaaca ataagttcta ttttagttac gatcggtttc gtaatagtag ttataagcaa    540
aaacaaccac ggcaaggaac attttaaatc cttacatgcg attttcggtc tcataggttt    600
attagggtgt atacc                                                     615
```

```
<210> SEQ ID NO 201
<211> LENGTH: 587
<212> TYPE: DNA
<213> ORGANISM: Diabrotica virgifera virgifera

<400> SEQUENCE: 201
ggggatttta tttttttgaa agtttagtac atgtacatta tatttaaaaa cagtattgtt     60
taaatataaa ataaattctt gacgattgtc agacgtagaa aatgttacaa agtgtaaaaa    120
```

```
agtacgatac tattatcaga accattgatg atgatgaaga agttgaagat ttatcagaaa    180
acagtgatga ggaaatagag tttcaaccat ccaaacaaaa aactcgaagt aaggaggatt    240
ttgatacgga atttaatttt gtcagttccg tagaagaata taataaagat gtttggaatg    300
atttgactaa atacgttaaa aggaaagcaa acaaaaaac tgatgacaaa attaaaaaag     360
tcagaggcac acaagctgat gaggatcaaa caaacactga aatggtaca aatgatcttg      420 tcgattccga tatatctctt tcagaagatg aactaaaaca tgataggatt aaacttaaag    480
aaaagaaaaa gaaaaagta aaagctgaca atgatacaga agaatttttt gaagaggttg     540
aattaaattc tggagaaact gttagttttt atcagatgaa tctgtca                  587

<210> SEQ ID NO 202
<211> LENGTH: 559
<212> TYPE: DNA
<213> ORGANISM: Diabrotica virgifera virgifera

<400> SEQUENCE: 202
ggggacactt cctttcggtc cggctctgca tatcaaggt gcgaatttag tcattaaatt     60
gccaaatttt ccatttgtat tctctaaatc attcgtttgg taagaagatg gcagacttag    120
atgatttctt tgccaaaaaa gaccgcgaga agtccaaaag tacaaaaaaa tatgctacca    180
ctgaagaagt tgccaagaag ctagaagaca ctgcaaaaaa gactgacaaa ttaaagaaag    240
aacgtgttaa tgagggcgaa gatagtatag ttactgaaca agaccaagac gaatggaagg    300
acttcgagga agaaaagaaa gactacacag ggttaaagat aggaaactta gccatcggtc    360
aaaattcgga aagcagtact acgggagcta aggaaagtac cgaacagcaa caagaagatg    420
agcctggaca agatgtagac aagaaatctg gaccttggaa acgcatcgac gtcggggaag    480
cagcggaagt ggagaaagtt gaatataaac cggaaccgat acttcctaat gtatctaaga    540
ctggcactta tatccccc                                                  559

<210> SEQ ID NO 203
<211> LENGTH: 631
<212> TYPE: DNA
<213> ORGANISM: Diabrotica virgifera virgifera

<400> SEQUENCE: 203
gggggattga cgtgaagtta gcagctgcac gcagtgacag ctcagtgttt accgtcagaa     60
aattttaaat taaagaaat aaaatttaga atatgttgaa attgttcaaa gaaatatctt    120
caagtttggg gaaatctctt accaaaaggg gacttcaaac tacttccact ttacaacatg    180
atagcttatt tgtacatcga gatactcctg aagataatcc agatattgtc tttgaattca    240
ccccggaaaa taaaagagg gctgaagcta ttctagccat atatccagaa ggccacaaga    300
gggctgcaat gattccatta cttgatttag ctcaaagaca gtatggatgg ttaccaattt    360
ctgctatgca taaagtggct gaaatttaa acttgccaag aatgagggtg tatgaagtag     420
ctactttcta cactatgttt atgaggaaac ccacaggtaa atatcatgtt caaatttgta    480
ctacaactcc ttgctggtta agaggatcag atgagattct ggaagctatt aagaaaaatc    540
ttaagttaga agttggagag acaagcaaag acatgttatg gaccttatct ggggttgaat    600
gtctgggagc atgtgttaat gcccccatgg t                                   631

<210> SEQ ID NO 204
<211> LENGTH: 93
<212> TYPE: DNA
```

<213> ORGANISM: Diabrotica virgifera virgifera

<400> SEQUENCE: 204

```
taggatttttt cgtaaaacta atccacatcc ccatcaacaa cattatagtg ggatcataaa 60
tatattttc atatttatgt cagttcatac aat 93

<210> SEQ ID NO 205
<211> LENGTH: 614
<212> TYPE: DNA
<213> ORGANISM: Diabrotica virgifera virgifera
<400> SEQUENCE: 205
gggaataaaa aatttatttt atttatattt ttatttattt taaaataata aaatattttt 60
tagtaaaagt aaagaaaaat tttatttaat gatagttaat tagtattgtg agagaatatt 120
ttatttttat aaaagaaaaa tttatttttt gtaccttgtg tatcagggat tattaattaa 180
taattatata tttattattt tcgaatttaa aagagctaaa aaattaaaat ttttattgta 240
aaataaatat tttaaataat ttttttgtaa tgaaatgtta ttcgttttta aatatatcta 300
attttttaag aaataaatta aatttattta ttaacaatat atttataatt aaatattttt 360
atattattaa tattaaatat ttttagggat gagcttaaaa ataaaatttt attaaaattt 420
aatttttaaa taaaaattag gattaaaaat tttcatattt taaaatatgt tattatttat 480
ttttatatat tattattttt atttttttata aattttttat taaaatataa atttaaatta 540
tttaaattta gtaatgatga taatattagt attaaaaaat tgtatattta gtaaaaatat 600
ataggtttaa taaa 614

<210> SEQ ID NO 206
<211> LENGTH: 621
<212> TYPE: DNA
<213> ORGANISM: Diabrotica virgifera virgifera
<400> SEQUENCE: 206
ggggcttctc tgtgcatgtt tcaccatttt taataattta aaaacccgct attcgtaatt 60
ttgttggttg tctttacgga ttacttacaa ttttggaaat aaaatgactc ccggccgatc 120
atcaacgact acaaaagtgt ttgtaggaag tttgcctcca gacgctaccc cagaggattt 180
gaagaaactt ttcgagccct acgggaacat tgcagaatgc gacatcgcga acaaatgtgg 240
attcctccac ttggaggatg gcgaattggc aatgaaggcc attgacgaac taaatggtat 300
ggaatttatg ggttccaaaa tttcagtgga aaaggggcga gttaagccgc gaaggagtgg 360
cggtggaccc agaggtggaa gagaacgagg aggcccgtat tcaagagtta tggtggatcc 420
aacggatacg gcgcttctgc cggttacggt cgcgacgccg gtggctacgg cgccgcctat 480
ggagatcgcg cagccgccga tccgtacgct gcagctgatc catacagagg ggcttcagcc 540
ggtggtggct atcaggatag aggtgataga ggatacggtg ggcgacctgc tgagggttat 600
ggaaactcat acgctgctgc a 621

<210> SEQ ID NO 207
<211> LENGTH: 624
<212> TYPE: DNA
<213> ORGANISM: Diabrotica virgifera virgifera
<400> SEQUENCE: 207
gggggagtgt gtggtgagtg tcagttaaac gttaacgtta aacaagtatt ttattacatg 60
gtaacacacg tgttgtagga attcccttta aaaacgatgg atgtccttag tcgtcctgcg 120
```

```
gaagaatttg aaaatgacca aacagtggaa actatgtggg ctataaaagc cttcgaacat    180
gccgaagttt actttaacat tttatgttca gttgatccaa aattgctcaa actaacacca    240
gtagacgatt taatctataa agtctttaga gaagaattcc caaaactaga gtcgaagta     300 ataatagaaa atgaattgaa gagcacaaaa gaaaaaagca agtggagacc ttttttgtgaa   360 cgatttaaga ccattgcaga agactatagt tatggtactt tactgagagc agatgccaaa   420
gatgattata aagaggagaa caccatatta gttactagga ttcaatttta tgccatcgaa    480
ctggccagga atagggaggg agtcaatgac attctaagga aaaagttctg gcctgaagcc    540
aaggaagaga aagacgatta ggaagtattt aataaatctc agttttttta tacattttag    600
ttatttataa gttttttgta agtc                                           624

<210> SEQ ID NO 208
<211> LENGTH: 574
<212> TYPE: DNA
<213> ORGANISM: Diabrotica virgifera virgifera

<400> SEQUENCE: 208
ggggagcctt tattttttg tttcgacatg tcgcatgtcg agatccctg tatatcgggg       60 gcccctttta attgatacgt cggtagctac gcctctgctc ataccagacg gaaaagttga   120
tttaagcgct ccgtacctat cttgtttaaa agggtgtgca acaaagtttc gaagccacgg   180
taatccggaa atcacatata tcgaagaact tacgaaattt ggcaactatt acaacagaca   240
atttgttatt tcaagtataa tgcaacatcg gaatcattaa tttgttgctg ttcgtttagt   300
agttttttat aaaaatgggt ttgggaagaa gaaatggtag tagctgttgt agaaaatggc   360
ttataggaac ttgtttgtat atatttgttt tattactatt aatattttta atagtatttg   420
ttgtagtccc agtcgttttt aaatatagtg ttggaatcca agaagtata atatttccgt     480 catgggtaat cgacccgaaa aactattcaa acatcgacca atttgggatc aaaggggtga   540
aaaacttcta cgcgaacttg caagaagatg acaa                                574

<210> SEQ ID NO 209
<211> LENGTH: 600
<212> TYPE: DNA
<213> ORGANISM: Diabrotica virgifera virgifera

<400> SEQUENCE: 209
gggggagatg atgagcaacc aaaacaaaac attaacattt taatttaaca cacccatttg      60
attactaata acattttaaa aacggctctt aagacacgat gaattacgta tatctttgta   120
ttcttattgt aatattagtg ttagttaaga aaagtgaagc agtaagatgc tatcaatgcg   180
gatcagatga agatggcaaa tatgaagaca actgtggtgc ctatcaaaaa tttgacaaat   240
tgaatcacat tgccattgaa tgtaatagtg aggaaagtca tatgcctggt tctttttgta   300
tgaaatttac tcaacaaagt cctagaggtt ttatttggga tggcagatgg agacaagtaa   360
taagaagatg tgcatctgta gctgacacgg gagtaacagg agtatgtaac tggggggtgt   420
atgaaaatgg catttactgg gaagaatgtt attgttcaga agatgaatgt aatagtgcac   480
atatgactaa aatatcaata ttttcagtta ttagttttat cattttacca attgtgaggt   540
atatttggaa ctaaaagata tattatctta ttagtttgtt gactaatgaa agtagtcaga   600

<210> SEQ ID NO 210
<211> LENGTH: 574
<212> TYPE: DNA
```

<213> ORGANISM: Diabrotica virgifera virgifera

<400> SEQUENCE: 210

| | | |
|---|---|---|
| gggatcccgg tatatacacg acacgatttc aagtttacg ctcaatacac gcgtgaatcg | 60 |
| agtcacactc catttgagta tgacccttt ctagataata ttgaaatatt tctacacctg | 120 |
| atgttcttga taagtaagaa agagcattcg aaagcgtaac atttcgagtt tggtagcagc | 180 |
| atccgtcgct gaagcaaaca acggatttag tagcaggaga taaatttctt ttgatataat | 240 |
| ctatgataat ggaagtgaac tcgtttgctt caaccccacc tgaaccctca tgccatacat | 300 |
| agcaatggcc tttgccagtg gataaattat agaagctata gttgtgaaca tttagcttca | 360 |
| ttttataata tgcagctgat acttgtaatc ttggtgctgt taatattgcc tgtgcatcca | 420 |
| tagtcaaaac aagtttactg ttgtccttac tagcctcttc ttttagtttt tccttttcag | 480 |
| cacgagctaa attttttttc tccaaatgct gctgaaactg ttcatcattt attttgccga | 540 |
| cagaataccc agtgcaagtg tcgcactgat cttt | 574 |

<210> SEQ ID NO 211
<211> LENGTH: 227
<212> TYPE: DNA
<213> ORGANISM: Diabrotica virgifera virgifera

<400> SEQUENCE: 211

| | | |
|---|---|---|
| gggacttaga tttattcat catctcgtta aactgtacaa tgagaaacgg tcagatctgg | 60 |
| aggagcaaca gttgcatttg aacgttggtc tgaataagat cgccgaaact gtagaacagg | 120 |
| ttgaagaaat gcagaagagt ttggccgtca atctcagga gccacaggcc aaaaatgaag | 180 |
| ctgccaacgc taaactcagg cagatggtga agatcaaca agaagcc | 227 |

<210> SEQ ID NO 212
<211> LENGTH: 631
<212> TYPE: DNA
<213> ORGANISM: Diabrotica virgifera virgifera

<400> SEQUENCE: 212

| | | |
|---|---|---|
| ggggattatt tctgattttc gtttgctgct ttgttgtcta acatattgt aaaaatacag | 60 |
| ctaaaaactt ttaaaaatga gcgaagccaa ggaagcaatg gaagttgaag tggaaacagc | 120 |
| cccggtggct gaaaattcaa aatcttccat ggaggtaacc acagatacag gcaaaaatgt | 180 |
| aatggccccg ggagctgttg gatcaatcac ttgttcccctt catcctcttg taataatgaa | 240 |
| tgtatcagaa cattggacta gggaaagggc ccaagaagga gctgtgcaac aagtcattgg | 300 |
| agctttgatc ggcaaacaaa agggtagaaa tattgaagta atgaactcat ttgagctagt | 360 |
| atttacactt ataggaggtg atatagttat tgataaggat tattcaaca tgaaagaaga | 420 |
| gcaatttaaa caagtcttca gtgatttaga tttcattggc tggtacacaa caggtgacgc | 480 |
| cccaagtgaa atggatatca aggtccacaa gcaaatttgt gaaatcaatg agtctcccat | 540 |
| tttattgaag ctcaaccctt atgataaaaa tattgaacat ttaccagtaa acttatagga | 600 |
| atctgtgata gacttagtaa atggtgaagc c | 631 |

<210> SEQ ID NO 213
<211> LENGTH: 611
<212> TYPE: DNA
<213> ORGANISM: Diabrotica virgifera virgifera

<400> SEQUENCE: 213

| | | |
|---|---|---|
| ggggaagaga tgacaatatg gcgtcaaggt attagttgct aggacgtttt atttttcatt | 60 |

-continued

```
cgagagtttt acagtaataa atgagaaagt tgtaccgaaa ttattgtgat ttcgacgtaa      120
tatttctcag tctaactttg gattatgaac attatcacga aagttgatgg agaacatagg      180
cagagacaag aggactatgg agcatctaga atagcagtag agccaattca acacaagcat      240
ggatgacatg gataacatga ggaagaggac tttgttcagc agtggacctt tgaggctgga      300
tgataatgga ctccatcaat gaggatgtaa aggatatcac tttcatgtac tggagtacaa      360
tgtaacattg tgtaggcata atatttact cttttattt gacaaatatt taccaactcc       420
cttacatggg ggttgactaa tatttgacca cttctgaaaa tctcatttta tgttttttgc      480
atcaactgta ggcaatttgc tatacaattg caatattgtt tgaacgtcaa tattttgtta      540
aagtaaatta ttatctggtt ttgagtggta acttttttaa atgaattcca aaaattactt     600
tattagccta a                                                          611
```

<210> SEQ ID NO 214
<211> LENGTH: 569
<212> TYPE: DNA
<213> ORGANISM: Diabrotica virgifera virgifera

<400> SEQUENCE: 214

```
ggggatttca ttttcattt gtttgtaaac aaatttatgt aaaattgaca gtttgtgcaa       60
aagattatta tattctttgg tttttgtttg gctgaaaatg ttaaaaaatg ttgtattaaa     120
taataaatga atgacattat acctttcttg caaggatttc gtagattgtt tggaacaatg    180
tcccgatcta aagttagata gtttgttaac ccaaaagaag actatagaga atctagtcaa    240
attgtgattc cagtaccaga tataatacaa catttaaatg atactgttgt caaaatagaa    300
agtggtgtta agccagcaga agagaatgct ggagatggaa tttatttagg tactgctggg    360
atagcatata tgttctacca ccttagcaag gttccaacac tttcatcaaa gcaatctcag    420
tatttaagac aagctgtaac ttacctaaat ccggcaataa cagtagcaag ctgcaacaaa    480
acagatagta tcccctcttt catattagga aatgctggaa tttatgctgt agcagccaca    540
gttttcaaca gtttaggaga tctgaatca                                       569
```

<210> SEQ ID NO 215
<211> LENGTH: 630
<212> TYPE: DNA
<213> ORGANISM: Diabrotica virgifera virgifera

<400> SEQUENCE: 215

```
gggataatat agagataatt tcttcaccca gtgtgtactc tatactcagg ttttgactt       60 tatcaataat ttcatccatg atgaggtgaa actgtagcag gcttgacgta tgcctctttc    120
cacttgtatc ggcagcttct tattaataat ttcggcctgc atattattc tcctgtatat     180 gttttcggta gtcttgataa tatctgatgg tatgttttga ttacgtgaca ggtgaattac    240
gtcattcagc tctacgcggt cgaatgactt ttgtagatct atgaagcaac agtaaggcgg    300
gacgttgtat tcagtgccgg atttaccact aggccgacta ggccgcggcc tagtgccgca    360
agcaaaaggg ggccgcagcg ctttgtaaaa aaaactttat tggtaaaaaa attgtcacaa    420
cattgtcaaa aatagcaata acgataagaa actccttcca aaaagagtaa acgttacaag    480
acgggctgcc aaatggcatg ctgtaaaagc tattttactt aactactggg agctactacg    540
atgcaattaa aaaaaatatc agccgataca ggggaaacaa atgtgagccg agctgaagct    600
aatggaatca gtaaacaatt tttaaaatta                                      630
```

<210> SEQ ID NO 216
<211> LENGTH: 624
<212> TYPE: DNA
<213> ORGANISM: Diabrotica virgifera virgifera

<400> SEQUENCE: 216

| | | | | | |
|---|---|---|---|---|---|
| ggggacagca | atcgcagctg | ttttaaaaga | aagaaaattg | ttcccctict | tcgactgtgc | 60 |
| ctaccaaggt | ttcgcctctg | gtaacttggt | caaagatgct | gctgtggtaa | gaaaattcgc | 120 |
| cgccgaaggc | taggagttct | tctgtgccca | gagttttgcc | aagaacttcg | gtctctacaa | 180 |
| tgaacgtgtt | ggaaacctaa | cagtagcggt | tagcaaacca | gaccttatgg | cacctgtaaa | 240 |
| atcgcagctt | actctcatcg | tcagaggaat | gtactcaaac | ccacctagtc | acggagccag | 300 |
| gatagtatct | tttgtgctca | ataacccaga | tttggcaaag | cagtggcaag | ataatatcac | 360 |
| tacgatgtct | tcaagaataa | ttgaaatgag | gaccctgttg | agaaacgcat | tagaggagtt | 420 |
| gggcactcca | ggagactgga | gccatttaac | taaacacatc | ggaatgttct | cttacacagg | 480 |
| tctaaatgaa | atccagtcag | agcacttggt | gaagaaacat | catgtctacc | tgctgcgttc | 540 |
| tggaagaatt | agtataagtg | gttttgaacaa | tgacaacgtg | aactatgttg | ctaaagccat | 600 |
| ccatgaaaca | gtaaccaccc | tacc | | | | 624 |

<210> SEQ ID NO 217
<211> LENGTH: 362
<212> TYPE: DNA
<213> ORGANISM: Diabrotica virgifera virgifera

<400> SEQUENCE: 217

| | | | | | |
|---|---|---|---|---|---|
| ggggacagtc | gacatctgac | agtttctaca | gtatagttac | agtgttcagt | ggaaaatatt | 60 |
| caattaagac | tgcgattata | cgacacactt | tcactgtcaa | ggccgtcttt | cttgcatccc | 120 |
| taaaacgtac | atttgcgaca | aaaaaattga | ctgctgggac | ggcagcgatg | aagaaaactg | 180 |
| ctactacgaa | catatctgcc | aagagggga | ataccattgt | aataatggtt | attgtataaa | 240 |
| atcggagcaa | ttgtgtgatg | gctttccgga | ttgttctgat | aactcagacg | aaccatctgg | 300 |
| gtgtttagag | tattatttgt | caacaactac | tgatgttaca | agtccggaaa | atgattatga | 360 |
| gc | | | | | | 362 |

<210> SEQ ID NO 218
<211> LENGTH: 644
<212> TYPE: DNA
<213> ORGANISM: Diabrotica virgifera virgifera

<400> SEQUENCE: 218

| | | | | | |
|---|---|---|---|---|---|
| ggggttcgtg | gggtagaatt | tcagactttt | gacaaattaa | aattttgaac | aatttatttt | 60 |
| attaatttca | atcacattgc | agttttaaaa | agaattaaaa | atggtatccc | taaatcccgt | 120 |
| aagaattctc | aagcaagaag | ccgaggaaga | aagggcagag | attgcccgac | tcagtagttt | 180 |
| tgtaggtgct | atagctatag | gagatttggt | tagaagcacc | ttgggaccaa | aaggaatgga | 240 |
| taaaattta | gtatccagtg | gtagatctgc | aggatcagtt | gaagttacta | acgacggagc | 300 |
| aactatccta | aaatcggtgg | gtgttgataa | tcctgctgct | aaaattttgg | tggatatgtc | 360 |
| aaaagtccag | gatgatgaag | taggagatgg | caccacatca | gtgacagtat | tagcatctga | 420 |
| actacttaaa | gaagcagaaa | aacttgtaga | acagaaaatt | cacccacaaa | caatcattgc | 480 |
| cggttggagg | aaaagcagtag | atattgccag | aaaagctctt | ctagaaactg | ccaaagacaa | 540 |
| cagctctgat | tcggaaaagt | tcagagaaga | tctgatgaac | attgccagaa | ctacactcag | 600 |

```
ctcaaagatt ctttcacaac ataaagaata ttttgccaaa ctgg              644
```

<210> SEQ ID NO 219
<211> LENGTH: 637
<212> TYPE: DNA
<213> ORGANISM: Diabrotica virgifera virgifera

<400> SEQUENCE: 219

```
ggggagtgac agatgacaat aagaaagaat gaatgaaggg caaaatagct tttcatttta    60
atattatgtt caaaaataaa tttacttaga caatccataa aattaaggca actccgtaat   120
tatgacagaa acattagcag ccgaagaaaa acctttaaca aacaatggac gagcagcttt   180
tagtcccgta ccaactaaaa gaacatctgg aggactgatg aaactatcca gttatgtgct   240
agctcttcga ccatggtctc ttagtgcaag tttaattcca actctattag gatcgacaat   300
agcttacaaa tatccagggt cttcggattt taattatata actctatttt ttacgatatt   360
aacaattata tcagtgcatg gggctggtaa tgtagtgaat acatactttg actatgtaaa   420
gggcatagac aatcgaaaat cagacgatag aattcttgta gatcatatat tatcgaagga   480
tgaagttgta tcgttgggtg ctatcttata tttcgcagga tgtattggat ttattatatt   540
agcgaacata tctccagcaa aaatggaaca tttagcttta gtgtattttg ggggcttatc   600
gtcaagtttt ttatacaccg ggggcattgg ttttaaa                            637
```

<210> SEQ ID NO 220
<211> LENGTH: 271
<212> TYPE: DNA
<213> ORGANISM: Diabrotica virgifera virgifera

<400> SEQUENCE: 220

```
ggggactcca acgaaattaa tacgtacttt aaacggttta tttatatttt atttaatatt    60
aaactaattt taatacttac tactttccaa aaatttttat taaaacaata ccaaaaatta   120
aaaaaataaa agaataaaac acacacaaac acattgaaaa atgccacaaa taatgatttt   180
ctgaacaata attgttggca aaaatctaac caaatacgca ttttctgaaa aaaaattata   240
taacaaatat acttacaatc ataaaatgta c                                  271
```

<210> SEQ ID NO 221
<211> LENGTH: 80
<212> TYPE: DNA
<213> ORGANISM: Diabrotica virgifera virgifera

<400> SEQUENCE: 221

```
taaagctttg gataaaagac aagccgtact ttgtgtgctc gctgaaaact gtgacgagcc    60
tatgtataag aaactagtct                                                80
```

<210> SEQ ID NO 222
<211> LENGTH: 657
<212> TYPE: DNA
<213> ORGANISM: Diabrotica virgifera virgifera

<400> SEQUENCE: 222

```
gggggctctt taaattgtgg ttatgttgat ttatttataa agaataaat ttattttaaa    60
tatgttaaag aattggaatg atttagatgt agaacttcac tcagaggtaa aatgtggaat   120
tgaatcacta aaatttccta ctatgacacc agtgcaagcg tacactatac ctcagctttt   180
aaagaagaaa gatgttgcag ctgaagcagt tactggttct ggaaagactc tggcattcct   240
```

```
aataccaata ttacaaataa tgaagcaaag agaaactgaa gaaaaatggg ggaaacatca      300
agtaggggca gttgtcttat ctccaacaag agaattagcc ttgcaaacaa gagatgtact      360
tgataaactg ttagtcgatg ttaaaaatat atccaatatt ttattggttg gaggaaatag      420
tgttgaagaa gatgtaaata atttcaaatc acatggagga aatattataa tttgtactcc      480
tggcagacta gaagatttgt taactaggaa atatgattta aaccttccaa atcattaaa       540 gagtttggaa atccttatt tagatgaggc tgatagactt ttagatttag cttttcaaaa       600
gtccattgac acaattttaa gttatttgcc taggcaacga aggacaggct tattctc         657
```

```
<210> SEQ ID NO 223
<211> LENGTH: 541
<212> TYPE: DNA
<213> ORGANISM: Diabrotica virgifera virgifera

<400> SEQUENCE: 223
atatataact cggattacca cagtcaaagt gcataaaact taacaatacg caaaaaccgt       60
agcagtccgt ttatttcttt cctgcggcct tggctggagc cttcttggcc ttcttaggtt      120
ttgatttctt atctttcaag atttgtgccc ttctcctttc ttgcaatttt ctggatctaa      180
tcacgacgtt gtcggcactc acggtaatac cacgtttctt ggccaaaagt tcttccctgt      240
ttaactgtct cttttgattc ttcaaaatgg cttcacgttt gagtacagca gcatatggat      300
tcaacttaag catggcctta gcgttggtca atggattgag acgacgtaca cgacgtacaa      360
ccttcttttg aggagcacgt aatacagctt tgatttcatc agccttcaac aatctagata      420
gatcagtgtt ggccatttta ggctggggta gattgtaacc cttcttttcc aatgatgctg      480
ttttccatgt gccgaacaat ttatctaaac gttggaaagc tgattcagtc caaataacaa      540
a                                                                     541
```

```
<210> SEQ ID NO 224
<211> LENGTH: 650
<212> TYPE: DNA
<213> ORGANISM: Diabrotica virgifera virgifera

<400> SEQUENCE: 224
ggggacattt acgactgatg tgttgatatc ttcactgagg gttacctata atggatatca       60
tagagaaaac cttatcgtat aataacaaac taatagaacc cccacctgat aacattgtgg      120
tccaaaatga agataacgaa gaagttcact atgtaaatat tcatgaggtg cacgtcaaca      180
aagtcatcga gaaaaactg ggcaccaatc atttcgttct acttaattat gagcttaaac       240
ctataactga ccgtcttggt cttcttggag accacagtat tttgttcgta acattcctca      300
ataatattgg atccaaagaa catttgcaat ttttcgttaa gtattttcct tttactgaat      360
ctcaagcaca attcgctgat ggcatcggag catttgaaaa agaagcactg gtttataaat      420
tgttcaaaga gttttataag caaggtatca ctcaagccag taatgttgtc ccctactgct      480
atgtagtagc tcccaaaaaa tatttttatat taaatgatct tactctcgag agttatcaaa      540
ttttaaataa acatatttgc ttagaatacg atgtcgttgt agttgtttta caagctttag      600
cccagttaca ttccggtagt atagcgtacg aagaaaaatt aaagaagaat                 650
```

```
<210> SEQ ID NO 225
<211> LENGTH: 655
<212> TYPE: DNA
<213> ORGANISM: Diabrotica virgifera virgifera

<400> SEQUENCE: 225
```

```
gggcattgag ctcctgcata acaaaaacac tggaaagaat gataaaactt aggctcgaaa      60
gttggctaga aaaaaaacaa taaattatca caaacacaat ttggatttcg aaaaaaatca     120
ttctactgtg gaagctgtga gtcatttggt aacagatata aatttagcgt ttacgaaaaa     180
ttcttcagta atcgctcttt tattagatgt tgaagcagca tacgacaacg ttaatttaaa     240
tatactatat aacaaaatga tacaaatagg tctgccagaa tgcttctgtc aaaaaataat     300
aaaattgtat gactgtagaa aaatttatat atcggtaaat aataacacat ttggtccaag     360
agtagcgatg ggtggtttac ctcaaggagg aatattaagc cctttgttat atttaattta     420
cacttctgat atagaaaaaa atttaaactc aacaaaaatt ttacaatttg cagatgatgt     480
agttatttat caagaaaaca ttaaaataga aaatgcagtc aaatccattg aagaaggaga     540
caaacatatt aaaatatgga gtgaattaca tggactaaat atatctgatt ccaaaaccaa     600
attatgtatt tttacaagaa aacgaaaaga aatacccaat cacatcttaa taaac         655
```

<210> SEQ ID NO 226
<211> LENGTH: 521
<212> TYPE: DNA
<213> ORGANISM: Diabrotica virgifera virgifera

<400> SEQUENCE: 226

```
gggggaaacg atgacagttt tgaaagaagt aaaaaagcaa agagaacaca acagaaaaat      60
gaagcagaca aagatacaaa tgcagtcatg attagaatga tgaaagaact tatggagaaa     120
aatgaagaaa tgatgaatga ataaaaacag gtcaggaagg aacaagccga aaacaataag     180
caattaatgg aaatgaggca agagaatcag aacttgaaaa gagaagtaaa gcaactacag     240
gaaagaatcg aatacataga aaatacagt aagaagaaaa gcctgataat atcaggatta     300
aaaatggaca caaacgacga tagaaacatt agagaagaaa tggaaaattt cctagtcaga     360
gaactgcaag ttaaagtgaa attaaggaac gccacaaaaa ttggagagaa tctctgtgtt     420
atagaaacgg aaacaacgac tgaaaaaatg gagatattga aaaacaagag aaagttaaaa     480
aaccacaacg aacgcattta cataaacagt gacctaacga c                         521
```

<210> SEQ ID NO 227
<211> LENGTH: 627
<212> TYPE: DNA
<213> ORGANISM: Diabrotica virgifera virgifera

<400> SEQUENCE: 227

```
ggggagttcg ttcctgtacg tctgtctgtt cgttcgtgcg tgaccatttt tgatttctac      60
aattattgcc accgccatca ggagagtagc taaactcgga taacttaaat agtgttgtgc     120
ggattgtgat tttcgacatg ggagataaca agaataacga ttctcgaaga aaggtaaaga     180
aagtaaggaa agcggaagat ttagacgatt taaaacagga attagacatc gactatcata     240
agatctcacc agaagaacta tatcaaaggt ttcaaacaca cccagaaaac ggtcttagtc     300
atgcaaaagc gaaagaaaat ttggacaggg acggacccaa tgccctcaca ccaccaaaaa     360
caactcccga atgggtgaaa ttctgtaaaa atctcttcgg gggtttcgca ctcttacttt     420
ggattggtgc aatcatttgt ttcatcgcct actccataca ggctagtact gtagaagaac     480
cagcagatga taatctatat cttggcatcg tattagctgc cgttgttatc gttacaggta     540
tattttctta ttatcaagaa agcaaagttt caaaaattat ggaatctttc aagaacatgg     600
tgccccagtt cgcgaccgtt cttaggg                                         627
```

<210> SEQ ID NO 228
<211> LENGTH: 643
<212> TYPE: DNA
<213> ORGANISM: Diabrotica virgifera virgifera

<400> SEQUENCE: 228

```
agggggtgaca acagaaaaat atagaaaatc atcctctgtg tttccgtttt gaacttaact      60
tgtatttagt ttaaaaaata atcatgtcta gaggaagcag tgcaggtttt gaccgacaca     120
taacaatttt ctcgcccgaa ggccgactct atcaagtaga gtatgctttt aaagccatta     180
accaagccgg ccccacttcg gtagcagtcc gaggagtaga tgctgcggcg tgtgtgaccc     240
agagaaagat cccggataag ctgattgatc ccaacacaat tacacatctg ttccagttaa     300
cagaacacac tggatgtgtg atgactggca tgattgctga cagcaagtcc caggtgcaga     360
gagctagata tgaggctgcc gagttcaaat ataagtttgg atatgagatg ccaatcgatg     420
ccttgtgtag gagagtatcg gatatttccc aggtttatac gcagaatgct gagatgagac     480
ctttgggttg ctccatgctt ctgataggat atgaccaaga aatgggacca tgtgtccaca     540
aagctgaccc tgctggctat tactgtggct acagagcagt aagtgtagga tccaaacaaa     600
ctgaagccaa cagctaccta gagaagaagc taaagaagaa aac                       643
```

<210> SEQ ID NO 229
<211> LENGTH: 639
<212> TYPE: DNA
<213> ORGANISM: Diabrotica virgifera virgifera

<400> SEQUENCE: 229

```
gataacgatc acaaggcaat aaataatcat tagcaatttc aactgttaca ttttcattat      60
cattagcaaa aaccaggtca agtaaaactc cgttacaatt tgtgatgtga ttaagctgaa     120
ataggttgta aaatgcaaaa gtatcaacta agtatcagt agcagtgtta ctattattac      180
taaagacacc tcttttatca tggtaccatt cgctatttgg cagattgtag tctcctgtta     240
gaatgaactt gtgttcagga aaattgttac agacagattc tatactaata caatgattct     300
cataggatat taaggctgaa ttaggaggaa gatagactgt accaaatata taacattcat     360
tcagagtgca aacttcaaca aacagttcct ccaacttaca cgaacataag gcaatacaat     420
taaaattgaa aaatgtatcc attaatatat tataacaccc tgtaaattta gataataagt     480
attcttagat attaatttaa aattgttatt gtaataccat acaaaaaaaa acaaatagtc     540
tggctaattg gctatgtcaa agccattaat aaaaaaaatc cttatgggag ttttagcgt      600
ggcgatgccg attttcttca aaataatttt caatcggac                            639
```

<210> SEQ ID NO 230
<211> LENGTH: 238
<212> TYPE: DNA
<213> ORGANISM: Diabrotica virgifera virgifera
<220> FEATURE:
<221> NAME/KEY: misc_feature
<222> LOCATION: 139
<223> OTHER INFORMATION: n = A,T,C or G

<400> SEQUENCE: 230

```
gggtattaac ttttattatt aatttgtata tcgtcgtaat taaatatttt tttagaatta      60
aaatatttaa aattttata aaaaaattaa tcagatcaag gtgcagtgag agccaaattc     120
aataggaatt taccagccna ggctatggga catcgtattc gtattatgct gtacccatct     180
aagatatagt tgtttttata aatataaata agaaataaaa aatacgtttt ccaacccg      238
```

<210> SEQ ID NO 231
<211> LENGTH: 116
<212> TYPE: DNA
<213> ORGANISM: Diabrotica virgifera virgifera

<400> SEQUENCE: 231

```
gaaagttgtg tcttgaaaag tagaaatgac gtctaaagta tctcgtgata ctctatacga    60
gtgtgtgaat ggagtcttgg aaaatgccaa ggagaagaaa aggaactttt tggaaa        116
```

<210> SEQ ID NO 232
<211> LENGTH: 491
<212> TYPE: DNA
<213> ORGANISM: Diabrotica virgifera virgifera

<400> SEQUENCE: 232

```
cttatgtatt tagttatggt agtgtagtca tcttaacacc ccttcacccc tccctaacga    60
atctacgacc tagctcccgc acaacaaatg agctgccgtc ccgcaacgag gctttatgtg   120
tctgcttctt cttctttagc cccattctta ccccccagta tctctataga tagtctttcc   180
ttgttcccat atgagcagac atgtaaaacg catcaaactt tgggactcac ccatttcctt   240
acgccccgct caaatcgtca gattttgaa atatacactc ctttccatgt acttaactta   300
ccttatctta atctgacaat ttcgagtttt ttttaaggat agagtttttt tttcgagccc   360
cccttaacga actcccctgt gttaagagcc aatatatggt agaggtacat ctgcagggta   420
ccaggtttct ccccatatga taatctgacg cgctcgagta actgcaaaaa tccccgcttg   480
ggctccccta c                                                        491
```

<210> SEQ ID NO 233
<211> LENGTH: 645
<212> TYPE: DNA
<213> ORGANISM: Diabrotica virgifera virgifera

<400> SEQUENCE: 233

```
ggggatgttg tgatggattt tttgagatgt caattttata aatttaaaat ttaattaaaa    60
atcaaaaggg attttatttt atgtctgata gttactggta tattaaaact ataaaaaata   120
ttttaagttt gaaatgaata atgtatttat gttctatatt aaaaggaaga ccaaaacact   180
tacagagaag tttttactca gtgaaaaaat taattaaaga tgaagataac ttaggccgaa   240
gactttatca acaaattaaa gtcaaaggtc ctataactgt agctgattat atgaaggaag   300
tacttactaa ttctacaatg ggatattaca tgcataaaga tgttttttgga gtctcgggtg   360
atttatcac atctccagaa atcactcaga tgtttggaga aattgtagct gtttggttaa   420
taaatgagtg acaaaaatg gggtctccaa agccgctaca gatagttgaa ctgggaccag   480
gaagaggaac tttggccagt gatatcctga gagtgtttaa tcattttaaa gtactagagc   540
aaacacgctt acagcttgtt gagattagta caacgttaag tgaaattcaa gctaaaaagt   600
tgtgtaatca aaataatgta atcgatgaga atcagcctat ctaca                   645
```

<210> SEQ ID NO 234
<211> LENGTH: 662
<212> TYPE: DNA
<213> ORGANISM: Diabrotica virgifera virgifera

<400> SEQUENCE: 234

```
ggggataata agttcgattt tttacgaaaa tgacaagtat cgagactgtg gggaccattg    60
```

```
tcctgaaatt gctgaagttg gtgatcaatt tgatatgtct catcttgtac cgaaccggat    120
atcaaggcta cttcttggga gtaggaggaa cctggaatct aaacgaagaa aaaaatcccg    180
atgcagaaat tgtggcttcc ggcgtattcg taggatttat gatttacaca ttcgtctcgc    240
tgatcagcct ttgcttcgct agtggagatc acaaaacgac attcactgat attctgatga    300
atatagtagg gatttttatg tggatagctg ctggagctac agctcttcat tattggcttg    360
ggtacttgtc cgaatacaaa tacacgacaa tagattctga cgacaagtt ggtttggcgt     420 taggagcgat gtgtataata aatggagcgg tctatcttgt agacggagta ctttccgcaa    480
tctttatcct caaagccaaa atgcaataac tttcatcgta atataaatat atttatttag    540
gttatatact ttactttaag cagctcaagt ataccgtgac atcccactca tacatcaatg    600
tctataattg tttcatgaca aatcatttaa tagtatttta aagcattcat tcgttcaaca    660
cc                                                                   662

<210> SEQ ID NO 235
<211> LENGTH: 677
<212> TYPE: DNA
<213> ORGANISM: Diabrotica virgifera virgifera

<400> SEQUENCE: 235
ggggaggttg gtgtggtttt gtcaacaaat aggttgatct attttgtgt tctttaataa      60 taattgagaa ataattcgat aaaatgggta aaaaggcaga agtaggtact cccaagtacc    120
tggcaaataa aatgaaagcc aaaggtctgc aaaagcttcg atggtattgt caaatgtgtc    180
agaaacagtg cagagatgaa aatggtttca agtgccatac aacctctgaa tctcaccaaa    240
gacaactact gttgtttgca gacaactcca aaagtatat agatgacttc tcatttgatt     300
tcgcgaaggg atatatggag atccttcgaa gacaatttgg tacaaaaaga gtcaatgcta    360
acagagtcta tcaagaatac atacatgaca gggatcatgt ccacatgaat ggtactagat    420
gggtgacact tactgggattt gttaaatggt taggtaaaac tggacaagct gttgttgacg    480
aaacagagaa aggttggtac atcacttaca tagatagaag tcccgagacg gtagaaaagg    540
cagaatcgaa aaagaaaaaa gagaaaatgg ataagaacga tgaagagaag caaatagagt    600
ttgtagagaa gcaggctaga ttagcacaag agaaggcagg gccatcagtg gaaccaatct    660
atacagaatt agtgagg                                                   677

<210> SEQ ID NO 236
<211> LENGTH: 600
<212> TYPE: DNA
<213> ORGANISM: Diabrotica virgifera virgifera

<400> SEQUENCE: 236
ggggtacacg ctgggacccg aaagatggtg aactatgcct ggtcaggacg aagtcagggg     60
aaaccctgat ggaggtccgt agcgattctg acgtgcaaat cgatcgtcgg aactgggtat    120
aggggcgaaa gactaatcga accatctagt agctggttcc ctccgaagtt tccttcagga    180
tagctggcgc tcgttccgta cgagtttcat ccggtaaagc gaatgattag aggcattggg    240
gtcgaaacga cctcaaccta ttctcaaact ttaaatgggt gagatcttcg gcttgctcga    300
acttatgaag ccgtgagaaa cgaatcagag tgccaagtgg gccattttg gtaagcagaa     360 ctggcgctgt gggatgaacc aaacgttgag ttaaagcgcc aaaatcgacg cttatgggat    420
accatgaaag gcgttggtaa cttaagacag caggacggtg gccatggaag tcggaatccg    480
ccaaggagtg tgtaacaact cacctgccga agttactagc cctgaaaatg gatggcgcta    540
```

```
aagcgtcgtg cttatactca accgtcagcg gcatgtgcgg ttcgttaata gcgactatga      600
```

<210> SEQ ID NO 237
<211> LENGTH: 3928
<212> TYPE: DNA
<213> ORGANISM: Diabrotica virgifera virgifera

<400> SEQUENCE: 237

```
tgcagcgtga cccggtcgtg cccctctcta gagataatga gcattgcatg tctaagttat       60
aaaaaattac cacatatttt ttttgtcaca cttgtttgaa gtgcagttta tctatcttta      120
tacatatatt taaactttac tctacgaata atataatcta tagtactaca ataatatcag      180
tgttttagag aatcatataa atgaacagtt agacatggtc taaggacaa ttgagtattt       240
tgacaacagg actctacagt tttatctttt tagtgtgcat gtgttctcct ttttttttgc      300
aaatagcttc acctatataa tacttcatcc attttattag tacatccatt tagggtttag      360
ggttaatggt tttatagac taattttttt agtacatcta ttttattcta ttttagcctc       420
taaattaaga aaactaaaac tctattttag ttttttattt taataattta gatataaaat      480
agaataaaat aaagtgacta aaattaaac aaatacccctt taagaaatta aaaaaactaa       540
ggaaacattt tcttgtttc gagtagataa tgccagcctg ttaaacgccg tcgacgagtc       600
taacggacac caaccagcga accagcagcg tcgcgtcggg ccaagcgaag cagacggcac      660
ggcatctctg tcgctgcctc tggaccccctc tcgagagttc cgctccaccg ttggacttgc     720
tccgctgtcg gcatccagaa attgcgtggc ggagcggcag acgtgagccg gcacggcagg     780
cggcctcctc ctcctctcac ggcaccggca gctacggggg attcctttcc caccgctcct     840
tcgctttccc ttcctcgccc gccgtaataa atagacaccc cctccacacc ctctttcccc     900
aacctcgtgt tgttcggagc gcacacacac acaaccagat ctcccccaaa tccacccgtc     960
ggcacctccg cttcaaggta cgccgctcgt cctcccccccc ccccctctct accttctcta    1020
gatcggcgtt ccggtccatg catggttagg gcccggtagt tctacttctg ttcatgtttg    1080
tgttagatcc gtgtttgtgt tagatccgtg ctgctagcgt tcgtacacgg atgcgacctg    1140
tacgtcagac acgttctgat tgctaacttg ccagtgtttc tctttgggga atcctgggat    1200
ggctctagcc gttccgcaga cgggatcgat ttcatgattt ttttttgtttc gttgcatagg   1260
gtttggtttg cccttttcct ttatttcaat atatgccgtg cacttgtttg tcgggtcatc    1320
ttttcatgct tttttttgtc ttggttgtga tgatgtggtc tggttgggcg gtcgttctag    1380
atcggagtag aattctgttt caaactacct ggtggatttta ttaattttgg atctgtatgt   1440
gtgtgccata catattcata gttacgaatt gaagatgatg gatggaaata tcgatctagg    1500
ataggtatac atgttgatgc gggttttact gatgcatata cagagatgct ttttgttcgc    1560
ttggttgtga tgatgtggtg tggttgggcg gtcgttcatt cgttctagat cggagtagaa    1620
tactgtttca aactacctgg tgtatttatt aattttggaa ctgtatgtgt gtgtcataca    1680
tcttcatagt tacgagttta agatggatgg aaatatcgat ctaggatagg tatacatgtt    1740
gatgtgggtt ttactgatgc atatacatga tggcatatgc agcatctatt catatgctct    1800
aaccttgagt acctatctat tataataaac aagtatgttt tataattatt ttgatcttga    1860
tatacttgga tgatggcata tgcagcagct atatgtggat ttttttagcc ctgccttcat    1920
acgctattta tttgcttggt actgtttctt ttgtcgatgc tcaccctgtt gtttggtgtt    1980
acttctgcag accggtctct acgtacagtc cggactggcg ccttggcgcg gtaccacatg    2040
```

```
gttcgatatc aacaagtttg tacaaaaaag cagggggctt tctgattttt gacagcttct   2100
atagaagttt atcaagatgt tgatgccaaa aagaataga gtatgtattt acgaatacct   2160
cttcaaagag ggagtcatgg tagctaaaaa agattaccat gccccaaaac acctcgaact   2220
agaaactatc cctaaccttc aagtaattaa ggctttacaa tcacttaaat caaaaggtta   2280
cgtaaaggaa caattcgcct ggaggcatta ttattggtat ttgactaact ctggcatcga   2340
atacctccgc acattcttac acttacctgg agaaattgtc ccatctacct tgaaacgccc   2400
agcaaggaca gaaaccaccc gtcctagacc agctgctctc agatctgaga catctaaacc   2460
ttcagaagac cgtgcaggat acagaaggac tcctggaggc cctggagctg acaagaaagc   2520
tgatgttggt ccaggaactg agatgttga gttcaggcaa ggattcggac gtggacgggc   2580
accacaataa atttattgat aagttaattt ttataaattg atcagccaat aaaaagtttg   2640
gttaaaaaaa aaaaaaaaa aaaaaaaaa aaacagcttt cttgtacaaa gtggtcgata   2700
tcaggtccgc cttgtttctc ctctgtctct tgatctgact aatcttggtt tatgattcgt   2760
tgagtaattt tggggaaagc ttcgtccaca gtttttttc gatgaacagt gccgcagtgg   2820
cgctgatctt gtatgctatc ctgcaatcgt ggtgaactta tttcttttat atcctttact   2880
cccatgaaaa ggctagtaat cttctcgat gtaacatcgt ccagcactgc tattaccgtg   2940
tggtccatcc gacagtctgg ctgaacacat catacgatct atggagcaaa aatctatctt   3000
ccctgttctt taatgaagga cgtcattttc attagtatga tctaggaatg ttgcaacttg   3060
caaggaggcg tttctttctt tgaatttaac taactcgttg agtggccctg tttctcggac   3120
gtaaggcctt tgctgctcca cacatgtcca ttcgaatttt accgtgttta gcaagggcga   3180
aaagtttgca tcttgatgat ttagcttgac tatgcgattg ctttcctgga cccgtgcagc   3240
tgcccatcga ccactttgta caagaaagct gttttttttt tttttttttt tttttttttt   3300
taaccaaact ttttattggc tgatcaattt ataaaaatta acttatcaat aaatttattg   3360
tggtgcccgt ccacgtccga atccttgcct gaactcaaca tctccagttc ctggaccaac   3420
atcagctttc ttgtcagctc cagggcctcc aggagtcctt ctgtatcctg cacggtcttc   3480
tgaaggttta gatgtctcag atctgagagc agctggtcta ggacgggtgg tttctgtcct   3540
tgctgggcgt ttcaaggtag atgggacaat ttctccaggt aagtgtaaga atgtgcggag   3600
gtattcgatg ccagagttag tcaaatacca ataataatgc ctccaggcga attgttcctt   3660
tacgtaacct tttgatttaa gtgattgtaa agccttaatt acttgaaggt tagggatagt   3720
ttctagttcg aggtgttttg gggcatggta atcttttta gctaccatga ctccctcttt   3780
gaagaggtat tcgtaaatac atactctatt cttttttggc atcaacatct tgataaactt   3840
ctatagaagc tgtcaaaaat cagaaagccc cctgcttttt tgtacaaact tgttgatggg   3900
gttaggccgc caccgcggtg gagctcga                                      3928
```

<210> SEQ ID NO 238
<211> LENGTH: 4181
<212> TYPE: DNA
<213> ORGANISM: Diabrotica virgifera virgifera

<400> SEQUENCE: 238

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
```

| | | | | |
|---|---|---|---|---|
| ttgacaacag | gactctacag | ttttatcttt | ttagtgtgca | tgtgttctcc | tttttttttg | 300 |
| caaatagctt | cacctatata | atacttcatc | cattttatta | gtacatccat | ttagggttta | 360 |
| gggttaatgg | ttttatataga | ctaattttt | tagtacatct | attttattct | attttagcct | 420 |
| ctaaattaag | aaaactaaaa | ctctatttta | gtttttttat | ttaataattt | agatataaaa | 480 |
| tagaataaaa | taaagtgact | aaaaattaaa | caaatacct | ttaagaaatt | aaaaaaacta | 540 |
| aggaaacatt | tttcttgttt | cgagtagata | atgccagcct | gttaaacgcc | gtcgacgagt | 600 |
| ctaacggaca | ccaaccagcg | aaccagcagc | gtcgcgtcgg | gccaagcgaa | gcagacggca | 660 |
| cggcatctct | gtcgctgcct | ctggaccct | ctcgagagtt | ccgctccacc | gttggacttg | 720 |
| ctccgctgtc | ggcatccaga | aattgcgtgg | cggagcggca | gacgtgagcc | ggcacggcag | 780 |
| gcggcctcct | cctcctctca | cggcaccggc | agctacgggg | gattcctttc | ccaccgctcc | 840 |
| ttcgctttcc | cttcctcgcc | cgccgtaata | aatagacacc | ccctccacac | cctctttccc | 900 |
| caacctcgtg | ttgttcggag | cgcacacaca | cacaaccaga | tctcccccaa | atccacccgt | 960 |
| cggcacctcc | gcttcaaggt | acgccgctcg | tcctccccc | cccccctctc | taccttctct | 1020 |
| agatcggcgt | tccggtccat | gcatggttag | ggcccggtag | ttctacttct | gttcatgttt | 1080 |
| gtgttagatc | cgtgtttgtg | ttagatccgt | gctgctagcg | ttcgtacacg | gatgcgacct | 1140 |
| gtacgtcaga | cacgttctga | ttgctaactt | gccagtgttt | ctctttgggg | aatcctggga | 1200 |
| tggctctagc | cgttccgcag | acgggatcga | tttcatgatt | ttttttgttt | cgttgcatag | 1260 |
| ggtttggttt | gcccttttcc | tttatttcaa | tatatgccgt | gcacttgttt | gtcgggtcat | 1320 |
| cttttcatgc | tttttttgt | cttggttgtg | atgatgtggt | ctggttgggc | ggtcgttcta | 1380 |
| gatcggagta | gaattctgtt | tcaaactacc | tggtggattt | attaattttg | gatctgtatg | 1440 |
| tgtgtgccat | acatattcat | agttacgaat | tgaagatgat | ggatggaaat | atcgatctag | 1500 |
| gataggtata | catgttgatg | cgggttttac | tgatgcatat | acagagatgc | ttttgttcg | 1560 |
| cttggttgtg | atgatgtggt | gtggttgggc | ggtcgttcat | tcgttctaga | tcggagtaga | 1620 |
| atactgtttc | aaactacctg | gtgtatttat | taattttgga | actgtatgtg | tgtgtcatac | 1680 |
| atcttcatag | ttacgagttt | aagatggatg | gaaatatcga | tctaggatag | gtatacatgt | 1740 |
| tgatgtgggt | tttactgatg | catatacatg | atggcatatg | cagcatctat | tcatatgctc | 1800 |
| taaccttgag | tacctatcta | ttataataaa | caagtatgtt | ttataattat | tttgatcttg | 1860 |
| atatacttgg | atgatggcat | atgcagcagc | tatatgtgga | ttttttttagc | cctgccttca | 1920 |
| tacgctattt | atttgcttgg | tactgtttct | tttgtcgatg | ctcaccctgt | tgtttggtgt | 1980 |
| tacttctgca | gaccggtctc | tacgtacagt | ccggactggc | gccttggcgc | ggtaccacat | 2040 |
| ggttcgatat | caacaagttt | gtacaaaaaa | gcagggggct | ttttcacaat | gcaggcacca | 2100 |
| acgacaaagc | caaaaagaga | tccaatccac | tctgtccaag | ttttggcag | aaagaaatca | 2160 |
| gctacagccg | tagcttattg | caaaagaggt | agaggagtct | tgagggtaaa | tggcagacct | 2220 |
| ctcagccaag | tggagcctaa | aatgctccaa | gacaaacttc | aagaacccat | tcttcttctt | 2280 |
| ggaaaggaca | aattctctgc | tgttgacatc | agagttagag | taaatggtgg | tggacatgtt | 2340 |
| tcccaaattt | atgctattag | acaagctatc | tcaaaggctt | tggtagctta | ttaccaaaaa | 2400 |
| tatgttgatg | aagcatcaaa | gaaggaattg | aaggatatcc | ttatccaata | tgaccgtacc | 2460 |
| ttgttggtag | ccgatcccag | acgctgcgaa | cccaagaaat | tcggtggtcc | aggtgctcgt | 2520 |
| gcccgctacc | aaaaatctta | ccgttaagtt | ctttttaga | tttaatgttg | tgtttcttgt | 2580 |

```
atgtattaag atatcaacaa taaacacaat ttttcccgc aaaaaaaaaa aaaaaaaaaa    2640
aaaaaaaaaa cagctttctt gtacaaagtg gtcgatatca ggtccgcctt gtttctcctc    2700
tgtctcttga tctgactaat cttggtttat gattcgttga gtaattttgg ggaaagcttc    2760
gtccacagtt ttttttcgat gaacagtgcc gcagtggcgc tgatcttgta tgctatcctg    2820
caatcgtggt gaacttattt cttttatatc ctttactccc atgaaaaggc tagtaatctt    2880
tctcgatgta acatcgtcca gcactgctat taccgtgtgg tccatccgac agtctggctg    2940
aacacatcat acgatctatg gagcaaaaat ctatcttccc tgttctttaa tgaaggacgt    3000
cattttcatt agtatgatct aggaatgttg caacttgcaa ggaggcgttt ctttctttga    3060
atttaactaa ctcgttgagt ggccctgttt ctcggacgta aggcctttgc tgctccacac    3120
atgtccattc gaattttacc gtgtttagca agggcgaaaa gtttgcatct tgatgattta    3180
gcttgactat gcgattgctt tcctggaccc gtgcagctgc ccatcgacca ctttgtacaa    3240
gaaagctgtt tttttttttt tttttttttt ttttttttgc gggaaaaaat tgtgtttatt    3300
gttgatatct taatacatac aagaaacaca acattaaatc taaaaagaa cttaacggta     3360 agattttttgg tagcgggcac gagcacctgg accaccgaat ttcttgggtt cgcagcgtct    3420
gggatcggct accaacaagg tacggtcata ttggataagg atatccttca attccttctt    3480
tgatgcttca tcaacatatt tttggtaata agctaccaaa gcctttgaga tagcttgtct    3540
aatagcataa atttgggaaa catgtccacc accatttact ctaactctga tgtcaacagc    3600
agagaatttg tcctttccaa gaagaagaat gggttcttga agtttgtctt ggagcatttt    3660
aggctccact tggctgagag gtctgccatt taccctcaag actcctctac ctcttttgca    3720
ataagctacg gctgtagctg atttcttttct gccaaaaact tggacagagt ggattggatc    3780 tcttttttggc tttgtcgttg gtgcctgcat tgtgaaaaag ccccctgctt ttttgtacaa    3840
acttgttgat ggggttaggc cgccaccgcg gtggagctcg aattccggtc cgggtcacct    3900
ttgtccacca agatggaact gcggccgctc attaattaag tcaggcgcgc tctagttga     3960 agacacgttc atgtcttcat cgtaagaaga cactcagtag tcttcggcca gaatggccat    4020
ctggattcag caggcctaga aggccattta aatcctgagg atctggtctt cctaaggacc    4080
cgggatatcg gaccgattaa actttaattc ggtccgaagc ttgaagttcc tattccgaag    4140
ttcctattct ccagaaagta taggaacttc gcatgcctgc a                       4181
```

<210> SEQ ID NO 239
<211> LENGTH: 5247
<212> TYPE: DNA
<213> ORGANISM: Diabrotica virgifera virgifera

<400> SEQUENCE: 239

```
gtgcagcgtg acccggtcgt gcccctctct agagataatg agcattgcat gtctaagtta     60
taaaaaatta ccacatattt ttttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg tttttataga ctaattttttt tagtacatct attttattct attttagcct    420
ctaaattaag aaaactaaaa ctctattta gttttttttat ttaataattt agatataaaa    480
tagaataaaa taaagtgact aaaaattaaa caaatacccct ttaagaaatt aaaaaaacta    540
```

```
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctcccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt ttttttgttt cgttgcatag   1260
ggtttggttt gcccttttcc tttatttcaa tatatgccgt gcacttgttt gtcgggtcat   1320
cttttcatgc tttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat gaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920 tacgctattt atttgcttgg tactgttttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcagggggga gtagttgttt ttattgtgag   2100
atgatttcga agttcaccct ggtttttcttg gtttgcattg tcgcaccagc gataggtgat   2160
ccaccagttc cagaatggag tgacacttat agcgtagaag gaactatcca tttgccttat   2220
gcagaaatag tagagccttt ccatgcttgg tatgatgaa aatctaaaaa ttcgcgcatt   2280
gattactaca atgggacggc taagacatac caacttggag gaaatggaaa tggtgtccaa   2340
ctgaaagtag ttccattcac tacagaggag gtcctaaacc aaataacgtg cttccagatc   2400
aatggaactg aagacgatcc agtgactcct caatcgattt tgccagattt agaaggattt   2460
gaatatcaag gcatacagga gtatggagat agagaactag aggtatggtt tctaaaaact   2520
gtccagttag aaaaagaaaa cgaatacact ctatgggttg tccgagatga gcatggtaaa   2580
gctattccag ttaaatatga tatgagagga tacaattcgt tattgggaag ccactacgat   2640
cattactatt tgctatacac atcgaagtct tacaggacta caagattga tccctccgtt   2700 tttgaagtag aaactaatag tgaatgcaga agttttcctg gacccggaaa tcaacatgtt   2760
cacatcatga accccatggc cgaatacatt cgtcccgaaa aaagtgagca cgtgactca   2820 agctttggcg attttataaa taaccacaac aaaaattacg cagacacaaa agaacacgtt   2880
```

| | |
|---|---|
| tttagaaaag aggttttccg tcaaaacgtc aggttcatcg aatctgtcaa ccgacaaaat | 2940 |
| aaaggtaagt gttatagtag gggagcaaag taggtgtgct aaatttgcag tcactcgaga | 3000 |
| gttatggcga cctattgggt tgtgattatt aggtcctaaa accaaaaaaa gttaagtaaa | 3060 |
| attttccatt tccaacaatc gttttttccg attatagcgt catctatcca taattcgaaa | 3120 |
| aaatgtctct aataaaagtt gcttattttt acgaaaaaaa aaaaaaaaa aaaaaaaaa | 3180 |
| aaacagcttt cttgtacaaa gtggtcgata tcaggtccgc cttgtttctc ctctgtctct | 3240 |
| tgatctgact aatcttggtt tatgattcgt tgagtaattt tggggaaagc ttcgtccaca | 3300 |
| gttttttttc gatgaacagt gccgcagtgg cgctgatctt gtatgctatc ctgcaatcgt | 3360 |
| ggtgaactta tttcttttat atcctttact cccatgaaaa ggctagtaat cttctcgat | 3420 |
| gtaacatcgt ccagcactgc tattaccgtg tggtccatcc gacagtctgg ctgaacacat | 3480 |
| catacgatct atggagcaaa aatctatctt ccctgttctt taatgaagga cgtcattttc | 3540 |
| attagtatga tctaggaatg ttgcaacttg caaggaggcg tttctttctt tgaatttaac | 3600 |
| taactcgttg agtggccctg tttctcggac gtaaggcctt tgctgctcca cacatgtcca | 3660 |
| ttcgaatttt accgtgttta gcaagggcga aaagtttgca tcttgatgat ttagcttgac | 3720 |
| tatgcgattg ctttcctgga cccgtgcagc tgcccatcga ccactttgta caagaaagct | 3780 |
| gtttttttt tttttttttt tttttttttt tcgtaaaaat aagcaacttt tattagagac | 3840 |
| atttttcga attatggata gatgacgcta taatcggaaa aaacgattgt tggaaatgga | 3900 |
| aaatttact taactttttt tggttttagg acctaataat cacaacccaa taggtcgcca | 3960 |
| taactctcga gtgactgcaa atttagcaca cctactttgc tcccctacta taacacttac | 4020 |
| ctttattttg tcggttgaca gattcgatga acctgacgtt ttgacggaaa acctcttttc | 4080 |
| taaaaacgtg ttcttttgtg tctgcgtaat ttttgttgtg gttatttata aaatcgccaa | 4140 |
| agcttgagtc cacgtgctca ctttttcgg gacgaatgta ttcggccatg gggttcatga | 4200 |
| tgtgaacatg ttgatttccg ggtccaggaa aacttctgca ttcactatta gtttctactt | 4260 |
| caaaaacgga gggatcaatc ttgtgagtcc tgtaagactt cgatgtgtat agcaaatagt | 4320 |
| aatgatcgta gtggcttccc aataacgaat tgtatcctct catatcatat ttaactggaa | 4380 |
| tagctttacc atgctcatct cggacaaccc atagagtgta ttcgttttct ttttctaact | 4440 |
| ggacagtttt tagaaaccat acctctagtt ctctatctcc atactcctgt atgccttgat | 4500 |
| attcaaatcc ttctaaatct ggcaaaatcg attgaggagt cactggatcg tcttcagttc | 4560 |
| cattgatctg gaagcacgtt atttggttta ggacctcctc tgtagtgaat ggaactactt | 4620 |
| tcagttggac accatttcca tttcctccaa gttggtatgt cttagccgtc ccattgtagt | 4680 |
| aatcaatgcg cgaattttta gatttttcat cataccaagc atggaaaggc tctactattt | 4740 |
| ctgcataagg caaatggata gttccttcta cgctataagt gtcactccat tctggaactg | 4800 |
| gtggatcacc tatcgctggt gcgacaatgc aaaccaagaa aaccaggtg aacttcgaaa | 4860 |
| tcatctcaca ataaaaacaa ctactccccc ctgcttttt gtacaaactt gttgatgggg | 4920 |
| ttaggccgcc accgcggtgg agctcgaatt ccggtccggg tcacctttgt ccaccaagat | 4980 |
| ggaactgcgg ccgctcatta attaagtcag gcgcgcctct agttgaagac acgttcatgt | 5040 |
| cttcatcgta agaagacact cagtagtctt cggccagaat ggccatctgg attcagcagg | 5100 |
| cctagaaggc catttaaatc ctgaggatct ggtcttccta aggacccggg atatcggacc | 5160 |
| gattaaactt taattcggtc cgaagcttga agttcctatt ccgaagttcc tattctccag | 5220 |
| aaagtatagg aacttcgcat gcctgca | 5247 |

<210> SEQ ID NO 240
<211> LENGTH: 4939
<212> TYPE: DNA
<213> ORGANISM: Diabrotica virgifera virgifera

<400> SEQUENCE: 240

```
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggc taaaggaca attgagtatt      240
ttgacaacag gactctacag ttttatcttt ttagtgtgca tgtgttctcc tttttttttg     300
caaatagctt cacctatata atacttcatc cattttatta gtacatccat ttagggttta     360
gggttaatgg tttttataga ctaatttttt tagtacatct attttattct attttagcct     420
ctaaattaag aaaactaaaa ctctatttta gttttttat ttaataattt agatataaaa     480
tagaataaaa taaagtgact aaaaattaaa caaataccct ttaagaaatt aaaaaaacta     540
aggaaacatt tttcttgttt cgagtagata atgccagcct gttaaacgcc gtcgacgagt     600
ctaacggaca ccaaccagcg aaccagcagc gtcgcgtcgg gccaagcgaa gcagacggca     660
cggcatctct gtcgctgcct ctggaccct ctcgagagtt ccgctccacc gttggacttg     720
ctccgctgtc ggcatccaga aattgcgtgg cggagcggca gacgtgagcc ggcacggcag     780
gcggcctcct cctcctctca cggcaccggc agctacgggg gattcctttc ccaccgctcc     840
ttcgctttcc cttcctcgcc cgccgtaata aatagacacc ccctccacac cctctttccc     900
caacctcgtg ttgttcggag cgcacacaca caaaccaga tctcccccaa atccacccgt      960
cggcacctcc gcttcaaggt acgccgctcg tcctcccccc ccccctctc taccttctct    1020
agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gcccttttcc tttatttcaa tatatgccgt gcacttgttt gtcgggtcat    1320
cttttcatgc tttttttgt cttggttgtg atgatgtggc tggttgggc ggtcgttcta    1380
gatcggagta gaattctgtt tcaaactacc tggtggattt attaattttg gatctgtatg    1440
tgtgtgccat acatattcat agttacgaat tgaagatgat ggatggaaat atcgatctag    1500
gataggtata catgttgatg cgggttttac tgatgcatat acagagatgc ttttttgttcg    1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga tttttttagc cctgccttca    1920
tacgctattt atttgcttgg tactgtttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcaggggat tacaaactga actcaacaac    2100
```

```
ctcttttcat cttcgacccg tttgccggcg ttagcttgta aaacatttct gttaaaatca    2160
cgaaccatcc gttaaaagaa atggcagatg aatattttt tgctttaacc ctcaaaggta     2220
aaaacagtga atctgggat ccagaagcga agggagcaga ggattaccaa ggggggacaca    2280
aattgatcat taaacaagct tgttgggac ccgaagccca agaaggtgaa gtaaatgttg     2340
tacaagtaga agctatgacg tggaaagact cagttaaaat cccaattgcc acactaaaag    2400
ccggaggccc aaataaccaa gtattgttag atctgtcatt cccagaccca ccagtcacat    2460
tttcacttat acaaggtaat ggaccagttc acattgtagg ccatcattta attggtagtc    2520
cgatggaaga attcgatgaa atggatgaat tagaagagga aatgttggat gatgaagaag    2580
gggaagaagg agccgaggaa gatgaggatg aagatgaacc caaagccaaa aaagcaaaat    2640
cagcgactaa cgccaagggc aaaactcccg taaaaaacaa ttcaaaggct gcaagaaaat    2700
aaacaagttc atctaatccc caaaccacct cctttgtaat gttaagttag ttttttaatg    2760
tatctcggga gttgttatac atccattaac agatcaaccg taacaatttc tcttaaatat    2820
aagtataata ttttatgttt cttgacgtca taagattttg tgaaagtttc ttttattcca    2880
ggtgtaactc ttagttttaa tgtgatcaat attttttaagc tggaaacgta tttatttcct    2940
ttgaaatcat ccaattttgt tgtaaatatg cagccctcat taaaccattt tttgtagcaa    3000
aaaaaaaaa aaaaaaaaa aaaaaaaaac agctttcttg tacaaagtgg tcgatatcag      3060
gtccgccttg tttctcctct gtctcttgat ctgactaatc ttggtttatg attcgttgag    3120
taattttggg gaaagcttcg tccacagttt ttttttcgatg aacagtgccg cagtggcgct   3180
gatcttgtat gctatcctgc aatcgtggtg aacttattc ttttatatcc tttactccca     3240
tgaaaaggct agtaatcttt ctcgatgtaa catcgtccag cactgctatt accgtgtggt    3300
ccatccgaca gtctggctga acacatcata cgatctatgg agcaaaaatc tatcttccct    3360
gttctttaat gaaggacgtc attttcatta gtatgatcta ggaatgttgc aacttgcaag    3420
gaggcgtttc tttctttgaa tttaactaac tcgttgagtg gccctgtttc tcggacgtaa    3480
ggcctttgct gctccacaca tgtccattcg aattttaccg tgtttagcaa gggcgaaaag    3540
tttgcatctt gatgatttag cttgactatg cgattgcttt cctggacccg tgcagctgcc    3600
catcgaccac tttgtacaag aaagctgttt ttttttttt tttttttt tttttttgc        3660
tacaaaaaat ggtttaatga gggctgcata tttacaacaa aattggatga tttcaaagga    3720
aataaatacg tttccagctt aaaaatattg atcacattaa aactaagagt tacacctgga    3780
ataaaagaaa ctttcacaaa atcttatgac gtcaagaaac ataaaatatt atacttatat    3840
ttaagagaaa ttgttacggt tgatctgtta atggatgtat aacaactccc gagatacatt    3900
aaaaaactaa cttaacatta caaggaggt ggtttggga ttagatgaac ttgtttattt      3960
ctttgcagcc tttgaattgt ttttttacggg agttttgccc ttggcgttag tcgctgattt    4020
tgcttttttg gctttgggtt catcttcatc ctcatcttcc tcggctccct cttcccttc     4080
ttcatcatcc aacatttcct cttctaattc atccatttca tcgaattctt ccatcggact   4140
accaattaaa tgatggccta caatgtgaac tggtccatta ccttgtataa gtgaaaatgt    4200
gactggtggg tctgggaatg acagatctaa caatacttgg ttatttgggc ctccggcttt    4260
tagtgtggca attgggattt taactgagtc tttccacgtc atagcttcta cttgtacaac    4320
atttacttca ccttcttggg cttgggtcc caacaaagct tgtttaatga tcaatttgtg    4380
tccccctttgg taatcctctg ctcccttcgc ttctggatcc cagatttcac tgttttttacc   4440
tttgagggtt aaagcaaaaa aatattcatc tgccatttct tttaacggat ggttcgtgat    4500
```

```
tttaacagaa atgttttaca agctaacgcc ggcaaacggg tcgaagatga aaagaggttg    4560
ttgagttcag tttgtaatcc ccctgctttt ttgtacaaac ttgttgatgg ggttaggccg    4620
ccaccgcggt ggagctcgaa ttccggtccg ggtcaccttt gtccaccaag atggaactgc    4680
ggccgctcat taattaagtc aggcgcgcct ctagttgaag acacgttcat gtcttcatcg    4740
taagaagaca ctcagtagtc ttcggccaga atggccatct ggattcagca ggcctagaag    4800
gccatttaaa tcctgaggat ctggtcttcc taaggacccg ggatatcgga ccgattaaac    4860
tttaattcgg tccgaagctt gaagttccta ttccgaagtt cctattctcc agaaagtata    4920
ggaacttcgc atgcctgca                                                 4939

<210> SEQ ID NO 241
<211> LENGTH: 4661
<212> TYPE: DNA
<213> ORGANISM: Diabrotica virgifera virgifera

<400> SEQUENCE: 241
gtgcagcgtg acccggtcgt gccctctct agagataatg agcattgcat gtctaagtta      60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc ttttttttg    300 caaatagctt cacctatata atacttcatc cattttatta gtacatccat ttagggttta    360
gggttaatgg tttttataga ctaatttttt tagtacatct attttattct attttagcct    420
ctaaattaag aaaactaaaa ctctatttta gttttttat ttaataattt agatataaaa     480
tagaataaaa taaagtgact aaaaattaaa caaatacct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840 ttcgcttttcc cttcctcgcc cgccgtaata aatagacacc cctccacac cctctttccc    900 caacctcgtg ttgttcggag cgcacacaca cacaaccaga tctcccccaa atccaccgt    960 cggcacctcc gcttcaaggt acgccgctcg tcctccccc ccccctctc taccttctct    1020 agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gccctttccc tttatttcaa tatatgccgt gcacttgttt gtcgggtcat    1320
cttttcatgc ttttttttgt cttggttgtg atgatgtggt ctggtgggc ggtcgttcta    1380 gatcggagta gaattctgtt tcaaactacc tggtggattt attaatttg gatctgtatg    1440 tgtgtgccat acatattcat agttacgaat tgaagatgat ggatggaaat atcgatctag    1500
gataggtata catgttgatg cgggttttac tgatgcatat acagagatgc ttttgttcg    1560 cttggttgtg atgatgtggt gtggttgggc ggtcgttcat tcgttctaga tcggagtaga    1620
```

```
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga tttttttagc cctgccttca    1920
tacgctattt atttgcttgg tactgtttct tttgtcgatg ctcaccctgt tgtttggtgt    1980
tacttctgca gaccggtctc tacgtacagt ccggactggc gccttggcgc ggtaccacat    2040
ggttcgatat caacaagttt gtacaaaaaa gcaggggggtc taattctaat agcccgtatc    2100
tgccaagaga tttgtcaagt aggttttttc tgttttttt ttcttatcaa gtctaaagat    2160
attcagttac gaggtattag atgactggta ttagaggttc ctagaatttt ttgtttagat    2220
cagagttttg tgtatagatg gataactgtt ttgttagtcg tttgccacga aaattggaaa    2280
ttaagttttt ttgcagatac ggggtataga attagactgt caatatggaa acaatgagtt    2340
ttgtaaacat attgatgacg acaatgtatg ttcatgtcat atttcatatg catctataga    2400
tgtagtttga atatgcacaa ttcgttattt taaaaatgtc atctagacgt ttcaatggaa    2460
attagacatc tatagatgtt atgtctgtca acatgttaat atttgaggct atcagcaaca    2520
gtggcataag ctcaaaaact aagttttgag ataaatgcaa tctttgcatt catattttca    2580
ttatgtttat gagataaagc tacaaattat gtagcatcat ctagccaaat atagaggtag    2640
gttgtgtagg tccctgttaa tcggaagatt taattttgct gcttttattg atatattaat    2700
ctaaaaatgc tgaatttgtg acttagtcca ctgttgttct gagggcccca tttaaatgtt    2760
ttcaaaatat gtatagtcaa aactccttt acatgatgat aagaacgtag ggacatgtga    2820
ataaataccc tgattattta cgttgatggg aatctctctg aaaaaaaaaa aaaaaaaaa    2880
aaaaaaaaa cagctttctt gtacaaagtg gtcgatatca ggtccgcctt gtttctcctc    2940
tgtctcttga tctgactaat cttggtttat gattcgttga gtaattttgg ggaaagcttc    3000
gtccacagtt tttttcgat gaacagtgcc gcagtggcgc tgatcttgta tgctatcctg    3060
caatcgtggt gaacttattt cttttatatc ctttactccc atgaaaaggc tagtaatctt    3120
tctcgatgta acatcgtcca gcactgctat taccgtgtgg tccatccgac agtctggctg    3180
aacacatcat acgatctatg gagcaaaaat ctatcttccc tgttctttaa tgaaggacgt    3240
catttttcatt agtatgatct aggaatgttg caacttgcaa ggaggcgttt ctttctttga    3300
atttaactaa ctcgttgagt ggccctgttt ctcggacgta aggcctttgc tgctccacac    3360
atgtccattc gaattttacc gtgtttagca agggcgaaaa gtttgcatct tgatgattta    3420
gcttgactat gcgattgctt tcctggaccc gtgcagctgc ccatcgacca ctttgtacaa    3480
gaaagctgtt ttttttttt tttttttttt ttttttttca gagagattcc catcaacgta    3540
aataatcagg gtatttattc acatgtccct acgttcttat catcatgtaa aaggagtttt    3600
gactatacat attttgaaaa catttaaatg gggccctcag acaacagtg gactaagtca    3660
caaattcagc attttagat taatatatca ataaaagcag caaattaaa tcttccgatt    3720
aacagggacc tacacaacct acctctatat ttggctagat gatgctacat aatttgtagc    3780
tttatctcat aaacataatg aaaatatgaa tgcaaagatt gcatttatct caaaacttag    3840
tttttgagct tatgccactg ttgctgatag cctcaaatat taacatgttg acagacataa    3900
catctataga tgtctaattt ccattgaaac gtctagatga cattttttaaa ataacgaatt    3960
gtgcatattc aaactacatc tatagatgca tatgaaatat gacatgaaca tacattgtcg    4020
```

```
tcatcaatat gtttacaaaa ctcattgttt ccatattgac agtctaattc tatacccgt      4080 atctgcaaaa aaacttaatt tccaattttc gtggcaaacg actaacaaaa cagttatcca      4140
tctatacaca aaactctgat ctaaacaaaa aattctagga acctctaata ccagtcatct      4200
aatacctcgt aactgaatat ctttagactt gataagaaaa aaaaaacaga aaaaacctac      4260
ttgacaaatc tcttggcaga tacgggctat tagaattaga cccctgctt ttttgtacaa       4320 acttgttgat ggggttaggc cgccaccgcg gtggagctcg aattccggtc cgggtcacct      4380
ttgtccacca agatggaact gcggccgctc attaattaag tcaggcgcgc tctagttga      4440 agacacgttc atgtcttcat cgtaagaaga cactcagtag tcttcggcca gaatggccat     4500
ctggattcag caggcctaga aggccattta aatcctgagg atctggtctt cctaaggacc     4560
cgggatatcg gaccgattaa actttaattc ggtccgaagc ttgaagttcc tattccgaag     4620
ttcctattct ccagaaagta taggaacttc gcatgcctgc a                         4661

<210> SEQ ID NO 242
<211> LENGTH: 5116
<212> TYPE: DNA
<213> ORGANISM: Diabrotica virgifera virgifera

<400> SEQUENCE: 242
gtgcagcgtg acccggtcgt gcccctctct agagataatg agcattgcat gtctaagtta       60 taaaaatta ccacatattt ttttttgtcac acttgtttga agtgcagttt atctatcttt      120
atacatatat ttaaacttta ctctacgaat aatataatct atagtactac aataatatca      180
gtgttttaga gaatcatata aatgaacagt tagacatggt ctaaaggaca attgagtatt      240
ttgacaacag gactctacag ttttatcttt ttagtgtgca tgtgttctcc tttttttttg      300
caaatagctt cacctatata atacttcatc cattttatta gtacatccat ttagggttta     360
gggttaatgg ttttatagac taattttttt tagtacatct atttattct attttagcct      420 ctaaattaag aaaactaaaa ctctatttta gtttttttat ttaataatttt agatataaaa     480 tagaataaaa taaagtgact aaaaattaaa caaatacct ttaagaaatt aaaaaaacta      540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggaccct ctcgagagtt ccgctccacc gttggacttg       720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc     900
caacctcgtg ttgttcggag cgcacacaca caaaccaga tctcccccaa atccaccgt      960 cggcacctcc gcttcaaggt acgccgctcg tcctcccccc cccccctctc taccttctct    1020
agatcggcgt tccggtccat gcatggttag ggcccggtag ttctacttct gttcatgttt    1080
gtgttagatc cgtgtttgtg ttagatccgt gctgctagcg ttcgtacacg gatgcgacct    1140
gtacgtcaga cacgttctga ttgctaactt gccagtgttt ctctttgggg aatcctggga    1200
tggctctagc cgttccgcag acgggatcga tttcatgatt ttttttgttt cgttgcatag    1260
ggtttggttt gccctttcc tttatttcaa tatatgccgt gcacttgttt gtcgggtcat     1320
cttttcatgc ttttttttgt cttggttgtg atgatgtggc ctggttgggc ggtcgttcta    1380
gatcggagta gaattctgtt tcaaactacc tggtggattt attaatttg gatctgtatg    1440
```

```
tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920 tacgctattt atttgcttgg tactgtttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcaggggag tcgtcaacat caatttcaag   2100
tttcaagaaa aagcaaatca ctacgacttg ccggattttg tagtagtgtt aattttgtat   2160
taaaaaatca aaatgagttc tattggaact gggtacgatt tatcagcttc ccaattctct   2220
cctgatggaa gagtatttca agttgaatat gcaatgaaag cagttgaaaa tagtggcacc   2280
gtaataggcc tccgaggtac agatggcatt gtattggctg ctgaaaagct cattatgtca   2340
aaattgcatg aaccaagtac aaataaacga attttcaaca ttgataaaca cataggaatg   2400
gcattttcag gcttaatagc tgatgcaagg caaatcgttg agattgctag aaaagaagca   2460
tcaaattata gacatcaata tggttcaaat attcctctta aatacctaaa tgatagagta   2520
agcatgtaca tgcatgcata cactttatac agtgctgtta gaccatttgg ttgcagtgtc   2580
atcttggcca gttatgaaga tagtgaccca tctatgtatc tgattgatcc atctggagtt   2640
agctatggat actttggatg tgctacaggt aaagcaaaac agtctgcaaa gactgaaata   2700
gaaaaattga agatggggaa tctaacatgc aaagaacttg ttaaagaagc agccaaaatc   2760
atttatttgg tccatgatga gctgaaggat aagaattttg aactgaaact tcatgggta   2820 tgcaaagata cgaatggttt acataccaaa gtgcctgaat cagtgtttgc tgatgcagaa   2880
aaagctgcca acaagcaat ggaagcagat tcagaatcag atacagaaga tatgtaataa   2940
ctacatttag tttttaatat ttcgctgatg gtggctgttc ttacaatatt tcgtgtgtta   3000
tgttcatata ttatgtaata ctgtgagaat ttccattcca aggataggtt tataactttt   3060
ttttctaata aatacataac tttatgtcaa aaaaaaaaa aaaaaaaaa aaaaaaacag   3120 ctttcttgta caaagtggtc gatatcaggt ccgccttgtt tctcctctgt ctcttgatct   3180
gactaatctt ggtttatgat tcgttagta attttgggga aagcttcgtc cacagttttt   3240
tttcgatgaa cagtgccgca gtggcgctga tcttgtatgc tatcctgcaa tcgtggtgaa   3300
cttatttctt ttatatcctt tactcccatg aaaaggctag taatctttct cgatgtaaca   3360
tcgtccagca ctgctattac cgtgtggtcc atccgacagt ctggctgaac acatcatacg   3420
atctatggag caaaaatcta tcttccctgt tctttaatga aggacgtcat tttcattagt   3480
atgatctagg aatgttgcaa cttgcaagga ggcgtttctt tctttgaatt taactaactc   3540
gttgagtggc cctgtttctc ggacgtaagg cctttgctgc tccacacatg tccattcgaa   3600
ttttaccgtg tttagcaagg gcgaaaagtt tgcatcttga tgatttagct tgactatgcg   3660
attgctttcc tggacccgtg cagctgccca tcgaccactt tgtacaagaa agctgttttt   3720
tttttttttt tttttttttt ttttgacata agttatgta tttattagaa aaaaagtta   3780 taaacctatc cttgaaatgg aaattctcac agtattacat aatatatgaa cataacacac   3840
```

```
gaaatattgt aagaacagcc accatcagcg aaatattaaa aactaaatgt agttattaca    3900
tatcttctgt atctgattct gaatctgctt ccattgcttg tttggcagct ttttctgcat    3960
cagcaaacac tgattcaggc actttggtat gtaaaccatt cgtatctttg catacccatg    4020
aaagttccag ttcaaaattc ttatccttca gctcatcatg gaccaaataa atgattttgg    4080
ctgcttcttt aacaagttct ttgcatgtta gattccccat cttcaatttt tctatttcag    4140
tctttgcaga ctgttttgct ttacctgtag cacatccaaa gtatccatag ctaactccag    4200
atggatcaat cagatacata gatgggtcac tatcttcata actggccaag atgacactgc    4260
aaccaaatgg tctaacagca ctgtataaag tgtatgcatg catgtacatg cttactctat    4320
catttaggta tttaagagga atatttgaac catattgatg tctataattt gatgcttctt    4380
ttctagcaat ctcaacgatt tgccttgcat cagctattaa gcctgaaaat gccattccta    4440
tgtgtttatc aatgttgaaa attcgtttat ttgtacttgg ttcatgcaat tttgacataa    4500
tgagcttttc agcagccaat acaatgccat ctgtacctcg gaggcctatt acggtgccac    4560
tattttcaac tgctttcatt gcatattcaa cttgaaatac tcttccatca ggagagaatt    4620
gggaagctga taaatcgtac ccagttccaa tagaactcat tttgattttt taatacaaaa    4680
ttaacactac tacaaaatcc ggcaagtcgt agtgatttgc ttttcttga aacttgaaat    4740 tgatgttgac gactccccct gcttttttgt acaaacttgt tgatggggtt aggccgccac    4800
cgcggtggag ctcgaattcc ggtccgggtc acctttgtcc accaagatgg aactgcggcc    4860
gctcattaat taagtcaggc gcgcctctag ttgaagacac gttcatgtct tcatcgtaag    4920
aagacactca gtagtcttcg gccagaatgg ccatctggat tcagcaggcc tagaaggcca    4980
tttaaatcct gaggatctgg tcttcctaag gacccgggat atcggaccga ttaaacttta    5040
attcggtccg aagcttgaag ttcctattcc gaagttccta ttctccagaa agtataggaa    5100
cttcgcatgc ctgcag                                                    5116
```

<210> SEQ ID NO 243
<211> LENGTH: 4995
<212> TYPE: DNA
<213> ORGANISM: Diabrotica virgifera virgifera

<400> SEQUENCE: 243

```
gtgcagcgtg acccggtcgt gcccctctct agagataatg agcattgcat gtctaagtta      60
taaaaaatta ccacatattt tttttgtcac acttgtttga agtgcagttt atctatctttt    120 atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc ttttttttg      300 caaatagctt cacctatata atacttcatc cattttatta gtacatccat ttagggttta    360
gggttaatgg tttttataga ctaattttt tagtacatct attttattct attttagcct    420
ctaaattaag aaaactaaaa ctctatttta gtttttttat ttaataattt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttgacttg     720 ctccgctgtc ggcatccaga aattgcgtgg cggagcggca gacgtgagcc ggcacggcag    780
```

```
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctccccccc ccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt tttttgttt cgttgcatag    1260
ggtttggttt gcccttttcc tttatttcaa tatatgccgt gcacttgttt gtcgggtcat   1320
cttttcatgc tttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttgttcg    1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920
tacgctattt atttgcttgg tactgtttct tttgtcgatg ctcaccctgt gtttggtgt    1980
tacttctgca gaccggtctc tacgtacagt ccggactggc gccttggcgc ggtaccacat   2040
ggttcgatat caacaagttt gtacaaaaaa gcaggggct ttttcagcag ttgtcaaagc    2100
actgccacaa tgggtaaaat aatgaaatca ggaaaagtcg tattggtcct cggggccga    2160
tacgccggca gaaaagccgt agtcgtcaaa acctacgatg aaggtacatc agataaacaa   2220
tacggacatg ccttagtagc tggaattgat aggtacccaa ggaaaatcca caaacgcatg   2280
ggcaaaggca aaatgcacaa gaggtccaag atcaagcctt ttatcaaagt attgaactac   2340
aaccatctca tgcccactag atactctgta gatttggcat cagacttgaa agttgtaccc   2400
aaggacctca agatgccat gaagaggaag aaggctagat tccagacccg tgtcaaattt   2460
gaggaaaggt ataagcaagg aaagaacaaa tggttcttcc aaaaattgag gttctaggct   2520
gtagatttaa ttttataatt gtacactttt tattttgaga ataaaatgtg gataaatgca   2580
aaaaaaaaa aaaaaaaaaa aaaaaaaac agctttcttg tacaaagtgg tcgatatcag   2640
gtccgccttg tttctcctct gtctcttgat ctgactaatc ttggtttatg attcgttgag   2700
taatttggg gaaagcttcg tccacagttt tttttcgatg aacagtgccg cagtggcgct   2760
gatcttgtat gctatcctgc aatcgtggtg aacttatttc tttatatcc tttactccca    2820
tgaaaaggct agtaatcttt ctcgatgtaa catcgtccag cactgctatt accgtgtggt   2880
ccatccgaca gtctggctga acacatcata cgatctatgg agcaaaaatc tatcttccct   2940
gttctttaat gaaggacgtc attttcatta gtatgatcta ggaatgttgc aacttgcaag   3000
gaggcgtttc tttctttgaa tttaactaac tcgttgagtg ccctgtttc tcggacgtaa    3060
ggcctttgct gctccacaca tgtccattcg aattttaccg tgtttagcaa gggcgaaaag   3120
tttgcatctt gatgatttag cttgactatg cgattgcttt cctggacccg tgcagctgcc   3180
```

-continued

```
catcgaccac tttgtacaag aaagctgttt tttttttttt tttttttttt ttttttttgca    3240 tttatccaca ttttattctc aaaataaaaa gtgtacaatt ataaaattaa atctacagcc    3300
tagaacctca attttttggaa gaaccatttg ttctttcctt gcttatacct ttcctcaaat   3360
ttgacacggg tctggaatct agccttcttc ctcttcatgg catctttgag gtccttgggt    3420
acaactttca agtctgatgc caaatctaca gagtatctag tgggcatgag atggttgtag    3480
ttcaatactt tgataaaagg cttgatcttg gacctcttgt gcattttgcc tttgcccatg    3540
cgtttgtgga ttttccttgg gtacctatca attccagcta ctaaggcatg tccgtattgt    3600
ttatctgatg taccttcatc gtaggttttg acgactacgg cttttctgcc ggcgtatcgg    3660
cccccgagga ccaatacgac ttttcctgat ttcattattt tacccattgt ggcagtgctt    3720
tgacaactgc tgaaaagcc cctgcttttt tgtacaaac ttgttgatgg ggttaggccg     3780
ccaccgcggt ggagctcgaa ttccggtccg ggtcacctt gtccaccaag atggaactgc     3840
ggccgctcat taattaagtc aggcgcgcct ctagttgaag acacgttcat gtcttcatcg    3900
taagaagaca ctcagtagtc ttcggccaga atggccatct ggattcagca ggcctagaag   3960
gccatttaaa tcctgaggat ctggtcttcc taaggacccg ggatatcgga ccgattaaac   4020
tttaattcgg tccgaagctt gaagttccta ttccgaagtt cctattctcc agaaagtata   4080
ggaacttcgc atgcctgcag tgcagcgtga cccggtcgtg cccctctcta gagataatga   4140
gcattgcatg tctaagttat aaaaaattac cacatatttt ttttgtcaca cttgtttgaa   4200
gtgcagttta tctatcttta tacatatatt taaactttac tctacgaata atataatcta   4260
tagtactaca ataatatcag tgttttagag aatcatataa atgaacagtt agacatggtc   4320
taaaggacaa ttgagtattt tgacaacagg actctacagt tttatctttt tagtgtgcat   4380
gtgttctcct ttttttttgc aaatagcttc acctatataa tacttcatcc attttattag   4440
tacatccatt tagggtttag ggttaatggt ttttatagac taattttttt agtacatcta   4500
ttttattcta ttttagcctc taaattaaga aaactaaaac tctattttag ttttttttatt   4560 taataattta gatataaaat agaataaaat aaagtgacta aaaattaaac aaatacccct   4620
taagaaatta aaaaaactaa ggaaacattt ttcttgtttc gagtagataa tgccagcctg   4680
ttaaacgccg tcgacgagtc taacggacac caaccagcga accagcagcg tcgcgtcggg   4740
ccaagcgaag cagacggcac ggcatctctg tcgctgcctc tggacccctc tcgagagttc   4800
cgctccaccg ttggacttgc tccgctgtcg gcatccagaa attgcgtggc ggagcggcag   4860
acgtgagccg gcacggcagg cggcctcctc ctcctctcac ggcaccggca gctacggggg   4920
attcctttcc caccgctcct tcgctttccc ttcctcgccc gccgtaataa atagacaccc    4980
cctccacacc ctctt                                                    4995
```

<210> SEQ ID NO 244
<211> LENGTH: 7112
<212> TYPE: DNA
<213> ORGANISM: Diabrotica virgifera virgifera

<400> SEQUENCE: 244

```
gtgcagcgtg acccggtcgt gcccctctct agagataatg agcattgcat gtctaagtta     60
taaaaaatta ccacatattt ttttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
```

```
ttgacaacag gactctacag ttttatctttt ttagtgtgca tgtgttctcc tttttttttg      300
caaatagctt cacctatata atacttcatc cattttatta gtacatccat ttagggttta      360
gggttaatgg ttttttataga ctaattttttt tagtacatct attttattct attttagcct    420
ctaaattaag aaaactaaaa ctctatttta gttttttttat ttaataattt agatataaaa     480
tagaataaaa taaagtgact aaaaattaaa caaatacct ttaagaaatt aaaaaaacta       540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggacccct ctcgagagtt ccgctccacc gttggacttg      720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc      900
caacctcgtg ttgttcggag cgcacacaca acaaccaga tctcccccaa atccacccgt       960
cggcacctcc gcttcaaggt acgccgctcg tcctccccc ccccctctc taccttctct       1020 agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt ttttttgttt cgttgcatag     1260
ggtttggttt gccctttttcc tttatttcaa tatatgccgt gcacttgttt gtcgggtcat    1320
cttttcatgc ttttttttgt cttggttgtg atgatgtggt ctggttgggc ggtcgttcta    1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc ttttgttcg      1560 cttggttgtg atgatgtggt gtggttgggc ggtcgttcat tcgttctaga tcggagtaga     1620
atactgtttc aaactacctg gtgtatttat taattttgga actgtatgtg tgtgtcatac     1680
atcttcatag ttacgagttt aagatggatg gaaatatcga tctaggatag gtatacatgt     1740
tgatgtgggt tttactgatg catatacatg atggcatatg cagcatctat tcatatgctc     1800
taaccttgag tacctatcta ttataataaa caagtatgtt ttataattat ttgatcttg      1860 atatacttgg atgatggcat atgcagcagc tatatgtgga tttttttagc cctgccttca     1920
tacgctattt atttgcttgg tactgttttct tttgtcgatg ctcaccctgt tgtttggtgt    1980
tacttctgca gaccggtctc tacgtacagt ccggactggc gccttggcgc ggtaccacat     2040
ggttcgatat caacaagttt gtacaaaaaa gcaggggag ataaaacgaa gaatggcact      2100
agaacaagac ataatcaact acatcgaaga aaaacgttca atttggtatg acatgtgag     2160 aagagcagat catacaaggt ggatatcaaa gattacggat tggagcccaa taggaaagag    2220
aagaagaggt agaccccgaa tatcgtggag ggatgaagtg tacgaagcca tggaaagacg    2280
agacgttaaa gatggagaat ggtagaacag gaaggactgc agacgttggc tgaaaaaagg    2340
atagatagat agatatagaa atagaaatat ataggtgttt attagcgcgc tatggttatt    2400
atatggggaa tatataatga gaaaagcact cgacaaatgg aatggcggta tttctatcgc    2460
aggaaagaag atctcaaatc tcagatatgc agatgataca ccattaataa ctgcatccga    2520
agaagaaatg tccagtctgc tgcagctagt ggaagccgaa agcaatagat gtggtctcaa    2580
gatcaataaa caaaaaacaa aaattatgat agtagaatat ttaaattcat agtcccagga    2640
```

```
acgcaactca tcaatattgg caatatcatt ttaaagtcgt ctactttaaa atgtataata    2700
cgtgtctgaa ttgccgatat aaatgagtca gattaaataa attattggaa gaatttttta    2760
ctaggcaaca ccattttttgt ttatttagta ttattttgta ttttgagaac gacacccgac   2820
ttgggcgtcg aaacgttaat aaaatcattt ttaggtaaaa ttgtggctta tttcccattt    2880
gaatatactt aataacaata tttaaattca cttcagacaa cacgggcctt agaccagttt    2940
gaagtggtta acgagttcga ttatctagga tcctacatca gtaatacagg atgttgtgaa    3000
acagaaatac gtaggagaat aggcattgcc aaaaacgcta tgagtcgatt atcgaaaatc    3060
tggaaagatc gctccttgtc gaagaacacc aaaataagat tagtacgtgc attaattttt    3120
cccatattta attagggatc cgaaacatgg acaatgaaat cggacgacag aaaaaggatt    3180
gacgcctttg aaatgtggtg ctggagaaga atgcttcgga tctcatggac ggaacagaga    3240
acaaatcact caatcttcca agagcttaat attcagactc gactttcctc tacttgcctc    3300
tccaccgcct taaaattttt cggccatatt gcaagaagtg atgataatct ggagagactt    3360
ataatttcgg aaaaggttga agagcgcaga agtagaggtc gctcacctgc tcgatggacg    3420
gaccaagtac aggaagccag tggaaaaaca ttctctgaat ccatgaggga agctcaggac    3480
agaagccgac ggaaagagat agttgatcgt attatagggga atcacgacac tcagaaatga    3540
ggaaacgact gaggaggaga aggaggagga gcgtgctcat cactgtatat tattatacaa    3600
tttaattatt actatttaaa taatgtatga aacaatttt tcaatactgt gtttaagcaa     3660
tggtaatatc gacctcagtc atcccatcga taatgttatt gctgaataac attagcaact    3720
atttagcata gctctgtgat gtatcaaagc atcttgttaa taattggttt ccaatattcc    3780
gtaattcggg attacgagct ttacccacca aacgacacgt atttggtcaa gtagcggttt    3840
cgagcatttc aatcatcgcc acatccatca gcatttgtgt agtgaagtaa tctcctttaa    3900
tggagaaggt ggtaaaagac tctattttt ttgttagtgg tttattttg gtttgattga     3960
atacaaaaac attacaaaat tatatacaca atgaaattta ctgttttta tttggaatga    4020
gccataactt tactttgaaa ttaagttttt ttgacatttc gatttccact ttagaaatcg    4080
ttatcaaaaa aaaaaaaaaa aaaaaaaaa aaaaacagct ttcttgtaca aagtggtcga     4140
tatcaggtcc gccttgtttc tcctctgtct cttgatctga ctaatcttgg tttatgattc    4200
gttgagtaat tttggggaaa gcttcgtcca cagtttttt tcgatgaaca gtgccgcagt     4260
ggcgctgatc ttgtatgcta tcctgcaatc gtggtgaact tatttctttt atatccttta    4320
ctcccatgaa aaggctagta atctttctcg atgtaacatc gtccagcact gctattaccg    4380
tgtggtccat ccgacagtct ggctgaacac atcatacgat ctatggagca aaaatctatc    4440
ttccctgttc tttaatgaag gacgtcattt tcattagtat gatctaggaa tgttgcaact    4500
tgcaaggagg cgtttctttc tttgaattta actaactcgt tgagtggccc tgtttctcgg    4560
acgtaaggcc tttgctgctc cacacatgtc cattcgaatt ttaccgtgtt tagcaagggc    4620
gaaaagtttg catcttgatg atttagcttg actatgcgat tgcttcctg gacccgtgca    4680
gctgcccatc gaccactttg tacaagaaag ctgttttttt ttttttttt tttttttt     4740
tttgataacg atttctaaag tggaaatcga aatgtcaaaa aaacttaatt tcaaagtaaa    4800
gttatggctc attccaaata aaaaacagta aatttcattg tgtatataat tttgtaatgt    4860
ttttgtattc aatcaaacca aaaataaacc actaacaaaa aaaatagagt cttttaccac    4920
cttctccatt aaaggagatt acttcactac acaaatgctg atggatgtgg cgatgattga    4980
```

```
aatgctcgaa accgctactt gaccaaatac gtgtcgtttg gtgggtaaag ctcgtaatcc    5040
cgaattacgg aatattggaa accaattatt aacaagatgc tttgatacat cacagagcta    5100
tgctaaatag ttgctaatgt tattcagcaa taacattatc gatgggatga ctgaggtcga    5160
tattaccatt gcttaaacac agtattgaaa aatttgtttc atacattatt taaatagtaa    5220
taattaaatt gtataataat atacagtgat gagcacgctc ctcctccttc tcctcctcag    5280
tcgtttcctc atttctgagt gtcgtgattc cctataatac gatcaactat ctctttccgt    5340
cggcttctgt cctgagcttc cctcatggat tcagagaatg ttttttccact ggcttcctgt    5400 acttggtccg tccatcgagc aggtgagcga cctctacttc tgcgctcttc aacctttttcc    5460 gaaattataa gtctctccag attatcatca cttcttgcaa tatggccgaa aaattttaag    5520
gcggtggaga ggcaagtaga ggaaagtcga gtctgaatat taagctcttg gaagattgag    5580
tgatttgttc tctgttccgt ccatgagatc cgaagcattc ttctccagca ccacatttca    5640
aaggcgtcaa tccttttttct gtcgtccgat ttcattgtcc atgtttcgga tccctaatta    5700
aatatgggaa aaattaatgc acgtactaat cttatttttgg tgttcttcga caaggagcga    5760 tcttttccaga ttttcgataa tcgactcata gcgttttttgg caatgcctat tctcctacgt    5820
atttctgttt cacaacatcc tgtattactg atgtaggatc ctagataatc gaactcgtta    5880
accacttcaa actggtctaa ggcccgtgtt gtctgaagtg aatttaaata ttgttattaa    5940
gtatattcaa atgggaaata agccacaatt ttacctaaaa atgatttttat taacgtttcg    6000 acgcccaagt cgggtgtcgt tctcaaaata caaaataata ctaaatatac aaaaatggtg    6060
ttgcctagta aaaaattctt ccaataattt atttaatctg actcatttat atcggcaatt    6120
cagacacgta ttatacattt taaagtagac gactttaaaa tgatattgcc aatattgatg    6180
agttgcgttc ctgggactat gaatttaaat attctactat cataatttttt gttttttgtt    6240 tattgatctt gagaccacat ctattgcttt cggcttccac tagctgcagc agactggaca    6300
tttcttcttc ggatgcagtt attaatggtg tatcatctgc atatctgaga tttgagatct    6360
tctttcctgc gatagaaata ccgccattcc atttgtcgag tgcttttctc attatatatt    6420
ccccatataa taaccatagc gcgctaataa acacctatat atttctattt ctatatctat    6480
ctatctatcc tttttttcagc caacgtctgc agtccttcct gttctaccat tctccatctt    6540
taacgtctcg tctttccatg gcttcgtaca cttcatccct ccacgatatt cggggtctac    6600
ctcttcttct ctttcctatt gggctccaat ccgtaatctt tgatatccac cttgtatgat    6660
ctgctcttct cacatgtcca taccaaattg aacgtttttc ttcgatgtag ttgattatgt    6720
cttgttctag tgccattctt cgtttttatct ccccctgctt ttttgtacaa acttgttgat    6780
ggggttaggc cgccaccgcg gtggagctcg aattccggtc cgggtcacct ttgtccacca    6840
agatggaact gcggccgctc attaattaag tcaggcgcgc ctctagttga agacacgttc    6900
atgtcttcat cgtaagaaga cactcagtag tcttcggcca gaatggccat ctggattcag    6960
caggcctaga aggccatttta aatcctgagg atctggtctt cctaaggacc cgggatatcg    7020
gaccgattaa actttaattc ggtccgaagc ttgaagttcc tattccgaag ttcctattct    7080
ccagaaagta taggaacttc gcatgcctgc ag                                  7112
```

<210> SEQ ID NO 245  
<211> LENGTH: 4076  
<212> TYPE: DNA  
<213> ORGANISM: Diabrotica virgifera virgifera

<400> SEQUENCE: 245

```
gtgcagcgtg acccggtcgt gcccctctct agagataatg agcattgcat gtctaagtta    60
taaaaaatta ccacatattt tttttgtcac acttgtttga agtgcagttt atctatcttt   120
atacatatat ttaaacttta ctctacgaat aatataatct atagtactac aataatatca   180
gtgttttaga gaatcatata aatgaacagt tagacatgga ctaaaggaca attgagtatt   240
ttgacaacag gactctacag ttttatcttt ttagtgtgca tgtgttctcc ttttttttg    300
caaatagctt cacctatata atacttcatc cattttatta gtacatccat ttagggttta   360
gggttaatgg ttttatataga ctaattttt tagtacatct attttattct attttagcct   420
ctaaattaag aaaactaaaa ctctattta gtttttttat ttaataattt agatataaaa    480
tagaataaaa taaagtgact aaaaattaaa caaataccct ttaagaaatt aaaaaaacta   540
aggaaacatt tttcttgttt cgagtagata atgccagcct gttaaacgcc gtcgacgagt   600
ctaacggaca ccaaccagcg aaccagcagc gtcgcgtcgg gccaagcgaa gcagacggca   660
cggcatctct gtcgctgcct ctggacccct ctcgagagtt ccgctccacc gttggacttg   720
ctccgctgtc ggcatccaga aattgcgtgg cggagcggca gacgtgagcc ggcacggcag   780
gcggcctcct cctcctctca cggcaccggc agctacgggg gattcctttc ccaccgctcc   840
ttcgctttcc cttcctcgcc cgccgtaata aatagacacc ccctccacac cctctttccc   900
caacctcgtg ttgttcggag cgcacacaca cacaaccaga tctcccccaa atccacccgt   960
cggcacctcc gcttcaaggt acgccgctcg tcctccccc ccccctctc taccttctct  1020
agatcggcgt tccggtccat gcatggttag ggcccggtag ttctacttct gttcatgttt  1080
gtgttagatc cgtgtttgtg ttagatccgt gctgctagcg ttcgtacacg gatgcgacct  1140
gtacgtcaga cacgttctga ttgctaactt gccagtgttt ctctttgggg aatcctggga  1200
tggctctagc cgttccgcag acgggatcga tttcatgatt tttttttgttt cgttgcatag  1260
ggttggttt gcccttttcc tttatttcaa tatatgccgt gcacttgttt gtcgggtcat   1320
cttttcatgc tttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttgttcg   1560
cttggttgtg atgatgtggt gtggttgggc ggtcgttcat tcgttctaga tcggagtaga  1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920
tacgctattt atttgcttgg tactgttct tttgtcgatg ctcaccctgt tgtttggtgt   1980
tacttctgca gaccggtctc tacgtacagt ccggactggc gccttggcgc ggtaccacat   2040
ggttcgatat caacaagttt gtacaaaaaa gcagggggt gtagctttcc gcagcaaaaa   2100
gataggtggt taggcattat tttctaaaaa ccacatggat gaattgttgg caaattcagc   2160
cctagaggct gaaaaattta agccaaccgt agtaaataag cttattgatc taaattatga   2220
cttaggaagc cttttagcac aagacacaaa tgaatttgat acaaatttat taaggaggca   2280
gaaggaagat tatttgctta atttagctag agataacacc caattactat taaatcaaat   2340
```

| | |
|---|---:|
| atgggactta actacagaac gcctagaaga agctattgta gtgaaattac cacttcaaat | 2400 |
| aactttatta cctaggatga aaccactacc taagcccaaa cctttaacaa agtgggaaca | 2460 |
| gtttgccaaa acgaaaggta tacagaaaaa gaaaaaatcc aagttatcat gggaccagca | 2520 |
| actcaaaaag tgggtaccct tatatggatt taagcgagca caagctgaaa aaaaaaaaaa | 2580 |
| aaaaaaaaaa aaaaaaacag ctttcttgta caaagtggtc gatatcaggt ccgccttgtt | 2640 |
| tctcctctgt ctcttgatct gactaatctt ggtttatgat tcgttgagta attttgggga | 2700 |
| aagcttcgtc cacagttttt tttcgatgaa cagtgccgca gtggcgctga tcttgtatgc | 2760 |
| tatcctgcaa tcgtggtgaa cttatttctt ttatatcctt tactcccatg aaaaggctag | 2820 |
| taatctttct cgatgtaaca tcgtccagca ctgctattac cgtgtggtcc atccgacagt | 2880 |
| ctggctgaac acatcatacg atctatggag caaaaatcta tcttccctgt tctttaatga | 2940 |
| aggacgtcat tttcattagt atgatctagg aatgttgcaa cttgcaagga ggcgtttctt | 3000 |
| tctttgaatt taactaactc gttgagtggc cctgtttctc ggacgtaagg cctttgctgc | 3060 |
| tccacacatg tccattcgaa ttttaccgtg tttagcaagg gcgaaaagtt tgcatcttga | 3120 |
| tgatttagct tgactatgcg attgcttttcc tggacccgtg cagctgccca tcgaccactt | 3180 |
| tgtacaagaa agctgttttt ttttttttttt tttttttttt tttttcagct tgtgctcgct | 3240 |
| taaatccata taagggtacc cactttttga gttgctggtc ccatgataac ttggattttt | 3300 |
| tcttttttctg tatacctttc gttttggcaa actgttccca ctttgttaaa ggtttgggct | 3360 |
| taggtagtgg tttcatccta ggtaataaag ttatttgaag tggtaatttc actacaatag | 3420 |
| cttcttctag gcgttctgta gttaagtccc atatttgatt taatagtaat tgggtgttat | 3480 |
| ctctagctaa attaagcaaa taatcttcct tctgcctcct taataaattt gtatcaaatt | 3540 |
| catttgtgtc ttgtgctaaa aggcttccta agtcataatt tagatcaata agcttattta | 3600 |
| ctacggttgg cttaaatttt tcagcctcta gggctgaatt tgccaacaat tcatccatgt | 3660 |
| ggttttttaga aaataatgcc taaccaccta tcttttttgct gcggaaagct acacccccct | 3720 |
| gcttttttgt acaaacttgt tgatgggggtt aggccgccac cgcggtggag ctcgaattcc | 3780 |
| ggtccgggtc acctttgtcc accaagatgg aactgcggcc gctcattaat taagtcaggc | 3840 |
| gcgcctctag ttgaagacac gttcatgtct tcatcgtaag aagacactca gtagtcttcg | 3900 |
| gccagaatgg ccatctggat tcagcaggcc tagaaggcca tttaaatcct gaggatctgg | 3960 |
| tcttcctaag gacccgggat atcggaccga ttaaacttta attcggtccg aagcttgaag | 4020 |
| ttcctattcc gaagttccta ttctccagaa agtataggaa cttcgcatgc ctgcag | 4076 |

<210> SEQ ID NO 246
<211> LENGTH: 4415
<212> TYPE: DNA
<213> ORGANISM: Diabrotica virgifera virgifera

<400> SEQUENCE: 246

| | |
|---|---:|
| gtgcagcgtg acccggtcgt gcccctctct agagataatg agcattgcat gtctaagtta | 60 |
| taaaaaatta ccacatattt ttttttgtcac acttgtttga agtgcagttt atctatctttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag tttttatcttt ttagtgtgca tgtgttctcc tttttttttg | 300 |
| caaatagctt cacctatata atacttcatc cattttatta gtacatccat ttagggttta | 360 |
| gggttaatgg tttttataga ctaatttttt tagtacatct atttttattct attttagcct | 420 |

-continued

```
ctaaattaag aaaactaaaa ctctatttta gtttttttat ttaataattt agatataaaa      480
tagaataaaa taaagtgact aaaaattaaa caaatacect ttaagaaatt aaaaaaacta      540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggaccect ctcgagagtt ccgctccacc gttggacttg      720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc      900
caacctcgtg ttgttcggag cgcacacaca cacaaccaga tctcccccaa atccaccegt      960 cggcacctcc gcttcaaggt acgccgctcg tcctccccec cccecctctc taccttctct     1020 agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt ttttttgttt cgttgcatag     1260
ggtttggttt gccctttcc tttatttcaa tatatgccgt gcacttgttt gtcgggtcat      1320
cttttcatgc tttttttgt cttggttgtg atgatgtggt ctggttgggc ggtcgttcta      1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc ttttgttcg      1560 cttggttgtg atgatgtggt gtggttgggc ggtcgttcat tcgttctaga tcggagtaga     1620
atactgtttc aaactacctg gtgtatttat taattttgga actgtatgtg tgtgtcatac     1680
atcttcatag ttacgagttt aagatggatg gaaatatcga tctaggatag gtatacatgt     1740
tgatgtgggt tttactgatg catatacatg atggcatatg cagcatctat tcatatgctc     1800
taaccttgag tacctatcta ttataataaa caagtatgtt ttataattat tttgatcttg     1860
atatacttgg atgatggcat atgcagcagc tatatgtgga ttttttttagc cctgccttca    1920 tacgctattt atttgcttgg tactgttttct tttgtcgatg ctcaccctgt tgtttggtgt    1980
tacttctgca gggggggcagt tatttcgact tttcatgctt gtcataaaat aaaattaaaa    2040
tatatccggc gaggtgttga ctagcggatt tttttagatt caacaatctt attttataaa    2100 ataattgtt aaaatgatgc aaacagctaa taatgcatat tatcccgatt attccactgc      2160
tccaatgcaa cgtcaaatta accectatgc agataatgga gggagtgtag tagcaatagc     2220
aggtgaagac tttgtaataa ttggtgcaga tacacgtttg agtactggat tttccattta    2280
taccagagaa caaaacaaac ttttcccact atcaggcact actgttttgg gttgtgcagg    2340
atgttggtgt gacactctaa cattaaccag aatccttaaa tctcgcatgc agatgtacca    2400
acaagagcat aacaaaacaa tgtctacaac tgcatgtgcc cagatgttgt caaccatgct    2460
ctactacaag agattctttc cttattatat atcaaacatt ctagtaggtt tagataatga    2520
aggaaagggc tgtgtttaca gctatgatcc tattggacat tgtgaaaaag ctacgtatag    2580
agcaggtggt tcagctggag ctcttcttca gcctctgttg gacaatcaaa ttggacagaa    2640
gaacatgctt aaaacatctg ggaacctct tagtcaggag aaagctctgt ctacccttaa     2700
agatgtattt atttctgctg ctgaaagaga catctacact ggagatagcg tacttataaa    2760
```

-continued

```
tattattact aaagatggag taaaggaaga gtccttccag ttgagacggg attagaagca   2820
agtggttttg tttatatttt cttatgtgta attcaaatat actttctaaa taaacaaaaa   2880
aaaaaaaaaa aaaaaaaaaa aaaacagctt tcttgtacaa agtggtcgat atcaggtccg   2940
ccttgtttct cctctgtctc ttgatctgac taatcttggt ttatgattcg ttgagtaatt   3000
ttggggaaag cttcgtccac agtttttttt cgatgaacag tgccgcagtg gcgctgatct   3060
tgtatgctat cctgcaatcg tggtgaactt atttctttta tatcctttac tcccatgaaa   3120
aggctagtaa tctttctcga tgtaacatcg tccagcactg ctattaccgt gtggtccatc   3180
cgacagtctg gctgaacaca tcatacgatc tatggagcaa aaatctatct tccctgttct   3240
ttaatgaagg acgtcatttt cattagtatg atctaggaat gttgcaactt gcaaggaggc   3300
gtttctttct ttgaatttaa ctaactcgtt gagtggccct gtttctcgga cgtaaggcct   3360
ttgctgctcc acacatgtcc attcgaattt taccgtgttt agcaagggcg aaaagtttgc   3420
atcttgatga tttagcttga ctatgcgatt gctttcctgg acccgtgcag ctgcccatcg   3480
accactttgt acaagaaagc tgtttttttt tttttttttt tttttttttt tgtttattta   3540
gaaagtatat ttgaattaca cataagaaaa tataaacaaa accacttgct tctaatcccg   3600
tctcaactgg aaggactctt cctttactcc atctttagta ataatattta taagtacgct   3660
atctccagtg tagatgtctc tttcagcagc agaaataaat acatctttaa gggtagacag   3720
agctttctcc tgactaagag gttccccaga tgttttaagc atgttcttct gtccaatttg   3780
attgtccaac agaggctgaa gaagagctcc agctgaacca cctgctctat acgtagcttt   3840
ttcacaatgt ccaataggat catagctgta aacacagccc tttccttcat tatctaaacc   3900
tactagaatg tttgatatat aataaggaaa gaatctcttg tagtagagca tggttgacaa   3960
catctgggca catgcagttg tagacattgt tttgttatgc tcttgttggt acatctgcat   4020
gcgagattta aggattctgg ttaatgttag agtgtcacac caacatcctg cacaacccaa   4080
aacagtagtg cctgatagtg ggaaaagttt gttttgttct ctggtataaa tggaaaatcc   4140
agtactcaaa cgtgtatctg caccaattat tacaaagtct tcacctgcta ttgctactac   4200
actccctcca ttatctgcat aggggttaat ttgacgttgc attggagcag tggaataatc   4260
gggataatat gcattattag ctgtttgcat cattttaact aattatttta taaaataaga   4320
ttgttgaatc taaaaaaatc cgctagtcaa cacctcgccg gatatatttt aattttattt   4380
tatgacaagc atgaaaagtc gaaataactg ccccc                               4415
```

<210> SEQ ID NO 247
<211> LENGTH: 3389
<212> TYPE: DNA
<213> ORGANISM: Diabrotica virgifera virgifera

<400> SEQUENCE: 247

```
gtgcagcgtg acccggtcgt gcccctctct agagataatg agcattgcat gtctaagtta     60
taaaaaatta ccacatattt tttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg tttttataga ctaatttttt tagtacatct attttattct attttagcct    420
ctaaattaag aaaactaaaa ctctatttta gtttttttat ttaataattt agatataaaa    480
```

```
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840

ttcgctttcc cttcctcgcc cgccgtaata aatagacacc ccctccacac ccтсттттccc   900 caacctcgtt tgtcggag cgcacacaca cacaaccaga tctcccccaa atccacccgt      960
cggcacctcc gcttcaaggt acgccgctcg тccтccccccc cccccctctc taccttctct  1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgtTT ctctttgggg aatcctggga   1200

tggctctagc cgttccgcag acgggatcga tttcatgatt тттттттgттт cgttgcatag   1260 ggtttggttt gcccttttcc ттTaттттcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440

tgtgtgccat acatattcat agttacgaat tgaagatgat ggatggaaat atcgatctag   1500
gataggtata catgttgatg cgggttttac tgatgcatat acagagatgc tttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740

tgatgtgggt ttTactgatg catatacatg atggcatatg cagcatctat tcatatgctc   1800

taaccttgag tacctatcta ttataataaa caagtatgtt ttataattat tttgatcttg   1860
atatacttgg atgatggcat atgcagcagc tatatgtgga тТТТТТТТagc cctgccttca   1920

tacgctattt atttgcttgg tactgTTTct ttTgtcgatg ctcaccctgt tgtttggtgt   1980

tacttctgca ggggggantt tctctagttt gcaggaagca ggaatttcag taaagaaata   2040
agattaaaat ggcagacaaa gtagaaaagg ttgccagacc aatgaaattc ccttacacat   2100

tcagtgcaaa aattgcacaa ttcccaatca agcactactt gaagaaccaa tggatctgga   2160
aatactatgc tatttctctt gtagtatgtc ttccagtctt caactcgatt agtaaactgg   2220
ccaactctcc tggaaacgtt gctaaatggg cagagattcg cagaagagaa gctgctgaac   2280
atcatcacta agaaaatttt ttttatagta attagtctgc caattgtttt gttctaattt   2340
aatttctatt aaatacatgt agaaaaaaaa aaaaaaaaa aaaaaaaaa acagctttct    2400

tgtacaaagt ggtcgatatc aggtccgcct tgtttctcct ctgtctcttg atctgactaa   2460

tcttggttta tgattcgttg agtaattttg gggaaagctt cgtccacagt tttttttcga    2520

tgaacagtgc cgcagtggcg ctgatcttgt atgctatcct gcaatcgtgg tgaacttatt   2580

tcttttatat cctttactcc catgaaaagg ctagtaatct ttctcgatgt aacatcgtcc    2640
agcactgcta ttaccgtgtg gtccatccga cagtctggct gaacacatca tacgatctat   2700
ggagcaaaaa tctatcttcc ctgttcttta atgaaggacg tcattttcat tagtatgatc   2760

taggaatgtt gcaacttgca aggaggcgtt tctttctttg aatttaacta actcgttgag   2820
```

| | |
|---|---|
| tggccctgtt tctcggacgt aaggcctttg ctgctccaca catgtccatt cgaatttac | 2880 |
| cgtgtttagc aagggcgaaa agtttgcatc ttgatgattt agcttgacta tgcgattgct | 2940 |
| ttcctggacc cgtgcagctg cccatcgacc actttgtaca agaaagctgt tttttttttt | 3000 |
| tttttttttt tttttttct acatgtattt aatagaaatt aaattagaac aaaacaattg | 3060 |
| gcagactaat tactataaaa aaatttct tagtgatgat gttcagcagc ttctcttctg | 3120 |
| cgaatctctg cccatttagc aacgtttcca ggagagttgg ccagtttact aatcgagttg | 3180 |
| aagactggaa gacatactac aagagaaata gcatagtatt tccagatcca ttggttcttc | 3240 |
| aagtagtgct tgattgggaa ttgtgcaatt tttgcactga atgtgtaagg gaatttcatt | 3300 |
| ggtctggcaa ccttttctac tttgtctgcc attttaatct tatttcttta ctgaaattcc | 3360 |
| tgcttcctgc aaactagaga aaatcccc | 3389 |

<210> SEQ ID NO 248
<211> LENGTH: 3349
<212> TYPE: DNA
<213> ORGANISM: Diabrotica virgifera virgifera

<400> SEQUENCE: 248

| | |
|---|---|
| gtgcagcgtg acccggtcgt gccctctct agagataatg agcattgcat gtctaagtta | 60 |
| taaaaaatta ccacatattt tttttgtcac acttgtttga agtgcagttt atctatcttt | 120 |
| atacatatat ttaaacttta ctctacgaat aatataatct atagtactac aataatatca | 180 |
| gtgttttaga gaatcatata aatgaacagt tagacatggt ctaaaggaca attgagtatt | 240 |
| ttgacaacag gactctacag ttttatcttt ttagtgtgca tgtgttctcc tttttttttg | 300 |
| caaatagctt cacctatata atacttcatc cattttatta gtacatccat ttagggttta | 360 |
| gggttaatgg ttttttataga ctaattttt tagtacatct attttattct attttagcct | 420 |
| ctaaattaag aaaactaaaa ctctattta gttttttat ttaataattt agatataaaa | 480 |
| tagaataaaa taaagtgact aaaaattaaa caaatacct ttaagaaatt aaaaaaacta | 540 |
| aggaaacatt tttcttgttt cgagtagata atgccagcct gttaaacgcc gtcgacgagt | 600 |
| ctaacggaca ccaaccagcg aaccagcagc gtcgcgtcgg gccaagcgaa gcagacggca | 660 |
| cggcatctct gtcgctgcct ctggacccct ctcgagagtt ccgctccacc gttggacttg | 720 |
| ctccgctgtc ggcatccaga aattgcgtgg cggagcggca gacgtgagcc ggcacggcag | 780 |
| gcggcctcct cctcctctca cggcaccggc agctacgggg gattcctttc ccaccgctcc | 840 |
| ttcgcttttcc cttcctcgcc cgccgtaata aatagacacc ccctccacac cctctttccc | 900 |
| caacctcgtg ttgttcggag cgcacacaca cacaaccaga tctcccccaa atccacccgt | 960 |
| cggcacctcc gcttcaaggt acgccgctcg tcctcccccc cccccctctc taccttctct | 1020 |
| agatcggcgt tccggtccat gcatggttag ggcccggtag ttctacttct gttcatgttt | 1080 |
| gtgttagatc cgtgtttgtg ttagatccgt gctgctagcg ttcgtacacg gatgcgacct | 1140 |
| gtacgtcaga cacgttctga ttgctaactt gccagtgttt ctctttgggg aatcctggga | 1200 |
| tggctctagc cgttccgcag acgggatcga tttcatgatt ttttttgttt cgttgcatag | 1260 |
| ggtttggttt gccctttttcc tttatttcaa tatatgccgt gcacttgttt gtcgggtcat | 1320 |
| cttttcatgc ttttttttgt cttggttgtg atgatgtggt ctggttgggc ggtcgttcta | 1380 |
| gatcggagta gaattctgtt tcaaactacc tggtggattt attaattttg gatctgtatg | 1440 |
| tgtgtgccat acatattcat agttacgaat tgaaagtgat ggatggaaat atcgatctag | 1500 |
| gataggtata catgttgatg cgggttttac tgatgcatat acagagatgc tttttgttcg | 1560 |

```
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgtttct tttgtcgatg ctcaccctgt tgtttggtgt    1980
tacttctgca ggggggggg ggaggttaag ggaataaagc ccctataaaa tttttatcgg    2040
ctgtgaaaat ttcactacta ttttttttaaa gattttccta ccataataat gtcaaatgcc    2100
cattttaacc tctaatattt ttcgatattc tcgatttttta ttttataagc tcaaagagtt    2160 ataactttttt ttatgtgcac ctttgtacta aggtaactta ggttcaatgg aactattttt    2220
attcccagaa tattttatt tattcatgac ccacctttt actacacctt gtgcaattgt    2280
tatttatttt caaatagata tttaataatg aaaattgtaa ttcttcctcc aatccaaagg    2340
agtgtaaaat tttagcaga attacttccc ccagctttct tgtacaaagt ggtcgatatc    2400
aggtccgcct tgtttctcct ctgtctcttg atctgactaa tcttggttta tgattcgttg    2460
agtaattttg gggaaagctt cgtccacagt ttttttttcga tgaacagtgc cgcagtggcg    2520
ctgatcttgt atgctatcct gcaatcgtgg tgaacttatt tctttttatat cctttactcc    2580 catgaaaagg ctagtaatct ttctcgatgt aacatcgtcc agcactgcta ttaccgtgtg    2640
gtccatccga cagtctggct gaacacatca tacgatctat ggagcaaaaa tctatcttcc    2700 ctgttctttta atgaaggacg tcattttcat tagtatgatc taggaatgtt gcaacttgca    2760
aggaggcgtt tctttctttg aatttaacta actcgttgag tggccctgtt tctcggacgt    2820
aaggcctttg ctgctccaca catgtccatt cgaattttac cgtgtttagc aagggcgaaa    2880
agtttgcatc ttgatgattt agcttgacta tgcgattgct ttcctggacc cgtgcagctg    2940
cccatcgacc actttgtaca agaaagctgg gggaagtaat tctgctaaaa attttacact    3000
cctttggatt ggaggaagaa ttacaatttt cattattaaa tatctatttg aaaataaata    3060
acaattgcac aaggtgtagt aaaaaggtgg gtcatgaata aaataaaata ttctgggaat    3120
aaaaatagtt ccattgaacc taagttacct tagtacaaag gtgcacataa aaaaagttat    3180
aactctttga gcttataaaa taaaaatcga gaatatcgaa aaatattaga ggttaaaatg    3240
ggcatttgac attattatgg taggaaaatc tttaaaaaaa tagtagtgaa attttcacag    3300
ccgataaaaa ttttatagg gctttattcc cttaacctcc ccccccccc    3349
```

<210> SEQ ID NO 249
<211> LENGTH: 3953
<212> TYPE: DNA
<213> ORGANISM: Diabrotica virgifera virgifera

<400> SEQUENCE: 249

```
gtgcagcgtg acccggtcgt gccccctctct agagataatg agcattgcat gtctaagtta      60
taaaaaatta ccacatattt ttttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc tttttttttg     300
```

```
caaatagctt cacctatata atacttcatc cattttatta gtacatccat ttagggttta    360
gggttaatgg ttttttataga ctaattttttt tagtacatct attttattct attttagcct    420
```

```
caaatagctt cacctatata atacttcatc cattttatta gtacatccat ttagggttta    360
gggttaatgg ttttttataga ctaatttttt tagtacatct attttattct attttagcct    420
ctaaattaag aaaactaaaa ctctatttta gttttttttat ttaataattt agatataaaa    480
tagaataaaa taaagtgact aaaaattaaa caaataccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccacac cctctttccc    900
caacctcgtg ttgttcggag cgcacacaca cacaaccaga tctcccccaa atccacccgt    960
cggcacctcc gcttcaaggt acgccgctcg tcctccccc cccccctctc taccttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga tttcatgatt tttttgttt cgttgcatag   1260
ggtttggttt gccttttcc tttatttcaa tatatgccgt gcacttgttt gtcgggtcat   1320
cttttcatgc ttttttttgt cttggttgtg atgatgtggt ctggttgggc ggtcgttcta   1380
gatcggagta gaattctgtt tcaaactacc tggtggattt attaattttg gatctgtatg   1440
tgtgtgccat acatattcat agttacgaat tgaagatgat ggatggaaat atcgatctag   1500
gataggtata catgttgatg cgggttttac tgatgcatat acagagatgc ttttttgttcg   1560
cttggttgtg atgatgtggt gtggttgggc ggtcgttcat tcgttctaga tcggagtaga   1620
atactgtttc aaactacctg gtgtatttat taattttgga actgtatgtg tgtgtcatac   1680
atcttcatag ttacgagttt aagatggatg gaaatatcga tctaggatag gtatacatgt   1740
tgatgtgggt tttactgatg catatacatg atggcatatg cagcatctat tcatatgctc   1800
taaccttgag tacctatcta ttataataaa caagtatgtt ttataattat tttgatcttg   1860
atatacttgg atgatggcat atgcagcagc tatatgtgga ttttttttagc cctgccttca   1920
tacgctattt atttgcttgg tactgttct ttgtcgatg ctcaccctgt tgtttggtgt   1980
tacttctgca gcacgaacta acttggtttt taatacttca ataataaagc tttcaacttc   2040
gtctggtttc atctgtaact ccttttcgat gacatcaaaa gatatttcag gattactctc   2100
agcaagctgc atgaaggaaa gcagtctcat tttttgcata ttctgttcat gatttaaacc   2160
ttgtgcactc acaaattcct tatgttcatt gtaaaacttg aggtaggtgg acaaatttc   2220
actaacaaag atgtttaaaa ggtcatgtat taaatcaccc tccaaaaatc tgacaggttt   2280
tagtgataac aatggatcaa gaaggaatgt gttgggatca gctagtgctg atacaatgca   2340
acggatggcg tcttctctgg catgagaagc attttttgtca gtgtatgtac caagaagttc   2400
aatcatcact aaagcagcct gctcactttg atttgattta accagtactt catgtaaaag   2460
cctataaagc ttttgaagct gttcattaga cggaaggcaa ttggcaaact gttgctttag   2520
atggttgata tcttgaaaca ctaatttttac agattctgtc tgtttcgcaa tttgtattaa   2580
gtggtaatat acaggatacc gcattggaga acgatcatcc aatgattgga agagtaacca   2640
taatgctcta agacatacta aaccccagct ttcttgtaca aagtggtcga tatcaggtcc   2700
```

```
gccttgtttc tcctctgtct cttgatctga ctaatcttgg tttatgattc gttgagtaat    2760
tttggggaaa gcttcgtcca cagttttttt tcgatgaaca gtgccgcagt ggcgctgatc    2820
ttgtatgcta tcctgcaatc gtggtgaact tatttctttt atatcctttta ctcccatgaa   2880
aaggctagta atctttctcg atgtaacatc gtccagcact gctattaccg tgtggtccat    2940
ccgacagtct ggctgaacac atcatacgat ctatggagca aaaatctatc ttccctgttc    3000
tttaatgaag acgtcatttt tcattagtat gatctaggaa tgttgcaact tgcaaggagg    3060
cgtttctttc tttgaattta actaactcgt tgagtggccc tgtttctcgg acgtaaggcc    3120
tttgctgctc cacacatgtc cattcgaatt ttaccgtgtt tagcaagggc gaaaagtttg    3180
catcttgatg atttagcttg actatgcgat tgctttcctg gacccgtgca gctgcccatc    3240
gaccactttg tacaagaaag ctggggacgg ttttacgtgg ggtttagtat gtcttagagc    3300
attatggtta ctcttccaat cattggatga tcgttctcca atgcggtatc ctgtatatta    3360
ccacttaata caaattgcga aacagacaga atctgtaaaa ttagtgtttc aagatatcaa    3420
ccatctaaag caacagtttg ccaattgcct tccgtctaat gaacagcttc aaaagcttta    3480
taggctttta catgaagtac tggttaaatc aaatcaaagt gagcaggctg ctttagtgat    3540
gattgaactt cttggtacat acactgacaa aaatgcttct catgccagag aagacgccat    3600
ccgttgcatt gtatcagcac tagctgatcc caacacattc cttcttgatc cattgttatc    3660
actaaaacct gtcagatttt tggagggtga tttaatacat gacctttttaa acatctttgt   3720
tagtgaaaat ttgtccacct acctcaagtt ttacaatgaa cataaggaat ttgtgagtgc    3780
acaaggttta aatcatgaac agaatatgca aaaaatgaga ctgctttcct tcatgcagct    3840
tgctgagagt aatcctgaaa tatcttttga tgtcatcgaa aaggagttac agatgaaacc    3900
agacgaagtt gaaagcttta ttattgaagt attaaaaacc aagttagttc gtg          3953

<210> SEQ ID NO 250
<211> LENGTH: 3433
<212> TYPE: DNA
<213> ORGANISM: Diabrotica virgifera virgifera

<400> SEQUENCE: 250
gtgcagcgtg acccggtcgt gcccctctct agagataatg agcattgcat gtctaagtta     60
taaaaaatta ccacatattt ttttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggc ctaaaggaca attgagtatt    240
ttgacaacag gactctacag ttttatcttt ttagtgtgca tgtgttctcc ttttttttg     300
caaatagctt cacctatata atacttcatc cattttatta gtacatccat ttagggttta    360
gggttaatgg tttttataga ctaattttttt tagtacatct attttattct attttagcct   420
ctaaattaag aaaactaaaa ctctatttta gtttttttat ttaataattt agatataaaa    480
tagaataaaa taaagtgact aaaaattaaa caaatacct ttaagaaatt aaaaaaacta     540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggacccct ctcgagagtt ccgctccacc gttggacttg    720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
```

```
ttcgctttcc cttcctcgcc cgccgtaata aatagacacc ccctccacac cctctttccc      900
caacctcgtg ttgttcggag cgcacacaca cacaaccaga tctcccccaa atccacccgt      960
cggcacctcc gcttcaaggt acgccgctcg tcctcccccc ccccctctc taccttctct     1020
agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt ttttttgttt cgttgcatag     1260
ggtttggttt gccctttttcc tttatttcaa tatatgccgt gcacttgttt gtcgggtcat     1320
cttttcatgc ttttttttgt cttggttgtg atgatgtggt ctggttgggc ggtcgttcta     1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc ttttttgttcg    1560
cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920
tacgctattt atttgcttgg tactgtttct tttgtcgatg ctcaccctgt tgtttggtgt    1980
tacttctgca ggggggaaat atatactaca atgaagttttt taagatcgac agtgtgctac    2040
attgccatct tggcaattct ctttacccte tgtgccgatg aggttgaagg aaggagaaaa    2100
attttgatgg ggcgaaaaag cattaccagg acatatcttc gtggaaatgc tgttcctgcg    2160
tatgtgataa taatccttgt aggaattggt caactcatcc tgggagggat attgtacgtt    2220
gcattgagga agaagatcat tgctgcacct gtaacggcat catatgcagt ggctagacaa    2280
gaaccataaa ttttatttgt ctagaatatt attttctaaa tatgcatctt ttttaaatta    2340
ttgtctacgt aaataataag tctagaaata tataaaaatt gtcaaaaaaa aaaaaaaaa    2400
aaaaaaaaaa aaacagcttt cttgtacaaa gtggtcgata tcaggtccgc cttgtttctc    2460
ctctgtctct tgatctgact aatcttggtt tatgattcgt tgagtaattt tggggaaagc    2520
ttcgtccaca gttttttttc gatgaacagt gccgcagtgg cgctgatctt gtatgctatc    2580
ctgcaatcgt ggtgaactta tttcttttat atcctttact cccatgaaaa ggctagtaat    2640
ctttctcgat gtaacatcgt ccagcactgc tattaccgtg tggtccatcc gacagtctgg    2700
ctgaacacat catacgatct atggagcaaa aatctatctt ccctgttctt taatgaagga    2760
cgtcattttc attagtatga tctaggaatg ttgcaacttg caaggaggcg tttcttctt     2820
tgaatttaac taactcgttg agtggccctg tttctcggac gtaaggcctt tgctgctcca    2880
cacatgtcca ttcgaatttt accgtgttta gcaagggcga aaagtttgca tcttgatgat    2940
ttagcttgac tatgcgattg ctttcctgga cccgtgcagc tgcccatcga ccactttgta    3000
caagaaagct gtttttttt tttttttttt ttttttttt tgacaatttt tatatatttc     3060
tagacttatt atttacgtag acaataattt aaaaagatg catatttaga aaataatatt    3120
ctagacaaat aaaattatg gttcttgtct agccactgca tatgatgccg ttacaggtgc    3180
agcaatgatc ttcttcctca atgcaacgta caatatccct cccaggatga gttgaccaat    3240
```

| | | | |
|---|---|---|---|
| tcctacaagg | attattatca | catacgcagg aacagcattt ccacgaagat atgtcctggt | 3300 |
| aatgctttt | cgccccatca | aaattttct ccttccttca acctcatcgg cacagagggt | 3360 |
| aaagagaatt | gccaagatgg | caatgtagca cactgtcgat cttaaaaact tcattgtagt | 3420 |
| atatatttcc | ccc | | 3433 |

<210> SEQ ID NO 251
<211> LENGTH: 3121
<212> TYPE: DNA
<213> ORGANISM: Diabrotica virgifera virgifera

<400> SEQUENCE: 251

| | | | | |
|---|---|---|---|---|
| gtgcagcgtg | acccggtcgt | gcccctctct | agagataatg agcattgcat gtctaagtta | 60 |
| taaaaaatta | ccacatattt | tttttgtcac | acttgtttga agtgcagttt atctatcttt | 120 |
| atacatatat | ttaaacttta | ctctacgaat | aatataatct atagtactac aataatatca | 180 |
| gtgtttaga | gaatcatata | aatgaacagt | tagacatggc ctaaaggaca attgagtatt | 240 |
| ttgacaacag | gactctacag | ttttatcttt | ttagtgtgca tgtgttctcc ttttttttg | 300 |
| caaatagctt | cacctatata | atacttcatc | cattttatta gtacatccat ttagggttta | 360 |
| gggttaatgg | tttttataga | ctaattttt | tagtacatct atttattct atttagcct | 420 |
| ctaaattaag | aaaactaaaa | ctctatttta | gttttttat ttataatttt agatataaaa | 480 |
| tagaataaaa | taaagtgact | aaaaattaaa | caaatacct taagaaatt aaaaaaacta | 540 |
| aggaaacatt | tttcttgttt | cgagtagata | atgccagcct gttaaacgcc gtcgacgagt | 600 |
| ctaacggaca | ccaaccagcg | aaccagcagc | gtcgcgtcgg gccaagcgaa gcagacggca | 660 |
| cggcatctct | gtcgctgcct | ctggacccct | ctcgagagtt ccgctccacc gttggacttg | 720 |
| ctccgctgtc | ggcatccaga | aattgcgtgg | cggagcggca gacgtgagcc ggcacggcag | 780 |
| gcggcctcct | cctcctctca | cggcaccggc | agctacgggg gattcctttc ccaccgctcc | 840 |
| ttcgctttcc | cttcctcgcc | cgccgtaata | aatagacacc ccctccacac cctcttcc | 900 |
| caacctcgtg | ttgttcggag | cgcacacaca | cacaaccaga tctcccccaa atccacccgt | 960 |
| cggcacctcc | gcttcaaggt | acgccgctcg | tcctccccc cccccctctc taccttctct | 1020 |
| agatcggcgt | tccggtccat | gcatggttag | ggcccggtag ttctacttct gttcatgttt | 1080 |
| gtgttagatc | cgtgtttgtg | ttagatccgt | gctgctagcg ttcgtacacg gatgcgacct | 1140 |
| gtacgtcaga | cacgttctga | ttgctaactt | gccagtgttt ctctttgggg aatcctggga | 1200 |
| tggctctagc | cgttccgcag | acgggatcga | tttcatgatt tttttgttt cgttgcatag | 1260 |
| ggtttggttt | gcccttttcc | tttatttcaa | tatatgccgt gcacttgttt gtcgggtcat | 1320 |
| ctttcatgc | tttttttgt | cttggttgtg | atgatgtggt ctggttgggc ggtcgttcta | 1380 |
| gatcggagta | gaattctgtt | tcaaactacc | tggtggattt attaattttg gatctgtatg | 1440 |
| tgtgtgccat | acatattcat | agttacgaat | tgaagatgat ggatggaaat atcgatctag | 1500 |
| gataggtata | catgttgatg | cgggtttac | tgatgcatat acagagatgc ttttgttcg | 1560 |
| cttggttgtg | atgatgtggt | gtggttgggc | ggtcgttcat tcgttctaga tcggagtaga | 1620 |
| atactgttc | aaactacctg | gtgtatttat | taatttgga actgtatgtg tgtgtcatac | 1680 |
| atcttcatag | ttacgagttt | aagatggatg | gaaatatcga tctaggatag gtatacatgt | 1740 |
| tgatgtgggt | tttactgatg | catatacatg | atggcatatg cagcatctat tcatatgctc | 1800 |
| taaccttgag | tacctatcta | ttataataaa | caagtatgtt ttataattat tttgatcttg | 1860 |

| | | | | |
|---|---|---|---|---|
| atatacttgg | atgatggcat | atgcagcagc | tatatgtgga | ttttttttagc cctgccttca | 1920 |
| tacgctattt | atttgcttgg | tactgtttct | tttgtcgatg | ctcaccctgt tgtttggtgt | 1980 |
| tacttctgca | gctgttagtt | tcatcgtatt | attttttaaaa | tctaccacta catgttttc | 2040 |
| tgccaattcg | tccactccta | ctatcatgtc | atgtgacatg | tttggcatta ttacacattg | 2100 |
| tagtgcatac | atattcttgc | ccagtcgtac | cattactcgt | atgccttcat ttatagttgc | 2160 |
| caatgtccgt | tgtttgcgc | ccactaaatt | taccctaggt | attttataaa ttaaatttgt | 2220 |
| taagttatct | tcttctatta | gttttctgtt | gaccaatcag | ctttcttgta caaagtggtc | 2280 |
| gatatcaggt | ccgccttgtt | tctcctctgt | ctcttgatct | gactaatctt ggtttatgat | 2340 |
| tcgttgagta | attttgggga | aagcttcgtc | cacagttttt | tttcgatgaa cagtgccgca | 2400 |
| gtggcgctga | tcttgtatgc | tatcctgcaa | tcgtggtgaa | cttatttctt ttatatcctt | 2460 |
| tactcccatg | aaaaggctag | taatctttct | cgatgtaaca | tcgtccagca ctgctattac | 2520 |
| cgtgtggtcc | atccgacagt | ctggctgaac | acatcatacg | atctatggag caaaaatcta | 2580 |
| tcttccctgt | tctttaatga | aggacgtcat | tttcattagt | atgatctagg aatgttgcaa | 2640 |
| cttgcaagga | ggcgtttctt | tctttgaatt | taactaactc | gttgagtggc cctgtttctc | 2700 |
| ggacgtaagg | cctttgctgc | tccacacatg | tccattcgaa | ttttaccgtg tttagcaagg | 2760 |
| gcgaaaagtt | tgcatcttga | tgatttagct | tgactatgcg | attgctttcc tggacccgtg | 2820 |
| cagctgccca | tcgaccactt | tgtacaagaa | agctgattgg | tcaacagaaa actaatagaa | 2880 |
| gaagataact | taacaaattt | aatttataaa | atacctaggg | taaatttagt gggcgcaaac | 2940 |
| aaacggacat | tggcaactat | aaatgaaggc | atacgagtaa | tggtacgact gggcaagaat | 3000 |
| atgtatgcac | tacaatgtgt | aataatgcca | acatgtcac | atgacatgat agtaggagtg | 3060 |
| gacgaattgg | cagaaaaaca | tgtagtggta | gattttaaaa | ataatacgat gaaactaaca | 3120 |
| g | | | | | 3121 |

<210> SEQ ID NO 252
<211> LENGTH: 3758
<212> TYPE: DNA
<213> ORGANISM: Diabrotica virgifera virgifera

<400> SEQUENCE: 252

| | | | | |
|---|---|---|---|---|
| gtgcagcgtg | acccggtcgt | gcccctctct | agagataatg | agcattgcat gtctaagtta | 60 |
| taaaaaatta | ccacatattt | tttttgtcac | acttgtttga | agtgcagttt atctatcttt | 120 |
| atacatatat | ttaaacttta | ctctacgaat | aatataatct | atagtactac aataatatca | 180 |
| gtgttttaga | gaatcatata | aatgaacagt | tagacatggt | ctaaaggaca attgagtatt | 240 |
| ttgacaacag | gactctacag | ttttatcttt | ttagtgtgca | tgtgttctcc ttttttttg | 300 |
| caaatagctt | cacctatata | atacttcatc | cattttatta | gtacatccat ttagggttta | 360 |
| gggttaatgg | tttttataga | ctaatttttt | tagtacatct | attttattct attttagcct | 420 |
| ctaaattaag | aaaactaaaa | ctctatttta | gttttttat | ttaataattt agatataaaa | 480 |
| tagaataaaa | taaagtgact | aaaaattaaa | caaatacct | ttaagaaatt aaaaaaacta | 540 |
| aggaaacatt | tttcttgttt | cgagtagata | atgccagcct | gttaaacgcc gtcgacgagt | 600 |
| ctaacggaca | ccaaccagcg | aaccagcagc | gtcgcgtcgg | gccaagcgaa gcagacggca | 660 |
| cggcatctct | gtcgctgcct | ctggaccct | ctcgagagtt | ccgctccacc gttggacttg | 720 |
| ctccgctgtc | ggcatccaga | aattgcgtgg | cggagcggca | gacgtgagcc ggcacggcag | 780 |
| gcggcctcct | cctcctctca | cggcaccggc | agctacgggg | gattcctttc ccaccgctcc | 840 |

```
ttcgctttcc cttcctcgcc cgccgtaata aatagacacc ccctccacac cctctttccc      900
caacctcgtg ttgttcggag cgcacacaca cacaaccaga tctcccccaa atccacccgt      960
cggcacctcc gcttcaaggt acgccgctcg tcctccccc cccccctctc taccttctct      1020
agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt ttttttgttt cgttgcatag     1260
ggtttggttt gcccttttcc tttatttcaa tatatgccgt gcacttgttt gtcgggtcat     1320
cttttcatgc ttttttttgt cttggttgtg atgatgtggt ctggttgggc ggtcgttcta     1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc ttttgttcg      1560 cttggttgtg atgatgtggt gtggttgggc ggtcgttcat tcgttctaga tcggagtaga    1620
atactgtttc aaactacctg gtgtatttat taattttgga actgtatgtg tgtgtcatac     1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat tttgatcttg    1860
atatacttgg atgatggcat atgcagcagc tatatgtgga ttttttttagc cctgccttca    1920 tacgctattt atttgcttgg tactgtttct tttgtcgatg ctcaccctgt tgtttggtgt    1980
tacttctgca ggcaaattct atgttaattt gacgattatt ttaaaataac aaggaatgta    2040
gagttgtagg ttaaaaaatt agaataaaat ataatttaca accagtgaac actgatgagt   2100
tgtataaaat acataatata taaatattgt ttttgcaaga acttttcatg catggatgac   2160
caccattccc aatacagtcc ggagtgttta tagaaatgct cttttccaaa ttatttttc    2220 tcttaaacac aacacaatgt gcgagtaata tctaacttga aactgaacgt ttgactcaca   2280
ctgaattgca gtaacgcttg aaacgccact gtggtctata tcgggaatct gtgggcacgt   2340
tttgcgacag ttacttgtta gtacgcgata ctttgctctg tagaatgttt ccgattcaga   2400
gaggcaaaaa atcgcgtcgg tctcaaggtt cagagcgcca atcacagaag ttttttctaa   2460
acttaaaatc tagaaggagg catctagtgc gtcaataaaa gatttctaaa atattgttac   2520
ggaaggttgt cagtttagtt gtagtgtttt gggctgttcc cacgtaaaac cgtcccagct   2580
ttcttgtaca aagtggtcga tatcaggtcc gccttgtttc tcctctgtct cttgatctga   2640
ctaatcttgg tttatgattc gttgagtaat tttggggaaa gcttcgtcca cagttttttt   2700
tcgatgaaca gtgccgcagt ggcgctgatc ttgtatgcta tcctgcaatc gtggtgaact   2760 tatttcttt atatccttta ctcccatgaa aaggctagta atcttctcg atgtaacatc      2820 gtccagcact gctattaccg tgtggtccat ccgacagtct ggctgaacac atcatacgat   2880
ctatggagca aaaatctatc ttccctgttc tttaatgaag acgtcatttt tcattagtat   2940
gatctaggaa tgttgcaact tgcaaggagg cgtttctttc tttgaattta actaactcgt   3000
tgagtggccc tgtttctcgg acgtaaggcc tttgctgctc cacacatgtc cattcgaatt   3060
ttaccgtgtt tagcaagggc gaaaagtttg catcttgatg atttagcttg actatgcgat   3120
tgctttcctg gacccgtgca gctgcccatc gaccactttg tacaagaaag ctggggacgg   3180
```

-continued

```
ttttacgtgg gaacagccca aaacactaca actaaactga caaccttccg taacaatatt    3240
ttagaaatct tttattgacg cactagatgc ctccttctag attttaagtt tagaaaaaac    3300
ttctgtgatt ggcgctctga accttgagac cgacgcgatt ttttgcctct ctgaatcgga    3360
aacattctac agagcaaagt atcgcgtact aacaagtaac tgtcgcaaaa cgtgcccaca    3420
gattcccgat atagaccaca gtggcgtttc aagcgttact gcaattcagt gtgagtcaaa    3480
cgttcagttt caagttagat attactcgca cattgtgttg tgtttaagag aaaaaataat    3540
ttggaaaaga gcatttctat aaacactccg gactgtattg ggaatggtgg tcatccatgc    3600
atgaaaagtt cttgcaaaaa caatatttat atattatgta ttttatacaa ctcatcagtg    3660
ttcactggtt gtaaattata ttttattcta atttttttaac ctacaactct acattccttg    3720
ttattttaaa ataatcgtca aattaacata gaatttgc                            3758
```

UNITED STATES PATENT AND TRADEMARK OFFICE
CERTIFICATE OF CORRECTION

| | |
|---|---|
| PATENT NO. | : 9,686,995 B2 |
| APPLICATION NO. | : 13/791596 |
| DATED | : June 27, 2017 |
| INVENTOR(S) | : Karen E Broglie et al. |

Page 1 of 1

It is certified that error appears in the above-identified patent and that said Letters Patent is hereby corrected as shown below:

On the Title Page

Assignee should read:
--E. I. DU PONT DE NEMOURS AND COMPANY, WILMINGTON DE US--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*